US011634692B2

(12) United States Patent
Shah et al.

(10) Patent No.: US 11,634,692 B2
(45) Date of Patent: Apr. 25, 2023

(54) ALDEHYDE DEHYDROGENASE VARIANTS AND METHODS OF USING SAME

(71) Applicant: GENOMATICA, INC., San Diego, CA (US)

(72) Inventors: Amit Shah, San Diego, CA (US); Joseph Warner, Oceanside, CA (US)

(73) Assignee: GENOMATICA, INC., San Diego, CA (US)

( * ) Notice: Subject to any disclaimer, the term of this patent is extended or adjusted under 35 U.S.C. 154(b) by 0 days.

(21) Appl. No.: 17/280,181

(22) PCT Filed: Sep. 25, 2019

(86) PCT No.: PCT/US2019/052829
§ 371 (c)(1),
(2) Date: Mar. 25, 2021

(87) PCT Pub. No.: WO2020/068900
PCT Pub. Date: Apr. 2, 2020

(65) Prior Publication Data
US 2021/0348134 A1 Nov. 11, 2021

Related U.S. Application Data

(60) Provisional application No. 62/737,053, filed on Sep. 26, 2018, provisional application No. 62/740,830, filed on Oct. 3, 2018.

(51) Int. Cl.
*C12N 9/02* (2006.01)
*C12N 15/90* (2006.01)
*C12P 7/04* (2006.01)
*C12P 7/62* (2022.01)
*C12P 13/02* (2006.01)

(52) U.S. Cl.
CPC ............ *C12N 9/0008* (2013.01); *C12N 15/90* (2013.01); *C12P 7/04* (2013.01); *C12P 7/62* (2013.01); *C12P 13/02* (2013.01); *C12Y 102/01003* (2013.01)

(58) Field of Classification Search
None
See application file for complete search history.

(56) References Cited

U.S. PATENT DOCUMENTS

| | | | |
|---|---|---|---|
| 7,127,379 B2 | 10/2006 | Palsson et al. | |
| 7,135,315 B2 * | 11/2006 | Hoshino | C12N 9/0006 435/254.2 |
| 7,858,350 B2 | 12/2010 | Burk et al. | |
| 8,067,214 B2 | 11/2011 | Burk et al. | |
| 8,129,169 B2 | 3/2012 | Van Dien et al. | |
| 8,377,666 B2 | 2/2013 | Haselbeck et al. | |
| 9,017,983 B2 | 4/2015 | Burgard et al. | |
| 2002/0012939 A1 | 1/2002 | Palsson | |
| 2002/0168654 A1 | 11/2002 | Maranas et al. | |
| 2003/0059792 A1 | 3/2003 | Palsson et al. | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2009/0047719 A1 | 2/2009 | Burgard et al. | |
| 2012/0021478 A1 | 1/2012 | Osterhout et al. | |
| 2013/0029381 A1 | 1/2013 | Haselbeck et al. | |
| 2013/0066035 A1 | 3/2013 | Burgard et al. | |
| 2014/0030779 A1 | 1/2014 | Pharkya et al. | |
| 2014/0371417 A1 | 12/2014 | Pharkya et al. | |
| 2015/0148513 A1 | 5/2015 | Pharkya et al. | |

FOREIGN PATENT DOCUMENTS

| | | |
|---|---|---|
| WO | WO 2002/055995 | 7/2002 |
| WO | WO 2003/106998 | 12/2003 |
| WO | WO 2008/115840 | 9/2008 |
| WO | WO 2009/094485 | 7/2009 |
| WO | WO 2010/030711 | 3/2010 |
| WO | WO 2010/127319 | 11/2010 |
| WO | WO 2010/141920 | 12/2010 |
| WO | WO 2011/047101 | 4/2011 |
| WO | WO 2012/018624 | 2/2012 |
| WO | WO 2012/177619 | 12/2012 |
| WO | WO 2013/036764 | 3/2013 |

(Continued)

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Uniprot Accession No. A0A1I1SDY2, Nov. 22, 2017.*
Altschul et al., "Basic local alignment search tool," *J. Mol. Biol.* 215(3):403-410 (1990).
Bergquist et al., "Degenerate oligonucleotide gene shuffling (DOGS) and random drift mutagenesis (RNDM): two complementary techniques for enzyme evolution," *Biomol. Eng.*, 22:63-72 (2005).
Bergquist et al., "Degenerate oligonucleotide gene shuffling," *Methods Mol. Biol.*, 352:191-204 (2007).
Burgard et al., "Minimal reaction sets for *Escherichia coli* metabolism under different growth requirements and uptake environments," *Biotechnol. Prog.*, 17(5):791-797 (2001).

(Continued)

*Primary Examiner* — Richard G Hutson
(74) *Attorney, Agent, or Firm* — Greenberg Traurig, LLP

(57) ABSTRACT

The invention provides polypeptides and encoding nucleic acids of aldehyde dehydrogenase variants. The invention also provides cells expressing aldehyde dehydrogenase variants. The invention further provides methods for producing 3-hydroxybutyraldehyde (3-HBal) and/or 1,3-butanediol (1,3-BDO), or an ester or amide thereof, comprising culturing cells expressing an aldehyde dehydrogenase variant or using lysates of such cells. The invention additional provides methods for producing 4-hydroxybutyraldehyde (4-HBal) and/or 1,4-butanediol (1,4-BDO), or an ester or amide thereof, comprising culturing cells expressing an aldehyde dehydrogenase variant or using lysates of such cells.

26 Claims, 9 Drawing Sheets
Specification includes a Sequence Listing.

(56) References Cited

FOREIGN PATENT DOCUMENTS

| | | |
|---|---|---|
| WO | WO 2013/150153 | 10/2013 |
| WO | WO 2013/184602 | 12/2013 |
| WO | WO 2014/176514 | 10/2014 |
| WO | WO 2014/190251 | 11/2014 |
| WO | WO 2014/200994 | 12/2014 |
| WO | WO 2018/183664 | 10/2018 |

OTHER PUBLICATIONS

Burgard et al., "Optknock: a bilevel programming framework for identifying gene knockout strategies for microbial strain optimization," *Biotechnol. Bioeng.*, 84(6):647-657 (2003).
Coco et al., "DNA shuffling method for generating highly recombined genes and evolved enzymes," *Nat. Biotechnol.*, 19(4):354-359 (2001).
Colonna et al., "Synthesis and radiocarbon evidence of terephthalate polyesters completely prepared from renewable resource," *Green Chem.*, 13:2543-2548 (2011).
Currie et al., "Authentication and dating of biomass components of industrial materials; links to sustainable technology," *Nucl. Instrum. Methods Phys. Res. B*, 172:281-287 (2000).
EBI Accession No. GSP: BBP76764, "*Mycobacterium smegmatis* alpha-ketoglutarate decarboxylase SEQ:439" (2014).
EBI Accession No. GSP: BBR45068, "L. brevis coenzyme-A-acylating propionaldehyde dehydrogenase, SEQ 48" (2015).
EBI Accession No. GSP: BFS48689, "Mutant Clostridium saccharoperbutylacetinicum ALD-1 protein #49" (2018).
EBI Accession No. UNIPROT: A0A1H0T3I8, "Propionaldehyde dehydrogenase" (2017).
Fujii et al., "Error-prone rolling circle amplification: the simplest random mutagenesis protocol," *Nat. Protoc.*, 1(5):2493-2497 (2006).
Fujii et al., "One-step random mutagenesis by error-prone rolling circle amplification," *Nucleic Acids Res.*, 32(19):e145 (2004).
Gibbs et al., "Degenerate oligonucleotide gene shuffling (DOGS): a method for enhancing the frequency of recombination with family shuffling," *Gene*, 271(1):13-20 (2001).
Goswami et al., "Enzymatic strategies and biocatalysts for amide bond formation: tricks of the trade outside of the ribosome," *Mol. Biosyst.*, 11(2):338-353 (2015).
Hayes et al., "Combining computational and experimental screening for rapid optimization of protein properties," *Proc. Natl. Acad. Sci. USA*, 99(25):15926-15931 (2002).
Hibbert et al., "Directed evolution of biocatalytic processes," *Biomol. Eng.*, 22(1-3):11-19 (2005).
Hoffmeister et al., "Mitochondrial trans-2-enoyl-CoA reductase of wax ester fermentation from Euglena gracilis defines a new family of enzymes involved in lipid synthesis," *J. Biol. Chem.*, 280(6):4329-4338 (2005).
Houghten, "General method for the rapid solid-phase synthesis of large numbers of peptides: specificity of antigen-antibody interaction at the level of individual amino acids," *Proc. Natl. Acad. Sci. USA*, 82(15):5131-5135 (1985).
Huisman et al., "Enzyme Evolution for Chemical Process Applications" *Biocatalysis in the Pharmaceutical and Biotechnology Industries*, Patel ed., CRC Press, pp. 717-742 (2007).
Karlen et al., "Absolute determination of the activity of two $C^{14}$ dating standards," *Arkiv Geofysik*, 4:465-471 (1968).
Kretz et al., "Gene site saturation mutagenesis: a comprehensive mutagenesis approach," *Methods Enzymol.*, 388:3-11 (2004).
Lee et al., "A new approach to directed gene evolution by recombined extension on truncated templates (RETT)," *J. Molec. Catalysis*, 26:119-129 (2003).
Lin et al., "Fed-batch culture of a metabolically engineered *Escherichia coli* strain designed for high-level succinate production and yield under aerobic conditions," *Biotechnol. Bioeng.*, 90(6):775-779 (2005).
Low et al., "Mimicking somatic hypermutation: affinity maturation of antibodies displayed on bacteriophage using a bacterial mutator strain," *J. Mol. Biol.*, 260(3):359-368 (1996).

Lutz et al., "Creating multiple-crossover DNA libraries independent of sequence identity," *Proc. Natl. Acad. Sci. USA*, 98(20):11248-11253 (2001).
Lutz et al., "Rapid generation of incremental truncation libraries for protein engineering using alpha-phosphothioate nucleotides," *Nucleic Acids Res.*, 29(4):E16 (2001).
Mann, "An International Reference Material for Radiocarbon Dating," *Radiocarbon*, 25(2):519-527 (1983).
Merrifield, "Solid Phase Peptide Synthesis. I. The Synthesis of a Tetrapeptide," *J. Am. Chem. Soc.* 85:2149-2154 (1964).
Muller et al., "Nucleotide exchange and excision technology (NExT) DNA shuffling: a robust method for DNA fragmentation and directed evolution," *Nucleic Acids Res.*, 33(13):e117 (2005).
Ness et al., "Synthetic shuffling expands functional protein diversity by allowing amino acids to recombine independently," *Nat. Biotechnol.*, 20(12):1251-1255 (2002).
Ostermeier et al., "A combinatorial approach to hybrid enzymes independent of DNA homology," *Nat. Biotechnol.*, 17(12):1205-1209 (1999).
Ostermeier et al., "Combinatorial protein engineering by incremental truncation," *Proc. Natl. Acad. Sci. USA*, 96(7):3562-3567 (1999).
Otten et al., "Directed evolution: selecting today's biocatalysts," *Biomol. Eng.*, 22:1-9 (2005).
Pritchard et al., "A general model of error-prone PCR," *J. Theor. Biol.*, 234(4):497-509 (2005).
Rajpal et al., "A general method for greatly improving the affinity of antibodies by using combinatorial libraries," *Proc. Natl. Acad. Sci. USA*, 102(24):8466-8471 (2005).
Reetz et al., "Directed Evolution of an Enantioselective Enzyme through Combinatorial Multiple-Cassette Mutagenesis," *Angew. Chem. Int. Ed Engl.*, 40(19):3589-3591 (2001).
Reetz et al., "Iterative saturation mutagenesis (ISM) for rapid directed evolution of functional enzymes," *Nat. Protoc.*, 2(4):891-903 (2007).
Reetz et al., "Iterative saturation mutagenesis on the basis of B factors as a strategy for increasing protein thermostability,"*Angew. Chem. Int. Ed Engl.*, 45(46):7745-7751 (2006).
Reidhaar-Olson et al., "Combinatorial cassette mutagenesis as a probe of the informational content of protein sequences," *Science*, 241(4861):53-57 (1988).
Reidhaar-Olson et al., "Random mutagenesis of protein sequences using oligonucleotide cassettes," *Methods Enzymol.*, 208:564-586 (1991).
Selifonova et al., "Rapid evolution of novel traits in microorganisms," *Appl. Environ. Microbiol.*, 67(8):3645-3649 (2001).
Sen et al., "Developments in directed evolution for improving enzyme functions," *Appl. Biochem. Biotechnol.*, 143(3):212-223 (2007).
Shao et al., "Random-priming in vitro recombination: an effective tool for directed evolution," *Nucleic Acids Res.*, 26(2):681-683 (1998).
Sieber et al., "Libraries of hybrid proteins from distantly related sequences," *Nat. Biotechnol.*, 19(5):456-460 (2001).
Stemmer, "DNA shuffling by random fragmentation and reassembly: in vitro recombination for molecular evolution," *Proc. Natl. Acad. Sci. USA*, 91(22):10747-10751 (1994).
Stemmer, "Rapid evolution of a protein in vitro by DNA shuffling," *Nature*, 370(6488):389-391 (1994).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Wong et al., "Sequence saturation mutagenesis (SeSaM): a novel method for directed evolution," *Nucleic Acids Res.*, 32(3):e26 (2004).
Wong et al., "Sequence saturation mutagenesis with tunable mutation frequencies," *Anal. Biochem.*, 341(1):187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.*, 3(1):74-82 (2008).

(56) References Cited

OTHER PUBLICATIONS

Zhao et al., "Molecular evolution by staggered extension process (StEP) in vitro recombination," Nat. Biotechnol., 16(3):258-261 (1998).
Database RefSeq [Online] Feb. 27, 2017, "aldehyde dehydrogenase EutE [Clostridium puniceum]", retrieved from NCBI accession No. WP_077849585.1, Database accession No. WP_077849585.
Database RefSeq [Online] Aug. 18, 2017, "aldehyde dehydrogenase EutE [Petroclostridium xylanilyticum]", XP093010778, retrieved from NCBI accession No. WP_094548529.1, Database accession No. WP_094548529.

* cited by examiner

```
ALD-1    1   ------MIKDTLVSITKDLKLKTNVEMANLKNYKDSSCFGGVFEMVEMAISNAVHAQKILSLBYTKEQREKITTEIRKAA
ALD-2    1   ---MNTENIEQAIREILSEELSNPQSSTATNTVFGKM---GIFKTVNEAIAATKAAQENYA-QQPISVRNKVIDAIKBGF
ALD-3    1   MTVNEQLVQDIIKNVVASMQL-TQTNKTEL---------GVFDDMNQAIEAAKEAQLVVK-KMSMDQREKIISAIRRKT

ALD-1   75   LENKEILATMILEETHMGRYEDKILLKKHELVAKYTFGCTEDLPTTAWSGDNGLTVVEMSPYGVIGAITPSTNPTETVICNSI
ALD-2   75   RPYTEDMAERIHDETGMGTVSARIAKLNNALYNTPGPETLQEEABTGDGGLVMYEYAPFGVIGAVGPSTNPSETVIANAI
ALD-3   69   IEHARTLARMAVEETGMGNVGHFILKHQLVAEKTPGTEDITTTAWSGDRGLTLVEMGPFGVIGAITPCTNFSETICNTI

ALD-1  155   GMLAAGNTVVFNGHPGARKCVAFAVRMINKAIISC-GGPENLVTTIKNPTMQSLDAIRHPSIKLLCGTGGPGMVKTLLM
ALD-2  155   MMLAGGNTLFFGAHPGARNITRWTIEKLNELVADATGLBNLVV-SLETPSIERSVQEVMQHPDVAMLSITGGPAVVHQALI
ALD-3  149   GMLAGGNTVVFNPHPAAIKTSNFAVQLINEASLSA-GGPVNIACSVRKPTLDSSKIMMGSBQDIPLIAATGGPGVVTAVLQ

ALD-1  234   SGKRAIGAGAGAGNPPVIVDDTADIERAGSKSIIEGCSFDNNLPCTAEKEVFVEENVADDLISNMLKNNAV-IMEDQVSKLI
ALD-2  234   SGKKAVGAGAGAGNPPAMVDATAMIALAAHNIVDSAAFDNNLCTAEKEVVVERAAVKDELIMRMQQEGAFLVTDSADIEKLLA
ALD-3  228   SGKRGIGAGAGNPPVLVDETADIRKAABDIINGCTFDNNLPCTAEKEVVAIDALANELMNZMVKEQGCYATTKEQQEKLT

ALD-1  313   DIVLQKNNETQEYSINKKWVGKDAKLFLDEIDVESPSSVKCIICRVSASHPFVMTELMMPILPIVRVEDIDEAIEYAKIA
ALD-2  314   QMITGFKGAP------DRKFVGKDATYIILDQAGISYTGHPTLIILERAAKDEPLVTTEMLMPILPVVCCPDFDSVLATATEV
ALD-3  308   NLIVTFKG-------LNPRNCVGRDARTLLGSMIGIDVPSNIRCIIFKGEKEBPLHSEBLMMPILGIVRAKSFDDAVEKAVWL

ALD-1  393   EQMRKHSAYIYSKNIDMLNRFEREIDTTIFVKNAKSFAGVGYEAE---GFTFTIAGSTGEGITSARNFTEQRRCVLAG
ALD-2  389   EGGLHHTASIHSERNLPHTNKAABRLMTSIPYVNGPTYCGTGVATMGAHSGASALTIATPGEGTATSKYTYRERRLNSPE
ALD-3  382   EHGMRHSAHIBSKNVDRITTYAKAIDTALLVRNAPSYAAIGFGGE---GFCTFTIASRTGEGLTSASTFTERRRCVMSQ

ALD-1  469   ------------
ALD-2  469   GFSLRTWEA    477
ALD-3  458   SLCIR------  462
```

FIG. 3

```
ALD-1     1   M-------------------------------------------IKDTLVSITKDLKLKTNVENANLKNYKDDSSCF------
SEQ 13    1   M--------------------------------------------------SVNERMVQDI--------VQEVVAKM--------
SEQ 20    1   M--------------------------------------------------PINENMVQEI--------VQEVVAKM--------
SEQ 24    1   MNDGQIAAAVAKVLEAYGVEADPSAAAPAPAAPVAPAAPTAGSVSEMIARGIAKASSDDQIAQIVAKVVGDYSAQAAKPA

ALD-1    35   ----------GVFENVENAISMAVHAQKTLSLBYTKEQREKITTEIRKAALEN--KEILAIMTLEETMMGRYEDKIL
SEQ 13   20   ----QIASDVTGNHGVFQDMNAAIEAAKKTQKVVA-BMSMDQBEKITSNIBAKIKER--AEIFABMGVQETGMGNVGHNIL
SEQ 20   20   ----QIADAPTGKHGIFKEMNDAIEAAKKSQLIVK-EMSMDQBEKITTCIRKKIKEN--AEVMABMGVEETGMGNVGDEIL
SEQ 24   81   VVPGAASTEAGDGVFDTMDAAVDAAVLAGQQYL--LCSMTDRQRFVDGIREVILQKDTLELISRMAARETGMGNYEHKLI

ALD-1   100   KHELVAKYTPGTEDLITTAWSGDNGLHVVEMSPYGVIGAITPSTNPTHPVICNSIGMLAAGNTVVFNGHPGAKKCVAFAV
SEQ 13   94   KHQLVAEKTPGTEDIQTTAWSGGRGLTLIEMGSPFGVIGAITPCINPSEPVLCNTIGMLAGGNPVVFNPHPAAIKTSIYAV
SEQ 20   94   KHHLVADKTESTEVITTTAWSGERGLTLIEMGPEGVIGAITPCINPSETILCNTMGMLAGGNTVVENPHPAAIKTSIYAI
SEQ 24  160   KNRLAAEKTPCTEDLTTEAFSGDDGLTLVEYSPFGAIGAVAPTTNPTETIICNSIGMLAAGNSVIFSPHPRATKVSLLTY

ALD-1   180   EMINKAITSCGGPENLVTTIKNPTMDSLDAIIKHPSIKLLCGTGGFGMVKTLLMSGKKAIGAGAGNPVTVDDTAOIEKA
SEQ 13  174   NLINEASIEASGPDNIACTVENPTLESSNIMMKHKDIPLIAATGEGVVTAVLSSGKRGIGAGAGNPFALVDETAOIRKA
SEQ 20  174   NLLNEASLESSGPDNIAVTVEKPTLETSNVMMKHKDIPLIAATGEGVVTAVLSSGKRGIGAGAGNPFALVDETAOIRKA
SEQ 24  240   KLINQRLACLGAPANLVTVSKPSVENTNAMMABPKIRMLVATGGPGIVKAVMSTGKKAIGAGAGNPVVVDETAOIEKA

ALD-1   260   GKSTIEGCSFDNNLPCIAEKEYFVFENVADDLISNMLKNNAV-INEPQVSKLIDLVLQKNNETQEYSINEKWVGKDAKL
SEQ 13  254   AEDTVNGCTFDNNLPCTAKKEIVAVDSIADELMHYMISEQGCYLASKEEQCALTEVVLKG-GR------LNRKCVGRDAFT
SEQ 20  254   ATDIVNGCTFDNNLPCIARKEIVAVSSIVGELMHYLVTENDCYLASKEQKITEVVLAG--GK-------LNRKCVGRDART
SEQ 24  320   ALDIINGCSFDNNLPCIARKEIIAVAQIADYLIFSMKKQGAYQITDPAVLRKLQDLVLTAKGG-------PQTSCVGKSAVW

ALD-1   339   FLDEIDVESPSSVKCIICEVSASHPEVMTELMMPILPFIVRVKDIDEAIEYANIAEQMRRESAYIYSKNIDMLNKRHEIO
SEQ 13  328   LLGMIGVTVFDNIRCITFEGPKEHPLIAEELMMPTLGVVRAKDFFDAVEQAVWLEHGNRBSAHIHSKNVDNITKYAKAID
SEQ 20  328   LLSMIGVNAFAMIRCIVFFEGPKEHPLITTELMMPTLGVVRARDFFDAVEQAVWLEHGNRBSAHIHSENIDNITKYAKAID
SEQ 24  395   LINEIGIEVDSSVKVILMEVPKEHPFVQRELMMPTLPLVRVSDVDEAIAVALEVEHGNRHTAIMHSTNVRKLTEMAKLIQ

ALD-1   419   TTIFVKNAKSEAGVGYEAEGFTTETLAGSTGEGITSARNFTRQRRCVLAG------                           468
SEQ 13  408   TAILVKNGPSYAAIGFVGGEGFCTFTIASRTGEGLTSASAFTKRRRCVMCDSLCIR                            462
SEQ 20  408   TAILVKNAPSYAALGKGGEGYCTFTIASRTGEGLTSASAFTKRRRPCVMADSLCIR                            462
SEQ 24  475   TTFVKNGPSYAGLGVGGEGYITFTIAGPTGEGLTSAKSFARKRKCVMVEALNIR                              529
```

FIG. 4A

```
ALD-1    1    MIKD-TLVS----I--TKDLKLKTNVEMANLKNYEDDSSCFGVENVENAISNAVBAQKILSLHYTKEQREKIITEIRKAA
SEQ 30   1    MNNN-LFVS----PETKDLSLRTNVEMLKEPGCEGGSTYIGVEBNAETAIDEAVNAQKPLSLYTTKEQREKITEIRKVT
SEQ 33   1    MERNLSYLS----Q-TNDLKITKPTEGDKSNKE----SYLGVFKKVENAITKAIYAQKKLSLYTTKEDRERIEKSIRKAT
SEQ 37   1    MDVDVLVEKLVRQAIEEVKNKNLLNLDKFESVKN----YGIFGTMDAAVEASFVAQKQL-LNASMTKQKYVDTIKATI

ALD-1    75   L--ENKEILATMILEETHMGRYEDKILKBELVAKYTPGTEDLTTAWSGEMGLTVVEMSPYGVIGATTPSTMPTETVICN
SEQ 30   76   L---ENKEILAQMILEETHMGRYEDKILKHELVAKYTPGTEDLATTAWSGEMGLTVVEMSPYGVIGATTPSTMPTETVICN
SEQ 33   73   L---ENKEILARKMIVDETHMGRYEDKILKHELVAKYTPGTEDLITTAWSGEQGLTLVEMSPYGVIGATTPSTMPTETVICN
SEQ 37   76   LRKRNLELISRMSVEETETGKYEBHKLIKMRVAAEKTPGIERDLTTEAMTGEMGLTVEYCPFGVIGATTPTMPTETTICN

ALD-1    153  SIGMIAAGNTVVFNGHPGAKKCVAFAVEMINKAISCGGPENLVTTIKNPTMDSLDAIIKHPSIKLLCGTGGPGMVKTLL
SEQ 30   154  SIGMIASGNAVVENGHPGAKKCVAFAVDMINRAISCGGPRNLVTAIKNPTMESLDAIIKHPAIKLLCGTGGPGMVKTLL
SEQ 33   151  SIGMIAAGDSVVFNGHPGAKKCVAFAFAVDMINKEAVIREGGPENLVTTVENPTMESLNVIMAHPYIKLLCGTGGFGLIKTLL
SEQ 37   156  SISMIAGGNTVVFSPHFRAKNVSIKLVTMLNKEALEKAGAPDMLIATVKEPSIENTNIPMEHPKIRMLVATGGFAIVNKVM

ALD-1    233  NSGKNAIGAGAGNPPVIVDTADIENAGKSIIEGCSFDNNLPCIAEKEVFVFENVADDLISMMLKNNAVIINE-DQVSKL
SEQ 30   234  SSGKNSIGAGAGNPPVIVDTADIENAGKSIIEGCSFDNNLPCIAEKEVFVFENVADDLIKNMLKNNAVIINK-DQVSRL
SEQ 33   231  NSGKKAIGAGAGNPPVIVDSADIDKAAKNIIEGCSFDNNLPCIAEKEVFENVANDLIQNMIKNNAVLINE-MQVSKL
SEQ 37   236  STGKKAIGAGAGAGNPPVVDETADIEKAAIDIVNGCSFDNNVPCIAEKEVFAVDQVCDYLIHYMKLNGAYEIKDRLIQKL

ALD-1    312  IDEV-LQEMNETQEYSINKKWVGKDAKLFLDEIDVESPSSVECIICEVSASHPFVMTELMMFILPTVRKDIDEAIEYAK
SEQ 30   313  VBLV-LQEMNETSEYTINKKWVGKDAKLFLDEIDVESSSDVRCIICEVDADHPFVMTELMMFILPTVRKDIDEAIKYAK
SEQ 33   310  LDLVLLERADETLEYAINKKWVGKDAKLFLDKIGIEASDNVRCIICEVDAMBPFVMTELMMPILPTVRKDVDEAIECAK
SEQ 37   316  LDLVTNENGGPKV-----SFVGKSAPYILNKLGISVDENIKVIIMEVERMBHFVLEEMMPILPIVRTMDVDEAIECAY

ALD-1    391  IAEQNPRKHSAYIYSKNIDMLNKFEREIDTTIFVKMAKSFAGVGYEABGETTFTIAGSTGEGTTSARNFTKQRRCVLAG---
SEQ 30   392  IAEQNPRKHSAYIYSKNIEMLNKFEKEIDTTIFVKMAKSFAGVSYGVGAEGETTFFTIAGCTGEGTTSARNFTKQRRCVFVG---
SEQ 33   390  TAEQEMKRHSAYMYSKNIDMLNKFEKEIDTTIFVKMAKSFAGVGFGAEGETTFETIAGPTGEGTTSARNFTKQRRCVLAG---
SEQ 37   390  VAEHGMRHTAIMHSKNVDELTKMARLLETTIFVKNSPSYAGIGVGGSGTTFFTLAGPTGEGLTTARSFCRKRRCVMVDAF

ALD-1         ----
SEQ 30        ----
SEQ 33        ----
SEQ 37   470  NIR
```

FIG. 4B

```
ALD-1    1    MIKDTLVSITKDLKLKTNVENAMLKNYKDDSSCFGVFENVENAISMAVHAQKILSLHYTKEQREKIITEIRKAALENKEI
SEQ 38   1    MIKDTLVSITKDLKLKTNVENAMLKNYKDDSSCFGVFENVENAISMAVHAQKILSLHYTKEQREKIITEIRKAALENKEI
SEQ 40   1    MKDTLVSVTKDLKLKTNVENTMLKNYKDNSSCFGVFENAEMAISNAVHAQKILSLHYTKEQREKINEIRKAALENKEV
SEQ 44   1    MNKDTLIPTKDLKVKTNGENINLKNYKDNSSCFGVENVENAISSAVHAQKILSLHYTKEQREKIITEIRKAALQNKEV

ALD-1    81   LATMILEETHMGRYEDKILKHELVAKYTPGTEDLTTTAWSGDMGLTVVEMSPYGVIGAITPSTMPTETVICNSIGMIAAG
SEQ 38   81   LATMILEETHMGRYEDKILKHELVAKYTPGTEDLTTTAWSGDMGLTVVEMSPYGVIGAITPSTMPTETVICNSIGMIAAG
SEQ 40   81   LATMILEETHMGRYEDKILKHELVAKYTPGTEDLTTTAWSGDMGLTVVEMSPYGVIGAITPSTMPTETVLCNSIGMIAAG
SEQ 44   81   LATMILEETHMGRYEDKILKHELVAKYTPGTRDLTTTAWSGDMGLTVVEMSPYGVIGAITPSTMPTETVICNSIGMIAAG

ALD-1    161  NTVVFNGHPGAKKCVAFAVEMINKAIISCGGPENLVTTIKNPTMDSLDAIIKHPSIKLLCGTGGPGMVKTLLNSGKKAIG
SEQ 38   161  NTVVFNGHPGAKKCVAFAVEMINKAIISCGGPENLVTTIKNPTMDSLDAIIKHPSIKLLCGTGGPGMVKTLLNSGKKAIG
SEQ 40   161  NAVVFNGHPGAKKCVAFAVEMINKAIVSCGGPENLVTTIKNPTMESLNAIIKHPSIELLCGTGGPGMVKTLLNSGKKAIG
SEQ 44   161  NAVVFNGHFGAKKCVAFAVEMINKAIISCGGPENLVTTIKNPTMESLDAIIKHPSIKLLCGTGGPGMVKTLLNSGKKAIG

ALD-1    241  AGAGNPPVIVDDTADIEKAGKSIIEGCSFDMNLPCIAEKEVFVFENVADDLISNMLKANAVIINEDQVSKLIDIVLQKNN
SEQ 38   241  AGAGNPPVIVDDTADIEKAGKSIIEGCSFDMNLPCIAEKEVFVFENVADDLISNMLKANAVIINEDQVSKLIDIVLQKNN
SEQ 40   241  AGAGNPPVIVDDTADIEKAGKSIIEGCSFDMNLPCIAEKEVFVFEMIADDLISNMLKANAVIINEDQVSKLIDIVLQKNN
SEQ 44   241  AGAGNPPVIVDDTADIEKAGRSIIEGCSFDNNLPCIAEKEVFVFENVADDLISNMLKNNAVIINEDQISKLIDIVLQKNN

ALD-1    321  ETQEYSINKKWVGKDAKLFLDEIDVESPSSVKCIICEVSASHPFVMTELMMPILPIVRVKDIDEATEYAKIAEQNRKHSA
SEQ 38   321  ETQEYSINKKWVGKDAKLFLDEIDVESPSSVKCIICEVSASHPFVMTELMMPILPIVRVKDIDEATEYAKIAEQNRKHSA
SEQ 40   321  ETQEYSINKKWVGKDAKLFLDEIDVESPSNVKCIICEVNANHPFVMTELMMPILPIVRVKDIDEATEYAKIAEQNRKHSA
SEQ 44   321  ETQEYFINKKWVGKDAKLFLDEIDIESPSNVKCIICEVNENHPFVMTELMMPILPIVRVKDIDEATRYAKIAEQNRKHSA

ALD-1    401  YIYSKNIDNLNRFEREIDTTIFVENAKSFAGVGYEAEGFTFTIAGSTGEGITSARNFTQRRCVLAG 468
SEQ 38   401  YIYSKNIDNLNRFEREIDTTIFVENAKSFAGVGYEAEGFTFTIAGSTGEGITSARNFTQRRCVLAG 468
SEQ 40   401  YIYSKNIDNLNRFEREIDTTIFVENAKSFAGVGYEAEGFTFTIAGSTGEGITSARNFTQRRCVLAG 468
SEQ 44   401  YIYSKNIDNLNRFEREIDTTIFVENAKSFAGVGYEAEGFTFTIAGSTGEGITSARNFTQRRCVLAG 468
```

FIG. 4C

SEQUENCE LISTING

<160> NUMBER OF SEQ ID NOS: 129

<210> SEQ ID NO 1
<211> LENGTH: 468
<212> TYPE: PRT
<213> ORGANISM: Clostridium saccharoperbutylacetonicum

<400> SEQUENCE: 1

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Ser Ser
            20                  25                  30

Cys Phe Gly Val Phe Glu Asn Val Glu Asn Ala Ile Ser Asn Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
            115                 120                 125

Glu Met Ser Pro Tyr Gly Val Ile Gly Ala Ile Thr Pro Ser Thr Asn
        130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

```
Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Ser His Pro Phe Val Met Thr Glu
        355                 360                 365

Leu Met Met Pro Ile Leu Pro Ile Val Arg Val Lys Asp Ile Asp Glu
370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 2
<211> LENGTH: 477
<212> TYPE: PRT
<213> ORGANISM: Lactobacillus brevis

<400> SEQUENCE: 2

Met Asn Thr Glu Asn Ile Glu Gln Ala Ile Arg Lys Ile Leu Ser Glu
1               5                   10                  15

Glu Leu Ser Asn Pro Gln Ser Ser Thr Ala Thr Asn Thr Thr Val Pro
            20                  25                  30

Gly Lys Asn Gly Ile Phe Lys Thr Val Asn Glu Ala Ile Ala Ala Thr
        35                  40                  45

Lys Ala Ala Gln Glu Asn Tyr Ala Asp Gln Pro Ile Ser Val Arg Asn
50                  55                  60

Lys Val Ile Asp Ala Ile Arg Glu Gly Phe Arg Pro Tyr Ile Glu Asp
65                  70                  75                  80

Met Ala Lys Arg Ile His Asp Glu Thr Gly Met Gly Thr Val Ser Ala
                85                  90                  95

Lys Ile Ala Lys Leu Asn Asn Ala Leu Tyr Asn Thr Pro Gly Pro Glu
            100                 105                 110

Ile Leu Gln Pro Glu Ala Glu Thr Gly Asp Gly Gly Leu Val Met Tyr
        115                 120                 125

Glu Tyr Ala Pro Phe Gly Val Ile Gly Ala Val Gly Pro Ser Thr Asn
130                 135                 140

Pro Ser Glu Thr Val Ile Ala Asn Ala Ile Met Met Leu Ala Gly Gly
145                 150                 155                 160

Asn Thr Leu Phe Phe Gly Ala His Pro Gly Ala Lys Asn Ile Thr Arg
                165                 170                 175
```

```
Trp Thr Ile Glu Lys Leu Asn Glu Leu Val Ala Asp Ala Thr Gly Leu
            180                 185                 190

His Asn Leu Val Val Ser Leu Glu Thr Pro Ser Ile Glu Ser Val Gln
            195                 200                 205

Glu Val Met Gln His Pro Asp Val Ala Met Leu Ser Ile Thr Gly Gly
210                 215                 220

Pro Ala Val Val His Gln Ala Leu Ile Ser Gly Lys Lys Ala Val Gly
225                 230                 235                 240

Ala Gly Ala Gly Asn Pro Pro Ala Met Val Asp Ala Thr Ala Asn Ile
                245                 250                 255

Ala Leu Ala Ala His Asn Ile Val Asp Ser Ala Ala Phe Asp Asn Asn
            260                 265                 270

Ile Leu Cys Thr Ala Glu Lys Glu Val Val Glu Ala Ala Val Lys
            275                 280                 285

Asp Glu Leu Ile Met Arg Met Gln Gln Glu Gly Ala Phe Leu Val Thr
290                 295                 300

Asp Ser Ala Asp Ile Glu Lys Leu Ala Gln Met Thr Ile Gly Pro Lys
305                 310                 315                 320

Gly Ala Pro Asp Arg Lys Phe Val Gly Lys Asp Ala Thr Tyr Ile Leu
                325                 330                 335

Asp Gln Ala Gly Ile Ser Tyr Thr Gly Thr Pro Thr Leu Ile Ile Leu
            340                 345                 350

Glu Ala Ala Lys Asp His Pro Leu Val Thr Thr Glu Met Leu Met Pro
            355                 360                 365

Ile Leu Pro Val Val Cys Cys Pro Asp Phe Asp Ser Val Leu Ala Thr
            370                 375                 380

Ala Thr Glu Val Glu Gly Gly Leu His His Thr Ala Ser Ile His Ser
385                 390                 395                 400

Glu Asn Leu Pro His Ile Asn Lys Ala Ala His Arg Leu Asn Thr Ser
                405                 410                 415

Ile Phe Val Val Asn Gly Pro Thr Tyr Cys Gly Thr Gly Val Ala Thr
            420                 425                 430

Asn Gly Ala His Ser Gly Ala Ser Ala Leu Thr Ile Ala Thr Pro Thr
            435                 440                 445

Gly Glu Gly Thr Ala Thr Ser Lys Thr Tyr Thr Arg Arg Arg Arg Leu
450                 455                 460

Asn Ser Pro Glu Gly Phe Ser Leu Arg Thr Trp Glu Ala
465                 470                 475

<210> SEQ ID NO 3
<211> LENGTH: 462
<212> TYPE: PRT
<213> ORGANISM: Clostridium phytofermentans

<400> SEQUENCE: 3

Met Thr Val Asn Glu Gln Leu Val Gln Asp Ile Ile Lys Asn Val Val
1               5                   10                  15

Ala Ser Met Gln Leu Thr Gln Thr Asn Lys Thr Glu Leu Gly Val Phe
            20                  25                  30

Asp Asp Met Asn Gln Ala Ile Glu Ala Ala Lys Glu Ala Gln Leu Val
        35                  40                  45

Val Lys Lys Met Ser Met Asp Gln Arg Glu Lys Ile Ile Ser Ala Ile
    50                  55                  60

Arg Lys Lys Thr Ile Glu His Ala Glu Thr Leu Ala Arg Met Ala Val
```

```
            65                  70                  75                  80
        Glu Glu Thr Gly Met Gly Asn Val Gly His Lys Ile Leu Lys His Gln
                        85                  90                  95

Leu Val Ala Glu Lys Thr Pro Gly Thr Glu Asp Ile Thr Thr Thr Ala
                        100                 105                 110

Trp Ser Gly Asp Arg Gly Leu Thr Leu Val Glu Met Gly Pro Phe Gly
                        115                 120                 125

Val Ile Gly Ala Ile Thr Pro Cys Thr Asn Pro Ser Glu Thr Ile Ile
                        130                 135                 140

Cys Asn Thr Ile Gly Met Leu Ala Gly Gly Asn Thr Val Val Phe Asn
        145                 150                 155                 160

Pro His Pro Ala Ala Ile Lys Thr Ser Asn Phe Ala Val Gln Leu Ile
                        165                 170                 175

Asn Glu Ala Ser Leu Ser Ala Gly Gly Pro Val Asn Ile Ala Cys Ser
                        180                 185                 190

Val Arg Lys Pro Thr Leu Asp Ser Ser Lys Ile Met Met Ser His Gln
                        195                 200                 205

Asp Ile Pro Leu Ile Ala Ala Thr Gly Gly Pro Gly Val Val Thr Ala
                        210                 215                 220

Val Leu Gln Ser Gly Lys Arg Gly Ile Gly Ala Gly Ala Gly Asn Pro
        225                 230                 235                 240

Pro Val Leu Val Asp Glu Thr Ala Asp Ile Arg Lys Ala Ala Glu Asp
                        245                 250                 255

Ile Ile Asn Gly Cys Thr Phe Asp Asn Asn Leu Pro Cys Ile Ala Glu
                        260                 265                 270

Lys Glu Val Val Ala Ile Asp Ala Ile Ala Asn Glu Leu Met Asn Tyr
                        275                 280                 285

Met Val Lys Glu Gln Gly Cys Tyr Ala Ile Thr Lys Glu Gln Gln Glu
                        290                 295                 300

Lys Leu Thr Asn Leu Val Ile Thr Pro Lys Gly Leu Asn Arg Asn Cys
        305                 310                 315                 320

Val Gly Lys Asp Ala Arg Thr Leu Leu Gly Met Ile Gly Ile Asp Val
                        325                 330                 335

Pro Ser Asn Ile Arg Cys Ile Ile Phe Glu Gly Glu Lys Glu His Pro
                        340                 345                 350

Leu Ile Ser Glu Glu Leu Met Met Pro Ile Leu Gly Ile Val Arg Ala
                        355                 360                 365

Lys Ser Phe Asp Asp Ala Val Glu Lys Ala Val Trp Leu Glu His Gly
                        370                 375                 380

Asn Arg His Ser Ala His Ile His Ser Lys Asn Val Asp Arg Ile Thr
        385                 390                 395                 400

Thr Tyr Ala Lys Ala Ile Asp Thr Ala Ile Leu Val Lys Asn Ala Pro
                        405                 410                 415

Ser Tyr Ala Ala Ile Gly Phe Gly Gly Glu Gly Phe Cys Thr Phe Thr
                        420                 425                 430

Ile Ala Ser Arg Thr Gly Glu Gly Leu Thr Ser Ala Ser Thr Phe Thr
                        435                 440                 445

Lys Arg Arg Arg Cys Val Met Ser Asp Ser Leu Cys Ile Arg
        450                 455                 460

<210> SEQ ID NO 4
<211> LENGTH: 468
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 4

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
            115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Ser Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Arg Asp Ser Leu Asp
        195                 200                 205

Ala Ile Ile Lys His Pro Ser Ile Lys Leu Leu Val Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Ala Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Thr Glu Val Ser Ala Ser His Pro Phe Val Met Thr Glu
        355                 360                 365

Leu Met Met Pro Ile Leu Pro Ile Val Arg Val Lys Asp Ile Asp Glu
    370                 375                 380
```

```
Ala Ile Glu Tyr Ala Lys Ile Ala Glu Gln Asn His Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Pro Gly Phe Thr Thr Phe Thr Ile Ala Gly Ser Thr
        435                 440                 445

Gly Glu Gly Ile Thr Ser Ala Arg Asn Phe Thr Arg Gln Arg Arg Ile
    450                 455                 460

Val Leu Val Gly
465

<210> SEQ ID NO 5
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (11)..(11)
<223> OTHER INFORMATION: Any amino acid

<400> SEQUENCE: 5

Ile Xaa Pro Lys Gly Xaa Xaa Asn Arg Lys Xaa Val Gly Lys Asp
1               5                   10                  15

<210> SEQ ID NO 6
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid
<220> FEATURE:
<221> NAME/KEY: MOD_RES
<222> LOCATION: (13)..(13)
<223> OTHER INFORMATION: Any amino acid

<400> SEQUENCE: 6

Ser Tyr Ala Gly Xaa Gly Xaa Xaa Xaa Glu Gly Phe Xaa Thr Phe Thr
1               5                   10                  15

Ile Ala

<210> SEQ ID NO 7
<211> LENGTH: 468
<212> TYPE: PRT
<213> ORGANISM: Clostridium saccharoperbutylacetonicum
```

```
<400> SEQUENCE: 7

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
        370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
```

```
                405                 410                 415
Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 8
<211> LENGTH: 386
<212> TYPE: PRT
<213> ORGANISM: Roseburia inulinivorans

<400> SEQUENCE: 8

Met Gly Val Asn Glu Thr Gly Met Gly Asn Val Gly Asp Lys Ile Leu
1               5                   10                  15

Lys His His Leu Thr Ala Asp Lys Val Pro Gly Thr Glu Asp Ile Ser
            20                  25                  30

Thr Ile Ala Trp Ser Gly Asp Arg Gly Leu Thr Leu Val Glu Met Gly
        35                  40                  45

Pro Phe Gly Val Ile Gly Ala Ile Thr Pro Ala Thr Asn Pro Ser Glu
    50                  55                  60

Thr Val Ile Cys Asn Cys Ile Gly Met Leu Ala Gly Gly Asn Thr Val
65                  70                  75                  80

Val Phe Asn Pro His Pro Asn Ala Lys Lys Thr Thr Ile Tyr Thr Ile
                85                  90                  95

Asn Met Ile Asn Glu Ala Ser Ile Glu Ala Gly Gly Pro Asp Asn Ile
            100                 105                 110

Ala Val Thr Val Glu Ala Pro Thr Leu Asp Thr Ser Ala Ile Met Met
        115                 120                 125

Lys His Pro Ser Ile His Leu Leu Val Ala Thr Gly Gly Pro Gly Val
    130                 135                 140

Val Thr Ala Val Leu Ser Ser Gly Lys Arg Ala Ile Gly Ala Gly Ala
145                 150                 155                 160

Gly Asn Pro Pro Val Leu Val Asp Glu Thr Ala Asp Ile Arg Lys Ala
                165                 170                 175

Ala Gln Asp Ile Val Asn Gly Cys Thr Phe Asp Asn Asn Leu Pro Cys
            180                 185                 190

Ile Ala Glu Lys Glu Ile Val Ala Val Asp Ser Val Ala Asp Glu Leu
        195                 200                 205

Met Asn Tyr Met Ile Ser Glu Asn Gly Cys Tyr Leu Ala Ser Lys Glu
    210                 215                 220

Ile Gln Asp Lys Leu Val Gln Thr Val Phe Thr Pro Lys Gly Ala Leu
225                 230                 235                 240

Asn Arg Lys Cys Val Gly Arg Ser Ala Gln Thr Leu Leu Ala Met Val
                245                 250                 255

Gly Val Asn Val Gly Pro Glu Ile Arg Cys Ile Val Phe Glu Gly Gln
            260                 265                 270

Lys Glu His Pro Leu Ile Ala Glu Glu Leu Met Met Pro Ile Leu Gly
        275                 280                 285

Met Val Arg Val Lys Ser Phe Glu Glu Gly Val Glu Thr Ala Val Trp
    290                 295                 300
```

-continued

```
Leu Glu His Gly Asn Arg His Ser Ala His Ile His Ser Lys Asn Val
305                 310                 315                 320

Asp His Ile Thr Thr Tyr Ala Arg Ala Leu Asp Thr Ala Ile Leu Val
            325                 330                 335

Lys Asn Gly Pro Ser Tyr Ala Ala Leu Gly Phe Gly Gly Glu Gly Tyr
        340                 345                 350

Cys Thr Phe Thr Ile Ala Ser Arg Thr Gly Glu Gly Leu Thr Ala Ala
    355                 360                 365

His Ser Phe Thr Lys Ser Arg Arg Cys Thr Met Ser Asp Ser Leu Cys
370                 375                 380

Ile Arg
385

<210> SEQ ID NO 9
<211> LENGTH: 467
<212> TYPE: PRT
<213> ORGANISM: Bacillus sp.

<400> SEQUENCE: 9

Met Asn Pro Ala Glu Leu Pro His Gln Val His Glu Ser Gly Ala Asn
1               5                   10                  15

Gly Val Phe Asp Arg Ile Glu Asp Ala Ile Glu Ala Gly Tyr Ile Ala
            20                  25                  30

Gln Leu Asn Tyr Val Lys Gln Phe Gln Leu Lys Asp Arg Glu Lys Ile
        35                  40                  45

Ile Thr Ala Ile Arg Glu Ala Val Ile Glu Asn Lys Glu Lys Leu Ala
    50                  55                  60

Gln Met Val Phe Glu Glu Thr Lys Leu Gly Arg Tyr Glu Asp Lys Ile
65                  70                  75                  80

Ala Lys His Glu Leu Val Ala Arg Lys Thr Pro Gly Thr Glu Asp Ile
                85                  90                  95

Thr Thr Ala Ala Phe Ser Gly Asp Glu Gly Leu Thr Ile Ile Glu Gln
            100                 105                 110

Ala Pro Phe Gly Leu Val Gly Ala Val Thr Pro Val Thr Asn Pro Thr
        115                 120                 125

Glu Thr Ile Ile Asn Asn Ser Ile Ser Leu Leu Ala Ala Gly Asn Ala
    130                 135                 140

Val Val Leu Asn Val His Pro Ser Ser Lys Ala Ser Cys Ala Phe Val
145                 150                 155                 160

Val Asn Leu Ile Asn Gln Ala Ile Lys Asp Thr Gly Gly Pro Glu Asn
                165                 170                 175

Leu Val Ser Met Val Lys Asp Pro Thr Leu Glu Thr Leu Asn Arg Ile
            180                 185                 190

Ile Glu Ser Pro Lys Val Lys Leu Leu Val Gly Thr Gly Gly Leu Gly
        195                 200                 205

Met Val Lys Thr Leu Leu Lys Ser Gly Lys Lys Ala Ile Gly Ala Gly
    210                 215                 220

Ala Gly Asn Pro Pro Val Ile Val Asp Glu Thr Ala Asp Leu Lys Gln
225                 230                 235                 240

Ala Ala Lys Ser Ile Ile Glu Gly Ala Ser Phe Asp Asn Asn Leu Leu
                245                 250                 255

Cys Ile Ala Glu Lys Glu Leu Phe Val Ile Asp Ser Val Ala Asp Asp
            260                 265                 270

Leu Ile Phe His Met Leu Asn Glu Gly Ala Tyr Met Leu Asp Gln Gln
        275                 280                 285
```

```
Gln Leu Ser Lys Leu Met Ser Phe Ala Leu Glu Glu Asn Val His Gln
    290                 295                 300
Glu Ala Gly Gly Cys Ser Leu Asp Asn Lys Arg Glu Tyr His Val Ser
305                 310                 315                 320
Lys Asp Trp Val Gly Lys Asp Ala Val Ser Phe Leu Arg Gln Leu Gly
                325                 330                 335
Ile Ala His Glu Glu Asp Ile Lys Leu Leu Ile Cys Glu Val Asp Phe
                340                 345                 350
Asp His Pro Phe Val Gln Leu Glu Gln Met Met Pro Val Phe Pro Ile
            355                 360                 365
Val Arg Val Gly Asn Leu Asp Glu Ala Ile Glu Met Ala Leu Leu Ala
370                 375                 380
Glu His Gly Asn Arg His Thr Ala Ile Met His Ser Lys Asn Val Asp
385                 390                 395                 400
His Leu Thr Lys Phe Ala Arg Ala Ile Glu Thr Thr Ile Phe Val Lys
                405                 410                 415
Asn Ala Ser Ser Leu Ala Gly Val Gly Phe Gly Gly Glu Gly His Thr
                420                 425                 430
Thr Met Thr Ile Ala Gly Pro Thr Gly Glu Gly Ile Thr Ser Ala Lys
            435                 440                 445
Thr Phe Thr Arg Gln Arg Arg Cys Val Leu Ala Glu Gly Gly Phe Arg
450                 455                 460
Ile Ile Gly
465

<210> SEQ ID NO 10
<211> LENGTH: 467
<212> TYPE: PRT
<213> ORGANISM: Bacillus solani

<400> SEQUENCE: 10

Met Asn Pro Ala Glu Leu Pro His Gln Val His Glu Ser Gly Ala Asn
1               5                   10                  15
Gly Val Phe Asp Arg Ile Glu Asp Ala Ile Glu Ala Gly Tyr Ile Ala
                20                  25                  30
Gln Leu Asn Tyr Val Lys Gln Phe Gln Leu Lys Asp Arg Glu Lys Ile
                35                  40                  45
Ile Thr Ala Ile Arg Glu Ala Val Ile Glu Asn Lys Glu Lys Leu Ala
            50                  55                  60
Gln Met Val Phe Glu Thr Lys Leu Gly Arg Tyr Glu Asp Lys Ile
65              70                  75                  80
Ala Lys His Glu Leu Val Ala Arg Lys Thr Pro Gly Thr Glu Asp Ile
                85                  90                  95
Thr Thr Ala Ala Phe Ser Gly Asp Glu Gly Leu Thr Ile Ile Glu Gln
                100                 105                 110
Ala Pro Phe Gly Leu Val Gly Ala Val Thr Pro Val Thr Asn Pro Thr
            115                 120                 125
Glu Thr Ile Ile Asn Asn Ser Ile Ser Leu Leu Ala Ala Gly Asn Ala
        130                 135                 140
Val Val Leu Asn Val His Pro Ser Ser Lys Val Ser Cys Ala Phe Val
145                 150                 155                 160
Val Asn Leu Ile Asn Gln Ala Ile Lys Asp Thr Gly Gly Pro Glu Asn
                165                 170                 175
Leu Val Ser Met Val Lys Asp Pro Thr Leu Glu Thr Leu Asn Arg Ile
```

```
                180                 185                 190
Ile Glu Ser Pro Lys Val Lys Leu Leu Val Gly Thr Gly Pro Gly
            195                 200                 205
Met Val Lys Thr Leu Leu Lys Ser Gly Lys Lys Ala Ile Gly Ala Gly
        210                 215                 220
Ala Gly Asn Pro Pro Val Ile Val Asp Glu Thr Ala Asp Leu Lys Gln
225                 230                 235                 240
Ala Ala Lys Ser Ile Ile Glu Gly Ala Ser Phe Asp Asn Asn Leu Leu
            245                 250                 255
Cys Ile Ala Glu Lys Glu Leu Phe Val Ile Asp Ser Val Ala Asp Asp
            260                 265                 270
Leu Ile Phe His Met Leu Asn Glu Gly Ala Tyr Met Leu Asp Gln Gln
            275                 280                 285
Gln Leu Ser Lys Leu Met Ser Phe Ala Leu Glu Asn Val His Gln
        290                 295                 300
Glu Ala Gly Gly Cys Ser Leu Asp Asn Lys Arg Glu Tyr His Val Ser
305                 310                 315                 320
Lys Asp Trp Val Gly Lys Asp Ala Val Ser Phe Leu Arg Gln Leu Gly
            325                 330                 335
Ile Ala His Glu Glu Asp Ile Lys Leu Leu Ile Cys Glu Val Asp Phe
            340                 345                 350
Asp His Pro Phe Val Gln Leu Glu Gln Met Met Pro Val Phe Pro Ile
            355                 360                 365
Val Arg Val Gly Asn Leu Asp Glu Ala Ile Glu Met Ala Leu Leu Ala
        370                 375                 380
Glu His Gly Asn Arg His Thr Ala Ile Met His Ser Lys Asn Val Asp
385                 390                 395                 400
His Leu Thr Lys Phe Ala Arg Ala Ile Glu Thr Thr Ile Phe Val Lys
            405                 410                 415
Asn Ala Ser Ser Leu Ala Gly Val Gly Phe Gly Gly Glu Gly His Thr
            420                 425                 430
Thr Met Thr Ile Ala Gly Pro Thr Gly Glu Gly Ile Thr Ser Ala Lys
            435                 440                 445
Thr Phe Thr Arg Gln Arg Arg Cys Val Leu Ala Glu Gly Gly Phe Arg
        450                 455                 460
Ile Ile Gly
465

<210> SEQ ID NO 11
<211> LENGTH: 473
<212> TYPE: PRT
<213> ORGANISM: Terrisporobacter othiniensis

<400> SEQUENCE: 11

Met Asp Ile Asp Val Lys Leu Ile Glu Lys Met Val Ser Asp Ala Leu
1               5                   10                  15
Lys Glu Ile Lys Ile Glu Asn Ile Thr Gln Val Lys Asn Ser
            20                  25                  30
Ile Glu Asp Asn Tyr Gly Val Phe Lys Thr Ile Glu Gly Ala Ile Asp
            35                  40                  45
Ala Ser Tyr Val Ala Gln Lys Glu Leu Leu Phe Ser Lys Ile Ser Asp
        50                  55                  60
Arg Gln Lys Tyr Val Asp Ala Ile Arg Ser Ala Ile Leu Asn Gln Glu
65                  70                  75                  80
```

```
Asn Leu Glu Leu Ile Ser Lys Leu Ala Val Asp Glu Thr Glu Ile Gly
             85                  90                  95

Cys Tyr Glu His Lys Leu Ile Lys Asn Arg Leu Ala Ala Glu Lys Thr
        100                 105                 110

Pro Gly Thr Glu Asp Leu Ile Ser Ser Val Lys Thr Gly Asp Asp Gly
        115                 120                 125

Leu Thr Leu Val Glu Tyr Cys Pro Phe Gly Val Ile Gly Ala Ile Thr
130                 135                 140

Pro Thr Thr Asn Pro Thr Glu Thr Ile Ile Cys Asn Ser Ile Gly Met
145                 150                 155                 160

Ile Ala Gly Gly Asn Thr Val Val Phe Ser Pro His Pro Arg Ala Thr
                165                 170                 175

Lys Val Ser Gln Thr Ile Ile Lys Ile Leu Asn Lys Ala Leu Glu Glu
            180                 185                 190

Val Gly Ala Pro Lys Asn Leu Ile Thr Met Val Glu Lys Pro Ser Ile
        195                 200                 205

Glu Asn Thr Asn Lys Met Ile Glu Asn Pro Lys Val Arg Phe Leu Val
210                 215                 220

Ala Thr Gly Gly Pro Ser Ile Val Lys Lys Val Leu Ser Ser Gly Lys
225                 230                 235                 240

Lys Ala Ile Gly Ala Gly Ala Gly Asn Pro Pro Val Val Asp Glu
                245                 250                 255

Thr Ala Asp Ile Arg Lys Ala Ala Lys Asp Ile Ile Asp Gly Cys Ser
                260                 265                 270

Phe Asp Asn Asn Val Pro Cys Ile Ala Glu Lys Glu Val Phe Ala Val
            275                 280                 285

Ala Ser Ile Cys Asp Ser Leu Ile Glu Asn Met Lys Leu Asn Gly Ala
290                 295                 300

Tyr Leu Val Lys Asp Lys Lys Val Ile Glu Gln Leu Leu Ser Val Val
305                 310                 315                 320

Ala Lys Glu Asn Gly Ala Pro Lys Thr Asn Phe Val Gly Lys Ser Ala
                325                 330                 335

Lys Tyr Ile Leu Asp Lys Ile Gly Val Thr Val Asp Asp Asn Ile Lys
            340                 345                 350

Ala Ile Ile Met Glu Val Asp Lys Asp His Thr Phe Val Gln Glu Glu
            355                 360                 365

Met Met Met Pro Ile Leu Pro Ile Val Arg Val Glu Asp Val Asp Lys
        370                 375                 380

Ala Ile Glu Tyr Ala Gln Glu Ala Glu His Gly Asn Arg His Thr Ala
385                 390                 395                 400

Ile Met His Ser Lys Asn Ile Asp Lys Leu Ser Lys Met Ser Lys Ile
                405                 410                 415

Met Glu Thr Thr Ile Phe Val Lys Asn Ala Pro Ser Tyr Ala Gly Ile
            420                 425                 430

Gly Val Gly Gly Glu Gly His Ser Thr Phe Thr Ile Ala Gly Pro Thr
        435                 440                 445

Gly Glu Gly Leu Thr Ser Pro Lys Ser Phe Cys Arg Ile Arg Arg Cys
450                 455                 460

Val Val Ser Asp Ser Phe Ser Ile Arg
465                 470

<210> SEQ ID NO 12
<211> LENGTH: 457
<212> TYPE: PRT
```

<213> ORGANISM: Roseburia inulinivorans

<400> SEQUENCE: 12

```
Met Val His Asp Ile Val Gln Lys Val Met Ala Asn Met Gln Ile Ser
1               5                   10                  15

Gly Ser Val Ser Gly Met His Gly Val Phe Lys Asp Met Asn Asp Ala
            20                  25                  30

Ile Asn Ala Ser Ile Glu Ala Gln Lys Lys Val Cys Thr Met Thr Leu
        35                  40                  45

Asp Gln Arg Glu Gln Ile Ile Ser Leu Ile Arg Lys Lys Thr His Glu
    50                  55                  60

Asn Ala Glu Ile Leu Ala Asn Met Gly Val Asn Glu Thr Gly Met Gly
65                  70                  75                  80

Asn Val Gly Asp Lys Ile Leu Lys His His Leu Thr Ala Asp Lys Val
                85                  90                  95

Pro Gly Thr Glu Asp Ile Ser Thr Ile Ala Trp Ser Gly Asp Arg Gly
            100                 105                 110

Leu Thr Leu Val Glu Met Gly Pro Phe Gly Val Ile Gly Ala Ile Thr
        115                 120                 125

Pro Ala Thr Asn Pro Ser Glu Thr Val Ile Cys Asn Cys Ile Gly Met
    130                 135                 140

Leu Ala Gly Gly Asn Thr Val Val Phe Asn Pro His Pro Asn Ala Lys
145                 150                 155                 160

Lys Thr Thr Ile Tyr Thr Ile Asn Met Ile Asn Glu Ala Ser Ile Glu
                165                 170                 175

Ala Gly Gly Pro Asp Asn Ile Ala Val Thr Val Glu Ala Pro Thr Leu
            180                 185                 190

Asp Thr Ser Ala Ile Met Met Lys His Pro Ser Ile His Leu Leu Val
        195                 200                 205

Ala Thr Gly Gly Pro Gly Val Val Thr Ala Val Leu Ser Ser Gly Lys
    210                 215                 220

Arg Ala Ile Gly Ala Gly Ala Gly Asn Pro Pro Val Leu Val Asp Glu
225                 230                 235                 240

Thr Ala Asp Ile Arg Lys Ala Ala Gln Asp Ile Val Asn Gly Cys Thr
                245                 250                 255

Phe Asp Asn Asn Leu Pro Cys Ile Ala Glu Lys Glu Ile Val Ala Val
            260                 265                 270

Asp Ser Val Ala Asp Glu Leu Met Asn Tyr Met Ile Ser Glu Asn Gly
        275                 280                 285

Cys Tyr Leu Ala Ser Lys Glu Ile Gln Asp Lys Leu Val Gln Thr Val
    290                 295                 300

Phe Thr Pro Lys Gly Ala Leu Asn Arg Lys Cys Val Gly Arg Ser Ala
305                 310                 315                 320

Gln Thr Leu Leu Ala Met Val Gly Val Asn Val Gly Pro Glu Ile Arg
                325                 330                 335

Cys Ile Val Phe Glu Gly Gln Lys Glu His Pro Leu Ile Ala Glu Glu
            340                 345                 350

Leu Met Met Pro Ile Leu Gly Met Val Arg Val Lys Ser Phe Glu Glu
        355                 360                 365

Gly Val Glu Thr Ala Val Trp Leu Glu His Gly Asn Arg His Ser Ala
    370                 375                 380

His Ile His Ser Lys Asn Val Asp His Ile Thr Thr Tyr Ala Arg Ala
385                 390                 395                 400
```

```
Leu Asp Thr Ala Ile Leu Val Lys Asn Gly Pro Ser Tyr Ala Ala Leu
                405                 410                 415

Gly Phe Gly Gly Glu Gly Tyr Cys Thr Phe Thr Ile Ala Ser Arg Thr
            420                 425                 430

Gly Glu Gly Leu Thr Ala Ala His Ser Phe Thr Lys Ser Arg Arg Cys
        435                 440                 445

Thr Met Ser Asp Ser Leu Cys Ile Arg
    450                 455

<210> SEQ ID NO 13
<211> LENGTH: 462
<212> TYPE: PRT
<213> ORGANISM: Clostridium sp.

<400> SEQUENCE: 13

Met Ser Val Asn Glu Arg Met Val Gln Asp Ile Val Gln Glu Val Val
1               5                   10                  15

Ala Lys Met Gln Ile Ala Ser Asp Val Thr Gly Asn His Gly Val Phe
            20                  25                  30

Gln Asp Met Asn Ala Ala Ile Glu Ala Ala Lys Lys Thr Gln Lys Val
        35                  40                  45

Val Ala Arg Met Ser Met Asp Gln Arg Glu Lys Ile Ile Ser Asn Ile
    50                  55                  60

Arg Ala Lys Ile Lys Glu His Ala Glu Ile Phe Ala Arg Met Gly Val
65                  70                  75                  80

Gln Glu Thr Gly Met Gly Asn Val Gly His Lys Ile Leu Lys His Gln
                85                  90                  95

Leu Val Ala Glu Lys Thr Pro Gly Thr Glu Asp Ile Gln Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Val Leu
    130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Tyr Ala Val Asn Leu Ile
                165                 170                 175

Asn Glu Ala Ser Leu Glu Ala Gly Gly Pro Asp Asn Ile Ala Cys Thr
            180                 185                 190

Val Glu Asn Pro Thr Leu Glu Ser Ser Asn Ile Met Met Lys His Lys
        195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Ile Ala Asp Glu Leu Met His Tyr
        275                 280                 285

Met Ile Ser Glu Gln Gly Cys Tyr Leu Ala Ser Lys Glu Glu Gln Asp
    290                 295                 300

Ala Leu Thr Glu Val Val Leu Lys Gly Gly Arg Leu Asn Arg Lys Cys
305                 310                 315                 320
```

```
Val Gly Arg Asp Ala Lys Thr Leu Gly Met Ile Gly Val Thr Val
            325                 330                 335

Pro Asp Asn Ile Arg Cys Ile Thr Phe Glu Gly Pro Lys Glu His Pro
            340                 345                 350

Leu Ile Ala Glu Glu Leu Met Met Pro Ile Leu Gly Val Val Arg Ala
            355                 360                 365

Lys Asp Phe Asp Asp Ala Val Glu Gln Ala Val Trp Leu Glu His Gly
            370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
            405                 410                 415

Ser Tyr Ala Ala Ile Gly Phe Gly Gly Glu Gly Phe Cys Thr Phe Thr
            420                 425                 430

Ile Ala Ser Arg Thr Gly Glu Gly Leu Thr Ser Ala Ser Ala Phe Thr
            435                 440                 445

Lys Arg Arg Arg Cys Val Met Cys Asp Ser Leu Cys Ile Arg
            450                 455                 460

<210> SEQ ID NO 14
<211> LENGTH: 509
<212> TYPE: PRT
<213> ORGANISM: Bacillus selenitireducens

<400> SEQUENCE: 14

Met Ser Ile Ser Glu Asp Met Leu Lys Gln Ile Val Lys Ser Val Met
1               5                   10                  15

Asn Asn Val Glu Lys Glu Leu Gly Glu Ser Pro Lys Pro Gln Pro Arg
            20                  25                  30

Thr Ile Pro Val Thr Val Leu Asn Glu Val Thr Pro Val Lys Glu Ser
            35                  40                  45

Arg Asp Pro Ser Pro Val His Gln His Val Leu Gly Val Phe Pro Asp
50                  55                  60

Val Asp Gln Ala Val His Ala Ala Ala Gly Ser Gln Lys Glu Trp Val
65                  70                  75                  80

Lys Arg Pro Val Ser Glu Arg Arg Val Ile Leu Glu Ala Met Lys Gln
            85                  90                  95

Thr Val Asp Ser Gln Lys Glu Arg Tyr Ser Glu Leu Ala Val Glu Glu
            100                 105                 110

Thr Gly Leu Gly Asn Val Ala Asp Lys Ile Ala Lys His Glu Leu Ile
            115                 120                 125

Ile Thr Lys Thr Pro Gly Val Glu Asp Leu Arg Thr Asp Ala Val Ser
130                 135                 140

Gly Asp His Gly Leu Thr Ile Glu Glu Asp Ala Pro Phe Gly Val Ile
145                 150                 155                 160

Gly Ala Val Thr Pro Val Thr Asn Pro Thr Thr Thr Val Ile His Asn
            165                 170                 175

Ser Leu Val Met Leu Ala Ala Gly Asn Ala Val Val Phe Asn Val His
            180                 185                 190

Pro Ser Ser Lys Ala Thr Cys Gln Arg Val Val Ser Asp Leu Asn Ala
            195                 200                 205

Ala Ile Lys Asp Ala Gly Gly Pro Gln Asn Leu Ile Thr Met Ile Ala
            210                 215                 220

Glu Pro Thr Leu Asp Thr Leu Asn Gln Leu Ala Gly His Gln Glu Ile
```

```
                225                 230                 235                 240
        Arg Leu Leu Val Gly Thr Gly Gly Gln Gly Leu Val Arg Ser Leu Leu
                        245                 250                 255

Gln Ser Gly Lys Lys Ala Ile Gly Ala Gly Ala Gly Asn Pro Pro Val
                        260                 265                 270

Ile Val Asp Glu Thr Ala Asp Ile Glu Ala Ala Lys Ala Ile Ile
                        275                 280                 285

Leu Gly Ala Ser Phe Asp Asn Asn Ile Leu Cys Ile Ala Glu Lys Glu
                        290                 295                 300

Val Phe Ala Leu Asp Val Ile Tyr Asp Asp Leu Ile Tyr His Leu Leu
        305                 310                 315                 320

Gln Glu Gly Ala Tyr Met Leu Ser Glu Ser Glu Leu Ser Gln Val Met
                        325                 330                 335

Lys Thr Val Leu Val Gly Asp Ala Pro Ile Glu Ala Ala Lys Ser Cys
                        340                 345                 350

Ser Val Ser Val Arg Pro Asp Leu His Ile Ala Lys Ala Trp Val Gly
                        355                 360                 365

Lys Glu Ala Ser Ala Ile Leu Lys Ala Ala Thr Gly Lys Asp Leu Pro
                        370                 375                 380

Val Lys Leu Leu Ile Cys Asp Val Glu Ala Thr His Pro Phe Val Gln
        385                 390                 395                 400

Leu Glu Gln Met Met Pro Val Leu Pro Ile Val Arg Met Pro Asp Phe
                        405                 410                 415

Asp Ala Ala Val Glu Ala Ala Val Lys Ala Glu Lys Gly Asn Arg His
                        420                 425                 430

Thr Ala Val Ile His Ser Lys Asn Val Asp Arg Leu Thr Gln Phe Ala
                        435                 440                 445

Arg Arg Ile Glu Thr Thr Ile Phe Val Lys Asn Ala Ser Ser Leu Ala
                        450                 455                 460

Gly Val Gly Phe Gly Gly Glu Gly Tyr Ala Thr Met Thr Ile Ala Gly
        465                 470                 475                 480

Pro Thr Gly Glu Gly Ile Thr Ser Pro Arg Thr Phe Thr Arg Lys Arg
                        485                 490                 495

Arg Cys Val Leu Ala Glu Gly Gly Phe Arg Ile Ile Gly
                        500                 505

<210> SEQ ID NO 15
<211> LENGTH: 462
<212> TYPE: PRT
<213> ORGANISM: Blautia obeum

<400> SEQUENCE: 15

Met Pro Ile Ser Glu Ser Met Val Gln Asp Ile Gln Glu Val Met
        1               5                   10                  15

Ala Lys Met Gln Ile Ala Asp Ala Pro Thr Gly Lys His Gly Ile Phe
                        20                  25                  30

Lys Asp Met Asn Asp Ala Ile Glu Ala Lys Lys Ser Glu Leu Ile
                        35                  40                  45

Val Lys Lys Met Ser Met Asp Gln Arg Glu Lys Ile Ile Thr Cys Ile
                50                  55                  60

Arg Lys Lys Ile Lys Glu Asn Ala Glu Val Met Ala Arg Met Gly Val
        65                  70                  75                  80

Asp Glu Thr Gly Met Gly Asn Val Gly Asp Lys Ile Leu Lys His His
                        85                  90                  95
```

-continued

```
Leu Val Ala Asp Lys Thr Pro Gly Thr Glu Asp Ile Thr Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Ile Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Phe Ala Ile Asn Leu Val
                165                 170                 175

Asn Glu Ala Ser Leu Glu Ala Gly Gly Pro Asp Asn Ile Ala Val Thr
            180                 185                 190

Val Glu Lys Pro Thr Leu Glu Thr Ser Asn Ile Met Met Lys His Lys
        195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Val Val Asp Glu Thr Ala Asp Ile Arg Lys Ala Ala Gln Asp
                245                 250                 255

Ile Val Asn Gly Cys Thr Phe Asp Asn Asn Leu Pro Cys Ile Ala Glu
            260                 265                 270

Lys Glu Val Val Ala Val Ser Val Val Asp Glu Leu Met His Tyr
        275                 280                 285

Met Leu Thr Glu Asn Asp Cys Tyr Leu Ala Ser Lys Glu Glu Gln Asp
    290                 295                 300

Lys Leu Thr Glu Val Val Leu Ala Gly Gly Lys Leu Asn Arg Lys Cys
305                 310                 315                 320

Val Gly Arg Asp Ala Arg Thr Leu Leu Ser Met Ile Gly Val Asn Ala
                325                 330                 335

Pro Ala Asn Ile Arg Cys Ile Ile Phe Glu Gly Pro Lys Glu His Pro
            340                 345                 350

Leu Ile Thr Thr Glu Leu Met Met Pro Ile Leu Gly Ile Val Arg Ala
        355                 360                 365

Lys Asp Phe Asp Asp Ala Val Glu Gln Ala Val Trp Leu Glu His Gly
    370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ser Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
        435                 440                 445

Lys Arg Arg Arg Cys Val Met Ser Asp Ser Leu Cys Ile Arg
    450                 455                 460

<210> SEQ ID NO 16
<211> LENGTH: 478
<212> TYPE: PRT
<213> ORGANISM: Clostridium bolteae

<400> SEQUENCE: 16

Met Lys Glu Gly Val Ile Arg Leu Asp Met Asp Ile Lys Val Ile Glu
1               5                   10                  15
```

```
Gln Leu Val Glu Gln Ala Leu Lys Glu Ile Lys Ala Glu Gln Pro Leu
         20                  25                  30

Lys Phe Thr Ala Pro Lys Leu Glu Arg Tyr Gly Val Phe Lys Thr Met
             35                  40                  45

Asp Glu Ala Ile Ala Ala Ser Glu Glu Ala Gln Lys Lys Leu Leu Phe
         50                  55                  60

Ser Lys Ile Ser Asp Arg Gln Lys Tyr Val Asp Val Ile Arg Ser Thr
 65                  70                  75                  80

Ile Ile Lys Arg Glu Asn Leu Glu Leu Ile Ser Arg Leu Ser Val Glu
                 85                  90                  95

Glu Thr Glu Ile Gly Asp Tyr Glu His Lys Leu Ile Lys Asn Arg Leu
             100                 105                 110

Ala Ala Glu Lys Thr Pro Gly Thr Glu Asp Leu Leu Thr Glu Ala Ile
             115                 120                 125

Thr Gly Asp Asn Gly Leu Thr Leu Val Glu Tyr Cys Pro Phe Gly Val
 130                 135                 140

Ile Gly Ala Ile Thr Pro Thr Thr Asn Pro Thr Glu Thr Ile Ile Asn
145                 150                 155                 160

Asn Ser Ile Ser Met Ile Ala Gly Gly Asn Thr Val Val Phe Ser Pro
                 165                 170                 175

His Pro Arg Ala Lys Lys Val Ser Gln Met Thr Val Lys Met Leu Asn
             180                 185                 190

Lys Ala Leu Ile Asp Asn Gly Ala Pro Pro Asn Leu Ile Thr Met Val
             195                 200                 205

Glu Glu Pro Ser Ile Glu Asn Thr Asn Lys Met Ile Asp Asn Pro Ser
 210                 215                 220

Val Arg Leu Leu Val Ala Thr Gly Gly Pro Ser Ile Val Lys Lys Val
225                 230                 235                 240

Leu Ser Ser Gly Lys Lys Ala Ile Gly Ala Gly Ala Gly Asn Pro Pro
                 245                 250                 255

Val Val Val Asp Glu Thr Ala Asp Ile Asp Lys Ala Ala Lys Asp Ile
             260                 265                 270

Val Asp Gly Cys Ser Phe Asp Asn Asn Val Pro Cys Ile Ala Glu Lys
             275                 280                 285

Glu Val Phe Ala Val Asp Ser Ile Cys Asp Tyr Leu Ile His His Met
             290                 295                 300

Lys Glu Asn Gly Ala Tyr Gln Ile Thr Asp Pro Met Leu Leu Glu Gln
305                 310                 315                 320

Leu Val Ala Leu Val Thr Thr Glu Lys Gly Gly Pro Lys Thr Ser Phe
                 325                 330                 335

Val Gly Lys Ser Ala Arg Tyr Ile Leu Asp Lys Leu Gly Ile Thr Val
             340                 345                 350

Asp Ala Ser Val Arg Val Ile Ile Met Glu Val Pro Lys Asp His Leu
             355                 360                 365

Leu Val Gln Glu Glu Met Met Met Pro Ile Leu Pro Val Val Arg Val
 370                 375                 380

Ser Asp Val Asp Thr Ala Ile Glu Tyr Ala His Gln Ala Glu His Gly
385                 390                 395                 400

Asn Arg His Thr Ala Met Met His Ser Lys Asn Val Glu Lys Leu Ser
                 405                 410                 415

Lys Met Ala Lys Ile Met Glu Thr Thr Ile Phe Val Lys Asn Ala Pro
             420                 425                 430
```

```
Ser Tyr Ala Gly Ile Gly Val Gly Gly Glu Gly Tyr Thr Thr Phe Thr
            435                 440                 445

Ile Ala Gly Pro Thr Gly Glu Gly Leu Thr Ser Pro Arg Thr Phe Cys
450                 455                 460

Arg Lys Arg Lys Cys Val Met Thr Asp Ala Phe Ser Ile Arg
465                 470                 475
```

<210> SEQ ID NO 17
<211> LENGTH: 515
<212> TYPE: PRT
<213> ORGANISM: Jeotgalibacillus alimentarius

<400> SEQUENCE: 17

```
Met Ser Ile Ser Glu Glu Thr Leu Gln Gln Ile Ile Lys Ser Val Val
1               5                   10                  15

Thr Gln Val Glu Ser Glu Leu Gly His Lys His Ser Ala Pro Ala Thr
                20                  25                  30

Gly Ser Gln Ser Ala Thr Pro Val Ala Pro Val Lys Met Lys Ala Val
            35                  40                  45

Thr Asn Lys Pro Val Phe Lys Glu His Thr Tyr Arg Ser Ser Gly Glu
50                  55                  60

Gly Ile Tyr Thr Thr Val Asp Glu Ala Val Ser Arg Ser Ala Ala Ala
65                  70                  75                  80

Gln Lys Lys Tyr Val Lys His Phe Thr Met Asn Asp Arg Val Thr Val
                85                  90                  95

Leu Asn Ala Ile Lys Gln Thr Val Leu Ser Ser Lys Asp Thr Leu Ser
            100                 105                 110

Lys Met Ala Val Glu Glu Thr Gly Ile Gly Cys Tyr Glu Asp Lys Ile
        115                 120                 125

Gln Lys His Glu Leu Val Cys Lys Lys Thr Pro Gly Ile Glu Asp Leu
    130                 135                 140

Lys Thr Glu Ala Met Ser Gly Asp Asp Gly Leu Thr Ile Ile Glu Glu
145                 150                 155                 160

Ala Pro Phe Gly Val Ile Gly Ala Val Thr Pro Val Thr Asn Pro Thr
                165                 170                 175

Thr Thr Ile Ile Asn Asn Ser Leu Ser Met Leu Ala Ala Gly Asn Thr
            180                 185                 190

Val Val Phe Asn Val His Pro Ser Ser Lys Lys Val Cys Ser Tyr Leu
        195                 200                 205

Ile Arg Glu Leu His Gln Ser Ile Val Gln Ala Gly Gly Pro Ala Asp
    210                 215                 220

Leu Ile Thr Met Val Ala Asp Pro Thr Leu Asp Thr Leu Asn Glu Leu
225                 230                 235                 240

Ala Ala His Pro Asp Ile Arg Leu Leu Val Gly Thr Gly Gly Pro Gly
                245                 250                 255

Leu Val Lys Ser Leu Leu Gln Ser Gly Lys Lys Ala Ile Gly Ala Gly
            260                 265                 270

Ala Gly Asn Pro Pro Val Ile Val Asp Glu Thr Ala Asp Leu Val Asn
        275                 280                 285

Ala Ala Lys Ser Ile Ile Leu Gly Ala Ser Phe Asp His Asn Leu Leu
    290                 295                 300

Cys Ile Ala Glu Lys Glu Val Phe Val Leu Glu Glu Ala Ala Asn Glu
305                 310                 315                 320

Leu Ile Tyr Gln Met Leu Asp Gln Gly Ala Tyr Met Leu Asn Asn Glu
                325                 330                 335
```

```
Glu Leu Ser Arg Val Met Ser Leu Val Leu Thr Glu Asp Ser Ser Ser
            340                 345                 350

Pro Val Ala Gly Gly Cys Thr Gly Lys Pro Ser Lys Lys Tyr His Val
            355                 360                 365

Lys Lys Glu Trp Ile Gly Gln Ser Ala Ala Ile Ala Arg Ala Ala
370                 375                 380

Gly Ile Asn Lys Glu Asn Ile Lys Leu Leu Ile Cys Glu Thr Asp Pro
385                 390                 395                 400

Asp His Pro Phe Val Val Leu Glu Gln Met Met Pro Val Leu Pro Ile
                405                 410                 415

Val Lys Thr Gln Ser Phe Glu Glu Ala Val Glu Trp Ala Val Ala Ala
            420                 425                 430

Glu Lys Gly Asn Arg His Thr Ala Val Ile His Ser Thr Asn Val Asp
            435                 440                 445

Arg Met Thr Ala Phe Ala Arg Ala Ile Glu Thr Thr Ile Phe Val Lys
            450                 455                 460

Asn Ala Ser Ser Leu Ala Gly Val Gly Phe Gly Gly Glu Gly His Thr
465                 470                 475                 480

Thr Met Thr Ile Ala Gly Pro Thr Gly Glu Gly Val Thr Ser Ala Arg
                485                 490                 495

Ser Phe Thr Arg Lys Arg Arg Cys Val Leu Ala Glu Gly Gly Phe Arg
            500                 505                 510

Ile Ile Gly
        515

<210> SEQ ID NO 18
<211> LENGTH: 470
<212> TYPE: PRT
<213> ORGANISM: Clostridium hiranonis

<400> SEQUENCE: 18

Met Lys Met Glu Leu Asp Leu Ile Gln Glu Met Ile Lys Gln Val Leu
1               5                   10                  15

Glu Glu Ile Lys Glu Glu Gly Val Glu Val Ser Ser Lys Glu Glu Tyr
            20                  25                  30

Gly Tyr Gly Val Phe Asp Ser Met Val Glu Ala Ile Asp Ala Ser Glu
        35                  40                  45

Lys Ala Gln Lys Glu Leu Phe Glu Cys Ser Val Gln Gln Arg Asp Lys
    50                  55                  60

Phe Val Asp Ala Ile Arg Ala Glu Ile Leu Lys Lys Glu Asn Leu Glu
65                  70                  75                  80

Met Ile Ser Tyr Asp Ala Val Glu Glu Thr Lys Ile Gly Arg Val Glu
                85                  90                  95

Asp Lys Ile Ile Lys Asn Arg Val Ala Ala Glu Asn Thr Pro Gly Thr
            100                 105                 110

Glu Asp Leu Lys Thr Arg Ala Ile Thr Gly Asp Gly Leu Thr Ile
            115                 120                 125

Glu Glu Tyr Cys Pro Phe Gly Val Ile Gly Ser Ile Thr Pro Thr Thr
        130                 135                 140

Asn Pro Thr Glu Thr Leu Ile Asn Asn Ser Ile Ser Met Ile Ala Gly
145                 150                 155                 160

Gly Asn Thr Val Val Phe Ser Pro His Pro Arg Ala Lys Lys Val Ser
                165                 170                 175

Ile Lys Leu Val Lys Met Met Asn Lys Ala Leu Glu Glu Ala Gly Ala
```

```
            180                 185                 190
Pro Arg Asn Leu Ile Thr Met Val Lys Glu Pro Ser Ile Glu Asn Ser
        195                 200                 205
Lys Ile Met Met Glu Ser Pro Lys Val Arg Leu Leu Val Ala Thr Gly
    210                 215                 220
Gly Pro Ala Ile Val Lys Gln Val Leu Ser Ala Gly Lys Lys Ala Ile
225                 230                 235                 240
Gly Ala Gly Ala Gly Asn Pro Pro Val Val Asp Glu Thr Ala Asp
                245                 250                 255
Ile Glu Lys Ala Ala Lys Asp Ile Val Ser Gly Ala Ser Phe Asp Asn
            260                 265                 270
Asn Val Pro Cys Ile Ala Glu Lys Glu Val Phe Ala Val Glu Ser Val
        275                 280                 285
Val Asp Gln Leu Ile Tyr Tyr Met Lys Lys Asn Gly Ala Tyr Glu Ile
    290                 295                 300
Thr Ser Pro Glu Val Leu Glu Gln Leu Asp Lys Ala Val Ser Lys Glu
305                 310                 315                 320
Asn Gly Lys Pro Asn Pro Ser Leu Val Gly Lys Ser Ala Lys Glu Leu
                325                 330                 335
Leu Ala Leu Val Gly Ile Asn Val Asp Asp Val Lys Leu Val Ile
            340                 345                 350
Ala Arg Thr Asn Lys Asp His His Leu Val Thr Glu Glu Met Leu Met
        355                 360                 365
Pro Ile Leu Pro Ile Val Ser Val Ser Asp Val Asp Thr Ala Ile Asp
    370                 375                 380
Trp Ala Tyr Glu Ala Glu Ala Gly Asn Arg His Thr Ala Ile Met His
385                 390                 395                 400
Ser Lys Asn Val Asp Lys Leu Thr Lys Met Ala Lys Lys Leu Glu Ala
                405                 410                 415
Thr Ile Phe Val Lys Asn Ala Pro Ser Tyr Ala Gly Ile Gly Val Gly
            420                 425                 430
Gly Glu Gly His Thr Thr Phe Thr Ile Ala Gly Pro Thr Gly Glu Gly
        435                 440                 445
Ile Thr Ser Ala Lys Ser Phe Cys Arg Ile Arg Arg Cys Val Met Ser
    450                 455                 460
Glu Ala Leu Ser Ile Arg
465                 470

<210> SEQ ID NO 19
<211> LENGTH: 466
<212> TYPE: PRT
<213> ORGANISM: Thermoanaerobacter sp.

<400> SEQUENCE: 19

Met Ile Asp Glu Asn Leu Val Val Thr Ile Thr Lys Lys Ile Leu Asn
1               5                   10                  15
Glu Ile Asn Leu Lys Glu Ala Glu Lys Lys Glu Lys Asp Asn Pro
            20                  25                  30
Asp Leu Gly Ile Phe Asn Asp Val Asn Glu Ala Val Glu Cys Ala Lys
        35                  40                  45
Glu Ala Gln Lys Lys Phe Ala Leu Met Asp Leu Glu Lys Arg Glu Glu
    50                  55                  60
Ile Ile Ala Ala Ile Arg Glu Ala Cys Val Asn Asn Ala Arg Leu Leu
65                  70                  75                  80
```

```
Ala Glu Ile Ala Cys Ser Glu Thr Gly Arg Gly Arg Val Glu Asp Lys
                85                  90                  95

Val Ala Lys Asn Ile Leu Ala Ala Lys Lys Thr Pro Gly Thr Glu Asp
            100                 105                 110

Leu Lys Pro Thr Ala Trp Thr Gly Asp Arg Gly Leu Thr Leu Val Glu
        115                 120                 125

Met Ala Pro Val Gly Val Ile Ala Ser Ile Thr Pro Val Thr Asn Pro
    130                 135                 140

Thr Ala Thr Ile Ile Asn Asn Thr Ile Ser Met Leu Ala Ala Gly Asn
145                 150                 155                 160

Ala Val Val Phe Asn Pro His Pro Ser Ala Lys Lys Thr Ser Asn Lys
                165                 170                 175

Ala Val Glu Ile Ile Asn Glu Ala Ile Leu Lys Val Gly Ala Pro Asn
            180                 185                 190

Gly Leu Val Cys Ser Ile Asn Asn Pro Thr Ile Gln Thr Ala Gln Lys
        195                 200                 205

Leu Met Glu His Pro Glu Val Asn Met Val Val Thr Gly Gly Lys
    210                 215                 220

Ala Val Val Gln Thr Ala Leu Arg Cys Gly Lys Lys Val Ile Gly Ala
225                 230                 235                 240

Gly Ala Gly Asn Pro Pro Val Val Asp Glu Thr Ala Asp Ile Val
                245                 250                 255

Lys Ala Ala His Asp Ile Ala Cys Gly Ala Ser Phe Asp Asn Asn Leu
            260                 265                 270

Pro Cys Ile Ala Glu Lys Glu Ile Ile Ala Val Glu Arg Ile Ala Asp
        275                 280                 285

Thr Leu Leu Glu Arg Met Lys Arg Glu Gly Ala Tyr Val Leu His Gly
    290                 295                 300

Lys Asp Ile Asp Arg Met Thr Glu Leu Ile Phe Gln Gly Gly Ala Ile
305                 310                 315                 320

Asn Lys Asp Leu Ile Gly Arg Asp Ala His Phe Ile Leu Ser Gln Ile
                325                 330                 335

Gly Ile Glu Thr Gly Lys Asp Ile Arg Leu Val Val Met Pro Val Asp
            340                 345                 350

Val Ser His Pro Leu Val Tyr His Glu Gln Leu Met Pro Val Ile Pro
        355                 360                 365

Phe Val Thr Val Pro Thr Val Glu Glu Ala Ile Asn Leu Ala Val Lys
    370                 375                 380

Ala Glu Gly Gly Asn Arg His Thr Ala Met Met His Ser Lys Asn Val
385                 390                 395                 400

Glu Asn Met Thr Ala Phe Ala Arg Ala Ile Gln Thr Thr Ile Phe Val
                405                 410                 415

Lys Asn Ala Pro Ser Tyr Ala Gly Ile Gly Phe Gly Gly Glu Gly Tyr
            420                 425                 430

Thr Thr Phe Thr Ile Ala Gly Pro Thr Gly Glu Gly Leu Thr Ser Ala
        435                 440                 445

Arg Thr Phe Thr Arg Gln Arg Arg Cys Val Leu Val Asp Ala Phe Arg
    450                 455                 460

Ile Val
465

<210> SEQ ID NO 20
<211> LENGTH: 462
<212> TYPE: PRT
```

<213> ORGANISM: Clostridiales sp.

<400> SEQUENCE: 20

```
Met Pro Ile Asn Glu Asn Met Val Gln Glu Ile Val Gln Glu Val Met
1               5                   10                  15

Ala Lys Met Gln Ile Ala Asp Ala Pro Thr Gly Lys His Gly Ile Phe
            20                  25                  30

Lys Glu Met Asn Asp Ala Ile Glu Ala Ala Lys Lys Ser Gln Leu Ile
        35                  40                  45

Val Lys Lys Met Ser Met Asp Gln Arg Glu Lys Ile Ile Thr Cys Ile
    50                  55                  60

Arg Lys Lys Ile Lys Glu Asn Ala Glu Val Met Ala Arg Met Gly Val
65                  70                  75                  80

Glu Glu Thr Gly Met Gly Asn Val Gly Asp Lys Ile Leu Lys His His
                85                  90                  95

Leu Val Ala Asp Lys Thr Pro Gly Thr Glu Val Ile Thr Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Ile Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Tyr Ala Ile Asn Leu Leu
                165                 170                 175

Asn Glu Ala Ser Leu Glu Ser Gly Gly Pro Asp Asn Ile Ala Val Thr
            180                 185                 190

Val Glu Lys Pro Thr Leu Glu Thr Ser Asn Val Met Met Lys His Lys
        195                 200                 205

Asp Ile Pro Leu Ile Ala Ala Thr Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Thr Asp
                245                 250                 255

Ile Val Asn Gly Cys Thr Phe Asp Asn Asn Leu Pro Cys Ile Ala Glu
            260                 265                 270

Lys Glu Ile Val Ala Val Ser Ser Ile Val Asp Glu Leu Met His Tyr
        275                 280                 285

Leu Val Thr Glu Asn Asp Cys Tyr Leu Ala Ser Lys Glu Glu Gln Asp
    290                 295                 300

Lys Leu Thr Glu Val Val Leu Ala Gly Gly Lys Leu Asn Arg Lys Cys
305                 310                 315                 320

Val Gly Arg Asp Ala Arg Thr Leu Leu Ser Met Ile Gly Val Asn Ala
                325                 330                 335

Pro Ala Asn Ile Arg Cys Ile Val Phe Glu Gly Pro Lys Glu His Pro
            340                 345                 350

Leu Ile Thr Thr Glu Leu Met Met Pro Ile Leu Gly Val Val Arg Ala
        355                 360                 365

Arg Asp Phe Asp Asp Ala Val Glu Gln Ala Val Trp Leu Glu His Gly
    370                 375                 380

Asn Arg His Ser Ala His Ile His Ser Lys Asn Ile Asp Asn Ile Thr
385                 390                 395                 400
```

```
Lys Tyr Ala Lys Ala Ile Asp Thr Ala Ile Leu Val Lys Asn Ala Pro
                405                 410                 415

Ser Tyr Ala Ala Leu Gly Phe Gly Gly Glu Gly Tyr Cys Thr Phe Thr
            420                 425                 430

Ile Ala Ser Arg Thr Gly Glu Gly Leu Thr Cys Ala Ser Thr Phe Thr
            435                 440                 445

Lys Arg Arg Arg Cys Val Met Ala Asp Ser Leu Cys Ile Arg
450                 455                 460

<210> SEQ ID NO 21
<211> LENGTH: 468
<212> TYPE: PRT
<213> ORGANISM: Sebaldella termitidis

<400> SEQUENCE: 21

Met Leu Asp Gly Leu Gln Leu Glu Asp Ile Ile Lys Lys Val Ile Asn
1               5                   10                  15

Asp Val Lys Asn Glu Lys Asp Ile Asn Ile Thr Asn Lys Glu Asn Ser
            20                  25                  30

Cys Gly His Gly Ile Phe Thr Asn Ile Glu Thr Ala Val Asp Lys Ala
        35                  40                  45

Tyr Glu Ala Gln Gln Thr Tyr Asn Ser Arg Ser Leu Glu Glu Arg Arg
50                  55                  60

Asn Ile Ile Ser Asn Ile Arg Lys Glu Leu Leu Lys Tyr Thr Glu Glu
65                  70                  75                  80

Met Ala Glu Lys Thr Val Ala Glu Thr Lys Met Gly Arg Ile Lys Asp
                85                  90                  95

Lys Ile Leu Lys Asn Lys Leu Ala Ile Glu Lys Thr Pro Gly Val Glu
            100                 105                 110

Asp Leu Gly Thr Glu Val Phe Thr Gly Asp Asp Gly Leu Thr Leu Val
        115                 120                 125

Glu Leu Ser Ala Phe Gly Val Leu Gly Ser Val Thr Pro Val Thr Asn
130                 135                 140

Pro Thr Glu Thr Ile Ile Asn Asn Thr Ile Gly Ala Leu Ala Gly Gly
145                 150                 155                 160

Asn Ser Ile Val Phe Cys Pro His Pro Ser Ala Lys Asn Ile Cys Leu
                165                 170                 175

Trp Leu Ile Lys Lys Leu Asn Gly Ile Ile Thr Glu Ala Gly Gly Pro
            180                 185                 190

Glu Asn Leu Val Thr Ser Ala Ser Glu Ala Lys Lys Glu Asn Val Asp
        195                 200                 205

Ile Leu Phe Ser His Glu Lys Ile Asn Met Leu Val Ile Thr Gly Gly
210                 215                 220

Thr Glu Ile Val Lys Leu Ala Leu Lys Ser Gly Lys Lys Val Ile Gly
225                 230                 235                 240

Ala Gly Ala Gly Asn Pro Pro Val Ile Val Asp Glu Thr Ala Asp Ile
                245                 250                 255

Glu Lys Ala Ala Lys Asp Ile Val Asn Gly Ala Gly Phe Asp Asn Asn
            260                 265                 270

Leu Pro Cys Ile Ala Glu Lys Glu Val Leu Val Leu Glu Ser Val Ala
        275                 280                 285

Asp Tyr Leu Ile Phe Asn Met Glu Lys Ala Gly Ala Phe His Ile Thr
290                 295                 300

Asp Lys Glu Asp Ile Lys Lys Leu Glu Asp Thr Val Tyr Lys Asn Gly
305                 310                 315                 320
```

```
Met Val Asn Lys Glu Phe Ile Gly Lys Asp Ala Gly Phe Ile Leu Glu
                325                 330                 335

Lys Ser Gly Ile Lys Cys Ser Phe Asp Pro Ala Leu Ile Thr Leu Glu
            340                 345                 350

Thr Asp Ile Asn His Val Phe Val Gln Lys Glu Leu Met Met Pro Val
        355                 360                 365

Leu Ala Val Val Arg Gln Lys Asn Phe Glu Glu Ala Leu Lys Asn Ala
    370                 375                 380

Ile Leu Thr Glu His Gly Leu Lys His Thr Ala Val Met His Ser Gln
385                 390                 395                 400

Asn Val Thr Arg Leu Ser Ile Ala Ala Arg Glu Met Gln Thr Thr Ile
            405                 410                 415

Phe Val Lys Asn Ala Pro Ser Tyr Ala Ala Leu Gly Phe Gln Gly Glu
        420                 425                 430

Gly Tyr Thr Thr Phe Thr Ile Ala Gly Pro Thr Gly Glu Gly Leu Thr
    435                 440                 445

Ser Ala Arg Asn Phe Thr Arg Lys Arg Cys Val Leu Gly Gly Ser
450                 455                 460

Phe Ser Ile Arg
465

<210> SEQ ID NO 22
<211> LENGTH: 462
<212> TYPE: PRT
<213> ORGANISM: Eubacterium plexicaudatum

<400> SEQUENCE: 22

Met Ser Val Asn Asp Gln Met Val Gln Asp Ile Val Arg Gln Val Leu
1               5                   10                  15

Ala Asn Met Arg Ile Ser Ser Asp Ala Ser Gly Ser Arg Gly Val Phe
            20                  25                  30

Ser Asp Met Asn Glu Ala Val Glu Ala Ala Lys Lys Ala Gln Ala Val
        35                  40                  45

Ile Gly Lys Met Pro Met Asp His Arg Glu Lys Ile Ile Ser Ser Ile
    50                  55                  60

Arg Ala Lys Ile Met Glu Asn Ala Glu Ile Leu Ala Arg Met Gly Val
65                  70                  75                  80

Lys Glu Thr Gly Met Gly Asn Val Gly His Lys Ile Leu Lys His Gln
            85                  90                  95

Leu Val Ala Glu Lys Thr Pro Gly Thr Glu Asp Ile Thr Thr Lys Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Ile Leu
    130                 135                 140

Cys Asn Thr Ile Gly Met Val Ala Gly Asn Thr Val Phe Asn
145                 150                 155                 160

Pro His Pro Ala Ala Ile Lys Thr Ser Ile Phe Ala Val Asn Leu Val
            165                 170                 175

Asn Glu Ala Ser Val Glu Ala Gly Gly Pro Asp Asn Ile Ala Cys Thr
        180                 185                 190

Val Glu His Pro Thr Leu Asp Thr Ser Ala Ile Met Met Lys His Lys
    195                 200                 205

Asp Ile His Leu Ile Ala Ala Thr Gly Gly Pro Gly Val Val Thr Ala
```

```
        210                 215                 220
Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Ile Ala Asp Glu Leu Met His Tyr
        275                 280                 285

Met Ile Ser Glu Gln Gly Cys Tyr Leu Ala Ser Ala Lys Glu Gln Glu
    290                 295                 300

Ala Leu Ile Ser Val Val Leu Lys Gly Gly Gln Leu Asn Arg Asp Cys
305                 310                 315                 320

Val Gly Arg Asp Ala Lys Thr Leu Leu Gly Met Ile Gly Val Gln Ala
                325                 330                 335

Pro Asp Asn Ile Arg Cys Ile Thr Phe Glu Gly Pro Lys Glu His Pro
            340                 345                 350

Leu Ile Thr Glu Glu Leu Met Met Pro Ile Leu Gly Val Val Arg Ala
        355                 360                 365

Asp Ser Phe Glu Asp Ala Val Glu Lys Ala Val Trp Leu Glu His Gly
    370                 375                 380

Asn Arg His Ser Ala His Ile His Ser Lys Asn Val Asp His Ile Thr
385                 390                 395                 400

Thr Tyr Ala Lys Ala Ile Asp Thr Ala Ile Leu Val Lys Asn Gly Pro
                405                 410                 415

Ser Tyr Ala Ala Ile Gly Phe Gly Gly Glu Gly Tyr Cys Thr Phe Thr
            420                 425                 430

Ile Ala Ser Arg Thr Gly Glu Gly Leu Thr Ser Ala Ser Ala Phe Thr
        435                 440                 445

Lys Arg Arg Arg Cys Val Met Cys Asp Ser Leu Cys Ile Arg
    450                 455                 460

<210> SEQ ID NO 23
<211> LENGTH: 505
<212> TYPE: PRT
<213> ORGANISM: Escherichia sp.

<400> SEQUENCE: 23

Met Asn Asp Ile Glu Ile Ala Gln Ala Val Ser Thr Ile Leu Ser Lys
1               5                   10                  15

Phe Thr Lys Ala Thr Pro Asp Glu Ala Pro Ala Thr Ser Glu Ala Ala
                20                  25                  30

Arg Val Asp Gly Leu Asp Glu Ile Val Ala Lys Ala Leu Ala Gln His
            35                  40                  45

Ser Ser Val Arg Asp Ala Ser Ala Ile Ser Gln Val Ala Lys Val Ala
        50                  55                  60

Asn Ala Ser Thr Gly Ala Phe Asp Thr Met Asp Glu Ala Ile Ser Ala
65                  70                  75                  80

Ala Val Leu Ala Gln Val Gln Tyr Arg His Cys Ser Met Gln Asp Arg
                85                  90                  95

Ala Ser Phe Ile Asn Gly Ile Arg Asp Val Phe Leu Gln Glu Asp Val
            100                 105                 110

Leu Cys Ala Leu Ser Arg Met Ala Val Glu Glu Thr Gly Met Gly Asn
        115                 120                 125
```

```
Tyr Glu Asp Lys Leu Ile Lys Asn Arg Val Ala Ala Leu Lys Thr Pro
    130                 135                 140

Gly Ile Glu Asp Leu Thr Thr Ser Ala Val Ser Gly Asp Gly Gly Leu
145                 150                 155                 160

Thr Leu Ile Glu Tyr Ser Ala Phe Gly Val Ile Gly Ser Ile Thr Pro
                165                 170                 175

Thr Thr Asn Pro Thr Glu Thr Ile Ile Asn Asn Ser Ile Gly Met Leu
            180                 185                 190

Ala Ala Gly Asn Thr Val Val Phe Ser Pro His Pro Arg Ser Arg Lys
        195                 200                 205

Val Ser Leu Tyr Ala Val Glu Leu Ile Asn Asn Lys Leu Ala Gln Leu
210                 215                 220

Gly Ala Pro Ala Asn Met Val Val Thr Val Thr Lys Pro Ser Ile Asp
225                 230                 235                 240

Asn Thr Asn Val Leu Ile Asn Asp Pro Arg Ile Asn Met Leu Val Ala
                245                 250                 255

Thr Gly Gly Pro Ala Ile Val Lys Thr Val Met Ser Ser Gly Lys Lys
            260                 265                 270

Ala Ile Gly Ala Gly Ala Gly Asn Pro Pro Ala Val Val Asp Glu Thr
        275                 280                 285

Ala Asp Ile Glu Lys Ala Ala Arg Asp Ile Ile Lys Gly Cys Ser Phe
290                 295                 300

Asp Asn Asn Leu Pro Cys Val Ala Glu Lys Glu Val Ile Val Val Asn
305                 310                 315                 320

Gln Val Ala Asp Tyr Leu Ile His Cys Met Lys Lys Ser Gly Ala Tyr
                325                 330                 335

Leu Leu Cys Asp Lys Lys Leu Ser Gln Gln Leu Gln Ser Leu Val Leu
            340                 345                 350

Asn Glu Lys Gly Thr Gly Pro Asn Thr Ala Phe Val Gly Lys Asp Ala
        355                 360                 365

Arg Tyr Ile Leu Gln Gln Leu Gly Ile Gln Val Gly Asp Asp Ile Lys
370                 375                 380

Val Ile Leu Ile Glu Ala Glu Lys Thr His Pro Phe Val Val His Glu
385                 390                 395                 400

Leu Met Met Pro Val Leu Pro Val Val Arg Val Asp Asn Val Asp Glu
                405                 410                 415

Ala Ile Glu Leu Ala Val Lys Val Glu His Gly Asn Arg His Thr Ala
            420                 425                 430

Val Met His Ser Thr Asn Val Glu Lys Leu Thr Lys Met Ala Arg Leu
        435                 440                 445

Ile Gln Thr Thr Ile Phe Val Lys Asn Gly Pro Ser Tyr Ala Gly Leu
450                 455                 460

Gly Val Gly Gly Glu Gly His Ala Thr Phe Thr Ile Ala Gly Pro Thr
465                 470                 475                 480

Gly Glu Gly Leu Thr Ser Ala Arg Ser Phe Ala Arg Arg Arg Arg Cys
                485                 490                 495

Val Met Val Glu Ala Leu Asn Ile Arg
            500                 505

<210> SEQ ID NO 24
<211> LENGTH: 529
<212> TYPE: PRT
<213> ORGANISM: Rhodospirillum rubrum

<400> SEQUENCE: 24
```

```
Met Asn Asp Gly Gln Ile Ala Ala Val Ala Lys Val Leu Glu Ala
1               5                   10                  15

Tyr Gly Val Pro Ala Asp Pro Ser Ala Ala Pro Ala Pro Ala Ala
                20                  25              30

Pro Val Ala Pro Ala Ala Pro Thr Ala Gly Ser Val Ser Glu Met Ile
            35                  40                  45

Ala Arg Gly Ile Ala Lys Ala Ser Ser Asp Asp Gln Ile Ala Gln Ile
    50                  55                  60

Val Ala Lys Val Val Gly Asp Tyr Ser Ala Gln Ala Ala Lys Pro Ala
65                  70                  75                  80

Val Val Pro Gly Ala Ala Ala Ser Thr Glu Ala Gly Asp Gly Val Phe
                85                  90                  95

Asp Thr Met Asp Ala Ala Val Asp Ala Ala Val Leu Ala Gln Gln Gln
            100                 105                 110

Tyr Leu Leu Cys Ser Met Thr Asp Arg Gln Arg Phe Val Asp Gly Ile
        115                 120                 125

Arg Glu Val Ile Leu Gln Lys Asp Thr Leu Glu Leu Ile Ser Arg Met
    130                 135                 140

Ala Ala Glu Glu Thr Gly Met Gly Asn Tyr Glu His Lys Leu Ile Lys
145                 150                 155                 160

Asn Arg Leu Ala Ala Glu Lys Thr Pro Gly Thr Glu Asp Leu Thr Thr
                165                 170                 175

Glu Ala Phe Ser Gly Asp Asp Gly Leu Thr Leu Val Glu Tyr Ser Pro
            180                 185                 190

Phe Gly Ala Ile Gly Ala Val Ala Pro Thr Thr Asn Pro Thr Glu Thr
        195                 200                 205

Ile Ile Cys Asn Ser Ile Gly Met Leu Ala Ala Gly Asn Ser Val Ile
    210                 215                 220

Phe Ser Pro His Pro Arg Ala Thr Lys Val Ser Leu Leu Thr Val Lys
225                 230                 235                 240

Leu Ile Asn Gln Lys Leu Ala Cys Leu Gly Ala Pro Ala Asn Leu Val
                245                 250                 255

Val Thr Val Ser Lys Pro Ser Val Glu Asn Thr Asn Ala Met Met Ala
            260                 265                 270

His Pro Lys Ile Arg Met Leu Val Ala Thr Gly Gly Pro Gly Ile Val
        275                 280                 285

Lys Ala Val Met Ser Thr Gly Lys Lys Ala Ile Gly Ala Gly Ala Gly
    290                 295                 300

Asn Pro Pro Val Val Val Asp Glu Thr Ala Asp Ile Glu Lys Ala Ala
305                 310                 315                 320

Leu Asp Ile Ile Asn Gly Cys Ser Phe Asp Asn Asn Leu Pro Cys Ile
                325                 330                 335

Ala Glu Lys Glu Ile Ile Ala Val Ala Gln Ile Ala Asp Tyr Leu Ile
            340                 345                 350

Phe Ser Met Lys Lys Gln Gly Ala Tyr Gln Ile Thr Asp Pro Ala Val
        355                 360                 365

Leu Arg Lys Leu Gln Asp Leu Val Leu Thr Ala Lys Gly Gly Pro Gln
    370                 375                 380

Thr Ser Cys Val Gly Lys Ser Ala Val Trp Leu Leu Asn Lys Ile Gly
385                 390                 395                 400

Ile Glu Val Asp Ser Ser Val Lys Val Ile Leu Met Glu Val Pro Lys
                405                 410                 415
```

-continued

```
Glu His Pro Phe Val Gln Glu Leu Met Met Pro Ile Leu Pro Leu
            420                 425                 430

Val Arg Val Ser Asp Val Asp Glu Ala Ile Ala Val Ala Ile Glu Val
        435                 440                 445

Glu His Gly Asn Arg His Thr Ala Ile Met His Ser Thr Asn Val Arg
    450                 455                 460

Lys Leu Thr Lys Met Ala Lys Leu Ile Gln Thr Thr Ile Phe Val Lys
465                 470                 475                 480

Asn Gly Pro Ser Tyr Ala Gly Leu Gly Val Gly Gly Glu Gly Tyr Thr
                485                 490                 495

Thr Phe Thr Ile Ala Gly Pro Thr Gly Glu Gly Leu Thr Ser Ala Lys
            500                 505                 510

Ser Phe Ala Arg Lys Arg Lys Cys Val Met Val Glu Ala Leu Asn Ile
        515                 520                 525

Arg

<210> SEQ ID NO 25
<211> LENGTH: 472
<212> TYPE: PRT
<213> ORGANISM: Clostridium beijerinckii

<400> SEQUENCE: 25

Met Asp Val Asp Val Leu Val Glu Lys Leu Val Arg Gln Ala Ile
1               5                   10                  15

Glu Glu Val Lys Asn Lys Asn Leu Leu Asn Leu Asp Lys Phe Glu Ser
            20                  25                  30

Val Lys Asn Tyr Gly Ile Phe Gly Thr Met Asp Ala Ala Val Glu Ala
        35                  40                  45

Ser Phe Val Ala Gln Lys Gln Leu Leu Asn Ala Ser Met Thr Asp Lys
    50                  55                  60

Gln Lys Tyr Val Asp Thr Ile Lys Ala Thr Ile Leu Lys Lys Glu Asn
65                  70                  75                  80

Leu Glu Leu Ile Ser Arg Met Ser Val Glu Glu Thr Glu Ile Gly Lys
                85                  90                  95

Tyr Glu His Lys Leu Ile Lys Asn Arg Val Ala Ala Glu Lys Thr Pro
            100                 105                 110

Gly Ile Glu Asp Leu Thr Thr Glu Ala Met Thr Gly Asp Asn Gly Leu
        115                 120                 125

Thr Leu Val Glu Tyr Cys Pro Phe Gly Val Ile Gly Ala Ile Thr Pro
    130                 135                 140

Thr Thr Asn Pro Thr Glu Thr Ile Ile Cys Asn Ser Ile Ser Met Ile
145                 150                 155                 160

Ala Gly Gly Asn Thr Val Val Phe Ser Pro His Pro Arg Ala Lys Asn
                165                 170                 175

Val Ser Ile Lys Leu Val Thr Met Leu Asn Lys Ala Leu Glu Glu Ala
            180                 185                 190

Gly Ala Pro Asp Asn Leu Ile Ala Thr Val Lys Glu Pro Ser Ile Glu
        195                 200                 205

Asn Thr Asn Ile Met Met Glu His Pro Lys Ile Arg Met Leu Val Ala
    210                 215                 220

Thr Gly Gly Pro Ala Ile Val Asn Lys Val Met Ser Thr Gly Lys Lys
225                 230                 235                 240

Ala Ile Gly Ala Gly Ala Gly Asn Pro Pro Val Val Val Asp Glu Thr
                245                 250                 255
```

```
Ala Asp Ile Glu Lys Ala Ala Ile Asp Ile Val Asn Gly Cys Ser Phe
            260                 265                 270

Asp Asn Asn Val Pro Cys Ile Ala Glu Lys Glu Val Phe Ala Val Asp
            275                 280                 285

Gln Ile Cys Asp Tyr Leu Ile His Tyr Met Lys Leu Asn Gly Ala Tyr
        290                 295                 300

Glu Ile Lys Asp Arg Asp Leu Ile Gln Lys Leu Leu Asp Leu Val Thr
305                 310                 315                 320

Asn Glu Asn Gly Gly Pro Lys Val Ser Phe Val Gly Lys Ser Ala Pro
                325                 330                 335

Tyr Ile Leu Asn Lys Leu Gly Ile Ser Val Asp Glu Asn Ile Lys Val
        340                 345                 350

Ile Ile Met Glu Val Glu Lys Asn His His Phe Val Leu Glu Glu Met
                355                 360                 365

Met Met Pro Ile Leu Pro Ile Val Arg Thr Lys Asp Val Asp Glu Ala
        370                 375                 380

Ile Glu Cys Ala Tyr Val Ala Glu His Gly Asn Arg His Thr Ala Ile
385                 390                 395                 400

Met His Ser Lys Asn Val Asp Lys Leu Thr Lys Met Ala Arg Leu Leu
                405                 410                 415

Glu Thr Thr Ile Phe Val Lys Asn Ala Pro Ser Tyr Ala Gly Ile Gly
            420                 425                 430

Val Gly Gly Glu Gly Thr Thr Phe Thr Ile Ala Gly Pro Thr Gly
                435                 440                 445

Glu Gly Leu Thr Thr Ala Arg Ser Phe Cys Arg Lys Arg Arg Cys Val
450                 455                 460

Met Val Asp Ala Phe Asn Ile Arg
465                 470

<210> SEQ ID NO 26
<211> LENGTH: 468
<212> TYPE: PRT
<213> ORGANISM: Eubacterium hallii

<400> SEQUENCE: 26

Met Asn Ile Asp Val Glu Leu Ile Glu Lys Val Val Lys Lys Val Leu
1               5                   10                  15

Asn Asp Val Glu Thr Gly Ser Ser Glu Ser Glu Tyr Gly Tyr Gly Ile
            20                  25                  30

Phe Asp Thr Met Asp Glu Ala Ile Glu Ala Ser Ala Lys Ala Gln Lys
        35                  40                  45

Glu Tyr Met Asn His Ser Met Ala Asp Arg Gln Arg Tyr Val Glu Gly
50                  55                  60

Ile Arg Glu Val Val Cys Thr Lys Glu Asn Leu Glu Tyr Met Ser Lys
65                  70                  75                  80

Leu Ala Val Glu Glu Ser Gly Met Gly Ala Tyr Glu Tyr Lys Val Ile
                85                  90                  95

Lys Asn Arg Leu Ala Ala Val Lys Ser Pro Gly Val Glu Asp Leu Thr
            100                 105                 110

Thr Glu Ala Leu Ser Gly Asp Asp Gly Leu Thr Leu Val Glu Tyr Cys
        115                 120                 125

Pro Phe Gly Val Ile Gly Ala Ile Ala Pro Thr Thr Asn Pro Thr Glu
    130                 135                 140

Thr Val Ile Cys Asn Ser Ile Ala Met Leu Ala Gly Gly Asn Thr Val
145                 150                 155                 160
```

Val Phe Ser Pro His Pro Arg Ser Lys Gly Val Ser Ile Trp Leu Ile
            165                 170                 175

Lys Lys Leu Asn Ala Lys Leu Glu Glu Leu Gly Ala Pro Arg Asn Leu
        180                 185                 190

Ile Val Thr Val Lys Glu Pro Ser Ile Glu Asn Thr Asn Ile Met Met
    195                 200                 205

Asn His Pro Lys Val Arg Met Leu Val Ala Thr Gly Pro Gly Ile
210                 215                 220

Val Lys Ala Val Met Ser Thr Gly Lys Lys Ala Ile Gly Ala Gly Ala
225                 230                 235                 240

Gly Asn Pro Pro Val Val Val Asp Glu Thr Ala Asp Ile Glu Lys Ala
            245                 250                 255

Ala Lys Asp Ile Val Asn Gly Cys Ser Phe Asp Asn Asn Leu Pro Cys
        260                 265                 270

Ile Ala Glu Lys Glu Val Ile Ala Val Asp Gln Ile Ala Asp Tyr Leu
    275                 280                 285

Ile Phe Asn Met Lys Asn Asn Gly Ala Tyr Glu Val Lys Asp Pro Glu
290                 295                 300

Ile Ile Glu Lys Met Val Asp Leu Val Thr Lys Asp Arg Lys Lys Pro
305                 310                 315                 320

Ala Val Asn Phe Val Gly Lys Ser Ala Gln Tyr Ile Leu Asp Lys Val
            325                 330                 335

Gly Ile Lys Val Gly Pro Glu Val Lys Cys Ile Ile Met Glu Ala Pro
        340                 345                 350

Lys Asp His Pro Phe Val Gln Ile Glu Leu Met Met Pro Ile Leu Pro
    355                 360                 365

Ile Val Arg Val Pro Asn Val Asp Glu Ala Ile Asp Phe Ala Val Glu
370                 375                 380

Val Glu His Gly Asn Arg His Thr Ala Met Met His Ser Lys Asn Val
385                 390                 395                 400

Asp Lys Leu Thr Lys Met Ala Lys Glu Ile Glu Thr Thr Ile Phe Val
            405                 410                 415

Lys Asn Gly Pro Ser Tyr Ala Gly Ile Gly Val Gly Gly Met Gly Tyr
        420                 425                 430

Thr Thr Phe Thr Ile Ala Gly Pro Thr Gly Glu Gly Leu Thr Ser Ala
    435                 440                 445

Lys Ser Phe Cys Arg Lys Arg Arg Cys Val Leu Gln Asp Gly Leu His
450                 455                 460

Ile Arg Met Lys
465

<210> SEQ ID NO 27
<211> LENGTH: 532
<212> TYPE: PRT
<213> ORGANISM: Vibrio sp.

<400> SEQUENCE: 27

Met Asn Glu Gln Glu Ile Ala His Ala Val Glu Asn Val Leu Ser Lys
1               5                   10                  15

Tyr Thr Asn Val Thr Ala Gln Asn Ala Glu Pro Val Ser Tyr Ser Ser
            20                  25                  30

Asn Ala Ser Leu Glu Asn Ile Val Ser Gln Ala Leu Ala Gly Asn Met
        35                  40                  45

Val Lys Gln Pro Glu Thr Gln Thr Ala Pro Asp Leu Asn Ser Asn Ile

```
                50                  55                  60
Glu Asn Ile Val Ser Gln Ile Leu Ala Glu Asn Gln Ala Lys Pro Gln
 65                  70                  75                  80

Ser Val Gln Cys Gln Ser Ala Asn His Gly Thr Thr Glu Tyr Leu Gly
                 85                  90                  95

Cys Phe Ala Ser Met Glu Glu Ala Ile Ser Ala Ala Ser His Ala Gln
                100                 105                 110

Val Gln Tyr Arg His Cys Thr Met Gly Asp Arg Ala Ser Phe Val Lys
                115                 120                 125

Gly Ile Arg Glu Val Phe Thr Gln Asp Asp Val Leu Glu Lys Ile Ser
                130                 135                 140

Arg Met Ala Val Glu Glu Thr Gly Met Gly Asn Tyr Ala Asp Lys Leu
145                 150                 155                 160

Thr Lys Asn Arg Ile Ala Ala Thr Lys Thr Pro Gly Ile Glu Asp Leu
                165                 170                 175

Thr Thr Ser Ala Leu Ser Gly Asp Ser Gly Leu Thr Leu Thr Glu Phe
                180                 185                 190

Ser Ala Tyr Gly Val Ile Gly Ser Ile Thr Pro Thr Asn Pro Thr
                195                 200                 205

Glu Thr Ile Ile Asn Asn Ser Ile Gly Met Leu Ala Ala Gly Asn Thr
                210                 215                 220

Val Val Tyr Ser Pro His Pro Arg Ser Arg Asn Val Ser Leu Val Ala
225                 230                 235                 240

Val Asp Leu Ile Asn Arg Lys Leu Ala Glu Leu Gly Ala Pro Ala Asn
                245                 250                 255

Leu Val Val Thr Val Leu Glu Pro Ser Ile Asp Asn Thr Asn Ala Met
                260                 265                 270

Met Asn Asp Pro Arg Val Asn Met Leu Val Ala Thr Gly Gly Pro Ser
                275                 280                 285

Ile Val Lys Thr Val Met Ser Thr Gly Lys Lys Ala Ile Gly Ala Gly
                290                 295                 300

Ala Gly Asn Pro Pro Ala Val Val Asp Glu Thr Ala Asn Ile Glu Lys
305                 310                 315                 320

Ala Ala Lys Asp Ile Ile Asn Gly Cys Ala Phe Asp Asn Asn Leu Pro
                325                 330                 335

Cys Ile Ala Glu Lys Glu Val Ile Val Asn Glu Val Ala Asp Tyr
                340                 345                 350

Leu Ile His Cys Met Lys Lys Ser Gly Ala Tyr Leu Leu Cys Asp Lys
                355                 360                 365

Gln Lys Ile Gln Gln Leu Gln Ser Leu Val Leu Asn Glu Lys Gly Thr
                370                 375                 380

Gly Pro Asn Thr Ser Phe Val Gly Lys Gly Ala Arg Tyr Ile Leu Asp
385                 390                 395                 400

Lys Leu Asn Ile Gln Val Ser Asp Asp Ile Lys Val Ile Leu Ile Glu
                405                 410                 415

Thr Glu Arg Asn His Pro Phe Val Val His Glu Leu Met Met Pro Ile
                420                 425                 430

Leu Pro Val Val Arg Val Glu Asn Val Asp Glu Ala Ile Asp Leu Ala
                435                 440                 445

Ile Lys Val Glu His Gly Asn Arg His Thr Ala Ile Met His Ser Thr
                450                 455                 460

Asn Val Glu Lys Leu Ser Lys Met Ala Arg Leu Ile Gln Thr Thr Ile
465                 470                 475                 480
```

Phe Val Lys Asn Gly Pro Ser Tyr Ser Gly Ile Gly Val Gly Gly Glu
                485                 490                 495

Gly His Thr Thr Phe Thr Ile Ala Gly Pro Thr Gly Glu Gly Ile Thr
            500                 505                 510

Ser Ala Arg Ser Phe Ala Arg Tyr Arg Arg Cys Val Met Val Glu Ala
        515                 520                 525

Leu Asn Ile Arg
    530

<210> SEQ ID NO 28
<211> LENGTH: 464
<212> TYPE: PRT
<213> ORGANISM: Rhodopseudomonas palustris

<400> SEQUENCE: 28

Met Val Ala Lys Ala Ile Arg Asp His Ala Gly Thr Ala Gln Pro Ser
1               5                   10                  15

Gly Asn Ala Ala Thr Ser Ser Ala Val Ser Asp Gly Val Phe Glu
            20                  25                  30

Thr Met Asp Ala Ala Val Glu Ala Ala Ala Leu Ala Gln Gln Gln Tyr
        35                  40                  45

Leu Leu Cys Ser Met Ser Asp Arg Ala Arg Phe Val Gln Gly Ile Arg
    50                  55                  60

Asp Val Ile Leu Asn Gln Asp Thr Leu Glu Lys Met Ser Arg Met Ala
65                  70                  75                  80

Val Glu Glu Thr Gly Met Gly Asn Tyr Glu His Lys Leu Ile Lys Asn
                85                  90                  95

Arg Leu Ala Gly Glu Lys Thr Pro Gly Ile Glu Asp Leu Thr Thr Asp
            100                 105                 110

Ala Phe Ser Gly Asp Asn Gly Leu Thr Leu Val Glu Tyr Ser Pro Phe
        115                 120                 125

Gly Val Ile Gly Ala Ile Thr Pro Thr Thr Asn Pro Thr Glu Thr Ile
    130                 135                 140

Val Cys Asn Ser Ile Gly Met Leu Ala Ala Gly Asn Ser Val Val Phe
145                 150                 155                 160

Ser Pro His Pro Arg Ala Arg Gln Val Ser Leu Leu Leu Val Arg Leu
                165                 170                 175

Ile Asn Gln Lys Leu Ala Ala Leu Gly Ala Pro Glu Asn Leu Val Val
            180                 185                 190

Thr Val Glu Lys Pro Ser Ile Glu Asn Thr Asn Ala Met Met Ala His
        195                 200                 205

Pro Lys Val Arg Met Leu Val Ala Thr Gly Gly Pro Ala Ile Val Lys
    210                 215                 220

Ala Val Leu Ser Thr Gly Lys Lys Ala Ile Gly Ala Gly Ala Gly Asn
225                 230                 235                 240

Pro Pro Val Val Val Asp Glu Thr Ala Asn Ile Glu Lys Ala Ala Cys
                245                 250                 255

Asp Ile Val Asn Gly Cys Ser Phe Asp Asn Asn Leu Pro Cys Val Ala
            260                 265                 270

Glu Lys Glu Ile Ile Ala Val Ala Gln Ile Ala Asp Tyr Leu Ile Phe
        275                 280                 285

Asn Leu Lys Lys Asn Gly Ala Tyr Glu Ile Lys Asp Pro Ala Val Leu
    290                 295                 300

Gln Gln Leu Gln Asp Leu Val Leu Thr Ala Lys Gly Gly Pro Gln Thr

```
              305                 310                 315                 320
Lys Cys Val Gly Lys Ser Ala Val Trp Leu Leu Ser Gln Ile Gly Ile
                325                 330                 335

Ser Val Asp Ala Ser Ile Lys Ile Ile Leu Met Glu Val Pro Arg Glu
                340                 345                 350

His Pro Phe Val Gln Glu Glu Leu Met Met Pro Ile Leu Pro Leu Val
                355                 360                 365

Arg Val Glu Thr Val Asp Asp Ala Ile Asp Leu Ala Ile Glu Val Glu
                370                 375                 380

His Asp Asn Arg His Thr Ala Ile Met His Ser Thr Asp Val Arg Lys
385                 390                 395                 400

Leu Thr Lys Met Ala Lys Leu Ile Gln Thr Thr Ile Phe Val Lys Asn
                405                 410                 415

Gly Pro Ser Tyr Ala Gly Leu Gly Ala Gly Gly Glu Gly Tyr Ser Thr
                420                 425                 430

Phe Thr Ile Ala Gly Pro Thr Gly Glu Gly Leu Thr Ser Ala Lys Ser
                435                 440                 445

Phe Ala Arg Arg Arg Lys Cys Val Met Val Glu Ala Leu Asn Ile Arg
                450                 455                 460

<210> SEQ ID NO 29
<211> LENGTH: 468
<212> TYPE: PRT
<213> ORGANISM: Desulfatibacillum alkenivorans

<400> SEQUENCE: 29

Met Ser Val Lys Glu Phe Ala Leu Glu Asp Met Val Ala Ser Val Ile
1               5                   10                  15

Met Glu Met Met Asn Lys Asp Asp Ser Cys Gln Pro Thr Gly Asp
                20                  25                  30

Gly Ile Tyr Glu Thr Ile Asp Glu Ala Val Ala Lys Ala Lys Ala Ala
                35                  40                  45

Gln Pro Arg Leu Ile Ser Leu Ser Leu Glu Lys Arg Glu Ala Ile Leu
50                  55                  60

Thr Ala Ile Arg Lys Ile Ser Leu Glu Lys Asn Glu Glu Trp Ala Lys
65                  70                  75                  80

Ala Thr Val Ala Glu Thr Gly Leu Gly Arg Val Glu Asp Lys Ile Ala
                85                  90                  95

Glu Asn Ile Leu Ala Ala Thr Lys Thr Pro Gly Thr Glu Asp Leu Asp
                100                 105                 110

Ala Lys Ala Leu Ser Gly Asp Ala Gly Leu Thr Leu Ile Glu Tyr Ala
                115                 120                 125

Pro Phe Gly Val Ile Gly Ser Leu Thr Pro Val Thr Asn Ala Thr Gly
                130                 135                 140

Thr Leu Ile Asn Asn Thr Ile Ser Met Leu Ala Gly Asn Thr Val
145                 150                 155                 160

Val Tyr Asn Val His Pro Ser Ala Leu Lys Ile Ser Thr Glu Val Ile
                165                 170                 175

Arg Thr Phe His Lys Val Ile Val Glu Asn Gly Gly Pro Glu Gly Cys
                180                 185                 190

Val Gly Met Val Ala Thr Pro Thr Met Glu Thr Ala Gly Glu Ile Met
                195                 200                 205

Ala His Pro Asp Ile Asn Val Leu Val Ala Thr Gly Gly Ala Gly Val
                210                 215                 220
```

Val Lys Ala Val Leu Ser Ser Gly Lys Lys Ala Ile Gly Ala Gly Ala
225                 230                 235                 240

Gly Asn Pro Pro Val Leu Val Asp Glu Thr Ala Cys Ile Arg Lys Ala
            245                 250                 255

Ala Glu Glu Ile Ile Ala Gly His Ser Ile Asn Asn Asn Ile Phe Cys
        260                 265                 270

Ile Ser Glu Lys Glu Val Ile Ala Val Asp Glu Val Ala Asp Asn Leu
    275                 280                 285

Leu Lys Phe Met Glu Glu Thr Gly Lys Ala Ala Ile Leu Thr Pro Glu
290                 295                 300

Glu Ala Gln Lys Val Thr Glu Thr Val Ile His Asp Asn His Val Val
305                 310                 315                 320

Lys Asp Tyr Val Gly Lys Asn Ala Ser Val Ile Ile Glu Gly Ala Gly
            325                 330                 335

Leu Thr Arg Leu Ala Gly Lys Lys Asp Leu Arg Cys Leu Val Phe Glu
        340                 345                 350

Ala Asp Cys Lys His Pro Met Val Trp Ile Glu Gln Met Met Pro Val
    355                 360                 365

Leu Pro Met Val Arg Val Lys Asp Val Trp Glu Gly Ile Asp Leu Ala
370                 375                 380

Val Lys Val Glu Gln Gly Asn Arg His Thr Ala Met Met His Ser Thr
385                 390                 395                 400

Asn Val Glu His Leu Thr Ala Leu Ala Arg Ala Ile Gln Thr Thr Ile
            405                 410                 415

Phe Val Lys Asn Gly Pro Ser Tyr Ser Gly Ile Gly Leu Asn Gly Glu
        420                 425                 430

Gly His Ala Thr Phe Thr Ile Ala Gly Pro Thr Gly Glu Gly Ile Thr
    435                 440                 445

Ser Ala Lys Ser Phe Cys Arg Gln Arg Arg Cys Val Leu Ile Asp Ser
450                 455                 460

Phe Arg Ile Val
465

<210> SEQ ID NO 30
<211> LENGTH: 469
<212> TYPE: PRT
<213> ORGANISM: Clostridium saccharobutylicum

<400> SEQUENCE: 30

Met Asn Asn Leu Phe Val Ser Pro Glu Thr Lys Asp Leu Lys Leu
1               5                   10                  15

Arg Thr Asn Val Glu Asn Leu Lys Phe Lys Gly Cys Glu Gly Gly Ser
            20                  25                  30

Thr Tyr Ile Gly Val Phe Glu Asn Ala Glu Thr Ala Ile Asp Glu Ala
        35                  40                  45

Val Asn Ala Gln Lys Arg Leu Ser Leu Tyr Tyr Thr Lys Glu Gln Arg
    50                  55                  60

Glu Lys Ile Ile Thr Glu Ile Arg Lys Val Thr Leu Lys Asn Lys Glu
65                  70                  75                  80

Ile Leu Ala Gln Met Ile Leu Glu Glu Thr His Met Gly Arg Tyr Glu
                85                  90                  95

Asp Lys Ile Leu Lys His Glu Leu Val Ala Lys Tyr Thr Pro Gly Thr
            100                 105                 110

Glu Asp Leu Ala Thr Thr Ala Trp Ser Gly Asp Asn Gly Leu Thr Val
        115                 120                 125

```
Val Glu Met Ser Pro Tyr Gly Val Ile Gly Ala Ile Thr Pro Ser Thr
    130                 135                 140

Asn Pro Thr Glu Thr Ile Ile Cys Asn Ser Ile Gly Met Ile Ala Ser
145                 150                 155                 160

Gly Asn Ala Val Val Phe Asn Gly His Pro Gly Ala Lys Lys Cys Val
                165                 170                 175

Ala Phe Ala Val Asp Met Ile Asn Arg Ala Ile Ile Ser Cys Gly Gly
                180                 185                 190

Pro Arg Asn Leu Val Thr Ala Ile Lys Asn Pro Thr Met Glu Ser Leu
                195                 200                 205

Asp Ala Ile Ile Lys His Pro Ala Ile Lys Leu Leu Cys Gly Thr Gly
210                 215                 220

Gly Pro Gly Met Val Lys Thr Leu Leu Ser Ser Gly Lys Lys Ser Ile
225                 230                 235                 240

Gly Ala Gly Ala Gly Asn Pro Pro Val Ile Val Asp Asp Thr Ala Asp
                245                 250                 255

Ile Glu Lys Ala Gly Lys Ser Ile Ile Glu Gly Cys Ser Phe Asp Asn
                260                 265                 270

Asn Leu Pro Cys Ile Ala Glu Lys Glu Val Phe Val Phe Glu Asn Val
                275                 280                 285

Ala Asp Asp Leu Ile Lys Asn Met Leu Lys Asn Asn Ala Val Ile Ile
290                 295                 300

Asn Lys Asp Gln Val Ser Arg Leu Val Asn Leu Val Leu Gln Lys Asn
305                 310                 315                 320

Asn Glu Thr Ser Glu Tyr Thr Ile Asn Lys Lys Trp Val Gly Lys Asp
                325                 330                 335

Ala Lys Leu Phe Leu Asp Glu Ile Asp Val Glu Ser Ser Ser Asp Val
                340                 345                 350

Arg Cys Ile Ile Cys Glu Val Asp Ala Asp His Pro Phe Val Met Thr
                355                 360                 365

Glu Leu Met Met Pro Ile Leu Pro Ile Val Arg Val Lys Asp Ile Asp
370                 375                 380

Glu Ala Ile Lys Tyr Ala Lys Ile Ala Glu Gln Asn Arg Lys His Ser
385                 390                 395                 400

Ala Tyr Ile Tyr Ser Lys Asn Ile Glu Asn Leu Asn Arg Phe Glu Lys
                405                 410                 415

Glu Ile Asp Thr Thr Ile Phe Val Lys Asn Ala Lys Ser Phe Ala Gly
                420                 425                 430

Val Gly Tyr Gly Ala Glu Gly Phe Thr Thr Phe Thr Ile Ala Gly Cys
                435                 440                 445

Thr Gly Glu Gly Ile Thr Ser Ala Arg Asn Phe Thr Arg Gln Arg Arg
                450                 455                 460

Cys Val Phe Val Gly
465

<210> SEQ ID NO 31
<211> LENGTH: 468
<212> TYPE: PRT
<213> ORGANISM: Clostridium sp.

<400> SEQUENCE: 31

Met Asn Lys Asp Thr Thr Ile Ser Glu Thr Glu Asn Leu Lys Phe Lys
1               5                   10                  15

Thr Asn Ile Lys Asn Ala Asp Leu Lys Asn Tyr Glu Asn Ser Thr Ser
```

-continued

```
             20                  25                  30
Tyr Ser Gly Val Phe Glu Asp Val Glu Val Ala Ile Asn Lys Ala Ile
         35                  40                  45

Thr Ala Gln Lys Glu Phe Ser Leu Tyr Tyr Thr Lys Glu Gln Arg Glu
 50                  55                  60

Lys Ile Leu Thr Glu Ile Arg Lys Ala Thr Leu Lys Asn Lys Lys Ile
 65                  70                  75                  80

Leu Ala Lys Met Ile Leu Asp Glu Thr His Met Gly Arg Tyr Glu Asp
                 85                  90                  95

Lys Ile Leu Lys His Glu Leu Val Ala Lys Tyr Thr Pro Gly Ile Glu
                100                 105                 110

Asp Leu Thr Thr Thr Ala Trp Ser Gly Asp Asn Gly Leu Thr Val Val
                115                 120                 125

Glu Met Ala Pro Tyr Gly Val Ile Gly Ala Ile Thr Pro Ser Thr Asn
        130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Ser Ala Lys Lys Cys Val Ala
                165                 170                 175

Phe Ala Val Asp Met Ile Asn Lys Ala Ile Val Ser Cys Gly Gly Pro
                180                 185                 190

Lys Asn Leu Ile Thr Ala Val Lys Asn Pro Thr Met Glu Ser Leu Asp
        195                 200                 205

Ala Ile Ile Lys His Pro Glu Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Asn Ile Ile Glu Gly Cys Ser Phe Asp Asn Asn
                260                 265                 270

Leu Pro Cys Ile Ala Glu Lys Glu Val Phe Val Phe Asp Asn Val Ala
        275                 280                 285

Asp Asn Leu Ile Asp Asn Met Leu Lys Asn Asn Ala Val Ile Ile Asn
        290                 295                 300

Lys Asp Lys Ile Thr Lys Leu Leu Asn Leu Ile Leu Gln Lys Asn Asn
305                 310                 315                 320

Glu Thr Gln Glu Tyr Asn Ile Asn Lys Lys Trp Val Gly Lys Asp Ala
                325                 330                 335

Lys Leu Phe Leu Asn Glu Ile Asp Val Glu Ala Pro Ser Ser Val Arg
                340                 345                 350

Cys Ile Cys Glu Val Glu Pro Asp His Pro Phe Val Met Thr Glu
        355                 360                 365

Leu Met Met Pro Ile Leu Pro Ile Val Arg Val Lys Asn Ile Asp Asp
        370                 375                 380

Ala Ile Gln Tyr Ala Lys Ile Ala Glu Gln Ser Arg Lys His Ser Ala
385                 390                 395                 400

Tyr Ile Tyr Ser Lys Asn Ile Asp Asn Leu Asn Arg Phe Glu Lys Glu
                405                 410                 415

Ile Asp Thr Thr Ile Phe Val Lys Asn Ala Lys Ser Phe Ala Gly Val
                420                 425                 430

Gly Tyr Asn Ala Glu Gly Phe Thr Thr Phe Thr Ile Ala Gly Cys Thr
                435                 440                 445
```

```
Gly Glu Gly Ile Thr Ser Ala Arg Asn Phe Thr Arg Gln Arg Cys
    450                 455                 460
Val Leu Ala Gly
465

<210> SEQ ID NO 32
<211> LENGTH: 467
<212> TYPE: PRT
<213> ORGANISM: Clostridium taeniosporum

<400> SEQUENCE: 32

Met Glu Arg Asn Leu Ser Val Leu Ser Gln Lys Lys Asn Leu Lys Ile
1               5                   10                  15

Thr Arg Lys Val Glu Gly Asn Lys Ser Ile Asn Lys Glu Ser Tyr Leu
            20                  25                  30

Gly Val Phe Glu Lys Val Asp Asn Ala Ile Thr Lys Ala Ile Tyr Ala
        35                  40                  45

Gln Arg Lys Leu Ser Leu Tyr Tyr Thr Lys Glu Asp Arg Glu Arg Ile
    50                  55                  60

Ile Glu Gly Ile Arg Lys Ala Thr Leu Glu Asn Lys Glu Ile Leu Ala
65                  70                  75                  80

Lys Met Ile Val Asp Glu Thr His Met Gly Arg Tyr Glu Asp Lys Ile
                85                  90                  95

Leu Lys His Glu Leu Val Ala Lys Tyr Thr Pro Gly Thr Glu Asp Leu
            100                 105                 110

Ile Thr Thr Ala Trp Ser Gly Asp Gln Gly Leu Thr Leu Val Glu Met
        115                 120                 125

Ser Pro Tyr Gly Val Ile Gly Ala Ile Thr Pro Ser Thr Asn Pro Thr
    130                 135                 140

Glu Thr Val Ile Cys Asn Ser Ile Gly Met Ile Ala Ala Gly Asn Ser
145                 150                 155                 160

Val Val Phe Asn Gly His Pro Gly Ala Lys Lys Cys Val Ala Phe Ala
                165                 170                 175

Val Asp Met Ile Asn Lys Ala Ile Ile Lys Cys Gly Gly Pro Glu Asn
            180                 185                 190

Leu Val Thr Thr Val Glu Asn Pro Thr Met Asp Ser Leu Asn Val Ile
        195                 200                 205

Met Lys His Pro Tyr Val Lys Leu Leu Cys Gly Thr Gly Gly Pro Gly
    210                 215                 220

Leu Ile Lys Thr Leu Leu Asn Ser Gly Lys Lys Ala Ile Gly Ala Gly
225                 230                 235                 240

Ala Gly Asn Pro Pro Val Ile Val Asp Asp Ser Ala Asp Ile Lys His
                245                 250                 255

Ala Ala Lys Ser Ile Ile Glu Gly Cys Ser Phe Asp Asn Asn Leu Pro
            260                 265                 270

Cys Ile Ala Glu Lys Glu Val Phe Val Phe Glu Asn Val Ala Asp Asp
        275                 280                 285

Leu Ile Gln Asn Met Leu Lys Asn Asn Ala Val Leu Ile Asn Glu Asn
    290                 295                 300

Glu Val Ser Lys Leu Leu Asp Leu Val Leu Ile Glu Lys Lys Asp Glu
305                 310                 315                 320

Pro Ser Gly Tyr Val Ile Asn Lys Lys Trp Val Gly Lys Asp Ala Lys
                325                 330                 335

Leu Phe Leu Asp Lys Ile Gly Lys Lys Val Ser Asp Asp Val Lys Cys
```

```
            340                 345                 350
Ile Ile Cys Glu Val Asp Val Asn His Pro Phe Val Met Thr Glu Leu
        355                 360                 365

Met Met Pro Ile Leu Ala Ile Ala Arg Val Lys Asp Ile Asp Glu Ala
    370                 375                 380

Ile Glu Cys Ala Lys Thr Ala Glu Gln Gly Lys Arg His Ser Ala Tyr
385                 390                 395                 400

Met Tyr Ser Lys Asn Ile Asp Asn Leu Asn Arg Phe Glu Lys Glu Ile
            405                 410                 415

Asp Thr Thr Ile Phe Val Lys Asn Ala Lys Ser Phe Ala Gly Val Gly
                420                 425                 430

Phe Gly Ala Glu Gly Phe Thr Thr Phe Thr Ile Ala Gly Pro Thr Gly
            435                 440                 445

Glu Gly Ile Thr Ser Ala Arg Asn Phe Thr Arg Gln Arg Arg Cys Val
        450                 455                 460

Leu Ala Gly
465

<210> SEQ ID NO 33
<211> LENGTH: 467
<212> TYPE: PRT
<213> ORGANISM: Clostridium botulinum

<400> SEQUENCE: 33

Met Glu Arg Asn Leu Ser Val Leu Ser Gln Thr Asn Asp Leu Lys Ile
1               5                   10                  15

Thr Lys Arg Thr Glu Gly Asp Lys Ser Asn Asn Lys Glu Ser Tyr Leu
            20                  25                  30

Gly Val Phe Lys Lys Val Glu Asn Ala Ile Thr Lys Ala Ile Tyr Ala
        35                  40                  45

Gln Lys Lys Leu Ser Leu Tyr Tyr Thr Lys Glu Asp Arg Glu Arg Ile
    50                  55                  60

Ile Lys Ser Ile Arg Lys Ala Thr Leu Glu Asn Lys Glu Ile Leu Ala
65                  70                  75                  80

Lys Met Ile Val Asp Glu Thr His Met Gly Arg Tyr Glu Asp Lys Ile
                85                  90                  95

Leu Lys His Glu Leu Val Ala Lys Tyr Thr Pro Gly Thr Glu Asp Leu
            100                 105                 110

Ile Thr Thr Ala Trp Ser Gly Asp Gln Gly Leu Thr Leu Val Glu Met
        115                 120                 125

Ser Pro Tyr Gly Val Ile Gly Ala Ile Thr Pro Ser Thr Asn Pro Thr
    130                 135                 140

Glu Thr Val Ile Cys Asn Ser Ile Gly Met Ile Ala Ala Gly Asp Ser
145                 150                 155                 160

Val Val Phe Asn Gly His Pro Gly Ala Lys Lys Cys Val Ala Phe Ala
                165                 170                 175

Val Asp Met Ile Asn Lys Ala Val Ile Arg Glu Gly Gly Pro Glu Asn
            180                 185                 190

Leu Val Thr Thr Val Glu Asn Pro Thr Met Glu Ser Leu Asn Val Ile
        195                 200                 205

Met Lys His Pro Tyr Ile Lys Leu Leu Cys Gly Thr Gly Gly Pro Gly
    210                 215                 220

Leu Ile Lys Thr Leu Leu Asn Ser Gly Lys Lys Ala Ile Gly Ala Gly
225                 230                 235                 240
```

```
Ala Gly Asn Pro Pro Val Ile Val Asp Asp Ser Ala Asp Ile Asp Lys
            245                 250                 255

Ala Ala Lys Asn Ile Ile Glu Gly Cys Ser Phe Asp Asn Asn Leu Pro
        260                 265                 270

Cys Ile Ala Glu Lys Glu Val Phe Val Phe Glu Asn Val Ala Asn Asp
    275                 280                 285

Leu Ile Gln Asn Met Ile Lys Asn Asn Ala Val Leu Ile Asn Glu Asn
290                 295                 300

Gln Val Ser Lys Leu Leu Asp Leu Val Leu Leu Glu Arg Lys Asp Glu
305                 310                 315                 320

Thr Leu Glu Tyr Ala Ile Asn Lys Lys Trp Val Gly Lys Asp Ala Lys
                325                 330                 335

Leu Phe Leu Asp Lys Ile Gly Ile Lys Ala Ser Asp Asn Val Arg Cys
            340                 345                 350

Ile Ile Cys Glu Val Asp Ala Asn His Pro Phe Val Met Thr Glu Leu
        355                 360                 365

Met Met Pro Ile Leu Pro Ile Val Arg Val Lys Asp Val Asp Glu Ala
    370                 375                 380

Ile Glu Cys Ala Lys Thr Ala Glu Gln Arg Lys Arg His Ser Ala Tyr
385                 390                 395                 400

Met Tyr Ser Lys Asn Ile Asp Asn Leu Asn Arg Phe Glu Lys Glu Ile
                405                 410                 415

Asp Thr Thr Ile Phe Val Lys Asn Ala Lys Ser Phe Ala Gly Val Gly
            420                 425                 430

Phe Gly Ala Glu Gly Phe Thr Thr Phe Thr Ile Ala Gly Pro Thr Gly
        435                 440                 445

Glu Gly Ile Thr Ser Ala Arg Asn Phe Thr Arg Gln Arg Arg Cys Val
    450                 455                 460

Leu Ala Gly
465

<210> SEQ ID NO 34
<211> LENGTH: 467
<212> TYPE: PRT
<213> ORGANISM: Clostridium botulinum

<400> SEQUENCE: 34

Met Lys Arg Asn Leu Ser Val Leu Leu Gln Thr Asn Asp Leu Lys Ile
1               5                   10                  15

Thr Lys Arg Thr Glu Gly Asp Lys Ser Asn Asn Lys Glu Ser Tyr Leu
            20                  25                  30

Gly Val Phe Lys Lys Val Glu Asn Ala Ile Thr Lys Ala Ile Tyr Ala
        35                  40                  45

Gln Lys Lys Leu Ser Leu Tyr Tyr Thr Lys Glu Asp Arg Glu Arg Ile
    50                  55                  60

Ile Lys Gly Ile Arg Lys Ala Thr Leu Glu Asn Lys Glu Ile Leu Ala
65                  70                  75                  80

Lys Met Ile Val Asp Glu Thr His Met Gly Arg Tyr Glu Asp Lys Ile
                85                  90                  95

Leu Lys His Glu Leu Val Ala Lys Tyr Thr Pro Gly Thr Glu Asp Leu
            100                 105                 110

Ile Thr Thr Ala Trp Ser Gly Asp Gln Gly Leu Thr Leu Val Glu Met
        115                 120                 125

Ser Pro Tyr Gly Val Ile Gly Ala Ile Thr Pro Ser Thr Asn Pro Thr
    130                 135                 140
```

Glu Thr Val Ile Cys Asn Ser Ile Gly Met Ile Ala Ala Gly Asp Ser
145                 150                 155                 160

Val Val Phe Asn Gly His Pro Gly Ala Lys Lys Cys Val Ala Phe Ala
                165                 170                 175

Val Asp Met Ile Asn Lys Ala Val Ile Lys Ala Gly Gly Pro Glu Asn
            180                 185                 190

Leu Val Thr Thr Val Glu Asn Pro Thr Met Glu Ser Leu Asn Val Ile
        195                 200                 205

Met Lys His Pro Tyr Ile Lys Leu Leu Cys Gly Thr Gly Gly Pro Gly
    210                 215                 220

Leu Ile Lys Thr Leu Leu Asn Ser Gly Lys Lys Ala Ile Gly Ala Gly
225                 230                 235                 240

Ala Gly Asn Pro Pro Val Ile Val Asp Asp Ser Ala Asp Ile Asn Lys
                245                 250                 255

Ala Ala Lys Asn Ile Ile Glu Gly Cys Ser Phe Asp Asn Asn Ser Pro
            260                 265                 270

Cys Ile Ala Glu Lys Glu Val Phe Val Phe Glu Asn Val Ala Asn Asp
        275                 280                 285

Leu Ile Gln Asn Met Ile Lys Asn Asn Ala Val Leu Ile Asn Glu Asn
    290                 295                 300

Gln Val Ser Lys Leu Leu Asp Leu Val Leu Leu Glu Arg Lys Asp Glu
305                 310                 315                 320

Thr Leu Glu Tyr Ala Ile Asn Lys Lys Trp Val Gly Lys Asp Ala Lys
                325                 330                 335

Leu Phe Leu Asp Lys Ile Gly Ile Lys Ser Ser Asp Asn Val Arg Cys
            340                 345                 350

Ile Ile Cys Glu Val Asp Ala Asn His Pro Phe Val Met Thr Glu Leu
        355                 360                 365

Met Met Pro Ile Leu Pro Ile Val Arg Val Lys Asp Val Asp Glu Ala
    370                 375                 380

Ile Glu Cys Ala Lys Thr Ala Glu Gln Arg Lys Arg His Ser Ala Tyr
385                 390                 395                 400

Met Tyr Ser Lys Asn Ile Asp Asn Leu Asn Arg Phe Glu Lys Glu Ile
                405                 410                 415

Asp Thr Thr Ile Phe Val Lys Asn Ala Lys Ser Phe Ala Gly Val Gly
            420                 425                 430

Phe Gly Ala Glu Gly Phe Thr Thr Phe Thr Ile Ala Gly Pro Thr Gly
        435                 440                 445

Glu Gly Ile Thr Ser Ala Arg Asn Phe Thr Arg Gln Arg Arg Cys Val
    450                 455                 460

Leu Ala Gly
465

<210> SEQ ID NO 35
<211> LENGTH: 467
<212> TYPE: PRT
<213> ORGANISM: Clostridium botulinum

<400> SEQUENCE: 35

Met Lys Arg Asn Leu Ser Val Leu Leu Gln Thr Asn Asp Leu Lys Ile
1               5                   10                  15

Thr Lys Arg Thr Glu Gly Asp Lys Ser Asn Asn Lys Glu Ser Tyr Leu
            20                  25                  30

Gly Val Phe Lys Lys Val Glu Asn Ala Ile Thr Glu Ala Ile Tyr Ala

```
                35                  40                  45
Gln Lys Lys Leu Ser Leu Tyr Tyr Thr Lys Glu Asp Arg Glu Arg Ile
 50                  55                  60

Ile Lys Gly Ile Arg Lys Ala Thr Leu Glu Asn Lys Glu Ile Leu Ala
 65                  70                  75                  80

Lys Met Ile Val Asp Glu Thr His Met Gly Arg Tyr Glu Asp Lys Ile
                 85                  90                  95

Leu Lys His Glu Leu Val Ala Lys Tyr Thr Pro Gly Thr Glu Asp Leu
                100                 105                 110

Ile Thr Thr Ala Trp Ser Gly Asp Gln Gly Leu Thr Leu Val Glu Met
                115                 120                 125

Ser Pro Tyr Gly Val Ile Gly Ala Ile Thr Pro Ser Thr Asn Pro Thr
                130                 135                 140

Glu Thr Val Ile Cys Asn Ser Ile Gly Met Ile Ala Ala Gly Asp Ser
145                 150                 155                 160

Val Val Phe Asn Gly His Pro Gly Ala Lys Lys Cys Val Ala Phe Ala
                165                 170                 175

Val Asp Met Ile Asn Lys Ala Val Ile Lys Ala Gly Gly Pro Glu Asn
                180                 185                 190

Leu Val Thr Thr Val Glu Asn Pro Thr Met Glu Ser Leu Asn Val Ile
                195                 200                 205

Met Lys His Pro Tyr Ile Lys Leu Leu Cys Gly Thr Gly Gly Pro Gly
210                 215                 220

Leu Ile Lys Thr Leu Leu Asn Ser Gly Lys Lys Ala Ile Gly Ala Gly
225                 230                 235                 240

Ala Gly Asn Pro Pro Val Ile Val Asp Asp Ser Ala Asp Ile Asn Lys
                245                 250                 255

Ala Ala Lys Asn Ile Ile Glu Gly Cys Ser Phe Asp Asn Asn Ser Pro
                260                 265                 270

Cys Ile Ala Glu Lys Glu Val Phe Val Phe Glu Asn Val Ala Asn Asp
                275                 280                 285

Leu Ile Gln Asn Met Ile Lys Asn Asn Ala Val Leu Ile Asn Glu Asn
                290                 295                 300

Gln Val Ser Lys Leu Leu Asp Leu Val Leu Leu Glu Arg Lys Asp Glu
305                 310                 315                 320

Thr Leu Glu Tyr Ala Ile Asn Lys Lys Trp Val Gly Lys Asp Ala Lys
                325                 330                 335

Leu Phe Leu Asp Lys Ile Gly Ile Lys Ser Ser Asp Asn Val Arg Cys
                340                 345                 350

Ile Ile Cys Glu Val Asp Ala Asn His Pro Phe Val Met Thr Glu Leu
                355                 360                 365

Met Met Pro Ile Leu Pro Ile Val Arg Val Lys Asp Val Asp Glu Ala
                370                 375                 380

Ile Glu Cys Ala Lys Thr Ala Glu Gln Arg Lys Arg His Ser Ala Tyr
385                 390                 395                 400

Met Tyr Ser Lys Asn Ile Asp Asn Leu Asn Arg Phe Glu Lys Glu Ile
                405                 410                 415

Asp Thr Thr Ile Phe Val Lys Asn Ala Lys Ser Phe Ala Gly Val Gly
                420                 425                 430

Phe Gly Ala Glu Gly Phe Thr Thr Phe Thr Ile Ala Gly Pro Thr Gly
                435                 440                 445

Glu Gly Ile Thr Ser Ala Arg Asn Phe Thr Arg Gln Arg Arg Cys Val
                450                 455                 460
```

Leu Ala Gly
465

<210> SEQ ID NO 36
<211> LENGTH: 467
<212> TYPE: PRT
<213> ORGANISM: Clostridium botulinum

<400> SEQUENCE: 36

```
Met Lys Arg Asn Leu Ser Val Leu Leu Gln Thr Asn Asp Leu Lys Ile
1               5                   10                  15

Thr Lys Arg Thr Glu Gly Asp Lys Ser Asn Asn Lys Glu Ser Tyr Leu
            20                  25                  30

Gly Val Phe Lys Lys Val Glu Asn Ala Ile Thr Lys Ala Ile Tyr Ser
        35                  40                  45

Gln Lys Lys Leu Ser Leu Tyr Tyr Thr Lys Glu Asp Arg Glu Arg Ile
    50                  55                  60

Ile Lys Gly Ile Arg Lys Ala Thr Leu Glu Asn Lys Glu Ile Leu Ala
65                  70                  75                  80

Lys Met Ile Val Asp Glu Thr His Met Gly Arg Tyr Glu Asp Lys Ile
                85                  90                  95

Leu Lys His Glu Leu Val Ala Lys Tyr Thr Pro Gly Thr Glu Asp Leu
            100                 105                 110

Ile Thr Thr Ala Trp Ser Gly Asp Gln Gly Leu Thr Leu Val Glu Met
        115                 120                 125

Ser Pro Tyr Gly Val Ile Gly Ala Ile Thr Pro Ser Thr Asn Pro Thr
    130                 135                 140

Glu Thr Val Ile Cys Asn Ser Ile Gly Met Ile Ala Ala Gly Asp Ser
145                 150                 155                 160

Val Val Phe Asn Gly His Pro Gly Ala Lys Lys Cys Val Ala Phe Ala
                165                 170                 175

Val Asp Met Ile Asn Lys Ala Val Ile Lys Ala Gly Gly Pro Glu Asn
            180                 185                 190

Leu Val Thr Thr Val Glu Asn Pro Thr Met Glu Ser Leu Asn Val Ile
        195                 200                 205

Met Lys His Pro Tyr Ile Lys Leu Leu Cys Gly Thr Gly Gly Pro Gly
    210                 215                 220

Leu Ile Lys Thr Leu Leu Asn Ser Gly Lys Lys Ala Ile Gly Ala Gly
225                 230                 235                 240

Ala Gly Asn Pro Pro Val Ile Val Asp Asp Ser Ala Asp Ile Asn Lys
                245                 250                 255

Ala Ala Lys Asn Ile Ile Glu Gly Cys Ser Phe Asp Asn Asn Ser Pro
            260                 265                 270

Cys Ile Ala Glu Lys Glu Val Phe Val Phe Glu Asn Val Ala Asn Asp
        275                 280                 285

Leu Ile Gln Asn Met Ile Lys Asn Asn Ala Val Leu Ile Asn Glu Asn
    290                 295                 300

Gln Val Ser Lys Leu Leu Asp Leu Val Leu Leu Glu Arg Lys Asp Glu
305                 310                 315                 320

Thr Leu Glu Tyr Ala Ile Asn Lys Lys Trp Val Gly Lys Asp Ala Lys
                325                 330                 335

Leu Phe Leu Asp Lys Ile Gly Ile Lys Ser Ser Asp Asn Val Arg Cys
            340                 345                 350

Ile Ile Cys Glu Val Asp Ala Asn His Pro Phe Val Met Thr Glu Leu
```

```
                355                 360                 365
Met Met Pro Ile Leu Pro Ile Val Arg Val Lys Asp Val Asp Glu Ala
    370                 375                 380

Ile Glu Cys Ala Lys Thr Ala Glu Gln Arg Lys Arg His Ser Ala Tyr
385                 390                 395                 400

Met Tyr Ser Lys Asn Ile Asp Asn Leu Asn Arg Phe Glu Lys Glu Ile
                405                 410                 415

Asp Thr Thr Ile Phe Val Lys Asn Ala Lys Ser Phe Ala Gly Val Gly
                420                 425                 430

Phe Gly Ala Glu Gly Phe Thr Thr Phe Thr Ile Ala Gly Pro Thr Gly
            435                 440                 445

Glu Gly Ile Thr Ser Ala Arg Asn Phe Thr Arg Gln Arg Arg Cys Val
450                 455                 460

Leu Ala Gly
465

<210> SEQ ID NO 37
<211> LENGTH: 472
<212> TYPE: PRT
<213> ORGANISM: Clostridium beijerinckii

<400> SEQUENCE: 37

Met Asp Val Asp Val Leu Val Glu Lys Leu Val Arg Gln Ala Ile
1               5                   10                  15

Glu Glu Val Lys Asn Lys Asn Leu Leu Asn Leu Asp Lys Phe Glu Ser
                20                  25                  30

Val Lys Asn Tyr Gly Ile Phe Gly Thr Met Asp Ala Ala Val Glu Ala
            35                  40                  45

Ser Phe Val Ala Gln Lys Gln Leu Leu Asn Ala Ser Met Thr Asp Lys
    50                  55                  60

Gln Lys Tyr Val Asp Thr Ile Lys Ala Thr Ile Leu Lys Lys Glu Asn
65                  70                  75                  80

Leu Glu Leu Ile Ser Arg Met Ser Val Glu Glu Thr Glu Ile Gly Lys
                85                  90                  95

Tyr Glu His Lys Leu Ile Lys Asn Arg Val Ala Ala Glu Lys Thr Pro
                100                 105                 110

Gly Ile Glu Asp Leu Thr Thr Glu Ala Met Thr Gly Asp Asn Gly Leu
            115                 120                 125

Thr Leu Val Glu Tyr Cys Pro Phe Gly Val Ile Gly Ala Ile Thr Pro
    130                 135                 140

Thr Thr Asn Pro Thr Glu Thr Ile Ile Cys Asn Ser Ile Ser Met Ile
145                 150                 155                 160

Ala Gly Gly Asn Thr Val Val Phe Ser Pro His Pro Arg Ala Lys Asn
                165                 170                 175

Val Ser Ile Lys Leu Val Thr Met Leu Asn Lys Ala Leu Glu Glu Ala
                180                 185                 190

Gly Ala Pro Asp Asn Leu Ile Ala Thr Val Lys Glu Pro Ser Ile Glu
            195                 200                 205

Asn Thr Asn Ile Met Met Glu His Pro Lys Ile Arg Met Leu Val Ala
    210                 215                 220

Thr Gly Gly Pro Ala Ile Val Asn Lys Val Met Ser Thr Gly Lys Lys
225                 230                 235                 240

Ala Ile Gly Ala Gly Ala Gly Asn Pro Pro Val Val Asp Glu Thr
                245                 250                 255
```

```
Ala Asp Ile Glu Lys Ala Ile Asp Ile Val Asn Gly Cys Ser Phe
            260                 265                 270

Asp Asn Asn Val Pro Cys Ile Ala Glu Lys Glu Val Phe Ala Val Asp
            275                 280                 285

Gln Val Cys Asp Tyr Leu Ile His Tyr Met Lys Leu Asn Gly Ala Tyr
    290                 295                 300

Glu Ile Lys Asp Arg Asp Leu Ile Gln Lys Leu Leu Asp Leu Val Thr
305                 310                 315                 320

Asn Glu Asn Gly Gly Pro Lys Val Ser Phe Val Gly Lys Ser Ala Pro
                325                 330                 335

Tyr Ile Leu Asn Lys Leu Gly Ile Ser Val Asp Glu Asn Ile Lys Val
            340                 345                 350

Ile Ile Met Glu Val Glu Lys Asn His His Phe Val Leu Glu Glu Met
            355                 360                 365

Met Met Pro Ile Leu Pro Ile Val Arg Thr Lys Asp Val Asp Glu Ala
        370                 375                 380

Ile Glu Cys Ala Tyr Val Ala Glu His Gly Asn Arg His Thr Ala Ile
385                 390                 395                 400

Met His Ser Lys Asn Val Asp Lys Leu Thr Lys Met Ala Arg Leu Leu
                405                 410                 415

Glu Thr Thr Ile Phe Val Lys Asn Ser Pro Ser Tyr Ala Gly Ile Gly
            420                 425                 430

Val Gly Gly Glu Gly Thr Thr Thr Phe Thr Ile Ala Gly Pro Thr Gly
                435                 440                 445

Glu Gly Leu Thr Thr Ala Arg Ser Phe Cys Arg Lys Arg Cys Val
450                 455                 460

Met Val Asp Ala Phe Asn Ile Arg
465                 470

<210> SEQ ID NO 38
<211> LENGTH: 468
<212> TYPE: PRT
<213> ORGANISM: Clostridium saccharoperbutylacetonicum

<400> SEQUENCE: 38

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160
```

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Ser His Pro Phe Val Met Thr Glu
        355                 360                 365

Leu Met Met Pro Ile Leu Pro Ile Val Arg Val Lys Asp Ile Asp Glu
    370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 39
<211> LENGTH: 468
<212> TYPE: PRT
<213> ORGANISM: Clostridium sp.

<400> SEQUENCE: 39

Met Ile Lys Asp Thr Leu Val Ser Val Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Ser Ser Ala Val
        35                  40                  45

His Ala Gln Lys Ile Leu Ser Leu His Tyr Thr Lys Glu Gln Arg Glu

```
            50                  55                  60
Lys Ile Ile Thr Glu Ile Arg Lys Ala Ala Leu Gln Asn Lys Glu Val
 65                  70                  75                  80

Leu Ala Thr Met Ile Leu Glu Glu Thr His Met Gly Arg Cys Glu Asp
                 85                  90                  95

Lys Ile Leu Lys His Glu Leu Val Ala Lys Tyr Thr Pro Gly Thr Glu
                100                 105                 110

Asp Leu Thr Thr Thr Ala Trp Ser Gly Asp Asn Gly Leu Thr Val Val
                115                 120                 125

Glu Met Ser Pro Tyr Gly Val Ile Gly Ala Ile Thr Pro Ser Thr Asn
            130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
                180                 185                 190

Glu Asn Leu Val Thr Thr Ile Lys Asn Pro Thr Met Glu Ser Leu Asp
            195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
                260                 265                 270

Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
            290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Asn Val Lys
                340                 345                 350

Cys Ile Ile Cys Glu Val Asn Ala Asn His Pro Phe Val Met Thr Glu
            355                 360                 365

Leu Met Met Pro Ile Leu Pro Ile Val Arg Val Lys Asp Ile Asp Glu
            370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Phe Thr Ile Ala Gly Ser Thr
            435                 440                 445

Gly Glu Gly Ile Thr Ser Ala Arg Asn Phe Thr Arg Gln Arg Arg Cys
450                 455                 460

Val Leu Ala Gly
465
```

<210> SEQ ID NO 40
<211> LENGTH: 468
<212> TYPE: PRT
<213> ORGANISM: Clostridium beijerinckii

<400> SEQUENCE: 40

```
Met Ile Lys Asp Thr Leu Val Ser Val Thr Lys Asp Leu Lys Leu Lys
1               5                   10                  15

Thr Asn Val Glu Asn Thr Asn Leu Lys Asn Tyr Lys Asp Asn Ser Ser
            20                  25                  30

Cys Phe Gly Val Phe Glu Asn Ala Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Asn Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Leu Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Val Glu Met Ile Asn Lys Ala Ile Val Ser Cys Gly Gly Pro
            180                 185                 190

Glu Asn Leu Val Thr Thr Ile Lys Asn Pro Thr Met Glu Ser Leu Asn
        195                 200                 205

Ala Ile Ile Lys His Pro Ser Ile Glu Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Ile Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
```

```
             370                 375                 380
Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 41
<211> LENGTH: 468
<212> TYPE: PRT
<213> ORGANISM: Clostridium beijerinckii

<400> SEQUENCE: 41

Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Leu Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270
```

```
Leu Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
        355                 360                 365

Leu Met Met Pro Ile Leu Pro Ile Val Arg Val Lys Asp Ile Asp Glu
370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 42
<211> LENGTH: 468
<212> TYPE: PRT
<213> ORGANISM: Clostridium beijerinckii

<400> SEQUENCE: 42

Met Asn Lys Asp Thr Leu Ile Pro Thr Thr Lys Asp Leu Lys Val Lys
1               5                   10                  15

Thr Asn Gly Glu Asn Ile Asn Leu Lys Asn Tyr Lys Asp Asn Ser Ser
                20                  25                  30

Cys Phe Gly Val Phe Glu Asn Val Glu Asn Ala Ile Ser Ser Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175
```

```
Phe Ala Val Glu Met Ile Asn Lys Ala Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 43
<211> LENGTH: 468
<212> TYPE: PRT
<213> ORGANISM: Clostridium beijerinckii

<400> SEQUENCE: 43

Met Ile Lys Asp Thr Leu Val Ser Val Thr Lys Asp Leu Lys Leu Lys
1               5                   10                  15

Thr Asn Val Glu Asn Ile Asn Leu Lys Asn Tyr Lys Asp Asn 65                  70                  75                  80
Leu Ala Thr Met Ile Leu Glu Glu Thr His Met Gly Arg Tyr Glu Asp
                    85                  90                  95
Lys Ile Leu Lys His Glu Leu Val Ala Lys Tyr Thr Pro Gly Thr Glu
                100                 105                 110
Asp Leu Thr Thr Thr Ala Trp Ser Gly Asp Asn Gly Leu Thr Val Val
                115                 120                 125
Glu Met Ser Pro Tyr Gly Val Ile Gly Ala Ile Thr Pro Ser Thr Asn
        130                 135                 140
Pro Thr Glu Thr Val Ile Cys Asn Ser Ile Gly Met Ile Ala Ala Gly
145                 150                 155                 160
Asn Ala Val Val Phe Asn Gly His Pro Gly Ala Lys Lys Cys Val Ala
                165                 170                 175
Phe Ala Val Glu Met Ile Asn Lys Ala Ile Ile Ser Cys Gly Gly Pro
                180                 185                 190
Glu Asn Leu Val Thr Thr Ile Lys Asn Pro Thr Met Glu Ser Leu Asp
            195                 200                 205
Ala Ile Ile Lys His Pro Ser Ile Lys Leu Leu Cys Gly Thr Gly Gly
        210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Arg Ser Ile Ile Glu Gly Cys Ser Phe Asp Asn Asn
                260                 265                 270
Leu Pro Cys Ile Ala Glu Lys Glu Val Phe Val Phe Glu Asn Val Ala
            275                 280                 285
Asp Asp Leu Ile Ser Asn Met Leu Lys Asn Asn Ala Val Ile Ile Asn
        290                 295                 300
Glu Asp Gln Val Ser Lys Leu Ile Asp Leu Val Leu Gln Lys Asn Asn
305                 310                 315                 320
Glu Thr Gln Glu Tyr Phe Ile Asn Lys Lys Trp Val Gly Lys Asp Ala
                325                 330                 335
Lys Leu Phe Leu Asp Glu Ile Asp Val Glu Ser Pro Ser Asn Val Lys
            340                 345                 350
Cys Ile Ile Cys Glu Val Asn Ala Asn His Pro Phe Val Met Thr Glu
        355                 360                 365
Leu Met Met Pro Ile Leu Pro Ile Val Arg Val Lys Asp Ile Asp Glu
    370                 375                 380
Ala Ile Lys Tyr Ala Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
                405                 410                 415
Ile Asp Thr Thr Ile Phe Val Lys Asn Ala Lys Ser Phe Ala Gly Val
                420                 425                 430
Gly Tyr Glu Ala Glu Gly Phe Thr Thr Phe Thr Ile Ala Gly Ser Thr
            435                 440                 445
Gly Glu Gly Ile Thr Ser Ala Arg Asn Phe Thr Arg Gln Arg Arg Cys
        450                 455                 460
Val Leu Ala Gly
465

<210> SEQ ID NO 44

```
<211> LENGTH: 468
<212> TYPE: PRT
<213> ORGANISM: Clostridium beijerinckii

<400> SEQUENCE: 44
```

| | | | | | | | | | | | | | | |
|---|---|---|---|---|---|---|---|---|---|---|---|---|---|---|
| Met | Asn | Lys | Asp | Thr | Leu | Ile | Pro | Thr | Thr | Lys | Asp | Leu | Lys | Val | Lys |
| 1 | | | | 5 | | | | | 10 | | | | | 15 | |

Thr Asn Gly Glu Asn Ile Asn Leu Lys Asn Tyr Lys Asp Asn Ser Ser
          20                  25                  30

Cys Phe Gly Val Phe Glu Asn Val Glu Asn Ala Ile Ser Ser Ala Val
              35                  40                  45

His Ala Gln Lys Ile Leu Ser Leu His Tyr Thr Lys Glu Gln Arg Glu
 50                  55                  60

Lys Ile Ile Thr Glu Ile Arg Lys Ala Ala Leu Gln Asn Lys Glu Val
 65                  70                  75                  80

Leu Ala Thr Met Ile Leu Glu Glu Thr His Met Gly Arg Tyr Glu Asp
                  85                  90                  95

Lys Ile Leu Lys His Glu Leu Val Ala Lys Tyr Thr Pro Gly Thr Glu
              100                 105                 110

Asp Leu Thr Thr Thr Ala Trp Ser Gly Asp Asn Gly Leu Thr Val Val
              115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                  165                 170                 175

Phe Ala Val Glu Met Ile Asn Lys Ala Ile Ile Ser Cys Gly Gly Pro
              180                 185                 190

Glu Asn Leu Val Thr Thr Ile Lys Asn Pro Thr Met Glu Ser Leu Asp
              195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
              245                 250                 255

Glu Lys Ala Gly Arg Ser Ile Ile Glu Gly Cys Ser Phe Asp Asn Asn
              260                 265                 270

Leu Pro Cys Ile Ala Glu Lys Glu Val Phe Val Phe Glu Asn Val Ala
              275                 280                 285

Asp Asp Leu Ile Ser Asn Met Leu Lys Asn Asn Ala Val Ile Ile Asn
290                 295                 300

Glu Asp Gln Ile Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
              325                 330                 335

Lys Leu Phe Leu Asp Glu Ile Asp Ile Glu Ser Pro Ser Asn Val Lys
              340                 345                 350

Cys Ile Ile Cys Glu Val Asn Glu Asn His Pro Phe Val Met Thr Glu
              355                 360                 365

Leu Met Met Pro Ile Leu Pro Ile Val Arg Val Lys Asp Ile Asp Glu
              370                 375                 380

Ala Ile Arg Tyr Ala Lys Ile Ala Glu Gln Asn Arg Lys His Ser Ala

```
                385                 390                 395                 400
        Tyr Ile Tyr Ser Lys Asn Ile Asp Asn Leu Asn Arg Phe Glu Arg Glu
                        405                 410                 415

Ile Asp Thr Thr Ile Phe Val Lys Asn Ala Lys Ser Phe Ala Gly Val
                        420                 425                 430

Gly Tyr Glu Ala Glu Gly Phe Thr Phe Thr Ile Ala Gly Ser Thr
                        435                 440                 445

Gly Glu Gly Ile Thr Ser Ala Arg Asn Phe Thr Arg Gln Arg Arg Cys
        450                         455                 460

Val Leu Ala Gly
        465

<210> SEQ ID NO 45
<211> LENGTH: 468
<212> TYPE: PRT
<213> ORGANISM: Clostridium beijerinckii

<400> SEQUENCE: 45

Met Asn Lys Asp Thr Leu Ile Pro Thr Thr Lys Asp Leu Lys Val Lys
1               5                   10                  15

Thr Asn Asp Glu Asn Ile Asn Leu Lys Asn Tyr Lys Asp Asn Ser Ser
                20                  25                  30

Cys Phe Gly Val Phe Glu Asn Val Glu Asn Ala Ile Ser Ser Ala Val
            35                  40                  45

His Ala Gln Lys Ile Leu Ser Ile His Tyr Thr Lys Glu Gln Arg Glu
        50                  55                  60

Lys Ile Ile Thr Glu Ile Arg Lys Ala Ala Leu Gln Asn Lys Glu Ala
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Ser Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285
```

-continued

```
Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
                340                 345                 350

Cys Ile Ile Cys Glu Val Asn Ala Asn His Pro Phe Val Met Thr Glu
            355                 360                 365

Leu Met Met Pro Ile Leu Pro Ile Val Arg Val Lys Asp Ile Asp Glu
370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 46
<211> LENGTH: 468
<212> TYPE: PRT
<213> ORGANISM: Clostridium saccharoperbutylacetonicum

<400> SEQUENCE: 46

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
                20                  25                  30

Cys Phe Gly Val Phe Glu Asn Val Glu Asn Ala Ile Ser Asn Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190
```

```
Glu Asn Leu Val Thr Thr Ile Lys Asn Pro Thr Met Asp Ser Leu Asp
            195                 200                 205
Ala Ile Ile Lys His Pro Ser Ile Lys Leu Leu Cys Gly Thr Gly Gly
        210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Lys Ser Ile Ile Glu Gly Cys Ser Phe Asp Asn Asn
            260                 265                 270
Leu Pro Cys Ile Ala Glu Lys Glu Val Phe Val Phe Glu Asn Val Ala
        275                 280                 285
Asp Asp Leu Ile Ser Asn Met Leu Lys Asn Asn Ala Val Ile Ile Asn
    290                 295                 300
Glu Asp Gln Val Ser Lys Leu Ile Asp Leu Val Leu Gln Lys Asn Asn
305                 310                 315                 320
Glu Thr Gln Glu Tyr Ser Ile Asn Lys Lys Trp Val Gly Lys Asp Ala
                325                 330                 335
Lys Leu Phe Leu Asp Glu Ile Asp Val Glu Ser Pro Ser Ser Val Lys
            340                 345                 350
Cys Ile Ile Cys Glu Val Ser Ala Ser His Pro Phe Val Met Thr Glu
        355                 360                 365
Leu Met Met Pro Ile Leu Pro Ile Val Arg Val Lys Asp Ile Asp Glu
    370                 375                 380
Ala Ile Glu Tyr Ala Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
                405                 410                 415
Ile Asp Thr Thr Ile Phe Val Lys Asn Ala Lys Ser Phe Ala Gly Val
            420                 425                 430
Gly Tyr Glu Ala Glu Gly Phe Thr Thr Phe Thr Ile Ala Gly Ser Thr
        435                 440                 445
Gly Glu Gly Ile Thr Ser Ala Arg Asn Phe Thr Arg Gln Arg Arg Cys
    450                 455                 460
Val Leu Ala Gly
465

<210> SEQ ID NO 47
<211> LENGTH: 468
<212> TYPE: PRT
<213> ORGANISM: Clostridium beijerinckii

<400> SEQUENCE: 47

Met Asn Lys Asp Thr Leu Ile Pro Thr Thr Lys Asp Leu Lys Val Lys
1               5                   10                  15
Thr Asn Gly Glu Asn Ile Asn Leu Lys Asn Tyr Lys Asp Asn Ser Ser
            20                  25                  30
Cys Phe Gly Val Phe Glu Asn Val Glu Asn Ala Ile Ser Ser Ala Val
        35                  40                  45
His Ala Gln Lys Ile Leu Ser Leu His Tyr Thr Lys Glu Gln Arg Glu
    50                  55                  60
Lys Ile Ile Thr Glu Ile Arg Lys Ala Leu Gln Asn Lys Glu Val
65                  70                  75                  80
Leu Ala Thr Met Ile Leu Glu Glu Thr His Met Gly Arg Tyr Glu Asp
```

```
                85                  90                  95
Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
            115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 48
<211> LENGTH: 468
<212> TYPE: PRT
<213> ORGANISM: Clostridium beijerinckii
```

<400> SEQUENCE: 48

```
Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Leu Ile Lys Leu Leu Cys Gly Thr Gly Gly
210                 215                 220

Pro Gly Met Val Lys Thr Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Ala Val Ile Ile Asn
290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
        355                 360                 365

Leu Met Met Pro Ile Leu Pro Ile Val Arg Val Lys Asp Ile Asp Glu
        370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
```

-continued

```
                405                 410                 415
Ile Asp Thr Thr Ile Phe Val Lys Asn Ala Lys Ser Phe Ala Gly Val
                420                 425                 430
Gly Tyr Glu Ala Glu Gly Phe Thr Thr Phe Thr Ile Ala Gly Ser Thr
                435                 440                 445
Gly Glu Gly Ile Thr Ser Ala Arg Asn Phe Thr Arg Gln Arg Arg Cys
                450                 455                 460
Val Leu Ala Gly
465

<210> SEQ ID NO 49
<211> LENGTH: 468
<212> TYPE: PRT
<213> ORGANISM: Clostridium sp.

<400> SEQUENCE: 49

Met Asn Lys Asp Thr Thr Ile Ser Glu Thr Glu Asn Leu Lys Phe Lys
1               5                   10                  15
Thr Asn Ile Lys Asn Ala Asp Leu Lys Asn Tyr Glu Asn Ser Thr Ser
                20                  25                  30
Tyr Ser Gly Val Phe Glu Asp Val Glu Val Ala Ile Asn Lys Ala Ile
                35                  40                  45
Thr Ala Gln Lys Glu Phe Ser Leu Tyr Tyr Thr Lys Glu Gln Arg Glu
50                  55                  60
Lys Ile Leu Thr Glu Ile Arg Lys Ala Thr Leu Lys Asn Lys Lys Ile
65                  70                  75                  80
Leu Ala Lys Met Ile Leu Asp Glu Thr His Met Gly Arg Tyr Glu Asp
                85                  90                  95
Lys Ile Leu Lys His Glu Leu Val Ala Lys Tyr Thr Pro Gly Ile Glu
                100                 105                 110
Asp Leu Thr Thr Thr Ala Trp Ser Gly Asp Asn Gly Leu Thr Val Val
                115                 120                 125
Glu Met Ala Pro Tyr Gly Val Ile Gly Ala Ile Thr Pro Ser Thr Asn
                130                 135                 140
Pro Thr Glu Thr Val Ile Cys Asn Ser Ile Gly Met Ile Ala Ala Gly
145                 150                 155                 160
Asn Ala Val Val Phe Asn Gly His Pro Ser Ala Lys Lys Cys Val Ala
                165                 170                 175
Phe Ala Val Asp Met Ile Asn Lys Ala Ile Val Ser Cys Gly Gly Pro
                180                 185                 190
Lys Asn Leu Ile Thr Ala Val Lys Asn Pro Thr Met Glu Ser Leu Asp
                195                 200                 205
Ala Ile Ile Lys His Pro Glu Ile Lys Leu Leu Cys Gly Thr Gly Gly
                210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Lys Asn Ile Ile Glu Gly Cys Ser Phe Asp Asn Asn
                260                 265                 270
Leu Pro Cys Ile Ala Glu Lys Glu Val Phe Val Phe Asp Asn Val Ala
                275                 280                 285
Asp Asn Leu Ile Asp Asn Met Leu Lys Asn Asn Ala Val Ile Ile Asn
                290                 295                 300
```

-continued

```
Lys Asp Lys Ile Thr Lys Leu Leu Asn Leu Ile Leu Gln Lys Asn Asn
305                 310                 315                 320

Glu Thr Gln Glu Tyr Asn Ile Asn Lys Lys Trp Val Gly Lys Asp Ala
            325                 330                 335

Lys Leu Phe Leu Asn Glu Ile Asp Val Glu Ala Pro Ser Ser Val Arg
            340                 345                 350

Cys Ile Ile Cys Glu Val Glu Pro Asp His Pro Phe Val Met Thr Glu
            355                 360                 365

Leu Met Met Pro Ile Leu Pro Ile Val Arg Val Lys Asn Ile Asp Asp
370                 375                 380

Ala Ile Gln Tyr Ala Lys Ile Ala Glu Gln Ser Arg Lys His Ser Ala
385                 390                 395                 400

Tyr Ile Tyr Ser Lys Asn Ile Asp Asn Leu Asn Arg Phe Glu Lys Glu
            405                 410                 415

Ile Asp Thr Thr Ile Phe Val Lys Asn Ala Lys Ser Phe Ala Gly Val
            420                 425                 430

Gly Tyr Asn Ala Glu Gly Phe Thr Phe Thr Ile Ala Gly Cys Thr
            435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 50
<211> LENGTH: 469
<212> TYPE: PRT
<213> ORGANISM: Clostridium saccharobutylicum

<400> SEQUENCE: 50

Met Asn Asn Asn Leu Phe Val Ser Pro Glu Thr Lys Asp Leu Lys Leu
1               5                   10                  15

Arg Thr Asn Val Glu Asn Leu Lys Phe Lys Gly Cys Glu Gly Gly Ser
            20                  25                  30

Thr Tyr Ile Gly Val Phe Glu Asn Ala Glu Thr Ala Ile Asp Glu Ala
        35                  40                  45

Val Asn Ala Gln Lys Arg Leu Ser Leu Tyr Tyr Thr Lys Glu Gln Arg
50                  55                  60

Glu Lys Ile Ile Thr Glu Ile Arg Lys Val Thr Leu Asn Lys Glu
65                  70                  75                  80

Ile Leu Ala Gln Met Ile Leu Glu Glu Thr His Met Gly Arg Tyr Glu
                85                  90                  95

Asp Lys Ile Leu Lys His Glu Leu Val Ala Lys Tyr Thr Pro Gly Thr
            100                 105                 110

Glu Asp Leu Ala Thr Thr Ala Trp Ser Gly Asp Asn Gly Leu Thr Val
            115                 120                 125

Val Glu Met Ser Pro Tyr Gly Val Ile Gly Ala Ile Thr Pro Ser Thr
130                 135                 140

Asn Pro Thr Glu Thr Ile Ile Cys Asn Ser Ile Gly Met Ile Ala Ser
145                 150                 155                 160

Gly Asn Ala Val Val Phe Asn Gly His Pro Gly Ala Lys Lys Cys Val
            165                 170                 175

Ala Phe Ala Val Asp Met Ile Asn Arg Ala Ile Ile Ser Cys Gly Gly
            180                 185                 190

Pro Arg Asn Leu Val Thr Ala Ile Lys Asn Pro Thr Met Glu Ser Leu
            195                 200                 205
```

```
Asp Ala Ile Ile Lys His Pro Ala Ile Lys Leu Leu Cys Gly Thr Gly
            210                 215                 220
Gly Pro Gly Met Val Lys Thr Leu Leu Ser Ser Gly Lys Lys Ser Ile
225                 230                 235                 240
Gly Ala Gly Ala Gly Asn Pro Pro Val Ile Val Asp Asp Thr Ala Asp
                245                 250                 255
Ile Glu Lys Ala Gly Lys Ser Ile Ile Glu Gly Cys Ser Phe Asp Asn
                260                 265                 270
Asn Leu Pro Cys Ile Ala Glu Lys Glu Val Phe Val Phe Glu Asn Val
            275                 280                 285
Ala Asp Asp Leu Ile Lys Asn Met Leu Lys Asn Asn Ala Val Ile Ile
        290                 295                 300
Asn Lys Asp Gln Val Ser Arg Leu Val Asn Leu Val Leu Gln Lys Asn
305                 310                 315                 320
Asn Glu Thr Ser Glu Tyr Thr Ile Asn Lys Lys Trp Val Gly Lys Asp
                325                 330                 335
Ala Lys Leu Phe Leu Asp Glu Ile Asp Val Glu Ser Ser Asp Val
            340                 345                 350
Arg Cys Ile Ile Cys Glu Val Asp Ala Asp His Pro Phe Val Met Thr
        355                 360                 365
Glu Leu Met Met Pro Ile Leu Pro Ile Val Arg Val Lys Asp Ile Asp
370                 375                 380
Glu Ala Ile Lys Tyr Ala Lys Ile Ala Glu Gln Asn Arg Lys His Ser
385                 390                 395                 400
Ala Tyr Ile Tyr Ser Lys Asn Ile Glu Asn Leu Asn Arg Phe Glu Lys
                405                 410                 415
Glu Ile Asp Thr Thr Ile Phe Val Lys Asn Ala Lys Ser Phe Ala Gly
            420                 425                 430
Val Gly Tyr Gly Ala Glu Gly Phe Thr Thr Phe Thr Ile Ala Gly Cys
        435                 440                 445
Thr Gly Glu Gly Ile Thr Ser Ala Arg Asn Phe Thr Arg Gln Arg Arg
    450                 455                 460
Cys Val Phe Val Gly
465

<210> SEQ ID NO 51
<211> LENGTH: 467
<212> TYPE: PRT
<213> ORGANISM: Clostridium botulinum

<400> SEQUENCE: 51

Met Glu Arg Asn Leu Ser Val Leu Ser Gln Thr Asn Asp Leu Lys Ile
1               5                   10                  15
Thr Lys Arg Thr Glu Gly Asp Lys Ser Asn Asn Lys Glu Ser Tyr Leu
            20                  25                  30
Gly Val Phe Lys Lys Val Glu Asn Ala Ile Thr Lys Ala Ile Tyr Ala
        35                  40                  45
Gln Lys Lys Leu Ser Leu Tyr Tyr Thr Lys Glu Asp Arg Glu Arg Ile
    50                  55                  60
Ile Lys Ser Ile Arg Lys Ala Thr Leu Glu Asn Lys Glu Ile Leu Ala
65                  70                  75                  80
Lys Met Ile Val Asp Glu Thr His Met Gly Arg Tyr Glu Asp Lys Ile
                85                  90                  95
Leu Lys His Glu Leu Val Ala Lys Tyr Thr Pro Gly Thr Glu Asp Leu
```

Ile Thr Thr Ala Trp Ser Gly Asp Gln Gly Leu Thr Leu Val Glu Met
100                     105                     110

Ser Pro Tyr Gly Val Ile Gly Ala Ile Thr Pro Ser Thr Asn Pro Thr
115                     120                     125

Glu Thr Val Ile Cys Asn Ser Ile Gly Met Ile Ala Ala Gly Asp Ser
130                     135                     140

Val Val Phe Asn Gly His Pro Gly Ala Lys Lys Cys Val Ala Phe Ala
145                     150                     155                     160

Val Asp Met Ile Asn Lys Ala Val Ile Arg Glu Gly Gly Pro Glu Asn
165                     170                     175

Leu Val Thr Thr Val Glu Asn Pro Thr Met Glu Ser Leu Asn Val Ile
180                     185                     190

Met Lys His Pro Tyr Ile Lys Leu Leu Cys Gly Thr Gly Gly Pro Gly
195                     200                     205

Leu Ile Lys Thr Leu Leu Asn Ser Gly Lys Lys Ala Ile Gly Ala Gly
210                     215                     220

Ala Gly Asn Pro Pro Val Ile Val Asp Asp Ser Ala Asp Ile Asp Lys
225                     230                     235                     240

Ala Ala Lys Asn Ile Ile Glu Gly Cys Ser Phe Asp Asn Asn Leu Pro
245                     250                     255

Cys Ile Ala Glu Lys Glu Val Phe Val Phe Glu Asn Val Ala Asn Asp
260                     265                     270

Leu Ile Gln Asn Met Ile Lys Asn Asn Ala Val Leu Ile Asn Glu Asn
275                     280                     285

Gln Val Ser Lys Leu Leu Asp Leu Val Leu Leu Glu Arg Lys Asp Glu
290                     295                     300

Thr Leu Glu Tyr Ala Ile Asn Lys Lys Trp Val Gly Lys Asp Ala Lys
305                     310                     315                     320

Leu Phe Leu Asp Lys Ile Gly Ile Lys Ala Ser Asp Asn Val Arg Cys
325                     330                     335

Ile Ile Cys Glu Val Asp Ala Asn His Pro Phe Val Met Thr Glu Leu
340                     345                     350

Met Met Pro Ile Leu Pro Ile Val Arg Val Lys Asp Val Asp Glu Ala
355                     360                     365

Ile Glu Cys Ala Lys Thr Ala Glu Gln Arg Lys Arg His Ser Ala Tyr
370                     375                     380

Met Tyr Ser Lys Asn Ile Asp Asn Leu Asn Arg Phe Glu Lys Glu Ile
385                     390                     395                     400

Asp Thr Thr Ile Phe Val Lys Asn Ala Lys Ser Phe Ala Gly Val Gly
405                     410                     415

Phe Gly Ala Glu Gly Phe Thr Thr Phe Thr Ile Ala Gly Pro Thr Gly
420                     425                     430

Glu Gly Ile Thr Ser Ala Arg Asn Phe Thr Arg Gln Arg Arg Cys Val
435                     440                     445

Leu Ala Gly
450                     455                     460

465

<210> SEQ ID NO 52
<211> LENGTH: 527
<212> TYPE: PRT
<213> ORGANISM: Caldalkalibacillus thermarum

<400> SEQUENCE: 52

```
Met Asn Met Thr Glu Lys Asp Ile Glu Lys Ile Val Gln Ser Val Leu
1               5                   10                  15

His Asn Val Glu Ser Ala Leu Gly Lys Ser Ala Ser Ala Ser Pro Ser
            20                  25                  30

Val Ser Ala Val Ser Val Ala Ser Gly Glu Gly Ile Lys Pro Val Gln
            35                  40                  45

Phe Lys Gln Val Pro Val Phe Gln Gln Glu Thr Val Lys Ser Pro Asn
50                  55                  60

Arg Asn Arg Asn Leu Gly Gly Ala Glu Glu Lys Trp Gly Val Phe Asn
65                  70                  75                  80

His Met Glu Asp Ala Ile Glu Ala Ser Tyr Arg Ala Gln Met Glu Phe
                85                  90                  95

Val Lys His Phe Gln Leu Lys Asp Arg Glu Lys Ile Ile Thr Ala Ile
                100                 105                 110

Arg Glu Ala Val Leu Arg Glu Lys Glu Val Leu Ala Arg Lys Val Tyr
                115                 120                 125

Glu Glu Thr Lys Ile Gly Arg Tyr Glu Asp Lys Val Ala Lys His Glu
            130                 135                 140

Leu Ala Ala Leu Lys Thr Pro Gly Thr Glu Asp Leu Lys Thr Glu Ala
145                 150                 155                 160

Phe Ser Gly Asp Asn Gly Leu Thr Ile Val Glu Arg Ala Pro Tyr Gly
                165                 170                 175

Leu Ile Gly Ala Val Thr Pro Val Thr Asn Pro Thr Glu Thr Ile Ile
                180                 185                 190

Asn Asn Ala Ile Gly Met Leu Ala Ala Gly Asn Ala Val Val Phe Asn
                195                 200                 205

Val His Pro Ser Ser Lys Arg Ser Cys Ala Tyr Ala Val Gln Leu Ile
                210                 215                 220

Asn Lys Ala Ile Thr Glu Ala Gly Gly Pro His His Leu Val Thr Met
225                 230                 235                 240

Val Lys Glu Pro Thr Leu Asp Thr Leu Gln Thr Leu Ile Asp Ser Pro
                245                 250                 255

Lys Val Lys Leu Leu Val Gly Thr Gly Gly Pro Gly Leu Val Gln Thr
                260                 265                 270

Leu Leu Lys Ser Gly Lys Lys Ala Ile Gly Ala Gly Ala Gly Asn Pro
                275                 280                 285

Pro Val Ile Val Asp Asp Thr Ala Asp Leu Glu His Ala Ala Arg Ser
                290                 295                 300

Ile Ile Glu Gly Ala Ala Phe Asp Asn Asn Leu Leu Cys Ile Ala Glu
305                 310                 315                 320

Lys Glu Val Phe Val Leu Glu Ser Val Ala Asp Asp Leu Ile Phe His
                325                 330                 335

Met Leu Asn His Gly Ala Tyr Met Leu Gly Gln His Glu Val Glu Gln
                340                 345                 350

Val Met Ala Phe Ala Leu Glu Glu Gln Gly Asn Glu Gln Asn Arg Gly
                355                 360                 365

Cys Gly Phe Asn Pro Gln Arg His Tyr Gln Val Ser Lys Asp Trp Ile
                370                 375                 380

Gly Gln Asp Ala Arg Leu Phe Leu Glu His Ile Gly Val Gln Pro Pro
385                 390                 395                 400

Thr Glu Val Lys Leu Leu Ile Cys Asp Val Glu Phe Asp His Pro Phe
                405                 410                 415

Val Gln Leu Glu Gln Met Met Pro Val Leu Pro Ile Val Arg Val Lys
```

```
            420                 425                 430
Thr Leu Asp Glu Ala Ile Glu Lys Ala Val Met Ala Glu His Gly Asn
            435                 440                 445

Arg His Thr Ala Ile Met His Ser Lys Asn Val Asp His Leu Thr Lys
    450                 455                 460

Phe Ala Arg Ala Ile Gln Thr Thr Leu Phe Val Lys Asn Ala Ser Ser
465                 470                 475                 480

Leu Ala Gly Val Gly Tyr Gly Gly Glu Gly His Thr Thr Met Thr Ile
                485                 490                 495

Ala Gly Pro Thr Gly Glu Gly Val Thr Ser Ala Lys Thr Phe Thr Arg
            500                 505                 510

Glu Arg Arg Cys Val Leu Ala Glu Gly Gly Phe Arg Ile Ile Gly
            515                 520                 525

<210> SEQ ID NO 53
<211> LENGTH: 480
<212> TYPE: PRT
<213> ORGANISM: Pelosinus fermentans

<400> SEQUENCE: 53

Met Ser Ile Asp Gln Ala Leu Ile Glu Lys Ile Thr Leu Glu Ile Leu
1               5                   10                  15

Thr Lys Met Gln Thr Gly Ala Lys Ala Ala Pro Ala Gly Tyr Gly Asp
            20                  25                  30

Gly Ile Phe Glu Thr Val Asp Glu Ala Val Ala Ala Arg Lys Ala
            35                  40                  45

Tyr Gln Glu Leu Lys Thr Leu Ser Leu Glu Lys Arg Glu Val Leu Ile
    50                  55                  60

Lys Ala Met Arg Asp Val Ala Tyr Glu Asn Ala Thr Ile Leu Ala Gln
65                  70                  75                  80

Met Ala Val Asp Glu Ser Gly Met Gly Arg Val Ser Asp Lys Ile Ile
                85                  90                  95

Lys Asn Gln Val Ala Ala Leu Lys Thr Pro Gly Thr Glu Asp Leu Thr
            100                 105                 110

Thr Gln Ala Trp Ser Gly Asp Asn Gly Leu Thr Leu Ile Glu Met Gly
            115                 120                 125

Pro Tyr Gly Val Ile Gly Ala Ile Thr Pro Thr Thr Asn Pro Thr Glu
    130                 135                 140

Thr Val Ile Cys Asn Gly Ile Gly Met Ile Ala Ala Gly Asn Thr Val
145                 150                 155                 160

Phe Phe Ser Pro His Pro Thr Ala Lys Asn Thr Ser Met Lys Ile Ile
                165                 170                 175

Thr Leu Leu Asn Gln Ala Ile Val Lys Ala Gly Gly Pro Asn Asn Leu
            180                 185                 190

Leu Thr Ser Val Ala Asn Pro Ser Ile Lys Ala Ala Asn Glu Met Met
    195                 200                 205

Lys His Pro Gly Ile Asn Met Leu Val Ala Thr Gly Gly Pro Gly Val
210                 215                 220

Val Lys Ala Val Leu Ser Ser Gly Lys Lys Ala Ile Gly Ala Gly Ala
225                 230                 235                 240

Gly Asn Pro Pro Val Ile Val Asp Glu Thr Ala Asp Ile Glu Lys Ala
                245                 250                 255

Ala Arg Asp Ile Val Ala Gly Cys Ser Phe Asp Asn Asn Leu Pro Cys
            260                 265                 270
```

```
Ile Ala Glu Lys Glu Val Ile Ala Ile Gly Ser Ile Ala Asp Arg Leu
            275                 280                 285

Ile Thr Tyr Met Gln Lys Tyr Gly Ala Tyr Leu Ile Ser Gly Ser Asn
        290                 295                 300

Ile Asp Arg Leu Leu Asp Val Ile Met Thr Val Gln Glu Glu Lys Ile
305                 310                 315                 320

Ala Glu Gly Cys Thr Asp Lys Pro Lys Arg Ser Tyr Gly Ile Asn Lys
                325                 330                 335

Asp Tyr Val Gly Lys Asp Ala Lys Tyr Leu Leu Ser Lys Ile Gly Ile
            340                 345                 350

Asp Val Pro Asp Ser Val Arg Val Leu Cys Glu Thr Pro Ala Asp
            355                 360                 365

His Pro Phe Val Ile Glu Glu Leu Met Met Pro Val Leu Pro Val Val
        370                 375                 380

Gln Val Lys Asp Ile Asp Glu Ala Ile Glu Val Ala Val Arg Val Glu
385                 390                 395                 400

His Gly Asn Arg His Thr Ala Ala Met His Ser Lys Asn Val Asp His
                405                 410                 415

Leu Thr Arg Phe Ala Arg Ala Val Glu Thr Thr Ile Phe Val Lys Asn
            420                 425                 430

Ala Pro Ser Tyr Ala Gly Ile Gly Val Gly Gly Glu Gly Phe Thr Ser
        435                 440                 445

Phe Thr Leu Ala Gly Pro Thr Gly Glu Gly Ile Thr Ser Pro Arg Ser
        450                 455                 460

Phe Thr Arg Gln Arg Arg Cys Val Leu Val Asp Ala Phe Ser Ile Val
465                 470                 475                 480

<210> SEQ ID NO 54
<211> LENGTH: 479
<212> TYPE: PRT
<213> ORGANISM: Thermoanaerobacterium thermosaccharolyticum

<400> SEQUENCE: 54

Met Glu Ile Asn Asp Asn Met Ile Ser Glu Ile Ile Glu Arg Val Leu
1               5                   10                  15

Lys Glu Val Gln Lys Lys Ser Ile Asn Asp Arg Tyr Gln Asn Gly Ile
            20                  25                  30

Tyr Asp Arg Met Glu Asp Ala Ile Glu Ala Ala Tyr Glu Ala Gln Lys
        35                  40                  45

Lys Leu Met Lys Met Ser Ile Glu Gln Arg Glu Arg Leu Ile Ser Ala
    50                  55                  60

Met Arg Lys Ala Ile Leu Asp Asn Ala Lys Ser Cys Ala Lys Leu Ser
65                  70                  75                  80

Val Glu Glu Thr Gly Met Gly Arg Val Asp His Lys Tyr Leu Lys Leu
                85                  90                  95

Lys Leu Val Ala Glu Lys Thr Pro Gly Thr Glu Val Leu Thr Thr Lys
            100                 105                 110

Ala Tyr Ser Gly Asp Lys Gly Leu Thr Leu Val Glu Met Ala Pro Phe
        115                 120                 125

Gly Val Ile Gly Ser Ile Thr Pro Ser Thr Asn Pro Ala Glu Thr Val
    130                 135                 140

Cys Cys Asn Ser Ile Gly Met Ile Ala Ala Gly Asn Thr Val Val Phe
145                 150                 155                 160

Ser Pro His Pro Gly Ala Ile Lys Ser Ser Leu Met Ala Val Glu Phe
                165                 170                 175
```

```
Leu Asn Lys Ala Ile Ile Glu Ala Gly Gly Pro Glu Asn Leu Ile Thr
            180                 185                 190

Ser Val Arg Lys Pro Ser Ile Glu Phe Thr Asp Val Met Ile Asn His
        195                 200                 205

Pro Lys Ile Asn Leu Leu Val Ala Thr Gly Gly Pro Ala Ile Val Lys
    210                 215                 220

Lys Val Leu Ser Ser Gly Lys Lys Ala Ile Gly Ala Gly Ala Gly Asn
225                 230                 235                 240

Pro Pro Cys Val Val Asp Glu Thr Ala Asp Ile Lys Lys Ala Ala Arg
                245                 250                 255

Asp Ile Ile Leu Gly Cys Thr Phe Asp Asn Asn Leu Pro Cys Ile Ala
            260                 265                 270

Glu Lys Glu Val Ile Ala Val Glu Ser Ile Tyr Glu Glu Leu Ile Glu
        275                 280                 285

Asn Met Lys Lys Asn Gly Ala Tyr Glu Ile Thr Asp Asp Glu Ala Glu
    290                 295                 300

Lys Leu Ala Asp Ile Val Leu Thr Lys Lys Glu Leu Lys Ala Glu
305                 310                 315                 320

Gly Cys Ser Ile Asn Arg Pro Lys Phe Glu Tyr Ser Val Asn Lys Lys
                325                 330                 335

Trp Val Gly Lys Asp Ala Lys Val Leu Leu Glu Gln Ile Gly Ile Asn
            340                 345                 350

Val Gly Asp Asp Ile Val Cys Ile Ile Tyr Arg Cys Asp Lys Gln His
        355                 360                 365

Pro Phe Val Gln Glu Glu Leu Met Met Pro Ile Leu Pro Ile Val Lys
    370                 375                 380

Val Lys Asn Ile Asp Glu Ala Ile Asn Val Ala Val Glu Val Glu His
385                 390                 395                 400

Gly Asn His His Thr Ala Glu Met His Ser Lys Asn Ile Asp Asn Leu
                405                 410                 415

Thr Arg Phe Ala Lys Ala Ile Asn Thr Thr Ile Phe Val Lys Asn Ala
            420                 425                 430

Pro Ser Tyr Ala Gly Ile Gly Phe Gly Gly Glu Gly Tyr Thr Thr Phe
        435                 440                 445

Thr Ile Ala Gly Pro Thr Gly Glu Gly Leu Thr Cys Ala Ala Thr Phe
    450                 455                 460

Thr Arg Gln Arg Arg Cys Val Met Val Asp Ser Phe Arg Ile Val
465                 470                 475

<210> SEQ ID NO 55
<211> LENGTH: 480
<212> TYPE: PRT
<213> ORGANISM: Pelosinus fermentans

<400> SEQUENCE: 55

Met Ser Ile Asp Gln Ala Leu Ile Glu Lys Ile Thr Leu Glu Ile Leu
1               5                   10                  15

Thr Lys Met Gln Thr Gly Ala Lys Ala Ala Pro Ala Gly Tyr Gly Asp
            20                  25                  30

Gly Ile Phe Glu Thr Val Asp Glu Ala Val Ala Ala Arg Lys Ala
        35                  40                  45

Tyr Gln Glu Leu Lys Thr Leu Ser Leu Glu Lys Arg Glu Val Leu Ile
    50                  55                  60

Lys Ala Met Arg Asp Val Ala Tyr Glu Asn Ala Thr Ile Leu Ala Gln
```

```
                65                  70                  75                  80
           Met Ala Val Asp Glu Ser Gly Met Gly Arg Val Ser Asp Lys Ile Ile
                           85                  90                  95

Lys Asn Gln Val Ala Ala Leu Lys Thr Pro Gly Thr Glu Asp Leu Thr
                          100                 105                 110

Thr Gln Ala Trp Ser Gly Asp Asn Gly Leu Thr Leu Ile Glu Met Gly
                          115                 120                 125

Pro Tyr Gly Val Ile Gly Ala Ile Thr Pro Thr Asn Pro Thr Glu
           130                 135                 140

Thr Val Ile Cys Asn Gly Ile Gly Met Ile Ala Ala Gly Asn Thr Val
           145                 150                 155                 160

Phe Phe Ser Pro His Pro Thr Ala Lys Asn Thr Ser Met Lys Ile Ile
                              165                 170                 175

Thr Leu Leu Asn Gln Ala Ile Val Lys Ala Gly Gly Pro Asn Asn Leu
                          180                 185                 190

Leu Thr Ser Val Ala Asn Pro Ser Ile Lys Ala Ala Asn Glu Met Met
                          195                 200                 205

Lys His Pro Gly Ile Asn Met Leu Val Ala Thr Gly Gly Pro Gly Val
                          210                 215                 220

Val Lys Ala Val Leu Ser Ser Gly Lys Lys Ala Ile Gly Ala Gly Ala
           225                 230                 235                 240

Gly Asn Pro Pro Val Ile Val Asp Glu Thr Ala Asp Ile Glu Lys Ala
                              245                 250                 255

Ala Arg Asp Ile Val Ala Gly Cys Ser Phe Asp Asn Asn Leu Pro Cys
                          260                 265                 270

Ile Ala Glu Lys Glu Val Ile Ala Ile Gly Ser Ile Ala Asp Arg Leu
                          275                 280                 285

Ile Thr Tyr Met Gln Lys Tyr Gly Ala Tyr Leu Ile Ser Gly Ser Asn
                          290                 295                 300

Ile Asp Arg Leu Leu Asn Val Ile Met Thr Val Gln Glu Glu Lys Ile
           305                 310                 315                 320

Ala Glu Gly Cys Thr Asp Lys Pro Lys Arg Ser Tyr Gly Ile Asn Lys
                              325                 330                 335

Asp Tyr Val Gly Lys Asp Ala Lys Tyr Leu Leu Ser Lys Ile Gly Ile
                          340                 345                 350

Asp Val Pro Asp Ser Val Arg Val Val Leu Cys Glu Thr Pro Ala Asp
                          355                 360                 365

His Pro Phe Val Ile Glu Glu Leu Met Met Pro Val Leu Pro Val Val
                          370                 375                 380

Gln Val Lys Asp Ile Asp Glu Ala Ile Glu Val Ala Val Arg Val Glu
           385                 390                 395                 400

His Gly Asn Arg His Thr Ala Ala Met His Ser Lys Asn Val Asp His
                              405                 410                 415

Leu Thr Arg Phe Ala Arg Ala Val Glu Thr Thr Ile Phe Val Lys Asn
                          420                 425                 430

Ala Pro Ser Tyr Ala Gly Ile Gly Val Gly Gly Glu Gly Phe Thr Ser
                          435                 440                 445

Phe Thr Leu Ala Gly Pro Thr Gly Glu Gly Ile Thr Ser Pro Arg Ser
                          450                 455                 460

Phe Thr Arg Gln Arg Arg Cys Val Leu Val Asp Ala Phe Ser Ile Val
           465                 470                 475                 480

<210> SEQ ID NO 56
```

```
<211> LENGTH: 479
<212> TYPE: PRT
<213> ORGANISM: Desulfosporosinus sp.

<400> SEQUENCE: 56

Met Ser Val Asp Gln Ala Leu Ile Arg Lys Ile Thr Ser Glu Ile Leu
1               5                   10                  15

Ala Lys Met Gln Asn Arg Thr Val Ser Ala Cys Gln Asp Cys Asn Gly
            20                  25                  30

Ile Phe Thr Thr Val Asp Glu Ala Val Ala Ala Arg Ile Ala Tyr
        35                  40                  45

Gln Glu Leu Arg Thr Leu Ser Leu Glu Lys Arg Glu Leu Ile Lys
    50                  55                  60

Ala Met Arg Asn Val Ala Leu Glu Asn Ala Thr Met Leu Ala Glu Met
65                  70                  75                  80

Ala Val Lys Glu Ser Gly Met Gly Arg Val Glu Asp Lys Ile Ile Lys
                85                  90                  95

His Lys Leu Val Ala Val Lys Thr Pro Gly Thr Glu Asp Leu Arg Thr
            100                 105                 110

Glu Ala Trp Ser Gly Asp Ser Gly Leu Thr Leu Val Glu Met Gly Pro
        115                 120                 125

Tyr Gly Val Ile Gly Ala Ile Thr Pro Thr Thr Asn Pro Val Ala Thr
130                 135                 140

Ile Ile Cys Asn Gly Ile Gly Met Ile Ala Ala Gly Asn Ala Val Phe
145                 150                 155                 160

Phe Ser Pro His Pro Thr Ala Lys Asn Thr Ser Ile Lys Thr Ile Thr
                165                 170                 175

Leu Leu Asn Glu Ala Ile Val Lys Ala Gly Gly Pro Met Asn Leu Leu
            180                 185                 190

Thr Ser Val Ala Asp Pro Ser Ile Ser Ala Ala Asn Ala Met Met Lys
        195                 200                 205

His Ala Gly Ile Asn Leu Leu Val Ala Thr Gly Gly Pro Gly Val Val
    210                 215                 220

Lys Ala Val Leu Ser Ser Gly Lys Lys Ala Ile Gly Ala Gly Ala Gly
225                 230                 235                 240

Asn Pro Pro Val Ile Val Asp Glu Thr Ala Asp Ile Glu Lys Ala Ala
                245                 250                 255

Arg Asp Ile Ile Ala Gly Cys Ser Phe Asp Asn Asn Leu Pro Cys Ile
            260                 265                 270

Ala Glu Lys Glu Val Ile Ala Val Gly Cys Ile Ala Asp Arg Leu Ile
        275                 280                 285

Ser Asn Met Gln Lys Tyr Gly Ala Tyr Leu Ile Ser Gly Ser Lys Ile
    290                 295                 300

Asp Gln Met Leu Asp Val Val Met Thr Ala Thr Glu Glu Lys Met Ala
305                 310                 315                 320

Glu Gly Cys Thr Ala Lys Pro Ile Lys Arg Tyr Gly Ile Asn Lys Asp
                325                 330                 335

Phe Val Gly Lys Asp Ala Lys Tyr Ile Leu Thr Gln Ile Gly Leu Asp
            340                 345                 350

Val Pro Asp Thr Ile Lys Val Ile Leu Cys Glu Thr Pro Ala Asp His
        355                 360                 365

Pro Phe Val Ile Glu Glu Leu Met Met Pro Ile Leu Pro Val Val Gln
    370                 375                 380

Val Lys Asp Ile Asp Ala Ala Ile Glu Leu Ala Val Lys Val Glu His
```

```
                385                 390                 395                 400
        Gly Asn Arg His Thr Ala Met Met His Ser Lys Asn Val Asp Asn Met
                        405                 410                 415

Thr Arg Phe Ala Lys Ala Ile Glu Thr Thr Ile Phe Val Lys Asn Ala
                        420                 425                 430

Pro Ser Tyr Ala Gly Ile Gly Val Gly Gly Glu Gly Phe Cys Thr Phe
                        435                 440                 445

Thr Ile Ala Gly Pro Thr Gly Glu Gly Leu Thr Thr Ala Arg Ser Phe
                        450                 455                 460

Thr Arg Gln Arg Arg Cys Val Leu Val Asp Ser Phe Ser Ile Ile
        465                 470                 475

<210> SEQ ID NO 57
<211> LENGTH: 482
<212> TYPE: PRT
<213> ORGANISM: Clostridium methylpentosum

<400> SEQUENCE: 57

Met Glu Ile Thr Pro Asn Gln Ile Asp Gln Ile Val Ala Asn Val Met
1               5                   10                  15

Ala Gln Leu Gly Gly Ser Ala Ala Pro Ala Ala Ser Tyr Asp Ser Thr
                20                  25                  30

Gln Tyr Ser Gly Arg Lys Tyr Ile Gly Ile Tyr Ala Thr Met Thr Glu
            35                  40                  45

Ala Ile Asp Ala Val Ala Asp Ala Tyr Lys Val Leu Arg Ser Met Thr
        50                  55                  60

Val Asp Gln Arg Glu Lys Ile Ile Glu Lys Ile Arg Glu Phe Thr Arg
65                  70                  75                  80

Ala Glu Ala Glu Ile Met Ala Lys Met Gly Val Glu Glu Thr Gly Met
                85                  90                  95

Gly Lys Val Glu His Lys Thr Leu Lys His His Leu Val Ala Asp Lys
                100                 105                 110

Thr Pro Gly Thr Glu Asp Ile Gln Thr Glu Ala Met Ser Gly Asp Gly
            115                 120                 125

Gly Leu Thr Leu Leu Glu Met Ala Pro Phe Gly Ile Ile Gly Ala Ile
        130                 135                 140

Ser Pro Ser Thr Asn Pro Ser Glu Thr Val Leu Cys Asn Ser Met Gly
145                 150                 155                 160

Met Ile Ala Gly Ala Asn Ala Val Val Phe Asn Pro His Pro Ser Ala
                165                 170                 175

Ile Cys Thr Ser Asn Tyr Ala Val Asp Leu Val Asn Arg Ala Ser Leu
            180                 185                 190

Ala Ala Gly Gly Pro Ala Asn Leu Cys Cys Ser Val Val Lys Pro Thr
        195                 200                 205

Met Gln Ser Ala Asp Asp Met Val Lys Asp Pro Arg Val Lys Met Leu
210                 215                 220

Val Cys Thr Gly Gly Pro Gly Val Val Arg Ala Met Leu Ser Ser Gly
225                 230                 235                 240

Lys Lys Ala Ile Gly Ala Gly Ala Gly Asn Pro Pro Val Ile Val Asp
                245                 250                 255

Asp Thr Ala Asp Ile Arg Lys Ala Ala Lys Asp Ile Ile Asp Gly Cys
            260                 265                 270

Thr Phe Asp Asn Asn Leu Pro Cys Ile Ala Glu Lys Glu Val Phe Ala
        275                 280                 285
```

```
Phe Ser Asn Ile Ala Asp Glu Leu Met Tyr Tyr Met Gln Gln Asn Gly
    290                 295                 300
Ala Tyr Phe Ile Ser Gly Glu Met Ala Asp Arg Leu Ala Lys Ile Val
305                 310                 315                 320
Leu Val Glu Lys Lys Asn Glu Lys Thr Gly Lys Ile Ser Tyr Ser Val
                325                 330                 335
Ser Arg Asp Trp Val Gly Arg Asp Ala Lys Lys Phe Leu Ala Ala Leu
            340                 345                 350
Asp Ile Glu Val Gly Asp Ala Val Arg Cys Val Ile Cys Glu Thr Asp
        355                 360                 365
Glu Asn His Leu Phe Val Gln Thr Glu Leu Met Met Pro Ile Leu Pro
370                 375                 380
Ile Val Arg Val Asn Asn Ile Asp Glu Ala Val Arg Met Ala Val Arg
385                 390                 395                 400
Ala Glu His Gly Asn Arg His Thr Ala His Met His Ser Lys Asn Ile
                405                 410                 415
Asp Asn Leu Thr Lys Phe Ala Arg Ala Val Glu Thr Thr Ile Phe Val
            420                 425                 430
Lys Asn Ala Pro Ser Tyr Ala Gly Ile Gly Phe Gly Ser Glu Gly His
        435                 440                 445
Thr Thr Phe Thr Ile Ala Gly Pro Thr Gly Glu Gly Leu Thr Ser Ala
    450                 455                 460
Arg Ser Phe Thr Arg Lys Arg Arg Cys Val Met Ser Asp Ser Phe Asn
465                 470                 475                 480
Ile Val

<210> SEQ ID NO 58
<211> LENGTH: 467
<212> TYPE: PRT
<213> ORGANISM: Thermoanaerobacterium saccharolyticum

<400> SEQUENCE: 58

Met Lys Val Lys Glu Glu Asp Ile Glu Ala Ile Val Lys Lys Val Leu
1               5                   10                  15
Ser Glu Phe Asn Phe Glu Lys Asn Thr Lys Ser Phe Arg Asp Phe Gly
            20                  25                  30
Val Phe Gln Asp Met Asn Asp Ala Ile Arg Ala Ala Lys Asp Ala Gln
        35                  40                  45
Lys Lys Leu Arg Asn Met Ser Met Glu Ser Arg Glu Lys Ile Ile Gln
    50                  55                  60
Asn Ile Arg Lys Lys Ile Met Glu Asn Lys Lys Ile Leu Ala Glu Met
65                  70                  75                  80
Gly Val Ser Glu Thr Gly Met Gly Lys Val Glu His Lys Ile Ile Lys
                85                  90                  95
His Glu Leu Val Ala Leu Lys Thr Pro Gly Thr Glu Asp Ile Val Thr
            100                 105                 110
Thr Ala Trp Ser Gly Asp Lys Gly Leu Thr Leu Val Glu Met Gly Pro
        115                 120                 125
Phe Gly Val Ile Gly Thr Ile Thr Pro Ser Thr Asn Pro Ser Glu Thr
    130                 135                 140
Val Leu Cys Asn Ser Ile Gly Met Ile Ala Ala Gly Asn Ser Val Val
145                 150                 155                 160
Phe Asn Pro His Pro Gly Ala Val Asn Val Ser Asn Tyr Ala Val Lys
                165                 170                 175
```

Leu Val Asn Glu Ala Val Met Glu Ala Gly Pro Glu Asn Leu Val
                180                 185                 190

Ala Ser Val Glu Lys Pro Thr Leu Glu Thr Gly Asn Ile Met Phe Lys
            195                 200                 205

Ser Pro Asp Val Ser Leu Leu Val Ala Thr Gly Pro Gly Val Val
        210                 215                 220

Thr Ser Val Leu Ser Ser Gly Lys Arg Ala Ile Gly Ala Gly Ala Gly
225                 230                 235                 240

Asn Pro Pro Val Val Asp Glu Thr Ala Asp Ile Lys Lys Ala Ala
                245                 250                 255

Lys Asp Ile Val Asp Gly Ala Thr Phe Asp Asn Asn Leu Pro Cys Ile
                260                 265                 270

Ala Glu Lys Glu Val Val Ser Val Asp Lys Ile Thr Asp Glu Leu Ile
            275                 280                 285

Tyr Tyr Met Gln Gln Asn Gly Cys Tyr Lys Ile Glu Gly Arg Glu Ile
        290                 295                 300

Glu Lys Leu Ile Glu Leu Val Leu Asp His Lys Gly Lys Ile Thr
305                 310                 315                 320

Leu Asn Arg Lys Trp Val Gly Lys Asp Ala His Leu Ile Leu Lys Ala
                325                 330                 335

Ile Gly Ile Asp Ala Asp Glu Ser Val Arg Cys Ile Ile Phe Glu Ala
                340                 345                 350

Glu Lys Asp Asn Pro Leu Val Glu Glu Leu Met Met Pro Ile Leu
            355                 360                 365

Gly Ile Val Arg Ala Lys Asn Val Asp Glu Ala Ile Met Ile Ala Thr
370                 375                 380

Glu Leu Glu His Gly Asn Arg His Ser Ala His Met His Ser Lys Asn
385                 390                 395                 400

Val Asp Asn Leu Thr Lys Phe Gly Lys Ile Ile Asp Thr Ala Ile Phe
                405                 410                 415

Val Lys Asn Ala Pro Ser Tyr Ala Ala Leu Gly Tyr Gly Gly Glu Gly
            420                 425                 430

Tyr Cys Thr Phe Thr Ile Ala Ser Arg Thr Gly Glu Gly Leu Thr Ser
        435                 440                 445

Ala Arg Thr Phe Thr Lys Ser Arg Arg Cys Val Leu Ala Asp Gly Leu
    450                 455                 460

Ser Ile Arg
465

<210> SEQ ID NO 59
<211> LENGTH: 467
<212> TYPE: PRT
<213> ORGANISM: Thermoanaerobacterium xylanolyticum

<400> SEQUENCE: 59

Met Lys Val Lys Glu Glu Asp Ile Glu Ala Ile Val Lys Lys Val Leu
1               5                   10                  15

Ser Glu Phe Asn Leu Glu Lys Thr Thr Ser Lys Tyr Gly Asp Val Gly
            20                  25                  30

Ile Phe Gln Asp Met Asn Asp Ala Ile Ser Ala Ala Lys Asp Ala Gln
        35                  40                  45

Lys Lys Leu Arg Asn Met Pro Met Glu Ser Arg Glu Lys Ile Ile Gln
    50                  55                  60

Asn Ile Arg Lys Lys Ile Met Glu Asn Lys Lys Ile Leu Ala Glu Met
65                  70                  75                  80

```
Gly Val Arg Glu Thr Gly Met Gly Arg Val Glu His Lys Ile Val Lys
                85                  90                  95

His Glu Leu Val Ala Leu Lys Thr Pro Gly Thr Glu Asp Ile Thr Thr
            100                 105                 110

Thr Ala Trp Ser Gly Asp Lys Gly Leu Thr Leu Val Glu Met Gly Pro
        115                 120                 125

Phe Gly Val Ile Gly Ala Ile Thr Pro Ser Thr Asn Pro Ser Glu Thr
    130                 135                 140

Val Leu Cys Asn Ser Ile Gly Met Ile Ala Ala Gly Asn Ser Val Val
145                 150                 155                 160

Phe Asn Pro His Pro Gly Ala Val Asn Val Ser Asn Tyr Ala Val Lys
                165                 170                 175

Leu Val Asn Glu Ala Ala Met Glu Ala Gly Gly Pro Glu Asn Leu Val
            180                 185                 190

Val Ser Val Glu Lys Pro Thr Leu Glu Thr Gly Asn Val Met Phe Lys
        195                 200                 205

Ser Ser Asp Val Ser Leu Leu Val Ala Thr Gly Gly Pro Gly Val Val
    210                 215                 220

Thr Ala Val Leu Ser Ser Gly Lys Arg Ala Ile Gly Ala Gly Ala Gly
225                 230                 235                 240

Asn Pro Pro Val Val Asp Glu Thr Ala Asp Ile Lys Lys Ala Ala
                245                 250                 255

Lys Asp Ile Ile Asp Gly Ala Thr Phe Asp Asn Asn Leu Pro Cys Ile
                260                 265                 270

Ala Glu Lys Glu Val Val Ser Val Asp Lys Ile Thr Asp Glu Leu Ile
            275                 280                 285

Tyr Tyr Met Gln Lys Asn Gly Cys Tyr Lys Ile Glu Gly Arg Glu Ile
        290                 295                 300

Glu Lys Leu Ile Glu Leu Val Leu Asp His Glu Gly Lys Thr Thr
305                 310                 315                 320

Leu Asn Arg Lys Trp Val Gly Lys Asp Ala His Leu Ile Leu Lys Ala
                325                 330                 335

Ile Gly Ile Asp Ala Asp Glu Ser Val Arg Cys Ile Ile Phe Glu Ala
            340                 345                 350

Glu Lys Asp Asn Pro Leu Val Val Glu Glu Leu Met Met Pro Ile Leu
        355                 360                 365

Gly Ile Val Arg Ala Lys Asn Val Asp Glu Ala Ile Met Ile Ala Thr
    370                 375                 380

Glu Leu Glu His Gly Asn Arg His Ser Ala His Met His Ser Lys Asn
385                 390                 395                 400

Ile Asp Asn Leu Thr Lys Phe Gly Lys Ile Ile Asp Thr Ala Ile Phe
                405                 410                 415

Val Lys Asn Ala Pro Ser Tyr Ala Ala Leu Gly Tyr Gly Gly Glu Gly
            420                 425                 430

Tyr Cys Thr Phe Thr Ile Ala Ser Arg Thr Gly Glu Gly Leu Thr Ser
        435                 440                 445

Ala Arg Thr Phe Thr Lys Ser Arg Arg Cys Val Leu Ala Asp Gly Leu
    450                 455                 460

Ser Ile Arg
465

<210> SEQ ID NO 60
<211> LENGTH: 477
```

```
<212> TYPE: PRT
<213> ORGANISM: Acetonema longum

<400> SEQUENCE: 60
```

| | | | | | | | | | | | | | | |
|---|---|---|---|---|---|---|---|---|---|---|---|---|---|---|
Met Val Asp Gln Thr Leu Ile Glu Gln Ile Thr Arg Ala Val Leu Thr
1               5                   10                  15

Gln Met Lys Ala Gly Lys Asp Ala Ala Val Ser Gly Asp Gly Ile Phe
            20                  25                  30

Ala Thr Val Asp Gln Ala Val Ala Ala Arg Gln Ala Tyr Gln Glu
        35                  40                  45

Leu Arg Leu Leu Thr Leu Glu Lys Arg Glu Thr Leu Ile Arg Ala Ile
    50                  55                  60

Arg Asp Ala Ala Phe Ala Asn Ala Ala Val Ile Ala Gln Met Ala Val
65              70                  75                  80

Gln Glu Ser Gly Met Gly Arg Val Glu Asp Lys Ile Leu Lys Asn Gln
                85                  90                  95

Leu Ala Ala Arg Lys Thr Pro Gly Thr Glu Asp Leu Thr Ser Arg Ala
            100                 105                 110

Trp Ser Gly Asp His Gly Leu Thr Leu Val Glu Met Ala Pro Tyr Gly
        115                 120                 125

Val Ile Gly Ala Ile Thr Pro Thr Asn Pro Ser Glu Thr Val Ile
    130                 135                 140

Cys Asn Ser Ile Gly Met Ile Ala Ala Gly Asn Ser Ile Val Phe Ser
145             150                 155                 160

Pro His Pro Thr Ala Gln Asn Thr Ser Leu Thr Thr Ile Arg Leu Leu
                165                 170                 175

Asn Glu Ala Ile Val Lys Ala Gly Gly Pro Asp Asn Leu Leu Thr Ala
            180                 185                 190

Val Ala Glu Pro Ser Ile Glu Ala Ala Asn Ala Met Met Arg His Pro
        195                 200                 205

Gly Ile Gln Met Leu Val Ala Thr Gly Gly Pro Ala Val Val Lys Ala
    210                 215                 220

Val Leu Ser Ser Gly Lys Lys Ala Ile Gly Ala Gly Ala Gly Asn Pro
225             230                 235                 240

Pro Ala Val Val Asp Glu Thr Ala Asp Ile Ala Lys Ala Ala Lys Asp
                245                 250                 255

Ile Val Ala Gly Cys Ser Phe Asp Asn Asn Leu Pro Cys Ile Ala Glu
            260                 265                 270

Lys Glu Ile Ile Ala Val Gly Arg Ile Ala Asp Glu Leu Ile Ser Tyr
        275                 280                 285

Leu Gln Lys Tyr Gly Ala Tyr Leu Ile Ser Gly Arg Asp Ile Glu Arg
    290                 295                 300

Leu Met Glu Val Val Leu Thr Glu Arg Thr Glu Met Ala Pro Gly
305             310                 315                 320

Cys Val Gly Lys Pro Arg Arg Val Tyr Gly Val Asn Lys Asp Tyr Ile
                325                 330                 335

Gly Lys Asp Ala Lys Phe Ile Leu Ser Lys Ile Asn Ile Gln Ala Pro
            340                 345                 350

Asp His Ile Arg Val Ile Leu Cys Glu Thr Pro Ala Asp His Pro Phe
        355                 360                 365

Val Leu Glu Glu Leu Met Met Pro Val Leu Pro Leu Val Ser Val Arg
    370                 375                 380

Asp Ile Asp Ala Ala Ile Asp Leu Ala Val Lys Val Glu His Gly Asn
385             390                 395                 400

```
Arg His Thr Ala Val Met His Ser Lys Asn Val Asp Tyr Met Thr Arg
                405                 410                 415

Leu Ala Lys Ala Ile Glu Thr Thr Ile Phe Val Lys Asn Ala Pro Ser
            420                 425                 430

Tyr Ala Gly Ile Gly Val Gly Gly Glu Gly Phe Thr Thr Phe Thr Ile
        435                 440                 445

Ala Gly Pro Thr Gly Glu Gly Leu Thr Ser Ala Arg Ser Phe Thr Arg
    450                 455                 460

Gln Arg Arg Cys Ala Leu Val Asp Ala Phe Ser Ile Val
465                 470                 475

<210> SEQ ID NO 61
<211> LENGTH: 465
<212> TYPE: PRT
<213> ORGANISM: Geobacillus thermoglucosidans

<400> SEQUENCE: 61

Met Ser Val Asp Ala Gln Lys Ile Glu Lys Leu Val Arg Lys Ile Leu
1               5                   10                  15

Glu Glu Met Glu Glu Lys Lys Pro Ala Glu Thr Glu Cys Glu Trp
            20                  25                  30

Gly Ile Phe Asp His Met Asn Gln Ala Ile Glu Ala Ala Glu Ile Ala
        35                  40                  45

Gln Lys Glu Leu Val Gln Leu Ser Leu Gly Gln Arg Gly Lys Leu Ile
    50                  55                  60

Glu Ala Ile Arg Lys Ala Ala Lys Glu Asn Ala Glu Lys Phe Ala Arg
65                  70                  75                  80

Met Ala Val Asp Glu Thr Gly Met Gly Lys Tyr Glu Asp Lys Ile Val
                85                  90                  95

Lys Asn Leu Leu Ala Ala Glu Lys Thr Pro Gly Ile Glu Asp Leu Arg
            100                 105                 110

Thr Glu Val Phe Ser Gly Asp Asp Gly Leu Thr Leu Val Glu Leu Ser
        115                 120                 125

Pro Tyr Gly Val Ile Gly Ala Ile Thr Pro Thr Thr Asn Pro Thr Glu
    130                 135                 140

Thr Ile Ile Cys Asn Ser Ile Gly Met Ile Ala Ala Gly Asn Ala Val
145                 150                 155                 160

Val Phe Ser Pro His Pro Arg Ala Lys Asn Thr Ser Leu Tyr Ala Ile
                165                 170                 175

Lys Ile Phe Asn Gln Ala Ile Val Glu Ala Gly Gly Pro Lys Asn Leu
            180                 185                 190

Ile Thr Thr Val Ala Asn Pro Ser Ile Glu Gln Ala Glu Ile Met Met
        195                 200                 205

Lys His Lys Thr Ile Lys Met Leu Val Ala Thr Gly Gly Pro Gly Val
    210                 215                 220

Val Lys Ala Val Leu Ser Ser Gly Lys Lys Ala Ile Gly Ala Gly Ala
225                 230                 235                 240

Gly Asn Pro Pro Val Val Val Asp Glu Thr Ala Asp Ile Glu Lys Ala
                245                 250                 255

Ala Lys Asp Ile Ile Ala Gly Cys Ser Phe Asp Asn Asn Leu Pro Cys
            260                 265                 270

Val Ala Glu Lys Glu Val Ile Ala Val Glu Ser Ile Ala Asp Arg Leu
        275                 280                 285

Ile Asp Tyr Met Lys Lys His Gly Ala Tyr Glu Ile Thr Asn Lys Glu
```

```
              290                 295                 300
Gln Ile Gln Gln Leu Thr Asp Leu Val Glu Asn Gly His Ala Asn
305                 310                 315                 320

Lys Glu Phe Val Gly Lys Asp Ala Ala Tyr Ile Leu Lys His Ile Gly
                325                 330                 335

Ile Asn Val Pro Pro Asp Ile Arg Val Ala Ile Met Glu Val Asp Gly
                340                 345                 350

Lys His Pro Leu Val Thr Val Glu Leu Met Met Pro Ile Leu Pro Ile
            355                 360                 365

Val Arg Val Lys Asn Val Asp Gln Ala Ile Glu Leu Ala Val Glu Val
        370                 375                 380

Glu His Gly Phe Arg His Thr Ala Ile Met His Ser Lys Asn Val Asp
385                 390                 395                 400

His Leu Thr Lys Phe Ala Lys Ala Ile Gln Thr Thr Ile Phe Val Lys
                405                 410                 415

Asn Ala Pro Ser Tyr Ala Gly Ile Gly Val Gly Gly Glu Gly Tyr Ala
                420                 425                 430

Thr Phe Thr Ile Ala Gly Pro Thr Gly Glu Gly Leu Thr Ser Ala Lys
            435                 440                 445

Asp Phe Ala Arg Lys Arg Lys Cys Val Leu Val Asp Ala Leu Ser Ile
        450                 455                 460

Arg
465

<210> SEQ ID NO 62
<211> LENGTH: 463
<212> TYPE: PRT
<213> ORGANISM: Geobacillus sp.

<400> SEQUENCE: 62

Met Asp Ala Gln Lys Ile Glu Lys Leu Val Arg Lys Ile Leu Glu Glu
1               5                   10                  15

Met Glu Glu Lys Lys Pro Ala Glu Thr Glu Cys Glu Trp Gly Ile
            20                  25                  30

Phe Asp His Met Asn Gln Ala Ile Glu Ala Ala Glu Ile Ala Gln Lys
        35                  40                  45

Glu Leu Val Gln Leu Ser Leu Gly Gln Arg Gly Lys Leu Ile Glu Ala
    50                  55                  60

Ile Arg Lys Ala Ala Lys Glu Asn Ala Glu Lys Phe Ala Arg Met Ala
65                  70                  75                  80

Val Asp Glu Thr Gly Met Gly Lys Tyr Glu Asp Lys Ile Val Lys Asn
                85                  90                  95

Leu Leu Ala Ala Glu Lys Thr Pro Gly Ile Glu Asp Leu Arg Thr Glu
            100                 105                 110

Val Phe Ser Gly Asp Asp Gly Leu Thr Leu Val Glu Leu Ser Pro Tyr
        115                 120                 125

Gly Val Ile Gly Ala Ile Thr Pro Thr Thr Asn Pro Thr Glu Thr Ile
    130                 135                 140

Ile Cys Asn Ser Ile Gly Met Ile Ala Ala Gly Asn Ala Val Val Phe
145                 150                 155                 160

Ser Pro His Pro Arg Ala Lys Asn Thr Ser Leu Tyr Ala Ile Lys Ile
                165                 170                 175

Phe Asn Gln Ala Ile Val Glu Ala Gly Gly Pro Lys Asn Leu Ile Thr
            180                 185                 190
```

```
Thr Val Ala Asn Pro Ser Ile Glu Gln Ala Glu Ile Met Lys His
            195                 200                 205

Lys Thr Ile Lys Met Leu Val Ala Thr Gly Gly Pro Gly Val Lys
    210                 215                 220

Ala Val Leu Ser Ser Gly Lys Ala Ile Gly Ala Gly Ala Gly Asn
225                 230                 235                 240

Pro Pro Val Val Asp Glu Thr Ala Asp Ile Glu Lys Ala Ala Lys
                245                 250                 255

Asp Ile Ile Ala Gly Cys Ser Phe Asp Asn Asn Leu Pro Cys Val Ala
                260                 265                 270

Glu Lys Glu Val Ile Ala Val Glu Ser Ile Ala Asp Arg Leu Ile Asp
        275                 280                 285

Tyr Met Lys Lys His Gly Ala Tyr Glu Ile Thr Asn Lys Glu Gln Ile
    290                 295                 300

Gln Gln Leu Thr Asp Leu Val Val Glu Asn Gly His Ala Asn Lys Glu
305                 310                 315                 320

Phe Val Gly Lys Asp Ala Ala Tyr Ile Leu Lys His Ile Gly Ile Asn
                325                 330                 335

Val Pro Pro Asp Thr Arg Val Ala Ile Met Glu Val Asp Gly Lys His
                340                 345                 350

Pro Leu Val Thr Val Glu Leu Met Met Pro Ile Leu Pro Ile Val Arg
        355                 360                 365

Val Lys Asn Val Asp Gln Ala Ile Glu Leu Ala Val Glu Val Glu His
    370                 375                 380

Gly Phe Arg His Thr Ala Ile Met His Ser Lys Asn Val Asp His Leu
385                 390                 395                 400

Thr Lys Phe Ala Lys Ala Ile Gln Thr Thr Ile Phe Val Lys Asn Ala
                405                 410                 415

Pro Ser Tyr Ala Gly Ile Gly Val Gly Gly Glu Gly Tyr Ala Thr Phe
                420                 425                 430

Thr Ile Ala Gly Pro Thr Gly Glu Gly Leu Thr Ser Ala Lys Asp Phe
        435                 440                 445

Ala Arg Lys Arg Lys Cys Val Leu Val Asp Ala Leu Ser Ile Arg
    450                 455                 460

<210> SEQ ID NO 63
<211> LENGTH: 463
<212> TYPE: PRT
<213> ORGANISM: Geobacillus thermoglucosidasius

<400> SEQUENCE: 63

Met Asp Ala Gln Lys Ile Glu Lys Leu Val Arg Lys Ile Leu Glu Glu
1               5                   10                  15

Met Glu Glu Lys Lys Pro Ala Glu Thr Glu Cys Glu Trp Gly Ile
            20                  25                  30

Phe Asp His Met Asn Gln Ala Ile Glu Ala Ala Glu Ile Ala Gln Lys
        35                  40                  45

Glu Phe Val Gln Leu Ser Leu Gly Gln Arg Gly Lys Leu Ile Glu Ala
    50                  55                  60

Ile Arg Lys Ala Ala Lys Glu Asn Ala Glu Lys Phe Ala Arg Met Ala
65                  70                  75                  80

Val Asp Glu Thr Gly Met Gly Lys Tyr Glu Asp Lys Ile Val Lys Asn
                85                  90                  95

Leu Leu Ala Ala Glu Lys Thr Pro Gly Ile Glu Asp Leu Arg Thr Glu
                100                 105                 110
```

Val Phe Ser Gly Asp Asp Gly Leu Thr Leu Val Glu Leu Ser Pro Tyr
            115                 120                 125

Gly Val Ile Gly Ala Ile Thr Pro Thr Thr Asn Pro Thr Glu Thr Ile
        130                 135                 140

Ile Cys Asn Ser Ile Gly Met Ile Ala Ala Gly Asn Ala Val Val Phe
145                 150                 155                 160

Ser Pro His Pro Arg Ala Lys Asn Thr Ser Leu Tyr Ala Ile Lys Ile
                165                 170                 175

Phe Asn Gln Ala Ile Val Glu Ala Gly Gly Pro Lys Asn Leu Ile Thr
            180                 185                 190

Thr Val Ala Asn Pro Ser Ile Glu Gln Ala Glu Ile Met Met Lys His
        195                 200                 205

Lys Thr Ile Lys Met Leu Val Ala Thr Gly Gly Pro Gly Val Val Lys
210                 215                 220

Ala Val Leu Ser Ser Gly Lys Lys Ala Ile Gly Ala Gly Ala Gly Asn
225                 230                 235                 240

Pro Pro Val Val Val Asp Glu Thr Ala Asp Ile Glu Lys Ala Ala Lys
                245                 250                 255

Asp Ile Ile Ala Gly Cys Ser Phe Asp Asn Asn Leu Pro Cys Val Ala
            260                 265                 270

Glu Lys Glu Val Ile Ala Val Glu Ser Ile Ala Asp Arg Leu Ile Asp
        275                 280                 285

Tyr Met Lys Lys His Gly Ala Tyr Glu Ile Thr Asn Lys Glu Gln Ile
290                 295                 300

Gln Gln Leu Thr Asp Leu Val Val Glu Asn Gly His Ala Asn Lys Glu
305                 310                 315                 320

Phe Val Gly Lys Asp Ala Ala Tyr Ile Leu Lys His Ile Gly Ile Asn
                325                 330                 335

Val Pro Pro Asp Ile Arg Val Ala Ile Met Glu Val Asp Gly Lys His
            340                 345                 350

Pro Leu Val Thr Val Glu Leu Met Met Pro Ile Leu Pro Ile Val Arg
        355                 360                 365

Val Lys Asn Val Asp Gln Ala Ile Glu Leu Ala Val Glu Val Glu His
370                 375                 380

Gly Phe Arg His Thr Ala Ile Met His Ser Lys Asn Val Asp His Leu
385                 390                 395                 400

Thr Lys Phe Ala Lys Ala Ile Gln Thr Thr Ile Phe Val Lys Asn Ala
                405                 410                 415

Pro Ser Tyr Ala Gly Ile Gly Val Gly Gly Glu Gly Tyr Ala Thr Phe
            420                 425                 430

Thr Ile Ala Gly Pro Thr Gly Glu Gly Leu Thr Ser Ala Lys Asp Phe
        435                 440                 445

Ala Arg Lys Arg Lys Cys Val Leu Val Asp Ala Leu Ser Ile Arg
450                 455                 460

<210> SEQ ID NO 64
<211> LENGTH: 463
<212> TYPE: PRT
<213> ORGANISM: Bacillus azotoformans

<400> SEQUENCE: 64

Met Ala Val Glu Ala Lys Ala Ile Glu Glu Ile Val Lys Lys Ile Leu
1               5                   10                  15

Glu Glu Met Met Ile Lys Lys Asp Ala Cys Ile Thr Gly Tyr Gly Ile

```
            20                  25                  30
Phe Glu Asp Met Asn Glu Ala Ile Glu Ala Ala Thr Ile Ala Gln Lys
             35                  40                  45
Glu Leu Leu Lys Leu Ser Leu Glu Gln Arg Gly Asn Leu Ile Thr Ala
 50                  55                  60
Ile Arg Lys Ala Ala Lys Asp Asn Ala Glu Thr Phe Ala Gln Met Ala
 65                  70                  75                  80
Val Asp Glu Thr Gly Met Gly Asn Tyr Gly Asp Lys Val Ile Lys Asn
                 85                  90                  95
Leu Ile Ala Ala Glu Lys Thr Pro Gly Ile Glu Asp Leu Thr Thr Glu
                100                 105                 110
Ala Phe Ser Gly Asp His Gly Leu Thr Leu Val Glu Leu Ser Pro Tyr
            115                 120                 125
Gly Val Ile Gly Ser Ile Thr Pro Thr Thr Asn Pro Thr Glu Thr Val
            130                 135                 140
Ile Cys Asn Ser Ile Gly Met Ile Ala Ala Gly Asn Ala Val Val Phe
145                 150                 155                 160
Ser Pro His Pro Thr Ala Lys Asn Thr Ser Leu Lys Ala Ile Glu Val
                165                 170                 175
Ile Asn Lys Ala Ile Ile Lys Ala Gly Gly Pro Pro Asn Leu Ile Thr
                180                 185                 190
Ser Val Ala Asn Pro Thr Ile Asp Gln Ala Asn Ile Met Met Lys His
            195                 200                 205
Lys Lys Ile Lys Leu Leu Val Ala Thr Gly Gly Pro Gly Val Val Lys
    210                 215                 220
Ala Val Leu Ser Ser Gly Lys Lys Ala Ile Gly Ala Gly Ala Gly Asn
225                 230                 235                 240
Pro Pro Ala Val Val Asp Glu Thr Ala Asn Leu Glu Lys Ala Ala Arg
                245                 250                 255
Asp Ile Ile Asp Gly Cys Ser Phe Asp Asn Asn Leu Pro Cys Thr Ala
                260                 265                 270
Glu Lys Glu Val Ile Val Val Asp Ser Val Ala Asp Tyr Leu Val Ser
            275                 280                 285
Tyr Met Lys Lys His Gly Ala Phe Leu Ile Thr Asp Lys Glu Gln Ile
    290                 295                 300
Gln Lys Leu Thr Glu Leu Val Val Asp Asn Gly His Ala Asn Lys Glu
305                 310                 315                 320
Leu Val Gly Lys Ser Val Ala His Ile Leu Gln Arg Ile Gly Ile Glu
                325                 330                 335
Val Pro Ser Asp Ala Arg Val Ala Ile Leu Asn Val Glu Arg Asn His
                340                 345                 350
Pro Leu Val Lys Ala Glu Leu Met Met Pro Ile Leu Pro Val Val Arg
            355                 360                 365
Val Glu Asn Val Asp Ala Ala Ile Glu Leu Ala Val Glu Ala Glu Gln
            370                 375                 380
Gly Phe Arg His Thr Ala Ile Met His Ser Thr Asn Ile Asp Asn Leu
385                 390                 395                 400
Thr Lys Phe Ser Lys Glu Ile Gln Thr Thr Ile Phe Val Lys Asn Gly
                405                 410                 415
Pro Ser Tyr Ala Gly Ile Gly Ile Gly Gly Glu Gly Tyr Ala Thr Phe
                420                 425                 430
Thr Ile Ala Gly Pro Thr Gly Glu Gly Leu Thr Ser Ala Lys Asp Phe
            435                 440                 445
```

```
Ala Arg Arg Arg Lys Cys Val Leu Val Asp Gly Leu Ser Ile Arg
    450             455             460
```

<210> SEQ ID NO 65
<211> LENGTH: 503
<212> TYPE: PRT
<213> ORGANISM: Clostridium sticklandii

<400> SEQUENCE: 65

```
Met Lys Ala Gly Asp Ile Val Gln Asp Phe Ile Thr Glu Arg Asp Val
1               5                   10                  15

Glu Lys Ile Ile Glu Gln Val Leu Ser Lys Leu Glu Pro Val Ile Glu
            20                  25                  30

Gln Val Lys Pro Lys Glu Ile Asn Met Leu Pro Asn Lys Thr Asn Ile
        35                  40                  45

Asp Phe Ser Gln Asn Ala Asn Gly Ile Phe Glu Ser Ile Asp Leu Ala
    50                  55                  60

Val Glu Ser Ala Leu Glu Ala His Ile Ile Leu Thr Ser Tyr Lys Leu
65                  70                  75                  80

Glu Asp Arg Glu Lys Met Ile Gln Ser Ile Arg Lys Glu Val Leu Gly
                85                  90                  95

Asp Ile Glu Asn Ile Ala Arg Leu Val Tyr Glu Glu Thr Lys Leu Gly
            100                 105                 110

Lys Tyr Glu Asp Lys Ile Ala Lys Ile Asn Leu Ala Ala Ser Lys Thr
        115                 120                 125

Pro Gly Thr Glu Asp Ile Lys Thr Ser Ala Ile Ser Gly Asp Tyr Gly
    130                 135                 140

Leu Thr Ile Glu Glu Met Ala Pro Phe Gly Val Ile Gly Ala Val Thr
145                 150                 155                 160

Pro Val Thr Asn Pro Val Glu Thr Leu Ile Asn Asn Ala Ile Ser Met
                165                 170                 175

Ile Ser Gly Gly Asn Ser Val Val Phe Asn Val His Pro Ser Ser Lys
            180                 185                 190

Lys Ser Ser Ala Tyr Thr Val Glu Leu Ile Asn Lys Ala Val Leu Lys
        195                 200                 205

Ala Gly Gly Pro Gln Asn Leu Val Thr Met Val Lys Glu Pro Thr Ile
    210                 215                 220

Glu Thr Val Asn Gln Leu Ser Ser His Pro Arg Ile Ser Met Met Val
225                 230                 235                 240

Gly Thr Gly Gly Pro Gly Leu Val Lys Ser Leu Leu Lys Ser Gly Lys
                245                 250                 255

Lys Thr Ile Gly Ala Gly Ala Gly Asn Pro Pro Val Val Val Asp Glu
            260                 265                 270

Thr Ala Asp Met Asn Leu Ala Ala Lys Gly Ile Ile Glu Gly Ala Ser
        275                 280                 285

Phe Asp Asn Asn Ile Leu Cys Ile Ala Glu Lys Glu Val Phe Val Val
    290                 295                 300

Asn Glu Val Ala Asp Asp Leu Ile Tyr Asn Met Leu Ser Ser Gly Ala
305                 310                 315                 320

Tyr Met Leu Asn Gln Glu Glu Leu Glu Lys Val Met Lys Leu Thr Leu
                325                 330                 335

Val Glu Asp Glu Asp Leu Gly Ala Lys Ser Cys Thr Leu Ser Pro Lys
            340                 345                 350

Lys Lys Tyr His Val His Lys Asn Trp Val Gly Lys Asp Ala Ser Lys
```

```
                    355                 360                 365
Ile Leu Ser Glu Ile Gly Ile Thr Lys Gln Asp Val Lys Leu Leu Ile
            370                 375                 380

Cys Glu Val Asp Ser Asp His Pro Tyr Val Thr Leu Glu Gln Met Met
385                 390                 395                 400

Pro Ile Leu Pro Leu Val Arg Cys Ser Asp Val Asp Glu Ala Ile Lys
                405                 410                 415

Leu Ala Val Lys Ala Glu Gly Thr Asn Lys His Thr Ala Ser Ile Phe
            420                 425                 430

Ser Arg Asn Val Asp Asn Met Thr Lys Phe Ala Arg Ala Ile Asn Thr
            435                 440                 445

Thr Ile Phe Val Lys Asn Ala Pro Thr Leu Ala Gly Val Gly Tyr Lys
            450                 455                 460

Gly Glu Gly Asn Ala Thr Phe Thr Ile Ala Gly Pro Thr Gly Glu Gly
465                 470                 475                 480

Ile Thr Ser Ala Lys Thr Phe Thr Arg Val Arg Arg Cys Val Leu Ala
                485                 490                 495

Glu Gly Gly Phe Arg Ile Val
                500

<210> SEQ ID NO 66
<211> LENGTH: 482
<212> TYPE: PRT
<213> ORGANISM: Thermincola potens

<400> SEQUENCE: 66

Met Ala Ile Glu Ala Tyr Gln Ile Glu Lys Ile Val Glu Glu Val Met
1               5                   10                  15

Arg Lys Met Val Ser Gly Gly Ser Gly Asp Ser Phe Ala Gly Lys Ala
            20                  25                  30

Lys Gly Ile Phe Glu Ser Val Asp Glu Ala Val Lys Ala Ala Lys Ala
        35                  40                  45

Ala Gln Lys Glu Leu Val Ala Met Arg Ile Glu Lys Arg Glu Met Leu
    50                  55                  60

Leu Lys Ala Met Arg Glu Ala Ala Ile Ala His Ala Glu Glu Leu Ala
65                  70                  75                  80

Arg Leu Ala Val Glu Glu Thr Gly Met Gly Arg Val Thr Asp Lys Ile
                85                  90                  95

Ile Lys Asn Arg Val Ala Ala Glu Lys Thr Pro Gly Thr Glu Asn Leu
            100                 105                 110

Gln Pro Ser Ala Val Thr Gly Asp Arg Gly Leu Thr Leu Ile Glu Arg
        115                 120                 125

Ala Pro Tyr Gly Val Ile Gly Ala Ile Thr Pro Ser Thr Asn Pro Cys
    130                 135                 140

Ala Thr Val Ile Asn Asn Ser Ile Ser Met Val Ala Ala Gly Asn Ser
145                 150                 155                 160

Val Val Phe Ser Val His Pro Gly Ala Lys Lys Ala Ser Leu Leu Thr
                165                 170                 175

Val Glu Ile Leu Asn Glu Ala Ile Glu Lys Ala Gly Gly Pro Ala Asn
            180                 185                 190

Val Leu Thr Ala Val Ala Ser Pro Ser Leu Glu Asn Thr Asn Ala Leu
        195                 200                 205

Met Lys His Pro Asp Ile Lys Leu Leu Val Ala Thr Gly Gly Pro Gly
    210                 215                 220
```

```
Leu Val Lys Ala Val Leu Ser Ser Gly Lys Lys Ala Ile Gly Ala Gly
225                 230                 235                 240

Ala Gly Asn Pro Pro Ala Leu Val Asp Glu Thr Ala Asp Leu Glu Arg
            245                 250                 255

Ala Ala Lys Ser Ile Val Ala Gly Ala Ser Phe Asp Asn Asn Leu Pro
            260                 265                 270

Cys Ile Ala Glu Lys Glu Val Ile Val Asp Tyr Val Ala Asn Gln
            275                 280                 285

Leu Ile Ser Tyr Met Lys Gln Asn Gly Ala Tyr Leu Ala Asn Asp Arg
    290                 295                 300

Glu Ile Lys Ala Leu Met Asp Leu Val Leu Thr Lys Asn Glu Asn Leu
305                 310                 315                 320

Lys Ala Glu Gly Cys Thr Val Lys Pro Glu Lys Leu Tyr Gly Ile
                325                 330                 335

Asn Lys Glu Tyr Val Gly Lys Asp Ala Ala Tyr Ile Met Lys Lys Ile
            340                 345                 350

Gly Val Asp Ile Pro Glu Asp Thr Lys Leu Ile Ile Cys Glu Val Asp
            355                 360                 365

Glu Asp His Pro Phe Val Leu Glu Glu Leu Met Met Pro Ile Leu Pro
    370                 375                 380

Ile Val Arg Val Pro Asn Val Gln Lys Ala Ile Glu Val Gly Val Arg
385                 390                 395                 400

Val Glu His Gly Asn Arg His Thr Ala Val Met His Ser Gln Asn Ile
                405                 410                 415

Asp Asn Leu Ser Ala Phe Ala Arg Ala Val Gln Thr Thr Ile Phe Val
            420                 425                 430

Lys Asn Gly Pro Ser Tyr Ala Gly Ile Gly Ile Gly Gly Glu Gly Tyr
            435                 440                 445

Thr Thr Phe Thr Ile Ala Gly Pro Thr Gly Glu Gly Leu Thr Ala Ala
    450                 455                 460

Ser Ser Phe Thr Arg Gln Arg Arg Cys Val Leu Val Asp Gly Phe Ser
465                 470                 475                 480

Ile Val

<210> SEQ ID NO 67
<211> LENGTH: 462
<212> TYPE: PRT
<213> ORGANISM: Clostridium sp.

<400> SEQUENCE: 67

Met Ser Val Asn Glu Gln Met Ile Gln Asp Ile Val Ser Glu Val Met
1               5                   10                  15

Ala Lys Met Gln Ile Ala Ser Glu Val Ser Asp Asn His Gly Ile Phe
            20                  25                  30

Ala Asp Met Asn Glu Ala Ile Glu Ala Ala Lys Lys Ala Gln Lys Ile
        35                  40                  45

Val Gly Arg Met Ser Met Asp Gln Arg Glu Lys Ile Ile Ser Asn Ile
    50                  55                  60

Arg Lys Lys Thr Val Glu Asn Ala Glu Ile Leu Ala Arg Met Gly Val
65                  70                  75                  80

Gln Glu Thr Gly Met Gly Asn Val Gly His Lys Ile Leu Lys His Gln
                85                  90                  95

Leu Val Ala Glu Lys Thr Pro Gly Thr Glu Asp Ile Thr Thr Thr Ala
            100                 105                 110
```

```
Trp Ser Gly Asp Arg Gly Leu Thr Leu Ile Glu Met Gly Pro Phe Gly
            115                 120                 125

Val Ile Gly Ala Ile Thr Pro Cys Thr Asn Pro Ser Glu Thr Val Leu
130                 135                 140

Cys Asn Thr Ile Gly Met Leu Ala Gly Gly Asn Thr Val Val Phe Asn
145                 150                 155                 160

Pro His Pro Gly Ala Ile Lys Thr Ser Ile Phe Ala Ile Asn Met Ile
                165                 170                 175

Asn Glu Ala Ser Leu Glu Ala Gly Gly Pro Asp Asn Ile Ala Cys Thr
            180                 185                 190

Val Glu Lys Pro Thr Leu Glu Ser Ser Asn Ile Met Met Lys His Lys
        195                 200                 205

Ala Ile His Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Val Ala Asp Glu Leu Met His Tyr
        275                 280                 285

Met Val Ser Glu Gln Gly Cys Tyr Leu Ala Ser Lys Glu Glu Gln Glu
    290                 295                 300

Ala Leu Thr Ala Val Val Leu Lys Asp Gly Arg Leu Asn Arg Asn Cys
305                 310                 315                 320

Val Gly Arg Asp Ala Lys Thr Leu Leu Gly Met Ile Gly Val Ser Val
                325                 330                 335

Pro Asp Asn Ile Arg Cys Ile Thr Phe Glu Gly Pro Lys Glu His Pro
            340                 345                 350

Leu Ile Ala Thr Glu Leu Met Met Pro Ile Leu Gly Val Val Arg Ala
        355                 360                 365

Lys Asp Phe Asp Asp Ala Val Glu Gln Ser Val Trp Leu Glu His Gly
    370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ala Ala Ile Gly Phe Gly Gly Glu Gly Phe Cys Thr Phe Thr
            420                 425                 430

Ile Ala Ser Arg Thr Gly Glu Gly Leu Thr Ser Ala Ser Thr Phe Thr
        435                 440                 445

Lys Arg Arg Arg Cys Val Met Ser Asp Ser Leu Cys Ile Arg
    450                 455                 460

<210> SEQ ID NO 68
<211> LENGTH: 470
<212> TYPE: PRT
<213> ORGANISM: Fusobacterium sp.

<400> SEQUENCE: 68

Met Arg Gly Glu Leu Met Glu Phe Glu Val Asn Asn Ile Glu Lys Ile
1               5                   10                  15

Val Glu Leu Ile Met Lys Lys Met Ala Glu Ser Asn Ile Ser Thr Ala
            20                  25                  30
```

```
Gly Asn Ser Lys Asn Gly Val Phe Asp Asn Val Asp Glu Ala Ile Glu
            35                  40                  45

Glu Ala Lys Lys Ala Gln Ala Ile Leu Phe Ser Ser Lys Leu Glu Leu
 50                  55                  60

Arg Glu Lys Ile Ile Ala Ser Ile Arg Asp Thr Leu Lys Ser His Val
 65                  70                  75                  80

Thr Glu Leu Ala Glu Leu Ala Val Lys Glu Thr Gly Met Gly Arg Val
                    85                  90                  95

Ser Asp Lys Glu Leu Lys Asn Lys Ile Ala Ile Glu Lys Thr Pro Gly
                100                 105                 110

Leu Glu Asp Leu Lys Ala Phe Ala Phe Ser Gly Asp Asp Gly Leu Thr
                115                 120                 125

Val Met Glu Leu Ser Pro Tyr Gly Val Ile Gly Ala Ile Thr Pro Ser
            130                 135                 140

Thr Asn Pro Ser Glu Thr Val Ile Cys Asn Ser Ile Gly Met Ile Ala
145                 150                 155                 160

Ala Gly Asn Ala Val Ile Phe Ala Pro His Pro Gly Ala Lys Arg Thr
                165                 170                 175

Ser Ile Arg Thr Val Glu Leu Ile Asn Glu Ala Ile Arg Lys Val Gly
            180                 185                 190

Gly Pro Asp Asn Leu Val Val Thr Ile Arg Glu Pro Ser Ile Glu Asn
            195                 200                 205

Thr Glu Lys Ile Ile Ala Asn Pro Asn Ile Lys Met Leu Val Ala Thr
210                 215                 220

Gly Gly Pro Gly Val Val Lys Thr Val Met Ser Ser Gly Lys Lys Ala
225                 230                 235                 240

Ile Gly Ala Gly Ala Gly Asn Pro Pro Val Leu Val Asp Glu Thr Ala
                245                 250                 255

Asp Ile Glu Lys Ala Ala Lys Asp Ile Ile Ala Gly Cys Ser Phe Asp
                260                 265                 270

Asn Asn Leu Pro Cys Thr Ala Glu Lys Glu Val Val Ala Val Asp Ser
            275                 280                 285

Ile Val Asn Tyr Leu Ile Phe Glu Met Gln Lys Asn Gly Ala Tyr Leu
            290                 295                 300

Leu Lys Asp Lys Lys Leu Ile Glu Lys Leu Leu Ser Leu Val Leu Lys
305                 310                 315                 320

Asn Asn Ser Pro Asp Arg Lys Tyr Val Gly Arg Asp Ala Lys Tyr Leu
                325                 330                 335

Leu Lys Gln Ile Gly Ile Glu Val Gly Asp Glu Ile Lys Val Ile Ile
                340                 345                 350

Val Glu Thr Asp Lys Asn His Pro Phe Ala Val Glu Glu Leu Leu Met
            355                 360                 365

Pro Ile Leu Pro Ile Val Lys Val Lys Asp Ala Leu Glu Gly Ile Lys
    370                 375                 380

Val Ala Lys Glu Leu Glu Arg Gly Leu Arg His Thr Ala Val Ile His
385                 390                 395                 400

Ser Lys Asn Ile Asp Ile Leu Thr Lys Tyr Ala Arg Glu Met Glu Thr
                405                 410                 415

Thr Ile Leu Val Lys Asn Gly Pro Ser Tyr Ala Gly Ile Gly Ile Gly
            420                 425                 430

Gly Glu Gly His Val Thr Phe Thr Ile Ala Gly Pro Thr Gly Glu Gly
            435                 440                 445
```

Leu Thr Ser Ala Lys Ser Phe Ala Arg Asn Arg Arg Cys Val Leu Val
450                 455                 460

Gly Gly Phe Ser Ile Lys
465                 470

<210> SEQ ID NO 69
<211> LENGTH: 470
<212> TYPE: PRT
<213> ORGANISM: Fusobacterium sp.

<400> SEQUENCE: 69

Met Arg Gly Glu Leu Met Glu Phe Glu Val Asn Asn Ile Glu Glu Ile
1               5                   10                  15

Val Glu Leu Ile Met Lys Lys Met Ala Glu Ser Asn Ile Ser Thr Ala
                20                  25                  30

Gly Asn Ser Lys Asn Gly Val Phe Asp Asn Val Asp Glu Ala Ile Glu
            35                  40                  45

Glu Ala Lys Lys Ala Gln Ala Ile Leu Phe Ser Ser Lys Leu Glu Leu
        50                  55                  60

Arg Glu Lys Ile Ile Ala Ser Ile Arg Asp Thr Leu Lys Asn His Val
65                  70                  75                  80

Ser Glu Leu Ala Glu Leu Ala Val Lys Glu Thr Gly Met Gly Arg Val
                85                  90                  95

Ala Asp Lys Glu Leu Lys Asn Lys Ile Ala Ile Glu Lys Thr Pro Gly
            100                 105                 110

Leu Glu Asp Leu Lys Ala Phe Ala Phe Ser Gly Asp Asp Gly Leu Thr
        115                 120                 125

Val Met Glu Leu Ser Pro Tyr Gly Val Ile Gly Ala Ile Thr Pro Ser
130                 135                 140

Thr Asn Pro Ser Glu Thr Val Ile Cys Asn Ser Ile Gly Met Ile Ala
145                 150                 155                 160

Ala Gly Asn Ala Val Ile Phe Ala Pro His Pro Gly Ala Lys Arg Thr
                165                 170                 175

Ser Ile Arg Thr Val Glu Leu Ile Asn Glu Ala Ile Arg Lys Val Gly
            180                 185                 190

Gly Pro Asp Asn Leu Val Val Thr Ile Arg Glu Pro Ser Ile Glu Asn
        195                 200                 205

Thr Glu Lys Ile Ile Ala Asn Pro Asn Ile Lys Met Leu Val Ala Thr
210                 215                 220

Gly Gly Pro Gly Val Val Lys Thr Val Met Ser Ser Gly Lys Lys Ala
225                 230                 235                 240

Ile Gly Ala Gly Ala Gly Asn Pro Pro Val Leu Val Asp Glu Thr Ala
                245                 250                 255

Asp Ile Glu Lys Ala Ala Lys Asp Ile Ile Ala Gly Cys Ser Phe Asp
            260                 265                 270

Asn Asn Leu Pro Cys Thr Ala Glu Lys Glu Val Val Ala Val Asp Ser
        275                 280                 285

Ile Val Asn Tyr Leu Ile Phe Glu Met Gln Lys Asn Gly Ala Tyr Leu
290                 295                 300

Leu Lys Asp Lys Glu Leu Ile Glu Lys Leu Leu Ser Leu Val Leu Lys
305                 310                 315                 320

Asn Asn Ser Pro Asp Arg Lys Tyr Val Gly Arg Asp Ala Lys Tyr Leu
                325                 330                 335

Leu Lys Gln Ile Gly Ile Glu Val Gly Asp Glu Ile Lys Val Ile Ile
            340                 345                 350

Val Glu Thr Asp Lys Asn His Pro Phe Ala Val Glu Leu Leu Met
            355                 360                 365

Pro Ile Leu Pro Ile Val Lys Val Lys Asp Ala Leu Glu Gly Ile Lys
        370                 375                 380

Val Ala Lys Glu Leu Glu Arg Gly Leu Arg His Thr Ala Val Ile His
385                 390                 395                 400

Ser Lys Asn Ile Asp Ile Leu Thr Lys Tyr Ala Arg Glu Met Glu Thr
                405                 410                 415

Thr Ile Leu Val Lys Asn Gly Pro Ser Tyr Ala Gly Ile Gly Ile Gly
            420                 425                 430

Gly Glu Gly His Val Thr Phe Thr Ile Ala Gly Pro Thr Gly Glu Gly
        435                 440                 445

Leu Thr Ser Ala Lys Ser Phe Ala Arg Asn Arg Arg Cys Val Leu Val
    450                 455                 460

Gly Gly Phe Ser Ile Lys
465             470

<210> SEQ ID NO 70
<211> LENGTH: 462
<212> TYPE: PRT
<213> ORGANISM: Ruminococcus sp.

<400> SEQUENCE: 70

Met Pro Ile Ser Glu Asn Met Val Gln Glu Ile Val Gln Glu Val Met
1               5                   10                  15

Ala Lys Met Gln Ile Ala Asp Ala Pro Ala Gly Lys His Gly Val Phe
            20                  25                  30

Lys Asp Met Asn Asp Ala Ile Glu Ala Ala Lys Lys Ala Gln Leu Val
        35                  40                  45

Val Lys Thr Met Ser Met Asp Gln Arg Glu Lys Ile Ile Thr Cys Ile
    50                  55                  60

Arg Lys Lys Ile Lys Glu Asn Ala Glu Val Leu Ala Arg Met Gly Val
65                  70                  75                  80

Glu Glu Thr Gly Met Gly Asn Val Gly Asp Lys Ile Leu Lys His His
            85                  90                  95

Leu Val Ala Asp Lys Thr Pro Gly Thr Glu Asp Ile Thr Thr Thr Ala
        100                 105                 110

Trp Ser Gly Asp Arg Gly Leu Thr Leu Ile Glu Met Gly Pro Phe Gly
    115                 120                 125

Val Ile Gly Ala Ile Thr Pro Cys Thr Asn Pro Ser Glu Thr Val Leu
    130                 135                 140

Cys Asn Thr Met Gly Met Leu Ala Gly Gly Asn Thr Val Val Phe Asn
145                 150                 155                 160

Pro His Pro Ala Ala Val Lys Thr Ser Ile Tyr Ala Ile Asn Leu Leu
                165                 170                 175

Asn Glu Ala Ser Leu Glu Ser Gly Gly Pro Asp Asn Ile Ala Val Thr
            180                 185                 190

Val Glu Lys Pro Thr Leu Glu Thr Ser Asn Ile Met Met Lys His Lys
        195                 200                 205

Asp Ile His Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Asp Thr Ala Asp Ile Arg Lys Ala Ala Gln Asp

```
            245                 250                 255
Ile Val Asn Gly Cys Thr Phe Asp Asn Asn Leu Pro Cys Ile Ala Glu
            260                 265                 270

Lys Glu Val Ala Val Ser Ser Val Val Asp Glu Leu Met His Tyr
            275                 280                 285

Met Ile Thr Glu Asn Asp Cys Tyr Leu Ala Ser Lys Glu Glu Gln Asp
            290                 295                 300

Lys Leu Val Glu Thr Val Leu Ala Gly Gly Lys Leu Asn Arg Lys Cys
305                 310                 315                 320

Val Gly Arg Asp Ala Lys Thr Leu Leu Ser Met Ile Gly Val Gln Ala
                325                 330                 335

Pro Ala Asn Thr Arg Cys Ile Ile Phe Glu Gly Pro Lys Glu His Pro
            340                 345                 350

Leu Ile Thr Thr Glu Leu Met Met Pro Ile Leu Gly Ile Val Arg Ala
            355                 360                 365

Lys Asp Phe Asp Asp Ala Val Glu Gln Ala Val Trp Leu Glu His Gly
            370                 375                 380

Asn Arg His Ser Ala His Ile His Ser Lys Asn Ile Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ser Ala Leu Gly Phe Gly Gly Glu Gly Phe Cys Thr Phe Thr
            420                 425                 430

Ile Ala Ser Arg Thr Gly Glu Gly Leu Thr Ser Ala Ser Thr Phe Thr
            435                 440                 445

Lys Arg Arg Arg Cys Val Met Thr Asp Ser Leu Cys Ile Arg
            450                 455                 460

<210> SEQ ID NO 71
<211> LENGTH: 465
<212> TYPE: PRT
<213> ORGANISM: Fusobacterium nucleatum

<400> SEQUENCE: 71

Met Glu Phe Glu Val Asn Asn Ile Glu Glu Ile Val Glu Leu Ile Met
1               5                   10                  15

Lys Lys Met Ala Glu Ser Asn Ile Ser Thr Ala Gly Asn Ser Lys Asn
            20                  25                  30

Gly Val Phe Asp Asn Val Asp Glu Ala Ile Glu Glu Ala Lys Lys Ala
        35                  40                  45

Gln Ala Ile Leu Phe Ser Ser Lys Leu Glu Leu Arg Glu Lys Ile Ile
    50                  55                  60

Ala Ser Ile Arg Asp Thr Leu Lys Asn His Val Thr Glu Leu Ala Glu
65                  70                  75                  80

Leu Ala Val Lys Glu Thr Gly Met Gly Arg Val Ala Asp Lys Glu Leu
                85                  90                  95

Lys Asn Lys Ile Ala Ile Glu Lys Thr Pro Gly Leu Glu Asp Leu Lys
            100                 105                 110

Ala Phe Ala Phe Ser Gly Asp Asp Gly Leu Thr Val Met Glu Leu Ser
        115                 120                 125

Pro Tyr Gly Val Ile Gly Ala Ile Thr Pro Ser Thr Asn Pro Ser Glu
    130                 135                 140

Thr Val Ile Cys Asn Ser Ile Gly Met Ile Ala Ala Gly Asn Ala Val
145                 150                 155                 160
```

-continued

```
Ile Phe Ala Pro His Pro Gly Ala Lys Arg Thr Ser Ile Arg Thr Val
                165                 170                 175

Glu Leu Ile Asn Glu Ala Ile Arg Lys Val Gly Gly Pro Asp Asn Leu
            180                 185                 190

Val Val Thr Ile Arg Glu Pro Ser Ile Glu Asn Thr Glu Lys Ile Ile
        195                 200                 205

Ala Asn Pro Asn Ile Lys Met Leu Val Ala Thr Gly Gly Pro Gly Val
    210                 215                 220

Val Lys Thr Val Met Ser Ser Gly Lys Lys Ala Ile Gly Ala Gly Ala
225                 230                 235                 240

Gly Asn Pro Pro Val Leu Val Asp Glu Thr Ala Asp Ile Glu Lys Ala
                245                 250                 255

Ala Lys Asp Ile Ile Ala Gly Cys Ser Phe Asp Asn Asn Leu Pro Cys
            260                 265                 270

Thr Ala Glu Lys Glu Val Val Ala Val Asp Ser Ile Val Asn Tyr Leu
        275                 280                 285

Ile Phe Glu Met Gln Lys Asn Gly Ala Tyr Leu Leu Lys Asp Lys Glu
    290                 295                 300

Leu Ile Glu Lys Leu Leu Ser Leu Val Leu Lys Asn Asn Ser Pro Asp
305                 310                 315                 320

Arg Lys Tyr Val Gly Arg Asp Ala Lys Tyr Leu Leu Lys Gln Ile Gly
                325                 330                 335

Ile Glu Val Gly Asp Glu Ile Lys Val Ile Val Glu Thr Asp Lys
            340                 345                 350

Asn His Pro Phe Ala Val Glu Glu Leu Leu Met Pro Ile Leu Pro Ile
        355                 360                 365

Val Lys Val Lys Asp Ala Leu Glu Gly Ile Lys Val Ala Lys Glu Leu
    370                 375                 380

Glu Arg Gly Leu Arg His Thr Ala Val Ile His Ser Lys Asn Ile Asp
385                 390                 395                 400

Ile Leu Thr Lys Tyr Ala Arg Glu Met Glu Thr Thr Ile Leu Val Lys
                405                 410                 415

Asn Gly Pro Ser Tyr Ala Gly Ile Gly Ile Gly Gly Glu Gly His Val
            420                 425                 430

Thr Phe Thr Ile Ala Gly Pro Thr Gly Glu Gly Leu Thr Ser Ala Lys
        435                 440                 445

Ser Phe Ala Arg Asn Arg Arg Cys Val Leu Val Gly Gly Phe Ser Ile
    450                 455                 460

Lys
465

<210> SEQ ID NO 72
<211> LENGTH: 465
<212> TYPE: PRT
<213> ORGANISM: Fusobacterium nucleatum

<400> SEQUENCE: 72

Met Glu Phe Glu Val Asn Asn Ile Glu Glu Ile Val Glu Leu Ile Met
1               5                   10                  15

Lys Lys Met Thr Glu Gly Gly Val Ser Thr Ser Asn Asn Ser Thr Asn
            20                  25                  30

Gly Val Phe Lys Asn Val Asp Glu Ala Ile Ala Glu Ala Lys Lys Ala
        35                  40                  45

Gln Thr Val Leu Phe Ser Ser Lys Leu Glu Leu Arg Glu Arg Ile Ile
    50                  55                  60
```

```
Ala Ser Ile Arg Asp Thr Leu Lys Ser His Ile Thr Glu Leu Ser Glu
 65                  70                  75                  80

Leu Ala Val Lys Glu Thr Gly Met Gly Arg Val Ala Asp Lys Glu Leu
                 85                  90                  95

Lys Asn Arg Ile Ala Ile Glu Lys Thr Pro Gly Leu Glu Asp Leu Lys
                100                 105                 110

Ala Phe Ala Phe Ser Gly Asp Asp Gly Leu Thr Val Met Glu Leu Ser
                115                 120                 125

Pro Tyr Gly Val Ile Gly Ala Ile Thr Pro Ser Thr Asn Pro Ser Glu
130                 135                 140

Thr Val Ile Cys Asn Ser Ile Gly Met Ile Ala Ala Gly Asn Ala Val
145                 150                 155                 160

Ile Phe Ala Pro His Pro Gly Ala Lys Arg Thr Ser Ile Arg Ala Val
                165                 170                 175

Glu Leu Ile Asn Glu Ala Ile Lys Lys Ala Gly Gly Pro Asp Asn Leu
                180                 185                 190

Val Val Thr Ile Ala Glu Pro Ser Ile Glu Asn Thr Glu Lys Ile Ile
                195                 200                 205

Ala Asn Pro Asn Ile Lys Met Val Val Ala Thr Gly Gly Pro Gly Val
210                 215                 220

Val Lys Thr Val Met Ser Ser Gly Lys Lys Ala Ile Gly Ala Gly Ala
225                 230                 235                 240

Gly Asn Pro Pro Val Leu Val Asp Glu Thr Ala Asp Ile Glu Lys Ala
                245                 250                 255

Ala Lys Asp Ile Ile Ala Gly Cys Ser Phe Asp Asn Asn Leu Pro Cys
                260                 265                 270

Thr Ala Glu Lys Glu Val Ile Ala Val Asp Ser Ile Val Asn Tyr Leu
                275                 280                 285

Ile Phe Glu Met Gln Lys Asn Gly Ala Tyr Leu Leu Lys Asp Lys Glu
                290                 295                 300

Leu Ile Glu Lys Leu Leu Ser Ile Val Leu Lys Asn Asn Ser Pro Asp
305                 310                 315                 320

Arg Lys Tyr Val Gly Lys Asp Ala Lys Tyr Leu Leu Lys Gln Ile Gly
                325                 330                 335

Ile Glu Val Gly Asp Glu Ile Lys Val Ile Val Glu Thr Asp Lys
                340                 345                 350

Asn His Pro Phe Ala Val Glu Glu Leu Leu Met Pro Ile Leu Pro Ile
                355                 360                 365

Val Lys Val Lys Asp Ala Leu Glu Gly Ile Lys Val Ala Lys Glu Leu
                370                 375                 380

Glu Lys Gly Leu Arg His Thr Ala Val Ile His Ser Lys Asn Ile Asp
385                 390                 395                 400

Ile Leu Ser Lys Tyr Ala Arg Glu Met Glu Thr Thr Ile Leu Val Lys
                405                 410                 415

Asn Gly Pro Ser Tyr Ala Gly Ile Gly Ile Gly Gly Glu Gly His Val
                420                 425                 430

Thr Phe Thr Ile Ala Gly Pro Thr Gly Glu Gly Leu Thr Ser Ala Arg
                435                 440                 445

Ser Phe Ala Arg Asn Arg Arg Cys Val Leu Val Gly Phe Ser Ile
                450                 455                 460

Lys
465
```

<210> SEQ ID NO 73
<211> LENGTH: 470
<212> TYPE: PRT
<213> ORGANISM: Fusobacterium sp.

<400> SEQUENCE: 73

```
Met Arg Gly Glu Leu Met Glu Phe Glu Val Asn Asn Ile Glu Glu Ile
1               5                   10                  15
Val Glu Leu Ile Met Lys Lys Met Ala Glu Ser Asn Ile Ser Thr Ala
            20                  25                  30
Gly Asn Ser Lys Asn Gly Val Phe Asp Asn Val Asp Gly Ala Ile Glu
        35                  40                  45
Glu Ala Lys Lys Ala Gln Ala Ile Leu Phe Ser Ser Lys Leu Glu Leu
    50                  55                  60
Arg Glu Lys Ile Ile Ala Ser Ile Arg Asp Thr Leu Lys Asn His Val
65                  70                  75                  80
Thr Glu Leu Ala Glu Leu Ala Val Lys Glu Thr Gly Met Gly Arg Val
                85                  90                  95
Ala Asp Lys Glu Leu Lys Asn Lys Ile Ala Ile Glu Lys Thr Pro Gly
            100                 105                 110
Leu Glu Asp Leu Lys Ala Phe Ala Phe Ser Gly Asp Gly Leu Thr
        115                 120                 125
Val Met Glu Leu Ser Pro Tyr Gly Val Ile Gly Ala Ile Thr Pro Ser
130                 135                 140
Thr Asn Pro Ser Glu Thr Val Ile Cys Asn Ser Ile Gly Met Ile Ala
145                 150                 155                 160
Ala Gly Asn Ala Val Ile Phe Ala Pro His Pro Gly Ala Lys Arg Thr
                165                 170                 175
Ser Ile Arg Thr Val Glu Leu Ile Asn Glu Ala Ile Arg Lys Val Gly
            180                 185                 190
Gly Pro Asp Asn Leu Ile Val Thr Ile Arg Glu Pro Ser Ile Glu Asn
        195                 200                 205
Thr Glu Lys Ile Ile Ala Asn Pro Asn Ile Lys Met Leu Val Ala Thr
    210                 215                 220
Gly Gly Pro Gly Val Val Lys Thr Val Met Ser Ser Gly Lys Lys Ala
225                 230                 235                 240
Ile Gly Ala Gly Ala Gly Asn Pro Pro Val Leu Val Asp Glu Thr Ala
                245                 250                 255
Asp Ile Glu Lys Ala Ala Lys Asp Ile Ile Ala Gly Cys Ser Phe Asp
            260                 265                 270
Asn Asn Leu Pro Cys Thr Ala Glu Lys Glu Val Val Ala Val Asp Ser
        275                 280                 285
Ile Val Asn Tyr Leu Ile Phe Glu Met Gln Lys Asn Gly Ala Tyr Leu
    290                 295                 300
Leu Lys Asp Lys Glu Leu Ile Glu Lys Leu Leu Ser Leu Val Leu Lys
305                 310                 315                 320
Asn Asn Ser Pro Asp Arg Lys Tyr Val Gly Arg Asp Ala Lys Tyr Leu
                325                 330                 335
Leu Lys Gln Ile Gly Ile Glu Val Gly Asp Glu Ile Lys Val Ile Ile
            340                 345                 350
Val Glu Thr Asp Lys Asn His Pro Phe Ala Val Glu Glu Leu Leu Met
        355                 360                 365
Pro Ile Leu Pro Ile Val Lys Val Lys Asp Ala Leu Glu Gly Ile Lys
    370                 375                 380
```

Val Ala Lys Glu Leu Glu Arg Gly Leu Arg His Thr Ala Val Ile His
385                 390                 395                 400

Ser Lys Asn Ile Asp Ile Leu Thr Lys Tyr Ala Arg Glu Met Glu Thr
                405                 410                 415

Thr Ile Leu Val Lys Asn Gly Pro Ser Tyr Ala Gly Ile Gly Ile Gly
            420                 425                 430

Gly Glu Gly His Val Thr Phe Thr Ile Ala Gly Pro Thr Gly Glu Gly
        435                 440                 445

Leu Thr Ser Ala Lys Ser Phe Ala Arg Asn Arg Arg Cys Val Leu Val
    450                 455                 460

Gly Gly Phe Ser Ile Lys
465             470

<210> SEQ ID NO 74
<211> LENGTH: 465
<212> TYPE: PRT
<213> ORGANISM: Fusobacterium nucleatum

<400> SEQUENCE: 74

Met Glu Phe Glu Val Asn Asn Leu Glu Ile Val Glu Leu Ile Met
1               5                   10                  15

Lys Lys Met Ser Glu Ser Ser Ile Ser Thr Ser Ser Asn Ser Lys Asn
                20                  25                  30

Gly Val Phe Glu Asn Val Asp Glu Ala Ile Ala Glu Ala Lys Lys Ala
            35                  40                  45

Gln Thr Ile Leu Phe Ser Ser Lys Leu Glu Leu Arg Glu Arg Ile Ile
    50                  55                  60

Ala Ser Ile Arg Asp Thr Leu Lys Pro Tyr Ile Thr Glu Leu Ser Glu
65                  70                  75                  80

Leu Ala Val Lys Glu Thr Gly Met Gly Arg Val Ser Asp Lys Glu Ile
                85                  90                  95

Lys Asn Arg Ile Ala Ile Glu Lys Thr Pro Gly Leu Glu Asp Leu Lys
            100                 105                 110

Ala Phe Ala Phe Ser Gly Asp Asp Gly Leu Thr Val Met Glu Leu Ser
        115                 120                 125

Pro Tyr Gly Val Ile Gly Ala Ile Thr Pro Ser Thr Asn Pro Ser Glu
    130                 135                 140

Thr Val Ile Cys Asn Ser Ile Gly Met Ile Ala Ala Gly Asn Ala Val
145                 150                 155                 160

Ile Phe Ala Pro His Pro Gly Ala Lys Arg Thr Ser Ile Arg Ala Val
                165                 170                 175

Glu Leu Ile Asn Glu Ala Ile Lys Lys Val Gly Gly Pro Asp Asn Leu
            180                 185                 190

Ile Val Thr Ile Thr Glu Pro Ser Ile Glu Asn Thr Glu Lys Ile Ile
        195                 200                 205

Ala Asn Pro Asn Ile Lys Met Val Val Ala Thr Gly Gly Pro Gly Val
    210                 215                 220

Val Lys Thr Val Met Ser Ser Gly Lys Lys Ala Ile Gly Ala Gly Ala
225                 230                 235                 240

Gly Asn Pro Pro Val Leu Val Asp Glu Thr Ala Asp Ile Glu Lys Ala
                245                 250                 255

Ala Lys Asp Ile Ile Ala Gly Cys Ser Phe Asp Asn Asn Leu Pro Cys
            260                 265                 270

Thr Ala Glu Lys Glu Val Ile Ala Val Asp Ser Ile Val Asn Tyr Leu

```
            275                 280                 285
Ile Phe Glu Met Gln Lys Asn Gly Ala Tyr Leu Leu Lys Asp Lys Asp
    290                 295                 300

Leu Ile Glu Lys Leu Leu Ser Ile Val Leu Lys Asn Asn Ser Pro Asp
305                 310                 315                 320

Arg Lys Tyr Val Gly Lys Asp Ala Lys Tyr Leu Leu Lys Gln Ile Gly
                325                 330                 335

Ile Glu Val Gly Asp Glu Ile Arg Val Ile Val Glu Thr Ser Lys
                340                 345                 350

Asp His Pro Phe Ala Val Glu Glu Leu Leu Met Pro Ile Leu Pro Ile
                355                 360                 365

Val Lys Val Lys Asp Ala Leu Glu Gly Ile Lys Val Ala Lys Glu Leu
    370                 375                 380

Glu Lys Gly Leu Arg His Thr Ala Ile Ile His Ser Lys Asn Ile Asp
385                 390                 395                 400

Ile Leu Ser Lys Tyr Ala Arg Glu Met Glu Thr Thr Ile Leu Val Lys
                405                 410                 415

Asn Gly Pro Ser Tyr Ala Gly Ile Gly Ile Gly Gly Glu Gly His Val
                420                 425                 430

Thr Phe Thr Ile Ala Gly Pro Thr Gly Glu Gly Leu Thr Ser Ala Arg
                435                 440                 445

Ser Phe Ala Arg Asn Arg Arg Cys Val Leu Val Gly Gly Phe Ser Ile
    450                 455                 460

Lys
465

<210> SEQ ID NO 75
<211> LENGTH: 465
<212> TYPE: PRT
<213> ORGANISM: Fusobacterium nucleatum

<400> SEQUENCE: 75

Met Glu Phe Glu Val Asn Asn Ile Glu Glu Ile Val Glu Leu Ile Met
1               5                   10                  15

Lys Lys Met Ser Glu Ser Gly Val Ser Thr Ser Asn Asn Ser Thr Asn
                20                  25                  30

Gly Val Phe Glu Asn Val Asp Glu Ala Ile Ala Glu Ala Lys Lys Ala
            35                  40                  45

Gln Thr Val Leu Phe Ser Ser Lys Leu Glu Leu Arg Glu Arg Ile Ile
    50                  55                  60

Ala Ser Ile Arg Asp Thr Leu Lys Thr His Ile Thr Glu Leu Ser Glu
65                  70                  75                  80

Leu Ala Val Lys Glu Thr Gly Met Gly Arg Val Ala Asp Lys Glu Leu
                85                  90                  95

Lys Asn Arg Ile Ala Ile Glu Lys Thr Pro Gly Leu Glu Asp Leu Lys
                100                 105                 110

Ala Phe Ala Phe Ser Gly Asp Asp Gly Leu Thr Val Met Glu Leu Ser
            115                 120                 125

Pro Tyr Gly Val Ile Gly Ala Ile Thr Pro Ser Thr Asn Pro Ser Glu
    130                 135                 140

Thr Val Ile Cys Asn Ser Ile Gly Met Ile Ala Ala Gly Asn Ala Val
145                 150                 155                 160

Ile Phe Ala Pro His Pro Gly Ala Lys Arg Thr Ser Ile Arg Ala Val
                165                 170                 175
```

```
Glu Leu Ile Asn Glu Ala Ile Lys Lys Ala Gly Gly Pro Asp Asn Leu
            180                 185                 190

Val Val Thr Ile Ala Glu Pro Ser Ile Glu Asn Thr Glu Lys Ile Ile
        195                 200                 205

Ala Asn Pro Asn Ile Lys Met Val Val Ala Thr Gly Gly Pro Gly Val
    210                 215                 220

Val Lys Thr Val Met Ser Ser Gly Lys Lys Ala Ile Gly Ala Gly Ala
225                 230                 235                 240

Gly Asn Pro Pro Ala Leu Val Asp Glu Thr Ala Asp Ile Glu Lys Ala
                245                 250                 255

Ala Lys Asp Ile Ile Ala Gly Cys Ser Phe Asp Asn Asn Leu Pro Cys
            260                 265                 270

Thr Ala Glu Lys Glu Val Ile Ala Val Asp Ser Ile Val Asn Tyr Leu
        275                 280                 285

Ile Phe Glu Met Gln Lys Asn Gly Ala Tyr Leu Leu Lys Asp Lys Glu
    290                 295                 300

Leu Ile Glu Lys Leu Leu Ser Ile Val Leu Lys Asn Asn Ser Pro Asp
305                 310                 315                 320

Arg Lys Tyr Val Gly Lys Asp Ala Lys Tyr Leu Leu Lys Gln Ile Gly
                325                 330                 335

Ile Glu Val Gly Asp Glu Ile Lys Val Ile Val Glu Thr Asp Lys
            340                 345                 350

Asn His Pro Phe Ala Val Glu Leu Leu Met Pro Ile Leu Pro Ile
        355                 360                 365

Val Lys Val Lys Asp Ala Leu Glu Gly Ile Lys Val Ala Lys Glu Leu
    370                 375                 380

Glu Lys Gly Leu Arg His Thr Ala Val Ile His Ser Lys Asn Ile Asp
385                 390                 395                 400

Ile Leu Ser Lys Tyr Ala Arg Glu Met Glu Thr Thr Ile Leu Val Lys
                405                 410                 415

Asn Gly Pro Ser Tyr Ala Gly Ile Gly Ile Gly Gly Glu Gly His Val
            420                 425                 430

Thr Phe Thr Ile Ala Gly Pro Thr Gly Glu Gly Leu Thr Ser Ala Arg
        435                 440                 445

Ser Phe Ala Arg Asn Arg Arg Cys Val Leu Val Gly Gly Phe Ser Ile
    450                 455                 460

Lys
465

<210> SEQ ID NO 76
<211> LENGTH: 470
<212> TYPE: PRT
<213> ORGANISM: Fusobacterium sp.

<400> SEQUENCE: 76

Met Arg Gly Glu Leu Met Glu Phe Glu Val Asn Asn Ile Glu Glu Ile
1               5                   10                  15

Val Glu Leu Ile Met Lys Lys Met Ala Glu Ser Asn Ile Ser Thr Ala
            20                  25                  30

Gly Asn Ser Lys Asn Gly Val Phe Asp Asn Val Asp Glu Ala Ile Glu
        35                  40                  45

Glu Ala Lys Lys Ala Gln Ala Ile Leu Phe Ser Ser Lys Leu Glu Leu
    50                  55                  60

Arg Glu Lys Ile Ile Ala Ser Ile Arg Asp Thr Leu Lys Asn His Val
65                  70                  75                  80
```

```
Thr Glu Leu Ala Glu Leu Ala Val Lys Glu Thr Gly Met Gly Arg Val
                85                  90                  95

Ala Asp Lys Glu Leu Lys Asn Lys Ile Ala Ile Glu Lys Thr Pro Gly
            100                 105                 110

Leu Glu Asp Leu Lys Ala Phe Ala Phe Ser Gly Asp Asp Gly Leu Thr
        115                 120                 125

Val Met Glu Leu Ser Pro Tyr Gly Val Ile Gly Ala Ile Thr Pro Ser
130                 135                 140

Thr Asn Pro Ser Glu Thr Val Ile Cys Asn Ser Ile Gly Met Ile Ala
145                 150                 155                 160

Ala Gly Asn Ala Val Ile Phe Ala Pro His Pro Gly Ala Lys Arg Thr
                165                 170                 175

Ser Ile Arg Thr Val Glu Leu Ile Asn Glu Ala Ile Arg Lys Val Gly
            180                 185                 190

Gly Pro Asp Asn Leu Ile Val Thr Ile Arg Glu Pro Ser Ile Glu Asn
        195                 200                 205

Thr Glu Lys Ile Ile Ala Asn Pro Asn Ile Lys Met Leu Val Ala Thr
210                 215                 220

Gly Gly Pro Gly Val Val Lys Thr Val Met Ser Ser Gly Lys Lys Ala
225                 230                 235                 240

Ile Gly Ala Gly Ala Gly Asn Pro Pro Val Leu Val Asp Glu Thr Ala
                245                 250                 255

Asp Ile Glu Lys Ala Ala Lys Asp Ile Ile Ala Gly Cys Ser Phe Asp
            260                 265                 270

Asn Asn Leu Pro Cys Thr Ala Glu Lys Glu Val Val Ala Val Asp Ser
        275                 280                 285

Ile Val Asn Tyr Leu Ile Phe Glu Met Gln Lys Asn Gly Ala Tyr Leu
290                 295                 300

Leu Lys Asp Lys Glu Leu Ile Glu Lys Leu Leu Ser Leu Val Leu Lys
305                 310                 315                 320

Asn Asn Ser Pro Asp Arg Lys Tyr Val Gly Arg Asp Ala Lys Tyr Leu
                325                 330                 335

Leu Lys Gln Ile Gly Ile Glu Val Gly Asp Glu Ile Lys Val Ile Ile
            340                 345                 350

Val Glu Thr Asp Lys Asn His Pro Phe Ala Val Glu Glu Leu Leu Met
        355                 360                 365

Pro Ile Leu Pro Ile Val Lys Val Lys Asp Ala Leu Glu Gly Ile Lys
370                 375                 380

Val Ala Lys Glu Leu Glu Arg Gly Leu Arg His Thr Ala Val Ile His
385                 390                 395                 400

Ser Lys Asn Ile Asp Ile Leu Thr Lys Tyr Ala Arg Glu Met Glu Thr
                405                 410                 415

Thr Ile Leu Val Lys Asn Gly Pro Ser Tyr Ala Gly Ile Gly Ile Gly
            420                 425                 430

Gly Glu Gly His Val Thr Phe Thr Ile Ala Gly Pro Thr Gly Glu Gly
        435                 440                 445

Leu Thr Ser Ala Lys Ser Phe Ala Arg Asn Arg Arg Cys Val Leu Val
450                 455                 460

Gly Gly Phe Ser Ile Lys
465                 470

<210> SEQ ID NO 77
<211> LENGTH: 481
```

<212> TYPE: PRT
<213> ORGANISM: Clostridium asparagiforme

<400> SEQUENCE: 77

```
Met Glu Ile Glu Thr Arg Asp Ile Glu Arg Ile Val Arg Gln Val Met
1               5                   10                  15

Ala Ala Met Glu Gln Gln Gly Thr Ile Ala Gly Gly Ala Tyr Pro Pro
            20                  25                  30

Ala Pro Gly Ile Thr Ala Pro Arg Gly Asp Asn Gly Val Phe Glu Arg
        35                  40                  45

Val Glu Asp Ala Ile Asp Ala Ala Trp Ala Ala Gly Arg Val Trp Ala
    50                  55                  60

Phe His Tyr Lys Val Glu Asp Arg Arg Val Ile Glu Ala Ile Arg
65                  70                  75                  80

Val Met Ala Arg Glu Asn Ala Arg Thr Leu Ala Gln Met Val Arg Asp
                85                  90                  95

Glu Thr Gly Met Gly Arg Val Glu Asp Lys Val Glu Lys His Leu Ala
            100                 105                 110

Val Ala Asp Lys Thr Pro Gly Val Glu Cys Leu Thr Thr Asp Ala Ile
        115                 120                 125

Ser Gly Asp Gly Gly Leu Met Ile Glu Glu Tyr Ala Pro Phe Gly Val
    130                 135                 140

Ile Gly Ala Ile Thr Pro Ser Thr Asn Pro Thr Glu Thr Val Ile His
145                 150                 155                 160

Asn Thr Ile Ser Met Ile Ala Gly Gly Asn Ser Val Val Phe Asn Val
                165                 170                 175

His Pro Gly Ala Lys Lys Cys Cys Ala Phe Cys Leu Gln Leu Leu Asn
            180                 185                 190

Lys Thr Ile Val Glu Asn Gly Gly Pro Ala Asn Leu Ile Thr Met Gln
        195                 200                 205

Arg Asp Pro Thr Met Asp Ala Val Asn Lys Met Thr Ser Ser Pro Lys
    210                 215                 220

Ile Arg Leu Met Val Gly Thr Gly Gly Met Gly Met Val Asn Ala Leu
225                 230                 235                 240

Leu Arg Ser Gly Lys Lys Thr Ile Gly Ala Gly Ala Gly Asn Pro Pro
                245                 250                 255

Val Ile Val Asp Asp Thr Ala Asp Val Lys Leu Ala Ala Arg Glu Leu
            260                 265                 270

Tyr Trp Gly Ala Ser Phe Asp Asn Asn Leu Phe Cys Phe Ala Glu Lys
        275                 280                 285

Glu Val Phe Val Met Glu Ala Ser Ala Asp Gly Leu Ile Arg Gly Leu
    290                 295                 300

Val Glu Gln Gly Ala Tyr Leu Leu Thr Pro Ala Glu Thr Glu Ala Ile
305                 310                 315                 320

Val Lys Leu Ala Leu Ile Gln Lys Asp Gly Lys Tyr Glu Val Asn Lys
                325                 330                 335

Lys Trp Val Gly Lys Asp Ala Gly Leu Phe Leu Gln Ala Ile Gly Val
            340                 345                 350

Ser Gly His Glu Asn Thr Arg Leu Leu Ile Cys Asp Val Pro Lys Cys
        355                 360                 365

His Pro Tyr Val Met Val Glu Gln Leu Met Pro Val Leu Pro Ile Val
    370                 375                 380

Arg Cys Arg Thr Phe Asp Glu Cys Ile Gln Cys Ser Val Glu Ala Glu
385                 390                 395                 400
```

```
Gln Gly Asn Arg His Thr Ser Ser Ile Phe Ser Thr Asn Val Tyr Asn
            405                 410                 415

Met Thr Lys Phe Gly Lys Glu Ile Glu Thr Thr Ile Tyr Val Lys Asn
            420                 425                 430

Gly Ala Thr Leu Arg Gly Leu Gly Ile Gly Gly Glu Gly His Thr Thr
            435                 440                 445

Met Thr Ile Ala Gly Pro Thr Gly Glu Gly Leu Thr Cys Ala Arg Ser
            450                 455                 460

Phe Thr Arg Arg Arg Cys Met Leu Ala Glu Gly Gly Leu Arg Ile
465             470                 475                 480

Ile

<210> SEQ ID NO 78
<211> LENGTH: 462
<212> TYPE: PRT
<213> ORGANISM: Clostridium phytofermentans

<400> SEQUENCE: 78

Met Thr Val Asn Glu Gln Leu Val Gln Asp Ile Ile Lys Asn Val Val
1               5                   10                  15

Ala Ser Met Gln Leu Thr Gln Thr Asn Lys Thr Glu Leu Gly Val Phe
            20                  25                  30

Asp Asp Met Asn Gln Ala Ile Glu Ala Lys Glu Ala Gln Leu Val
            35                  40                  45

Val Lys Lys Met Ser Met Asp Gln Arg Glu Lys Ile Ile Ser Ala Ile
50                  55                  60

Arg Lys Lys Thr Ile Glu His Ala Glu Thr Leu Ala Arg Met Ala Val
65                  70                  75                  80

Glu Glu Thr Gly Met Gly Asn Val Gly His Lys Ile Leu Lys His Gln
            85                  90                  95

Leu Val Ala Glu Lys Thr Pro Gly Thr Glu Asp Ile Thr Thr Thr Ala
            100                 105                 110

Trp Ser Gly Asp Arg Gly Leu Thr Leu Val Glu Met Gly Pro Phe Gly
            115                 120                 125

Val Ile Gly Ala Ile Thr Pro Cys Thr Asn Pro Ser Glu Thr Ile Ile
            130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Asn Phe Ala Val Gln Leu Ile
            165                 170                 175

Asn Glu Ala Ser Leu Ser Ala Gly Gly Pro Val Asn Ile Ala Cys Ser
            180                 185                 190

Val Arg Lys Pro Thr Leu Asp Ser Ser Lys Ile Met Met Ser His Gln
            195                 200                 205

Asp Ile Pro Leu Ile Ala Ala Thr Gly Gly Pro Gly Val Val Thr Ala
            210                 215                 220

Val Leu Gln Ser Gly Lys Arg Gly Ile Gly Ala Gly Ala Gly Asn Pro
225                 230                 235                 240

Pro Val Leu Val Asp Glu Thr Ala Asp Ile Arg Lys Ala Ala Glu Asp
            245                 250                 255

Ile Ile Asn Gly Cys Thr Phe Asp Asn Asn Leu Pro Cys Ile Ala Glu
            260                 265                 270

Lys Glu Val Val Ala Ile Asp Ala Ile Ala Asn Glu Leu Met Asn Tyr
            275                 280                 285
```

```
Met Val Lys Glu Gln Gly Cys Tyr Ala Ile Thr Lys Glu Gln Gln Glu
    290                 295                 300

Lys Leu Thr Asn Leu Val Ile Thr Pro Lys Gly Leu Asn Arg Asn Cys
305                 310                 315                 320

Val Gly Lys Asp Ala Arg Thr Leu Leu Gly Met Ile Gly Ile Asp Val
                325                 330                 335

Pro Ser Asn Ile Arg Cys Ile Ile Phe Glu Gly Glu Lys Glu His Pro
            340                 345                 350

Leu Ile Ser Glu Glu Leu Met Met Pro Ile Leu Gly Ile Val Arg Ala
        355                 360                 365

Lys Ser Phe Asp Asp Ala Val Glu Lys Ala Val Trp Leu Glu His Gly
    370                 375                 380

Asn Arg His Ser Ala His Ile His Ser Lys Asn Val Asp Arg Ile Thr
385                 390                 395                 400

Thr Tyr Ala Lys Ala Ile Asp Thr Ala Ile Leu Val Lys Asn Ala Pro
                405                 410                 415

Ser Tyr Ala Ala Ile Gly Phe Gly Gly Glu Gly Phe Cys Thr Phe Thr
            420                 425                 430

Ile Ala Ser Arg Thr Gly Glu Gly Leu Thr Ser Ala Ser Thr Phe Thr
        435                 440                 445

Lys Arg Arg Arg Cys Val Met Ser Asp Ser Leu Cys Ile Arg
    450                 455                 460
```

<210> SEQ ID NO 79
<211> LENGTH: 470
<212> TYPE: PRT
<213> ORGANISM: Fusobacterium sp.

<400> SEQUENCE: 79

```
Met Arg Gly Glu Leu Met Glu Leu Glu Val Lys Asn Ile Glu Glu Ile
1               5                   10                  15

Val Asp Leu Ile Met Lys Lys Met Thr Glu Ser Asn Val Ala Val Ser
            20                  25                  30

Tyr Asp Ser Lys Asn Gly Val Phe Asp Asp Val Asp Val Ala Ile Ala
        35                  40                  45

Glu Ala Lys Lys Ala Gln Thr Val Leu Phe Ser Ser Lys Leu Glu Leu
    50                  55                  60

Arg Glu Arg Ile Ile Ala Ser Ile Arg Glu Thr Met Arg Ala His Ile
65                  70                  75                  80

Thr Glu Leu Ser Glu Leu Ala Val Lys Glu Thr Gly Met Gly Arg Val
                85                  90                  95

Lys Asp Lys Glu Gln Lys Asn Arg Val Ala Ile Asp Arg Thr Pro Gly
            100                 105                 110

Leu Glu Asp Leu Lys Ala Phe Ala Phe Ser Gly Asp Asp Gly Leu Thr
        115                 120                 125

Val Met Glu Phe Ser Pro Tyr Gly Val Ile Gly Ala Ile Thr Pro Ser
    130                 135                 140

Thr Asn Pro Ser Glu Thr Val Ile Cys Asn Ser Ile Gly Met Ile Ala
145                 150                 155                 160

Ala Gly Asn Ala Val Ile Phe Ala Pro His Pro Gly Ala Lys Arg Thr
                165                 170                 175

Ser Ile Arg Ala Val Glu Leu Ile Asn Glu Ala Ile Lys Lys Val Gly
            180                 185                 190

Gly Pro Glu Asn Leu Val Val Thr Ile Ser Glu Pro Ser Ile Glu Asn
```

```
                195                 200                 205
Thr Glu Lys Ile Ile Ala Asn Pro Asn Ile Lys Met Leu Val Ala Thr
    210                 215                 220
Gly Gly Pro Gly Val Val Lys Thr Val Met Ser Ser Gly Lys Lys Ala
225                 230                 235                 240
Ile Gly Ala Gly Ala Gly Asn Pro Pro Val Leu Val Asp Glu Thr Ala
                245                 250                 255
Asp Ile Glu Lys Ala Ala Lys Asp Ile Ile Asp Gly Cys Ser Phe Asp
            260                 265                 270
Asn Asn Leu Pro Cys Thr Ala Glu Lys Glu Val Ile Ala Val Asp Ser
        275                 280                 285
Ile Val Asn Tyr Leu Ile Phe Glu Met Gln Lys Asn Gly Ala Tyr Leu
    290                 295                 300
Leu Lys Asp Lys Glu Leu Ile Glu Lys Leu Val Ser Leu Val Leu Lys
305                 310                 315                 320
Asn Asn Ser Pro Asp Arg Lys Tyr Val Gly Lys Asp Ala Lys Tyr Ile
                325                 330                 335
Leu Lys Gln Leu Gly Ile Glu Val Gly Asp Glu Ile Arg Val Ile Ile
            340                 345                 350
Val Glu Thr Asp Lys Asn His Pro Phe Ala Val Glu Leu Leu Met
        355                 360                 365
Pro Val Leu Pro Ile Val Lys Val Lys Asp Ala Leu Glu Gly Ile Lys
    370                 375                 380
Val Ala Lys Glu Leu Glu Arg Gly Leu Arg His Thr Ala Ile Ile His
385                 390                 395                 400
Ser Lys Asn Ile Asp Ile Leu Ser Lys Tyr Ala Arg Glu Met Glu Thr
                405                 410                 415
Thr Ile Leu Val Lys Asn Gly Pro Ser Tyr Ala Gly Ile Gly Ile Gly
            420                 425                 430
Gly Glu Gly His Val Thr Phe Thr Ile Ala Gly Pro Thr Gly Glu Gly
        435                 440                 445
Leu Thr Ser Ala Arg Ser Phe Ala Arg Asn Arg Arg Cys Val Leu Val
    450                 455                 460
Gly Gly Phe Ser Ile Lys
465                 470

<210> SEQ ID NO 80
<211> LENGTH: 462
<212> TYPE: PRT
<213> ORGANISM: Lachnospiraceae bacterium

<400> SEQUENCE: 80

Met Ser Val Asn Glu Lys Met Val Gln Asp Ile Val Gln Glu Val Val
1               5                   10                  15
Ala Lys Met Gln Ile Ser Ser Asp Val Ser Gly Lys Lys Gly Val Phe
            20                  25                  30
Ser Asp Met Asn Glu Ala Ile Glu Ala Ser Lys Lys Ala Gln Lys Ile
        35                  40                  45
Val Ala Lys Met Ser Met Asp Gln Arg Glu Ala Ile Ile Ser Lys Ile
    50                  55                  60
Arg Glu Lys Ile Lys Glu Asn Ala Glu Ile Leu Ala Arg Met Gly Val
65                  70                  75                  80
Glu Glu Thr Gly Met Gly Asn Val Gly His Lys Ile Leu Lys His Gln
                85                  90                  95
```

Leu Val Ala Glu Lys Thr Pro Gly Thr Glu Asp Ile Thr Thr Thr Ala
            100                 105                 110

Trp Ser Gly Asp Arg Gly Leu Thr Leu Ile Glu Met Gly Pro Phe Gly
            115                 120                 125

Val Ile Gly Ala Ile Thr Pro Cys Thr Asn Pro Ser Glu Thr Val Leu
        130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Tyr Ala Val Asn Leu Leu
                165                 170                 175

Asn Glu Ala Ser Val Glu Val Gly Gly Pro Glu Asn Ile Ala Val Thr
            180                 185                 190

Val Glu His Pro Thr Met Glu Thr Ser Asp Val Met Met Lys His Lys
        195                 200                 205

Asp Ile His Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Ile Ala Asp Glu Leu Leu His Tyr
        275                 280                 285

Met Val Asn Glu Gln Gly Cys Tyr Met Ile Ser Lys Glu Glu Gln Asp
    290                 295                 300

Ala Leu Thr Glu Val Val Leu Lys Gly Gly Arg Leu Asn Arg Lys Cys
305                 310                 315                 320

Val Gly Arg Asp Ala Lys Thr Leu Leu Gly Met Ile Gly Ile Thr Val
                325                 330                 335

Pro Asp Asn Ile Arg Cys Ile Thr Phe Glu Gly Pro Lys Glu His Pro
            340                 345                 350

Leu Ile Ala Glu Glu Leu Met Met Pro Ile Leu Gly Val Val Arg Ala
        355                 360                 365

Lys Asp Phe Asp Asp Ala Val Glu Gln Ala Val Trp Leu Glu His Gly
    370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ala Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
        435                 440                 445

Lys Arg Arg Arg Cys Val Met Thr Asp Ser Leu Cys Ile Arg
    450                 455                 460

<210> SEQ ID NO 81
<211> LENGTH: 462
<212> TYPE: PRT
<213> ORGANISM: Ruminococcus gnavus

<400> SEQUENCE: 81

Met Ser Val Asn Glu Lys Met Val Gln Asp Ile Val Gln Glu Val Val
1               5                   10                  15

```
Ala Lys Met Gln Ile Ser Ser Asp Val Ser Gly Lys Lys Gly Val Phe
                20                  25                  30

Ser Asp Met Asn Glu Ala Ile Glu Ala Ser Lys Lys Ala Gln Lys Ile
                35                  40                  45

Val Ala Lys Met Ser Met Asp Gln Arg Glu Ala Ile Ile Ser Lys Ile
 50                  55                  60

Arg Glu Lys Ile Lys Glu Asn Ala Glu Ile Leu Ala Arg Met Gly Val
 65                  70                  75                  80

Glu Glu Thr Gly Met Gly Asn Val Gly His Lys Ile Leu Lys His Gln
                85                  90                  95

Leu Val Ala Glu Lys Thr Pro Gly Thr Glu Asp Ile Thr Thr Thr Ala
                100                 105                 110

Trp Ser Gly Asp Arg Gly Leu Thr Leu Ile Glu Met Gly Pro Phe Gly
                115                 120                 125

Val Ile Gly Ala Ile Thr Pro Cys Thr Asn Pro Ser Glu Thr Val Leu
 130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Tyr Ala Val Asn Leu Leu
                165                 170                 175

Asn Glu Ala Ser Val Glu Val Gly Gly Pro Glu Asn Ile Ala Val Thr
                180                 185                 190

Val Glu His Pro Thr Met Glu Thr Ser Asp Ile Met Met Lys His Lys
                195                 200                 205

Asp Ile His Leu Ile Ala Ala Thr Gly Gly Pro Gly Val Val Thr Ala
                210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
                260                 265                 270

Lys Glu Ile Val Ala Val Asp Ser Ile Ala Asp Glu Leu Leu His Tyr
                275                 280                 285

Met Val Ser Glu Gln Gly Cys Tyr Met Ile Ser Lys Glu Glu Gln Asp
290                 295                 300

Ala Leu Thr Glu Val Val Leu Lys Gly Gly Arg Leu Asn Arg Lys Cys
305                 310                 315                 320

Val Gly Arg Asp Ala Lys Thr Leu Leu Gly Met Ile Gly Ile Thr Val
                325                 330                 335

Pro Asp Asn Ile Arg Cys Ile Thr Phe Glu Gly Pro Lys Glu His Pro
                340                 345                 350

Leu Ile Ala Glu Glu Leu Met Met Pro Ile Leu Gly Val Val Arg Ala
                355                 360                 365

Lys Asp Phe Asp Asp Ala Val Glu Gln Ala Val Trp Leu Glu His Gly
                370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ala Ala Leu Gly Phe Gly Gly Glu Gly Tyr Cys Thr Phe Thr
                420                 425                 430
```

Ile Ala Ser Arg Thr Gly Glu Gly Leu Thr Ser Ala Ser Thr Phe Thr
            435                 440                 445

Lys Arg Arg Arg Cys Val Met Thr Asp Ser Leu Cys Ile Arg
450                 455                 460

<210> SEQ ID NO 82
<211> LENGTH: 462
<212> TYPE: PRT
<213> ORGANISM: Ruminococcus obeum

<400> SEQUENCE: 82

Met Pro Ile Ser Glu Ser Met Val Gln Asp Ile Val Gln Glu Val Met
1               5                   10                  15

Ala Lys Met Gln Ile Ala Asp Ala Pro Thr Gly Lys His Gly Val Phe
                20                  25                  30

Lys Glu Met Asn Asp Ala Ile Glu Ala Lys Lys Ala Glu Leu Ile
            35                  40                  45

Val Lys Lys Met Ser Met Asp Gln Arg Glu Lys Ile Ile Thr Cys Ile
50                  55                  60

Arg Lys Lys Ile Lys Glu Asn Ala Glu Val Met Ala Arg Met Gly Val
65                  70                  75                  80

Asp Glu Thr Gly Met Gly Asn Val Gly Asp Lys Ile Leu Lys His His
                85                  90                  95

Leu Val Ala Asp Lys Thr Pro Gly Thr Glu Asp Ile Thr Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Val Leu
130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Phe Ala Ile Asn Leu Val
                165                 170                 175

Asn Glu Ala Ser Leu Glu Ala Gly Gly Pro Asp Asn Ile Ala Val Thr
            180                 185                 190

Val Glu Lys Pro Thr Leu Glu Thr Ser Asn Ile Met Met Lys His Lys
        195                 200                 205

Asp Ile Pro Leu Ile Ala Ala Thr Gly Gly Pro Gly Val Val Thr Ala
210                 215                 220

Val Leu Ser Ser Gly Lys Arg Gly Ile Gly Ala Gly Ala Gly Asn Pro
225                 230                 235                 240

Pro Ala Val Val Asp Glu Thr Ala Asp Ile Arg Lys Ala Ala Gln Asp
                245                 250                 255

Ile Val Asn Gly Cys Thr Phe Asp Asn Asn Leu Pro Cys Ile Ala Glu
            260                 265                 270

Lys Glu Val Val Ala Val Ser Ser Val Val Asp Glu Leu Met His Tyr
        275                 280                 285

Met Leu Thr Glu Asn Asp Cys Tyr Leu Ala Ser Lys Glu Glu Gln Asp
290                 295                 300

Lys Leu Thr Glu Val Val Leu Ala Gly Gly Lys Leu Asn Arg Lys Cys
305                 310                 315                 320

Val Gly Arg Asp Ala Lys Thr Leu Leu Ser Met Ile Gly Val Asn Ala
                325                 330                 335

Pro Ala Asn Thr Arg Cys Ile Ile Phe Glu Gly Pro Lys Glu His Pro
            340                 345                 350

```
Leu Ile Thr Thr Glu Leu Met Met Pro Ile Leu Gly Val Val Arg Ala
            355                 360                 365

Arg Asp Phe Asp Asp Ala Val Glu Gln Ala Val Trp Leu Glu His Gly
    370                 375                 380

Asn Arg His Ser Ala His Ile His Ser Lys Asn Ile Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ser Ala Leu Gly Phe Gly Gly Glu Gly Tyr Cys Thr Phe Thr
                420                 425                 430

Ile Ala Ser Arg Thr Gly Glu Gly Leu Thr Ser Ala Ser Thr Phe Thr
            435                 440                 445

Lys Arg Arg Arg Cys Val Met Ser Asp Ser Leu Cys Ile Arg
    450                 455                 460
```

<210> SEQ ID NO 83
<211> LENGTH: 473
<212> TYPE: PRT
<213> ORGANISM: Clostridium saccharolyticum

<400> SEQUENCE: 83

```
Met Glu Ile Gly Ala Lys Glu Ile Glu Leu Ile Val Arg Glu Val Leu
1               5                   10                  15

Ala Gly Ile Glu Ser Arg Gly Pro Lys Leu Ser Tyr Ile Pro Ala Gln
                20                  25                  30

Ser Asp Asn Gly Val Phe Glu Arg Val Glu Asp Ala Ile Gly Ala Ala
            35                  40                  45

His Thr Ala Gln Arg Glu Trp Val Glu His Tyr Arg Val Glu Asp Arg
        50                  55                  60

Arg Arg Ile Ile Glu Ala Ile Arg Met Thr Ala Lys Ser His Ala Lys
65                  70                  75                  80

Thr Leu Ala Lys Leu Val Trp Glu Glu Thr Gly Met Gly Arg Phe Glu
                85                  90                  95

Asp Lys Ile Gln Lys His Met Ala Val Ile Glu Lys Thr Pro Gly Val
                100                 105                 110

Glu Cys Leu Thr Thr Asp Ala Ile Ser Gly Asp Glu Gly Leu Met Ile
            115                 120                 125

Glu Glu Tyr Ala Pro Phe Gly Val Ile Gly Ala Ile Thr Pro Ser Thr
        130                 135                 140

Asn Pro Thr Glu Thr Ile Ile Asn Asn Thr Ile Ser Met Ile Ala Gly
145                 150                 155                 160

Gly Asn Ala Val Val Phe Asn Val His Pro Gly Ala Lys Lys Cys Cys
                165                 170                 175

Ala His Cys Leu Lys Leu Leu His Gln Ala Ile Val Glu Asn Gly Gly
            180                 185                 190

Pro Ala Asn Leu Ile Thr Met Gln Lys Glu Pro Thr Met Glu Ala Val
        195                 200                 205

Thr Lys Met Thr Ser Asp Pro Arg Ile Arg Leu Met Val Gly Thr Gly
    210                 215                 220

Gly Met Pro Met Val Asn Ala Leu Leu Arg Ser Gly Lys Lys Thr Ile
225                 230                 235                 240

Gly Ala Gly Ala Gly Asn Pro Pro Val Ile Val Asp Asp Ser Ala Asp
                245                 250                 255

Val Ser Leu Ala Ala Arg Glu Ile Tyr Arg Gly Ala Ser Phe Asp Asn
```

260                 265                 270
Asn Ile Leu Cys Leu Ala Glu Lys Glu Val Phe Val Met Glu Lys Ala
            275                 280                 285

Ala Asp Glu Leu Val Asn Asn Leu Val Lys Glu Gly Ala Tyr Leu Leu
        290                 295                 300

Asn Pro Met Glu Leu Asn Glu Ile Leu Lys Phe Ala Met Ile Glu Lys
305                 310                 315                 320

Asn Gly Ser Cys Glu Val Asn Lys Lys Trp Val Gly Lys Asp Ala Gly
                325                 330                 335

Leu Phe Leu Glu Ala Ile Gly Val Ser Gly His Lys Asp Val Arg Leu
            340                 345                 350

Leu Ile Cys Glu Thr Asp Arg Asn His Pro Phe Val Met Val Glu Gln
        355                 360                 365

Leu Met Pro Ile Leu Pro Ile Val Arg Leu Arg Thr Phe Glu Glu Cys
    370                 375                 380

Val Glu Ser Ala Val Ala Ala Glu Ser Gly Asn Arg His Thr Ala Ser
385                 390                 395                 400

Met Phe Ser Arg Asn Val Glu Asn Met Thr Arg Phe Gly Lys Val Ile
                405                 410                 415

Glu Thr Thr Ile Phe Thr Lys Asn Gly Ser Thr Leu Lys Gly Val Gly
            420                 425                 430

Ile Gly Gly Glu Gly His Thr Thr Met Thr Ile Ala Gly Pro Thr Gly
        435                 440                 445

Glu Gly Leu Thr Cys Ala Arg Ser Phe Thr Arg Arg Arg Cys Met
    450                 455                 460

Leu Ala Glu Gly Gly Leu Arg Ile Ile
465                 470

<210> SEQ ID NO 84
<211> LENGTH: 471
<212> TYPE: PRT
<213> ORGANISM: Flavonifractor plautii

<400> SEQUENCE: 84

Met Asn Ile Asp Glu Asn Val Val Glu Ser Ile Val Lys Arg Val Val
1               5                   10                  15

Ser Gln Leu Ser Thr Glu Thr Ala Ser Ala Gln Thr Cys Pro Ser Gly
            20                  25                  30

Gly Asp Trp Gly Val Phe Glu Ser Met Asn Asp Ala Val Asp Ala Ala
        35                  40                  45

Val Glu Ala Gln Arg Glu Tyr Leu Asn Arg Ser Met His Asp Arg Ala
    50                  55                  60

Cys Tyr Val Gln Ala Ile Arg Asp Val Val Leu Asp Gln Glu Asn Leu
65                  70                  75                  80

Glu Tyr Ile Ser Arg Leu Ala Val Glu Thr Gly Met Gly Gly Tyr
                85                  90                  95

Glu Tyr Lys Leu Ile Lys Asn Arg Leu Ala Ala Val Lys Thr Pro Gly
            100                 105                 110

Ile Glu Asp Leu Thr Thr Asp Ala Met Ser Gly Asp Gly Leu Thr
        115                 120                 125

Leu Val Glu Tyr Ser Pro Phe Gly Val Ile Gly Ser Ile Thr Pro Thr
    130                 135                 140

Thr Asn Pro Thr Glu Thr Ile Ile Cys Asn Ser Ile Gly Met Leu Ala
145                 150                 155                 160

Ala Gly Asn Ala Val Val Phe Ser Pro His Pro Arg Ala Lys Lys Val
            165                 170                 175

Ser Leu His Leu Ile Gln Leu Ile Asn Lys Ala Leu Cys Lys Ala Gly
            180                 185                 190

Ala Pro Ala Asn Leu Val Val Thr Val Ser Ala Pro Ser Ile Glu Asn
            195                 200                 205

Thr Asn Ala Met Met Ser His Pro Lys Ile Arg Met Leu Val Ala Thr
            210                 215                 220

Gly Gly Pro Ala Ile Val Lys Thr Val Leu Ser Gly Lys Lys Ala
225             230                 235                 240

Ile Gly Ala Gly Ala Gly Asn Pro Pro Val Val Asp Glu Thr Ala
                245                 250                 255

Asp Ile Glu Lys Ala Ala Lys Asp Ile Val Asp Gly Cys Ser Phe Asp
            260                 265                 270

Asn Asn Leu Pro Cys Ile Ala Glu Lys Glu Val Ile Ala Val Asp Ser
            275                 280                 285

Val Ala Asp Tyr Leu Ile Phe Asn Met Lys Lys Asn Gly Ala Tyr Glu
            290                 295                 300

Val Lys Asp Pro Ala Val Ile Ser Gln Leu Val Glu Leu Val Thr Lys
305             310                 315                 320

Glu Gly Lys Ser Pro Lys Thr Glu Phe Val Gly Lys Ser Ala Lys Tyr
                325                 330                 335

Ile Leu Asp Lys Ile Gly Ile Thr Val Gly Asp Val Lys Val Ile
            340                 345                 350

Leu Met Glu Ala Lys Glu Asp His Pro Phe Val Gln Val Glu Leu Met
            355                 360                 365

Met Pro Ile Leu Pro Leu Val Arg Val Pro Asp Val Asp Gln Ala Ile
            370                 375                 380

Glu Met Ala Val Arg Val Glu His Gly Asn Arg His Thr Ala Met Met
385             390                 395                 400

His Ser Arg Asn Val Glu Lys Leu Thr Lys Met Ala Lys Leu Ile Gln
                405                 410                 415

Thr Thr Ile Phe Val Lys Asn Gly Pro Ser Tyr Ala Gly Ile Gly Val
            420                 425                 430

Gly Gly Glu Gly Tyr Thr Thr Phe Thr Ile Ala Gly Pro Thr Gly Glu
            435                 440                 445

Gly Leu Thr Ser Ala Lys Ser Phe Ala Arg Arg Arg Cys Val Leu
            450                 455                 460

Val Gly Gly Met Asp Val Arg
465             470

<210> SEQ ID NO 85
<211> LENGTH: 462
<212> TYPE: PRT
<213> ORGANISM: Ruminococcus obeum

<400> SEQUENCE: 85

Met Pro Ile Ser Glu Ser Met Val Gln Asp Ile Val Gln Glu Val Met
1               5                   10                  15

Ala Lys Met Gln Ile Ala Asp Ala Pro Thr Gly Lys His Gly Ile Phe
            20                  25                  30

Lys Asp Met Asn Asp Ala Ile Glu Ala Ala Lys Lys Ser Glu Leu Ile
            35                  40                  45

Val Lys Lys Met Ser Met Asp Gln Arg Glu Lys Ile Ile Thr Cys Ile
50              55                  60

Arg Lys Lys Ile Lys Glu Asn Ala Glu Val Met Ala Arg Met Gly Val
65                  70                  75                  80

Asp Glu Thr Gly Met Gly Asn Val Gly Asp Lys Ile Leu Lys His His
            85                  90                  95

Leu Val Ala Asp Lys Thr Pro Gly Thr Glu Asp Ile Thr Thr Thr Ala
            100                 105                 110

Trp Ser Gly Asp Arg Gly Leu Thr Leu Ile Glu Met Gly Pro Phe Gly
            115                 120                 125

Val Ile Gly Ala Ile Thr Pro Cys Thr Asn Pro Ser Glu Thr Ile Leu
130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Phe Ala Ile Asn Leu Val
                165                 170                 175

Asn Glu Ala Ser Leu Glu Ala Gly Gly Pro Asp Asn Ile Ala Val Thr
            180                 185                 190

Val Glu Lys Pro Thr Leu Glu Thr Ser Asn Ile Met Met Lys His Lys
            195                 200                 205

Asp Ile Pro Leu Ile Ala Ala Thr Gly Gly Pro Gly Val Val Thr Ala
210                 215                 220

Val Leu Ser Ser Gly Lys Arg Gly Ile Gly Ala Gly Ala Gly Asn Pro
225                 230                 235                 240

Pro Ala Val Val Asp Glu Thr Ala Asp Ile Arg Lys Ala Ala Gln Asp
                245                 250                 255

Ile Val Asn Gly Cys Thr Phe Asp Asn Asn Leu Pro Cys Ile Ala Glu
            260                 265                 270

Lys Glu Val Val Ala Val Ser Ser Val Val Asp Glu Leu Met His Tyr
            275                 280                 285

Met Leu Thr Glu Asn Asp Cys Tyr Leu Ala Ser Lys Glu Glu Gln Asp
290                 295                 300

Lys Leu Thr Glu Val Val Leu Ala Gly Gly Lys Leu Asn Arg Lys Cys
305                 310                 315                 320

Val Gly Arg Asp Ala Arg Thr Leu Leu Ser Met Ile Gly Val Asn Ala
                325                 330                 335

Pro Ala Asn Ile Arg Cys Ile Ile Phe Glu Gly Pro Lys Glu His Pro
            340                 345                 350

Leu Ile Thr Thr Glu Leu Met Met Pro Ile Leu Gly Ile Val Arg Ala
            355                 360                 365

Lys Asp Phe Asp Asp Ala Val Glu Gln Ala Val Trp Leu Glu His Gly
            370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ser Ala Leu Gly Phe Gly Gly Glu Gly Tyr Cys Thr Phe Thr
            420                 425                 430

Ile Ala Ser Arg Thr Gly Glu Gly Leu Thr Ser Ala Ser Thr Phe Thr
            435                 440                 445

Lys Arg Arg Arg Cys Val Met Ser Asp Ser Leu Cys Ile Arg
450                 455                 460

<210> SEQ ID NO 86
<211> LENGTH: 469

```
<212> TYPE: PRT
<213> ORGANISM: Clostridium carboxidivorans

<400> SEQUENCE: 86
```

| | | | | | | | | | | | | | | |
|---|---|---|---|---|---|---|---|---|---|---|---|---|---|---|
| Met<br>1 | Glu | Leu | Gln | Ser<br>5 | Asn | Glu | Leu | Ser | Leu<br>10 | Ile | Ile | Glu | Lys | Val<br>15 | Leu |

Lys Glu Met Asn Lys Lys Glu Leu Lys Glu Val Ser Asp Gly Val
                20              25              30

Phe Asp Thr Met Glu Glu Ala Ile Glu Ala Ala Tyr Glu Ala Gln Lys
            35              40              45

Lys Phe Ser Ser Tyr Thr Ile Glu Gln Arg Glu Lys Leu Ile Ala Ala
        50              55              60

Met Arg Lys Ala Ile Ile Asp Asn Ala Met Glu Ile Ala Asn Leu Cys
65              70              75              80

Val Asn Glu Ser Gly Met Gly Arg Val Asp His Lys Tyr Leu Lys Leu
                85              90              95

Lys Leu Thr Ala Glu Lys Thr Pro Gly Thr Glu Val Leu Gln Thr Thr
            100             105             110

Ala Phe Thr Gly Asp Lys Gly Leu Thr Leu Val Glu Asn Gly Ala Phe
        115             120             125

Gly Val Ile Gly Ser Ile Thr Pro Ser Thr Asn Pro Ala Ala Thr Val
130             135             140

Ala Cys Asn Gly Ile Gly Met Leu Ala Gly Asn Thr Ala Val Phe
145             150             155             160

Ser Pro His Pro Gly Ala Phe Arg Ser Ser Leu Ala Met Leu Arg Ala
                165             170             175

Leu Asn Lys Ala Ile Lys Glu Ala Gly Gly Pro Asp Asn Leu Leu Thr
            180             185             190

Ser Val Lys Lys Pro Ser Ile Glu Ser Thr Asn Ser Met Met Lys Asn
        195             200             205

Asp Lys Ile Arg Met Val Val Ala Thr Gly Gly Pro Gly Ile Val Lys
210             215             220

Met Val Leu Ser Ser Gly Arg Lys Ala Ile Gly Ala Gly Ala Gly Asn
225             230             235             240

Pro Pro Val Val Val Asp Glu Thr Ala Asp Ile Lys Lys Ala Arg
                245             250             255

Asp Ile Ile Ala Gly Cys Thr Phe Asp Asn Asn Leu Pro Cys Ile Ala
            260             265             270

Glu Lys Glu Ala Leu Val Val Glu Ala Val Tyr Glu Glu Leu Ile Lys
        275             280             285

Glu Met Lys Asn Asn Arg Ala Val Tyr Glu Leu Asn Asp Glu Glu Ala
290             295             300

Ala Lys Val Ala Glu Leu Val Leu Val His Asn Lys Glu Lys Asn Thr
305             310             315             320

Tyr Ser Ile Asn Lys Ala Phe Val Gly Lys Asp Ala Lys Tyr Ile Leu
                325             330             335

Gln Asn Ile Gly Lys Asn Asp Ala Glu Gly Val Glu Cys Leu Ile Tyr
            340             345             350

Arg Ala Glu Asn Ser His Pro Phe Val Gln Glu Leu Met Met Pro
        355             360             365

Ile Leu Pro Ile Val Lys Thr Lys Asp Phe Glu Glu Ala Leu Lys Leu
            370             375             380

Ala Val Gln Asp Glu His Gly Asn Arg His Thr Ala Ile Met His Ser
385             390             395             400

```
Lys Asn Val Asp Asn Leu Thr Lys Met Ala Arg Ala Ile Asp Thr Thr
                405                 410                 415

Ile Phe Val Lys Asn Ala Pro Ser Tyr Ala Gly Ile Gly Phe Gly Gly
                420                 425                 430

Glu Gly Tyr Thr Thr Phe Thr Ile Ala Gly Pro Thr Gly Glu Gly Leu
                435                 440                 445

Thr Asn Ala Val Ser Phe Thr Arg Lys Arg Cys Thr Met Ala Glu
450                 455                 460

Ser Phe Arg Ile Val
465

<210> SEQ ID NO 87
<211> LENGTH: 469
<212> TYPE: PRT
<213> ORGANISM: Fusobacterium ulcerans

<400> SEQUENCE: 87

Met Asn Leu Glu Ala Asn Asn Met Asp Glu Ile Val Ala Leu Ile Met
1               5                   10                  15

Lys Glu Leu Lys Lys Thr Asp Ile Lys Ala Gly Cys Gln Ser Cys Glu
                20                  25                  30

Ser Pro Lys Asn Gly Val Phe Ser Met Asp Glu Ala Ile Ala Ala
            35                  40                  45

Ala Lys Lys Ala Gln Glu Ile Leu Phe Ser Ser Arg Leu Glu Met Arg
    50                  55                  60

Glu Lys Ile Val Ala Ser Ile Arg Glu Val Met Lys Asp Tyr Val Val
65                  70                  75                  80

Glu Leu Ala Glu Leu Gly Val Lys Glu Thr Gly Met Gly Arg Ala Ala
                85                  90                  95

Asp Lys Ala Leu Lys His Gln Val Thr Ile Glu Lys Thr Pro Gly Val
                100                 105                 110

Glu Asp Leu Arg Ala Phe Ala Phe Ser Gly Asp Asp Gly Leu Thr Val
                115                 120                 125

Met Glu Leu Ser Pro Tyr Gly Val Ile Gly Ala Ile Thr Pro Ser Thr
                130                 135                 140

Asn Pro Ser Glu Thr Ile Ile Cys Asn Ser Ile Gly Met Ile Ser Ala
145                 150                 155                 160

Gly Asn Ser Val Val Phe Ala Pro His Pro Gly Ala Lys Arg Thr Ser
                165                 170                 175

Ile Lys Thr Val Glu Ile Ile Asn Glu Ala Val Arg Lys Ala Gly Gly
                180                 185                 190

Pro Glu Asn Leu Val Val Thr Ile Ala Glu Pro Ser Ile Glu Asn Thr
                195                 200                 205

Asn Arg Met Met Glu Asn Pro Asp Ile Lys Met Leu Val Ala Thr Gly
        210                 215                 220

Gly Pro Gly Val Val Lys Ser Val Met Ser Ser Gly Lys Lys Ala Ile
225                 230                 235                 240

Gly Ala Gly Ala Gly Asn Pro Pro Val Leu Val Asp Glu Thr Ala Asp
                245                 250                 255

Ile Glu Lys Ala Ala Arg Asp Ile Val Ala Gly Cys Ser Phe Asp Asn
                260                 265                 270

Asn Leu Pro Cys Ile Ala Glu Lys Glu Val Val Ala Val Asp Ser Ile
            275                 280                 285

Thr Asp Tyr Leu Ile Phe Glu Met Gln Lys Asn Gly Ala Tyr Leu Ile
```

```
            290                 295                 300
Lys Asp Lys Ser Val Ile Asp Arg Leu Val Ala Met Val Leu Lys Asn
305                 310                 315                 320

Gly Ser Pro Asn Arg Ala Tyr Val Gly Lys Asp Ala Ser Tyr Ile Leu
                325                 330                 335

Lys Asp Leu Gly Ile Asn Val Gly Gly Glu Ile Arg Val Ile Ile Thr
            340                 345                 350

Glu Ala Asp Lys Asp His Pro Phe Ala Val Glu Glu Leu Leu Met Pro
                355                 360                 365

Ile Leu Pro Ile Ile Arg Val Lys Asn Ala Leu Glu Gly Ile Glu Val
            370                 375                 380

Ser Lys Lys Leu Glu His Gly Leu Arg His Thr Ala Met Ile His Ser
385                 390                 395                 400

Lys Asn Ile Asp Ile Leu Thr Lys Tyr Ala Arg Asp Met Glu Thr Thr
                405                 410                 415

Ile Leu Val Lys Asn Gly Pro Ser Phe Ala Gly Ile Gly Val Gly Gly
            420                 425                 430

Glu Gly His Thr Thr Phe Thr Ile Ala Gly Pro Thr Gly Glu Gly Leu
                435                 440                 445

Thr Ser Ala Lys Ser Phe Ala Arg Asn Arg Arg Cys Val Leu Val Gly
            450                 455                 460

Gly Leu Ser Ile Lys
465

<210> SEQ ID NO 88
<211> LENGTH: 469
<212> TYPE: PRT
<213> ORGANISM: Fusobacterium sp.

<400> SEQUENCE: 88

Met Asn Leu Glu Ala Asn Asn Met Asp Glu Ile Val Ala Leu Ile Met
1               5                   10                  15

Lys Glu Leu Lys Lys Thr Asp Ile Lys Ala Gly Cys Gln Ser Cys Glu
                20                  25                  30

Ser Leu Lys Asn Gly Val Phe Ser Met Asp Glu Ala Ile Ala Ala
            35                  40                  45

Ala Lys Lys Ala Gln Glu Ile Leu Phe Ser Ser Arg Leu Glu Met Arg
        50                  55                  60

Glu Lys Ile Val Ala Ser Ile Arg Glu Val Met Lys Asp Tyr Val Val
65                  70                  75                  80

Glu Leu Ala Glu Leu Gly Val Lys Glu Thr Gly Met Gly Arg Ala Ala
                85                  90                  95

Asp Lys Ala Leu Lys His Gln Val Thr Ile Glu Lys Thr Pro Gly Val
            100                 105                 110

Glu Asp Leu Arg Ala Phe Ala Phe Ser Gly Asp Gly Leu Thr Val
        115                 120                 125

Met Glu Leu Ser Pro Tyr Gly Val Ile Gly Ala Ile Thr Pro Ser Thr
130                 135                 140

Asn Pro Ser Glu Thr Ile Ile Cys Asn Ser Ile Gly Met Ile Ser Ala
145                 150                 155                 160

Gly Asn Ser Val Val Phe Ala Pro His Pro Gly Ala Lys Arg Thr Ser
                165                 170                 175

Ile Lys Thr Val Glu Ile Ile Asn Glu Ala Val Arg Arg Ala Gly Gly
            180                 185                 190
```

```
Pro Glu Asn Leu Val Val Thr Ile Ala Glu Pro Ser Ile Glu Asn Thr
195 200 205

Asn Arg Met Met Glu Asn Pro Asp Ile Lys Met Leu Val Ala Thr Gly
210 215 220

Gly Pro Gly Val Val Lys Ser Val Met Ser Ser Gly Lys Lys Ala Ile
225 230 235 240

Gly Ala Gly Ala Gly Asn Pro Pro Val Leu Val Asp Glu Thr Ala Asp
245 250 255

Ile Glu Lys Ala Ala Arg Asp Ile Val Ala Gly Cys Ser Phe Asp Asn
260 265 270

Asn Leu Pro Cys Ile Ala Glu Lys Glu Val Val Ala Val Asp Ser Ile
275 280 285

Thr Asp Tyr Leu Ile Phe Glu Met Gln Lys Asn Gly Ala Tyr Leu Ile
290 295 300

Lys Asp Lys Ser Val Ile Asp Arg Leu Val Ala Met Val Leu Lys Asn
305 310 315 320

Gly Ser Pro Asn Arg Ala Tyr Val Gly Lys Asp Ala Ser Tyr Ile Leu
325 330 335

Lys Asp Leu Gly Ile Asn Val Gly Asp Glu Ile Arg Val Ile Ile Thr
340 345 350

Glu Thr Asp Lys Asp His Pro Phe Ala Val Glu Glu Leu Leu Met Pro
355 360 365

Ile Leu Pro Ile Ile Arg Val Lys Asn Ala Leu Glu Gly Ile Glu Val
370 375 380

Ser Lys Lys Leu Glu His Gly Leu Arg His Thr Ala Met Ile His Ser
385 390 395 400

Lys Asn Ile Asp Ile Leu Thr Lys Tyr Ala Arg Asp Met Glu Thr Thr
405 410 415

Ile Leu Val Lys Asn Gly Pro Ser Phe Ala Gly Ile Gly Val Gly Gly
420 425 430

Glu Gly His Thr Thr Phe Thr Ile Ala Gly Pro Thr Gly Glu Gly Leu
435 440 445

Thr Ser Ala Lys Ser Phe Ala Arg Asn Arg Arg Cys Val Leu Val Gly
450 455 460

Gly Leu Ser Ile Lys
465

<210> SEQ ID NO 89
<211> LENGTH: 469
<212> TYPE: PRT
<213> ORGANISM: Clostridium carboxidivorans

<400> SEQUENCE: 89

Met Glu Leu Glu Ser Asn Glu Leu Ser Val Ile Ile Glu Lys Val Leu
1 5 10 15

Lys Glu Met Asn Lys Lys Glu Phe Gly Lys Lys Glu Ser Asp Gly Ile
20 25 30

Phe Asp Thr Met Asp Glu Ala Val Glu Ala Ser Tyr Glu Ala Gln Lys
35 40 45

Lys Tyr Ser Ser Tyr Ser Leu Glu Gln Arg Glu Lys Leu Ile Gln Ala
50 55 60

Met Arg Lys Ala Ile Met Asp Asn Ala Met Glu Val Ala Asn Leu Cys
65 70 75 80

Val Lys Glu Ser Gly Met Gly Arg Val Asp His Lys Tyr Leu Lys Leu
85 90 95

-continued

```
Lys Leu Ile Val Glu Lys Thr Gln Gly Thr Glu Ile Leu Arg Pro Glu
        100                 105                 110

Val Tyr Thr Gly Asp Asn Gly Leu Thr Leu Ile Glu His Gly Ala Phe
    115                 120                 125

Gly Val Ile Gly Ala Ile Thr Pro Ser Thr Asn Pro Ala Ala Thr Val
    130                 135                 140

Ala Cys Asn Ser Ile Cys Met Leu Ala Gly Gly Asn Thr Val Val Phe
145                 150                 155                 160

Ser Pro His Pro Gly Ala Leu Asn Ser Cys Leu Thr Met Ile Arg Ile
                165                 170                 175

Leu Asn Lys Ala Ile Lys Glu Ala Gly Gly Pro Glu Asn Leu Ile Thr
            180                 185                 190

Ser Val Lys Ala Pro Ser Ile Glu Asn Thr Asn Ile Met Ile Asn His
        195                 200                 205

Lys Arg Ile Arg Leu Val Val Ala Thr Gly Gly Pro Gly Ile Val Lys
    210                 215                 220

Leu Val Leu Ser Ser Gly Lys Lys Ala Ile Gly Ala Gly Ala Gly Asn
225                 230                 235                 240

Pro Pro Val Val Val Asp Glu Thr Ala Asp Ile Pro Lys Ala Ala Arg
                245                 250                 255

Asp Ile Ile Ala Gly Cys Ser Phe Asp Asn Asn Leu Pro Cys Ile Ala
            260                 265                 270

Glu Lys Glu Ala Ile Val Val Glu Ser Val Tyr Glu Glu Leu Ile Lys
        275                 280                 285

Glu Phe Lys Lys Asn Arg Val Val Tyr Glu Leu Thr Asp Glu Glu Ala
    290                 295                 300

Glu Lys Leu Val Gly Lys Val Leu Asn Tyr Asp Glu Lys Asn Lys Lys
305                 310                 315                 320

Tyr Ser Ile Asn Lys Lys Phe Val Gly Lys Asp Ala Lys Tyr Leu Leu
                325                 330                 335

Glu Ser Ile Gly Lys Asp Ala Gly Thr Gly Val Glu Cys Leu Ile Tyr
            340                 345                 350

Arg Ala Glu Asn Ser His Pro Phe Val Gln Glu Glu Leu Met Met Pro
        355                 360                 365

Ile Leu Pro Ile Val Lys Val Lys Asn Val Asp Glu Ala Ile Glu Thr
    370                 375                 380

Ala Val Glu Asp Glu His Gly Asn Arg His Thr Ala Met Met His Ser
385                 390                 395                 400

Lys Asn Val Val Asn Leu Thr Lys Met Ala Arg Ala Ile Asp Thr Thr
                405                 410                 415

Ile Phe Val Lys Asn Ala Pro Ser Tyr Ala Gly Ile Gly Phe Gly Gly
            420                 425                 430

Glu Gly His Thr Thr Phe Thr Ile Ala Gly Pro Thr Gly Glu Gly Ile
        435                 440                 445

Thr Asn Ala Val Thr Phe Thr Arg Gln Arg Arg Cys Thr Met Val Asp
    450                 455                 460

Ser Phe Arg Ile Val
465
```

<210> SEQ ID NO 90
<211> LENGTH: 471
<212> TYPE: PRT
<213> ORGANISM: Clostridium sp.

<400> SEQUENCE: 90

```
Met Glu Met Asp Met Lys Val Ile Glu Gln Leu Val Ala Gln Ala Leu
1               5                   10                  15
Lys Glu Met Lys Ala Glu Pro Ala Ala Phe Ala Glu Lys Lys Glu
            20                  25                  30
Glu Asn Tyr Gly Val Phe Ser Thr Met Asp Glu Ala Ile Glu Ala Ser
        35                  40                  45
Glu Lys Ala Gln Lys Ala Leu Leu Phe Ser Lys Ile Gln Asp Arg Gln
    50                  55                  60
Lys Tyr Val Asp Ile Ile Arg Ala Ala Ile Leu Lys Arg Glu Asn Leu
65                  70                  75                  80
Glu Leu Ile Ser Arg Met Ala Val Glu Glu Thr Glu Ile Gly Lys Tyr
                85                  90                  95
Glu His Lys Leu Ile Lys Asn Arg Leu Ala Ala Glu Lys Thr Pro Gly
            100                 105                 110
Thr Glu Asp Leu Thr Thr Glu Ala Gln Thr Gly Asp His Gly Leu Thr
        115                 120                 125
Leu Val Glu Tyr Cys Pro Phe Gly Val Ile Gly Ala Ile Thr Pro Thr
    130                 135                 140
Thr Asn Pro Thr Glu Thr Ile Ile Cys Asn Ser Ile Ser Met Ile Ala
145                 150                 155                 160
Gly Gly Asn Thr Val Val Phe Ser Pro His Pro Arg Ala Lys Lys Val
                165                 170                 175
Ser Gln Leu Leu Val Lys Met Leu Asn Lys Ala Leu Met Glu Gly Gly
            180                 185                 190
Ala Pro Ala Asn Leu Ile Thr Met Val Glu Glu Pro Ser Ile Glu Asn
        195                 200                 205
Thr Asn Lys Met Ile Glu His Pro Gly Val Arg Leu Leu Val Ala Thr
    210                 215                 220
Gly Gly Pro Ala Ile Val Lys Lys Val Leu Ser Ser Gly Lys Lys Ala
225                 230                 235                 240
Ile Gly Ala Gly Ala Gly Asn Pro Pro Val Val Val Asp Glu Thr Ala
                245                 250                 255
Asp Ile Glu Lys Ala Ala Arg Asp Ile Val Asp Gly Cys Ser Phe Asp
            260                 265                 270
Asn Asn Val Pro Cys Ile Ala Glu Lys Glu Val Phe Ala Val Asp Ser
        275                 280                 285
Ile Cys Asp Tyr Leu Ile Gln Asn Met Lys Leu Asn Gly Ala Tyr Glu
    290                 295                 300
Ile Arg Asp Ala Glu Thr Ile Glu Arg Leu Asp Ala Leu Val Thr Asn
305                 310                 315                 320
Glu Lys Gly Gly Pro Lys Thr Ser Phe Val Gly Lys Ser Ala Lys Tyr
                325                 330                 335
Ile Leu Asp Lys Met Gly Ile Pro Ala Asp Asp Ser Val Lys Val Ile
            340                 345                 350
Ile Met Glu Val Arg Arg Asp His Leu Val Thr Glu Glu Met Met
    355                 360                 365
Met Pro Ile Leu Pro Ile Val Arg Val Ser Asp Val Asp Thr Ala Ile
        370                 375                 380
Glu Tyr Ala His Asp Ala Glu His Gly Asn Arg His Thr Ala Met Met
385                 390                 395                 400
His Ser Lys Asn Val Glu Lys Leu Ser Lys Met Ala Lys Leu Leu Glu
                405                 410                 415
```

```
Thr Thr Ile Phe Val Lys Asn Ala Pro Ser Tyr Ala Gly Ile Gly Ala
                420                 425                 430

Gly Gly Glu Gly His Ala Thr Phe Thr Ile Ala Gly Pro Thr Gly Glu
                435                 440                 445

Gly Leu Thr Ser Ala Arg Ser Phe Cys Arg Lys Arg Arg Cys Val Met
            450                 455                 460

Ser Asp Ala Phe Ser Ile Arg
465                 470

<210> SEQ ID NO 91
<211> LENGTH: 469
<212> TYPE: PRT
<213> ORGANISM: Fusobacterium varium

<400> SEQUENCE: 91

Met Asn Leu Glu Ala Asn Asn Met Asp Glu Ile Val Ala Leu Ile Met
1               5                   10                  15

Lys Glu Leu Lys Lys Thr Asp Ile Lys Thr Val Cys Gln Ser Cys Glu
            20                  25                  30

Asn Pro Lys Asn Gly Val Phe Ser Met Asp Glu Ala Ile Thr Ala
            35                  40                  45

Ala Lys Lys Ala Gln Glu Ile Leu Phe Ser Ser Arg Leu Glu Met Arg
50                  55                  60

Glu Lys Ile Val Ala Ser Ile Arg Glu Val Met Lys Asp Tyr Val Leu
65                  70                  75                  80

Glu Leu Ala Glu Leu Gly Val Lys Glu Thr Gly Met Gly Arg Val Ala
            85                  90                  95

Asp Lys Ala Leu Lys His Gln Val Thr Ile Glu Lys Thr Pro Gly Val
            100                 105                 110

Glu Asp Leu Lys Ala Phe Ala Phe Ser Gly Asp Asp Gly Leu Thr Val
            115                 120                 125

Met Glu Leu Ser Pro Tyr Gly Val Ile Gly Ala Ile Thr Pro Ser Thr
        130                 135                 140

Asn Pro Ser Glu Thr Ile Ile Cys Asn Ser Ile Gly Met Ile Ser Ala
145                 150                 155                 160

Gly Asn Ser Ile Val Phe Ala Pro His Pro Gly Ala Lys Arg Thr Ser
                165                 170                 175

Ile Lys Thr Val Glu Ile Ile Asn Glu Ala Val Arg Lys Val Gly Gly
            180                 185                 190

Pro Glu Asn Leu Val Val Thr Ile Ala Glu Pro Ser Ile Glu Asn Thr
        195                 200                 205

Asn Lys Met Met Ala Asn Pro Asp Ile Lys Met Leu Val Ala Thr Gly
210                 215                 220

Gly Pro Gly Val Val Lys Ser Val Met Ser Ser Gly Lys Lys Ala Ile
225                 230                 235                 240

Gly Ala Gly Ala Gly Asn Pro Pro Val Leu Val Asp Glu Thr Ala Asp
                245                 250                 255

Ile Glu Lys Ala Ala Lys Asp Ile Val Ala Gly Cys Ser Phe Asp Asn
            260                 265                 270

Asn Leu Pro Cys Ile Ala Glu Lys Glu Val Val Ala Val Asp Ser Ile
        275                 280                 285

Thr Asp Tyr Leu Ile Phe Glu Met Gln Lys Asn Gly Ala Tyr Leu Ile
    290                 295                 300

Lys Asp Lys Ala Val Ile Glu Arg Leu Ala Gly Met Val Leu Lys Asn
```

```
305                 310                 315                 320
Gly Ser Pro Asn Arg Ala Tyr Val Gly Lys Asp Ala Ser Tyr Ile Leu
            325                 330                 335

Lys Asp Leu Gly Ile Asn Val Gly Asp Glu Ile Arg Val Ile Ile Ala
            340                 345                 350

Glu Thr Asp Lys Glu His Pro Phe Ala Val Glu Glu Leu Leu Met Pro
            355                 360                 365

Ile Leu Pro Ile Ile Arg Val Lys Asn Ala Leu Glu Gly Ile Glu Val
            370                 375                 380

Ser Lys Lys Leu Glu His Gly Leu Arg His Thr Ala Met Ile His Ser
385                 390                 395                 400

Lys Asn Ile Asp Val Leu Thr Lys Tyr Ala Arg Asp Met Glu Thr Thr
            405                 410                 415

Ile Leu Val Lys Asn Gly Pro Ser Phe Ala Gly Ile Gly Val Gly Gly
            420                 425                 430

Glu Gly His Thr Thr Phe Thr Ile Ala Gly Pro Thr Gly Gly Leu
            435                 440                 445

Thr Ser Ala Lys Ser Phe Ala Arg Asn Arg Arg Cys Val Leu Val Gly
            450                 455                 460

Gly Leu Ser Ile Lys
465

<210> SEQ ID NO 92
<211> LENGTH: 482
<212> TYPE: PRT
<213> ORGANISM: Clostridium celatum

<400> SEQUENCE: 92

Met Asp Asp Asn Thr Lys Leu Ile Gln Asp Ile Val Ala Lys Val Ile
1               5                   10                  15

Ser Glu Ile Gly Thr Lys Glu Ile Glu Glu Ala Cys Cys Gly Asn
            20                  25                  30

Gly Ser Cys Gly Gly Ser Cys Gly Cys Asn Lys Glu Lys Tyr Val Phe
            35                  40                  45

Glu Asp Val Asp Ser Ala Val Ala Ala Lys Lys Ala Tyr Lys Glu
        50                  55                  60

Leu Lys Gln Leu Thr Ile Lys Asp Arg Glu Asn Ile Ile Thr Lys Ile
65              70                  75                  80

Arg Glu Lys Cys Leu Thr Tyr Ser Glu Arg Leu Ser Ile Met Ala Val
            85                  90                  95

Asp Glu Thr Gly Met Gly Lys Val Glu Asp Lys Ile Thr Lys His Val
            100                 105                 110

Leu Val Ala Arg Lys Thr Pro Gly Thr Glu Asp Leu Thr Thr Ala
            115                 120                 125

Trp Ser Gly Asp Gly Leu Thr Leu Val Glu Arg Gly Ala Phe Gly
130             135                 140

Val Ile Ala Ala Ile Thr Pro Ser Thr Asn Pro Thr Ala Thr Ile Phe
145             150                 155                 160

Cys Asn Ser Ile Gly Met Ile Ala Ala Gly Asn Ser Val Val Phe Ala
            165                 170                 175

Pro His Pro Ala Ala Lys Ser Cys Ser Lys Phe Ala Val Lys Leu Ile
            180                 185                 190

Asn Glu Ala Ser Ile Glu Val Gly Gly Pro Glu Asn Ile Val Val Thr
            195                 200                 205
```

```
Phe Glu Asn Pro Ser Ile Glu Ile Thr Ser Ala Leu Met Lys His Lys
    210                 215                 220

Asp Ile Pro Phe Ile Ser Ala Thr Gly Gly Pro Gly Val Val Thr Gln
225                 230                 235                 240

Ala Cys Ser Ser Gly Lys Arg Ala Ile Gly Ala Gly Ala Gly Asn Pro
                245                 250                 255

Pro Val Leu Val Asp Glu Thr Ala Asp Ile Lys His Ala Ala Lys Ser
                260                 265                 270

Ile Ile Ala Gly Ala Thr Phe Asp Asn Asn Leu Pro Cys Ile Ala Glu
                275                 280                 285

Lys Glu Val Val Ala Leu Asp Ser Ile Cys Asp Glu Leu Ile Glu Asp
    290                 295                 300

Met Gln Lys Glu Gly Ala Tyr Phe Leu Asn Ser Thr Glu Leu Ile Asn
305                 310                 315                 320

Arg Leu Ile Asp Thr Val Leu Ile Arg Lys Asp Gly Lys Val Thr Leu
                325                 330                 335

Asn Arg Asn Phe Val Gly Arg Asp Ala Lys Ile Ile Leu Asp Ala Ile
                340                 345                 350

Gly Val Tyr Ala Asp Asp Ser Val Lys Cys Ile Ile Phe Glu Gly Cys
                355                 360                 365

Lys Ser Asn Leu Leu Ile Val Glu Glu Leu Met Met Pro Ile Leu Gly
    370                 375                 380

Ile Val Arg Val Lys Asp Phe Asn Thr Ala Val Asp Val Ala Val Glu
385                 390                 395                 400

Leu Glu His Gly Asn Arg His Ser Ala His Ile His Ser Lys Arg Ile
                405                 410                 415

Asp Arg Leu Thr Tyr Phe Ala Arg Glu Ile Asp Thr Ala Ile Phe Val
                420                 425                 430

Lys Asn Ala Pro Ser Tyr Ser Ala Leu Gly Val Glu Ala Glu Gly Tyr
                435                 440                 445

Pro Thr Phe Thr Ile Ala Ser Arg Thr Gly Glu Gly Leu Ser Ser Ala
                450                 455                 460

Lys Thr Phe Ser Lys Ser Arg Arg Cys Ile Met Lys Asp Ala Leu Ser
465                 470                 475                 480

Ile Lys

<210> SEQ ID NO 93
<211> LENGTH: 462
<212> TYPE: PRT
<213> ORGANISM: Clostridium sp.

<400> SEQUENCE: 93

Met Ser Val Asn Glu Arg Met Val Gln Asp Ile Val Gln Glu Val Val
1               5                   10                  15

Ala Lys Met Gln Ile Ala Ser Asp Val Thr Gly Asn His Gly Val Phe
                20                  25                  30

Gln Asp Met Asn Ala Ala Ile Glu Ala Ala Lys Lys Thr Gln Lys Val
                35                  40                  45

Val Ala Arg Met Ser Met Asp Gln Arg Glu Lys Ile Ile Ser Asn Ile
            50                  55                  60

Arg Ala Lys Ile Lys Glu His Ala Glu Ile Phe Ala Arg Met Gly Val
65              70                  75                  80

Gln Glu Thr Gly Met Gly Asn Val Gly His Lys Ile Leu Lys His Gln
                85                  90                  95
```

```
Leu Val Ala Glu Lys Thr Pro Gly Thr Glu Asp Ile Gln Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Val Leu
    130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Tyr Ala Val Asn Leu Ile
                165                 170                 175

Asn Glu Ala Ser Leu Glu Ala Gly Gly Pro Asp Asn Ile Ala Cys Thr
            180                 185                 190

Val Glu Asn Pro Thr Leu Glu Ser Ser Asn Ile Met Met Lys His Lys
        195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Ile Ala Asp Glu Leu Met His Tyr
        275                 280                 285

Met Ile Ser Glu Gln Gly Cys Tyr Leu Ala Ser Lys Glu Glu Gln Asp
    290                 295                 300

Ala Leu Thr Glu Val Val Leu Lys Gly Gly Arg Leu Asn Arg Lys Cys
305                 310                 315                 320

Val Gly Arg Asp Ala Lys Thr Leu Leu Gly Met Ile Gly Val Thr Val
                325                 330                 335

Pro Asp Asn Ile Arg Cys Ile Thr Phe Glu Gly Pro Lys Glu His Pro
            340                 345                 350

Leu Ile Ala Glu Glu Leu Met Met Pro Ile Leu Gly Val Val Arg Ala
        355                 360                 365

Lys Asp Phe Asp Asp Ala Val Glu Gln Ala Val Trp Leu Glu His Gly
    370                 375                 380

Asn Arg His Ser Ala His Ile His Ser Lys Asn Val Asp Asn Ile Thr
385                 390                 395                 400

Lys Tyr Ala Lys Ala Ile Asp Thr Ala Ile Leu Val Lys Asn Gly Pro
                405                 410                 415

Ser Tyr Ala Ala Ile Gly Phe Gly Gly Glu Gly Phe Cys Thr Phe Thr
            420                 425                 430

Ile Ala Ser Arg Thr Gly Glu Gly Leu Thr Ser Ala Ser Ala Phe Thr
        435                 440                 445

Lys Arg Arg Arg Cys Val Met Cys Asp Ser Leu Cys Ile Arg
    450                 455                 460

<210> SEQ ID NO 94
<211> LENGTH: 462
<212> TYPE: PRT
<213> ORGANISM: Lachnospiraceae bacterium

<400> SEQUENCE: 94

Met Ser Val Asn Glu Gln Met Val Gln Asp Ile Val Gln Glu Val Met
1               5                   10                  15
```

```
Ala Lys Met Gln Ile Thr Ser Asp Val Ser Gly Ser His Gly Val Phe
             20                  25                  30

Lys Asp Met Asn Glu Ala Ile Ala Ala Lys Lys Thr Gln Lys Ile
         35                  40                  45

Val Gly Lys Met Ser Met Asp Gln Arg Glu Lys Ile Ile Ser Asn Ile
 50                  55                  60

Arg Thr Lys Ile Lys Glu Asn Ala Glu Ile Met Ala Arg Met Gly Val
 65                  70                  75                  80

Gln Glu Thr Gly Met Gly Asn Val Gly His Lys Ile Leu Lys His Val
                 85                  90                  95

Leu Val Ala Glu Lys Thr Pro Gly Thr Glu Asp Ile Thr Thr Ala
             100                 105                 110

Trp Ser Gly Asp Arg Gly Leu Thr Leu Ile Glu Met Gly Pro Phe Gly
             115                 120                 125

Val Ile Gly Ala Ile Thr Pro Cys Thr Asn Pro Ser Glu Thr Val Leu
 130                 135                 140

Cys Asn Thr Ile Gly Met Leu Ala Gly Gly Asn Thr Val Val Phe Asn
145                 150                 155                 160

Pro His Pro Ala Ala Ile Lys Thr Ser Ile Phe Ala Ile Asn Leu Leu
                 165                 170                 175

Asn Glu Ala Ser Leu Glu Ala Gly Gly Pro Asp Asn Ile Ala Cys Thr
             180                 185                 190

Val Glu Lys Pro Thr Leu Ala Ser Ser Asp Ile Met Met Lys His Lys
             195                 200                 205

Asp Ile Pro Leu Ile Ala Ala Thr Gly Gly Pro Gly Val Val Thr Ala
             210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                 245                 250                 255

Ile Val Asn Gly Cys Thr Phe Asp Asn Asn Leu Pro Cys Ile Ala Glu
             260                 265                 270

Lys Glu Ile Val Ala Val Asp Ser Ile Ala Asp Glu Leu Met Tyr Tyr
             275                 280                 285

Met Val Ser Glu Gln Gly Cys Tyr Lys Ile Thr Lys Glu Glu Gln Asp
 290                 295                 300

Ala Leu Thr Ala Val Val Leu Lys Asp Gly Lys Leu Asn Arg Lys Cys
305                 310                 315                 320

Val Gly Arg Asp Ala Lys Thr Leu Leu Gly Met Ile Gly Val Thr Val
                 325                 330                 335

Pro Asp Asn Ile Arg Cys Ile Thr Phe Glu Gly Pro Lys Glu His Pro
             340                 345                 350

Leu Ile Ala Glu Glu Leu Met Met Pro Ile Leu Gly Val Val Arg Ala
             355                 360                 365

Lys Asp Phe Asp Asp Ala Val Glu Gln Ala Val Trp Leu Glu His Gly
             370                 375                 380

Asn Arg His Ser Ala His Ile His Ser Lys Asn Val Asp Asn Ile Thr
385                 390                 395                 400

Thr Tyr Ala Lys Ala Ile Asp Thr Ala Ile Leu Val Lys Asn Gly Pro
                 405                 410                 415

Ser Tyr Ala Ala Leu Gly Phe Gly Gly Glu Gly Tyr Cys Thr Phe Thr
             420                 425                 430
```

```
Ile Ala Ser Arg Thr Gly Glu Gly Leu Thr Ser Ala Ser Thr Phe Thr
            435                 440                 445

Lys Arg Arg Cys Val Met Thr Asp Ser Leu Cys Ile Arg
    450                 455                 460

<210> SEQ ID NO 95
<211> LENGTH: 463
<212> TYPE: PRT
<213> ORGANISM: Lachnospiraceae bacterium

<400> SEQUENCE: 95

Met Pro Val Ser Glu Ser Met Val Gln Asp Ile Val Lys Glu Val Val
1               5                   10                  15

Ala Arg Met Gln Leu Ser Gly Ser Ala Gly Thr Ala Gln His Gly Val
                20                  25                  30

Phe Thr Asp Met Asn Gln Ala Ile Glu Ala Ala Lys Glu Ala Glu Ala
            35                  40                  45

Lys Val Arg Cys Met Thr Met Asp Gln Arg Glu Gln Ile Val Ser Asn
    50                  55                  60

Ile Arg Arg Lys Thr His Glu Asn Ala Glu Leu Leu Ala Arg Met Gly
65                  70                  75                  80

Val Glu Glu Thr Gly Met Gly Asn Val Gly Asp Lys Ile Leu Lys His
                85                  90                  95

His Leu Leu Ala Asp Lys Thr Pro Gly Thr Glu Asp Ile Thr Thr Thr
            100                 105                 110

Ala Trp Ser Gly Asp Arg Gly Leu Thr Leu Ile Glu Met Gly Pro Phe
        115                 120                 125

Gly Val Ile Gly Ala Ile Thr Pro Cys Thr Asn Pro Ser Glu Thr Val
130                 135                 140

Leu Cys Asn Ser Met Gly Met Ile Ala Ala Gly Asn Thr Val Val Phe
145                 150                 155                 160

Asn Pro His Pro Gln Ala Ile Lys Thr Ser Ile Phe Ala Ile Asn Met
                165                 170                 175

Val Asn Glu Ala Ser Leu Glu Ala Gly Gly Pro Asp Asn Val Ala Cys
            180                 185                 190

Thr Val Ser Lys Pro Thr Leu Glu Thr Ser Asn Ile Met Met Lys His
        195                 200                 205

Lys Asp Ile Pro Leu Ile Ala Ala Thr Gly Gly Pro Gly Val Val Thr
    210                 215                 220

Ala Val Leu Ser Ser Gly Lys Arg Gly Ile Gly Ala Gly Ala Gly Asn
225                 230                 235                 240

Pro Pro Ala Leu Val Asp Glu Thr Ala Asp Val Arg Lys Ala Ala Ala
                245                 250                 255

Asp Ile Val Asn Gly Cys Thr Phe Asp Asn Asn Leu Pro Cys Ile Ala
            260                 265                 270

Glu Lys Glu Ile Val Ala Val Asp Ser Val Ala Asp Glu Leu Met Asn
        275                 280                 285

Tyr Met Ile Ser Glu Gln Gly Cys Tyr Leu Ile Ser Lys Glu Glu Gln
    290                 295                 300

Asp Lys Leu Thr Ala Thr Val Ile Thr Pro Lys Gly Leu Asn Arg Lys
305                 310                 315                 320

Cys Val Gly Arg Asp Ala Arg Thr Leu Leu Ser Met Ile Gly Ile Gln
                325                 330                 335

Ala Pro Glu Asn Ile Arg Cys Ile Val Phe Glu Gly Glu Lys Glu His
            340                 345                 350
```

```
Pro Leu Ile Ala Glu Glu Leu Met Met Pro Ile Leu Gly Leu Val Arg
        355                 360                 365

Ala Lys Asp Phe Asp Asp Ala Val Glu Lys Ala Val Trp Leu Glu His
    370                 375                 380

Gly Asn Arg His Ser Ala His Ile His Ser Lys Asn Val Asp Asn Ile
385                 390                 395                 400

Thr Lys Tyr Ala Lys Ala Ile Asp Thr Ala Ile Leu Val Lys Asn Ala
            405                 410                 415

Pro Ser Tyr Ala Ala Leu Gly Phe Gly Glu Gly Phe Cys Thr Phe
            420                 425                 430

Thr Ile Ala Ser Arg Thr Gly Glu Gly Leu Thr Ser Ala Ser Thr Phe
        435                 440                 445

Thr Lys Arg Arg Arg Cys Val Met Ser Asp Ser Leu Cys Ile Arg
    450                 455                 460
```

<210> SEQ ID NO 96
<211> LENGTH: 462
<212> TYPE: PRT
<213> ORGANISM: Ruminococcus sp.

<400> SEQUENCE: 96

```
Met Pro Ile Asn Glu Asn Met Val Gln Glu Ile Val Gln Glu Val Met
1               5                   10                  15

Ala Lys Met Gln Ile Ala Asp Ala Pro Thr Gly Lys His Gly Ile Phe
            20                  25                  30

Lys Glu Met Asn Asp Ala Ile Glu Ala Ala Lys Lys Ser Gln Leu Ile
        35                  40                  45

Val Lys Lys Met Ser Met Asp Gln Arg Glu Lys Ile Ile Thr Cys Ile
    50                  55                  60

Arg Lys Lys Ile Lys Glu Asn Ala Glu Val Met Ala Arg Met Gly Val
65                  70                  75                  80

Glu Glu Thr Gly Met Gly Asn Val Gly Asp Lys Ile Leu Lys His His
                85                  90                  95

Leu Val Ala Asp Lys Thr Pro Gly Thr Glu Val Ile Thr Thr Thr Ala
            100                 105                 110

Trp Ser Gly Asp Arg Gly Leu Thr Leu Ile Glu Met Gly Pro Phe Gly
        115                 120                 125

Val Ile Gly Ala Ile Thr Pro Cys Thr Asn Pro Ser Glu Thr Ile Leu
    130                 135                 140

Cys Asn Thr Met Gly Met Leu Ala Gly Gly Asn Thr Val Val Phe Asn
145                 150                 155                 160

Pro His Pro Ala Ala Ile Lys Thr Ser Ile Tyr Ala Ile Asn Leu Leu
                165                 170                 175

Asn Glu Ala Ser Leu Glu Ser Gly Gly Pro Asp Asn Ile Ala Val Thr
            180                 185                 190

Val Glu Lys Pro Thr Leu Glu Thr Ser Asn Val Met Met Lys His Lys
        195                 200                 205

Asp Ile Pro Leu Ile Ala Ala Thr Gly Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Thr Asp
                245                 250                 255

Ile Val Asn Gly Cys Thr Phe Asp Asn Asn Leu Pro Cys Ile Ala Glu
```

```
                260                 265                 270
Lys Glu Ile Val Ala Val Ser Ser Ile Val Asp Glu Leu Met His Tyr
            275                 280                 285
Leu Val Thr Glu Asn Asp Cys Tyr Leu Ala Ser Lys Glu Glu Gln Asp
        290                 295                 300
Lys Leu Thr Glu Val Val Leu Ala Gly Gly Lys Leu Asn Arg Lys Cys
305                 310                 315                 320
Val Gly Arg Asp Ala Arg Thr Leu Leu Ser Met Ile Gly Val Asn Ala
                325                 330                 335
Pro Ala Asn Ile Arg Cys Ile Val Phe Glu Gly Pro Lys Glu His Pro
            340                 345                 350
Leu Ile Thr Thr Glu Leu Met Met Pro Ile Leu Gly Val Val Arg Ala
        355                 360                 365
Arg Asp Phe Asp Asp Ala Val Glu Gln Ala Val Trp Leu Glu His Gly
    370                 375                 380
Asn Arg His Ser Ala His Ile His Ser Lys Asn Ile Asp Asn Ile Thr
385                 390                 395                 400
Lys Tyr Ala Lys Ala Ile Asp Thr Ala Ile Leu Val Lys Asn Ala Pro
                405                 410                 415
Ser Tyr Ala Ala Leu Gly Phe Gly Gly Glu Gly Tyr Cys Thr Phe Thr
            420                 425                 430
Ile Ala Ser Arg Thr Gly Glu Gly Leu Thr Cys Ala Ser Thr Phe Thr
        435                 440                 445
Lys Arg Arg Arg Cys Val Met Ala Asp Ser Leu Cys Ile Arg
    450                 455                 460

<210> SEQ ID NO 97
<211> LENGTH: 469
<212> TYPE: PRT
<213> ORGANISM: Acetobacterium woodii

<400> SEQUENCE: 97

Met Asn Ile Asp Thr Thr Gly Ile Glu Tyr Ile Val Lys Lys Val Met
1               5                   10                  15

Ala Glu Ile Asp Cys Ala Glu Glu Gly Gly Lys Pro Leu Lys Asp Gly
                20                  25                  30

Glu Leu Gly Ile Phe Asn Asp Met Glu Asn Ala Ile Asp Ala Ala Phe
            35                  40                  45

Ile Ala Gln Lys Ser Phe Met Arg Ala Ser Met Ala Phe Arg Ser Lys
        50                  55                  60

Ile Ile Ala Ala Met Arg Ala Glu Met Leu Lys Glu Asn Met Glu
65                  70                  75                  80

Met Ile Cys Gln Met Ala Val Glu Glu Thr Gly Met Gly Asn Tyr Glu
                85                  90                  95

His Lys Leu Leu Lys His Glu Leu Ala Ala Thr Lys Thr Pro Gly Val
            100                 105                 110

Glu Asp Leu Val Ala Asp Ala Phe Thr Gly Asp Asp Gly Leu Thr Leu
        115                 120                 125

Ile Glu Gln Ser Pro Phe Gly Val Ile Gly Ala Val Ser Pro Ser Thr
    130                 135                 140

Asn Pro Ser Glu Thr Ile Ile Cys Asn Gly Ile Gly Met Leu Ala Gly
145                 150                 155                 160

Gly Asn Thr Val Val Phe Ala Pro His Pro Ser Ala Lys Lys Thr Ser
                165                 170                 175
```

```
Ala Leu Val Val Lys Leu Leu Asn Lys Ala Ile Leu Glu Ala Gly Gly
            180                 185                 190

Pro Glu Asn Leu Ile Val Thr Thr Val Lys Pro Thr Ile Asp Ser Ala
            195                 200                 205

Asn Thr Met Phe Ala Ser Pro Lys Ile Thr Met Leu Cys Ala Thr Gly
            210                 215                 220

Gly Pro Gly Val Val Lys Ser Val Leu Gln Ser Gly Lys Lys Ala Ile
225                 230                 235                 240

Gly Ala Gly Ala Gly Asn Pro Pro Ala Leu Val Asp Glu Thr Ala Asp
            245                 250                 255

Ile Glu Lys Ala Gly Lys Asp Ile Ile Asp Gly Cys Cys Phe Asp Asn
            260                 265                 270

Asn Leu Pro Cys Ile Ala Glu Lys Glu Val Val Val Glu Gln Val
            275                 280                 285

Ala Asp Tyr Leu Ile Phe Asn Met Lys Lys Asn Gly Ala Tyr Glu Leu
            290                 295                 300

Lys Asp Ala Gln Lys Ile Lys Glu Leu Glu Leu Val Ile Pro Gly
305                 310                 315                 320

Gly Arg Leu Ser Arg Asp Tyr Val Gly Arg Ser Ala Lys Val Ile Leu
            325                 330                 335

Lys Gly Ile Gly Ile Glu Val Asp Asp Ser Val Arg Val Ile Ile
            340                 345                 350

Glu Thr Ser Lys Asp His Ile Phe Ala Val Glu Leu Met Met Pro
            355                 360                 365

Ile Leu Ala Ile Val Arg Val Lys Asp Val Ala Glu Gly Ile Asp Leu
            370                 375                 380

Ala Val Ser Leu Glu His Gly Asn Arg His Thr Ala Ile Met His Ser
385                 390                 395                 400

Thr Asn Ile Asn Asn Leu Thr Glu Met Ala Lys Arg Val Gln Thr Thr
            405                 410                 415

Ile Phe Val Lys Asn Gly Pro Ser Tyr Ala Gly Ile Gly Val Gly Gly
            420                 425                 430

Glu Gly Tyr Thr Thr Phe Thr Ile Ala Gly Pro Thr Gly Glu Gly Leu
            435                 440                 445

Thr Ser Ala Lys Thr Phe Thr Arg Lys Arg Arg Cys Val Leu Val Gly
450                 455                 460

Gly Phe Thr Ile Lys
465

<210> SEQ ID NO 98
<211> LENGTH: 497
<212> TYPE: PRT
<213> ORGANISM: Clostridium botulinum

<400> SEQUENCE: 98

Met Asn Asp Phe Asn Met Ile Asp Ile Glu Ser Ile Val Lys Asn Ile
1               5                   10                  15

Val Lys Glu Leu Thr Gly Asn Glu Lys Gly Gln Gly Ala Ile Thr Thr
            20                  25                  30

Ala Thr Ala Pro Lys Glu Ala Asn Pro Leu Val Asp Ile Glu Lys Lys
            35                  40                  45

Ile Met Gly Phe Met Asn Thr Pro Thr Met Pro Val Gly Glu Tyr Gly
            50                  55                  60

Val Phe Glu Asp Ile Asn Asp Ala Ile Glu Gln Ala Trp Leu Ala Glu
65                  70                  75                  80
```

-continued

```
Gln Glu Tyr Arg Lys Val Gly Leu Asp Lys Arg Thr Glu Ile Ile Glu
             85                  90                  95
Ala Phe Lys Ala Glu Val Arg Lys Asn Val Glu Ile Ser Arg Arg
            100                 105                 110
Thr Phe Glu Glu Thr Gly Met Gly Arg Tyr Glu Asp Lys Ile Leu Lys
            115                 120                 125
Asn Asn Leu Ala Leu Asp Lys Thr Pro Gly Val Glu Asp Leu Glu Ala
130                 135                 140
Gly Val Lys Thr Gly Asp Gly Gly Leu Thr Leu Tyr Glu Met Ser Pro
145                 150                 155                 160
Phe Gly Val Ile Gly Ala Ile Ala Pro Ser Thr Asn Pro Thr Glu Thr
                165                 170                 175
Ile Ile Asn Asn Gly Ile Ser Met Leu Ala Gly Gly Asn Thr Val Val
                180                 185                 190
Phe Ser Pro His Pro Gly Ala Lys Asp Val Ser Val Phe Ile Val Gln
            195                 200                 205
Leu Ile Asn Lys Ala Ile Glu Arg Ile Asn Gly Pro Lys Asn Leu Ile
            210                 215                 220
Val Thr Val Lys Asn Pro Asn Ile Glu Ser Thr Asn Ile Met Leu Ala
225                 230                 235                 240
His Pro Lys Val Asn Met Ile Cys Ala Thr Gly Gly Pro Gly Ile Val
                245                 250                 255
Lys Val Ala Leu Ser Ser Gly Lys Lys Ala Ile Gly Ala Gly Ala Gly
                260                 265                 270
Asn Pro Pro Val Val Asp Glu Thr Ala Asp Ile Glu Lys Ala Ala
            275                 280                 285
Val Asp Ile Ile Asp Gly Cys Ser Phe Asp Asn Asn Leu Pro Cys Ile
290                 295                 300
Cys Glu Lys Glu Val Ile Val Val Asp Lys Val Ala Asp Tyr Leu Lys
305                 310                 315                 320
Thr Cys Met Ser Lys Tyr Cys Ala Leu Glu Ile Thr Asp Lys Asn Met
                325                 330                 335
Leu Ala Gln Leu Glu Lys Leu Val Leu Thr Glu Asn Gly Thr Ile Asn
            340                 345                 350
Lys Gln Phe Val Gly Lys Asn Ala Asp Tyr Ile Met Ser Lys Leu Gly
            355                 360                 365
Val Asn Ile Asp Pro Ser Ile Arg Val Ile Phe Ala Glu Val Glu Ala
            370                 375                 380
Asn His Pro Phe Ala Val Glu Glu Leu Met Met Pro Ile Leu Pro Val
385                 390                 395                 400
Ile Arg Val Arg Asn Val Asp Glu Ala Ile Asp Leu Gly Val Glu Leu
                405                 410                 415
Glu His Gly Asn Arg His Thr Ala Ile Met His Ser Lys His Ile Asp
                420                 425                 430
Asn Leu Ser Lys Phe Ala Lys Ala Val Gln Thr Thr Ile Phe Val Lys
            435                 440                 445
Asn Ala Pro Ser Tyr Ala Gly Ile Gly Tyr Gly Ala Glu Gly His Gly
450                 455                 460
Thr Phe Thr Ile Ala Gly Pro Thr Gly Glu Gly Leu Thr Ser Ala Arg
465                 470                 475                 480
Thr Phe Thr Arg Lys Arg Arg Cys Val Met Val Asp Asn Phe Ser Ile
                485                 490                 495
```

Lys

<210> SEQ ID NO 99
<211> LENGTH: 497
<212> TYPE: PRT
<213> ORGANISM: Clostridium botulinum

<400> SEQUENCE: 99

Met Asn Asp Phe Asn Met Ile Asp Ile Glu Ser Ile Val Lys Asn Ile
1               5                   10                  15

Val Lys Glu Leu Thr Gly Asn Glu Lys Glu Gln Gly Ala Ile Ile Thr
            20                  25                  30

Ala Thr Ala Pro Lys Glu Val Asn Pro Leu Val Asp Ile Glu Lys Lys
        35                  40                  45

Ile Met Gly Phe Met Asn Thr Pro Thr Met Gln Ala Gly Glu Tyr Gly
    50                  55                  60

Val Phe Glu Asp Ile Asn Asp Ala Ile Glu Gln Ala Trp Leu Ala Glu
65                  70                  75                  80

Gln Glu Tyr Arg Lys Val Gly Leu Asp Lys Arg Thr Glu Ile Ile Glu
                85                  90                  95

Val Phe Lys Ala Glu Val Arg Lys Asn Val Glu Glu Ile Ser Arg Arg
            100                 105                 110

Thr Phe Glu Glu Thr Gly Met Gly Arg Tyr Glu Asp Lys Ile Leu Lys
        115                 120                 125

Asn Asn Leu Ala Leu Asp Lys Thr Pro Gly Val Glu Asp Leu Glu Ala
    130                 135                 140

Gly Val Lys Thr Gly Asp Gly Leu Thr Leu Tyr Glu Met Ser Pro
145                 150                 155                 160

Phe Gly Val Ile Gly Ala Ile Ala Pro Ser Thr Asn Pro Thr Glu Thr
                165                 170                 175

Ile Ile Asn Asn Gly Ile Ser Met Leu Ala Gly Gly Asn Thr Val Val
            180                 185                 190

Phe Ser Pro His Pro Gly Ala Lys Asp Val Ser Val Phe Ile Ile Gln
        195                 200                 205

Leu Ile Asn Lys Ala Ile Glu Arg Val Asn Gly Pro Lys Asn Leu Ile
    210                 215                 220

Val Thr Val Arg Asn Pro Asn Ile Glu Ser Thr Asn Ile Met Leu Ser
225                 230                 235                 240

His Pro Lys Val Asn Met Ile Cys Ala Thr Gly Gly Pro Gly Ile Val
                245                 250                 255

Lys Val Ala Leu Ser Ser Gly Lys Lys Ala Val Gly Ala Gly Ala Gly
            260                 265                 270

Asn Pro Pro Val Val Asp Glu Thr Ala Asp Ile Glu Lys Ala Ala
        275                 280                 285

Val Asp Ile Ile Asp Gly Cys Ser Phe Asp Asn Asn Leu Pro Cys Ile
    290                 295                 300

Cys Glu Lys Glu Val Ile Val Asp Lys Val Thr Asp Tyr Leu Lys
305                 310                 315                 320

Thr Cys Met Ser Lys Tyr Cys Ala Leu Glu Ile Thr Asp Lys Asn Met
                325                 330                 335

Leu Ala Gln Leu Glu Lys Leu Val Leu Thr Glu Asn Gly Thr Ile Asn
            340                 345                 350

Lys Lys Phe Val Gly Lys Asn Ala Asp Tyr Ile Met Ser Lys Leu Gly
        355                 360                 365

```
Ile Asn Ile Asp Pro Ser Ile Arg Val Ile Phe Ala Glu Val Gly Ala
        370                 375                 380

Asn His Pro Phe Ala Val Glu Glu Leu Met Met Pro Ile Leu Pro Ile
385                 390                 395                 400

Ile Arg Val Arg Asn Val Asp Glu Ala Ile Glu Leu Gly Val Glu Leu
                405                 410                 415

Glu His Gly Asn Arg His Thr Ala Ile Met His Ser Lys His Ile Asp
                420                 425                 430

Asn Leu Ser Lys Phe Ala Lys Ala Val Gln Thr Thr Ile Phe Val Lys
            435                 440                 445

Asn Ala Pro Ser Tyr Ala Gly Ile Gly Tyr Gly Ala Glu Gly His Gly
450                 455                 460

Thr Phe Thr Ile Ala Gly Pro Thr Gly Glu Gly Leu Thr Ser Ala Arg
465                 470                 475                 480

Thr Phe Thr Arg Lys Arg Arg Cys Val Met Val Asp Asn Phe Ser Ile
                485                 490                 495

Lys

<210> SEQ ID NO 100
<211> LENGTH: 497
<212> TYPE: PRT
<213> ORGANISM: Clostridium botulinum

<400> SEQUENCE: 100

Met Asn Asp Phe Asn Met Ile Asp Ile Glu Ser Ile Val Lys Asn Ile
1               5                   10                  15

Val Lys Glu Leu Thr Gly Asn Glu Lys Glu Gln Gly Thr Ile Thr Thr
                20                  25                  30

Ala Ala Val Pro Lys Glu Val Asn Pro Leu Val Asp Ile Glu Lys Lys
            35                  40                  45

Ile Met Gly Phe Val Asn Thr Pro Thr Met Pro Ile Gly Glu His Gly
        50                  55                  60

Val Phe Glu Asp Ile Asn Asp Ala Ile Glu Gln Ala Trp Ile Ala Glu
65                  70                  75                  80

Gln Glu Tyr Arg Lys Val Gly Leu Asp Lys Arg Thr Glu Ile Ile Glu
                85                  90                  95

Ala Phe Lys Ala Glu Val Arg Lys Asn Val Glu Glu Ile Ser Arg Arg
            100                 105                 110

Thr Phe Glu Glu Thr Gly Met Gly Arg Tyr Glu Asp Lys Ile Leu Lys
        115                 120                 125

Asn Asn Leu Ala Leu Asp Lys Thr Pro Gly Val Glu Asp Leu Glu Ala
    130                 135                 140

Gly Val Lys Thr Gly Asp Gly Leu Thr Leu Tyr Glu Met Ser Pro
145                 150                 155                 160

Phe Gly Val Ile Gly Ala Ile Ala Pro Ser Thr Asn Pro Thr Glu Thr
                165                 170                 175

Ile Ile Asn Asn Gly Ile Ser Met Leu Ala Gly Gly Asn Thr Val Val
            180                 185                 190

Phe Ser Pro His Pro Gly Ala Lys Asp Val Ser Val Phe Ile Ile Gln
        195                 200                 205

Leu Ile Asn Lys Ala Ile Glu Arg Val Asn Gly Pro Lys Asn Leu Ile
    210                 215                 220

Val Thr Val Arg Asn Pro Asn Ile Glu Ser Thr Asn Ile Met Leu Ala
225                 230                 235                 240
```

His Pro Lys Val Asn Met Ile Cys Ala Thr Gly Gly Pro Gly Ile Val
            245                 250                 255

Lys Val Ala Leu Ser Ser Gly Lys Lys Ala Ile Gly Ala Gly Ala Gly
        260                 265                 270

Asn Pro Pro Val Val Asp Glu Thr Ala Asp Ile Glu Lys Ala Ala
        275                 280                 285

Val Asp Ile Ile Asp Gly Cys Ser Phe Asp Asn Asn Leu Pro Cys Ile
    290                 295                 300

Cys Glu Lys Glu Val Ile Val Asp Lys Val Ala Asp Tyr Leu Lys
305                 310                 315                 320

Thr Cys Met Ser Lys Tyr Cys Ala Leu Glu Ile Thr Asp Lys Asn Met
            325                 330                 335

Leu Ala Gln Leu Glu Lys Leu Val Leu Thr Glu Asn Gly Thr Ile Asn
        340                 345                 350

Lys Lys Phe Val Gly Lys Asn Ala Asp Tyr Ile Met Ser Lys Leu Gly
        355                 360                 365

Val Asn Ile Asp Pro Ser Ile Arg Val Ile Phe Ala Glu Val Glu Ala
    370                 375                 380

Asn His Pro Phe Ala Val Glu Glu Leu Met Met Pro Ile Leu Pro Val
385                 390                 395                 400

Ile Arg Val Arg Asn Val Asp Glu Ala Ile Asp Leu Gly Val Glu Leu
            405                 410                 415

Glu His Gly Asn Arg His Thr Ala Ile Met His Ser Lys His Ile Asp
        420                 425                 430

Asn Leu Ser Lys Phe Ala Lys Ala Val Gln Thr Thr Ile Phe Val Lys
        435                 440                 445

Asn Ala Pro Ser Tyr Ala Gly Ile Gly Tyr Gly Ala Glu Gly His Gly
    450                 455                 460

Thr Phe Thr Ile Ala Gly Pro Thr Gly Glu Gly Leu Thr Ser Ala Arg
465                 470                 475                 480

Thr Phe Thr Arg Lys Arg Arg Cys Val Met Val Asp Asn Phe Ser Ile
            485                 490                 495

Lys

<210> SEQ ID NO 101
<211> LENGTH: 462
<212> TYPE: PRT
<213> ORGANISM: Eubacterium plexicaudatum

<400> SEQUENCE: 101

Met Ser Val Asn Asp Gln Met Val Gln Asp Ile Val Arg Gln Val Leu
1               5                   10                  15

Ala Asn Met Arg Ile Ser Ser Asp Ala Ser Gly Ser Arg Gly Val Phe
            20                  25                  30

Ser Asp Met Asn Glu Ala Val Glu Ala Ala Lys Lys Ala Gln Ala Val
        35                  40                  45

Ile Gly Lys Met Pro Met Asp His Arg Glu Lys Ile Ser Ser Ile
    50                  55                  60

Arg Ala Lys Ile Met Glu Asn Ala Glu Ile Leu Ala Arg Met Gly Val
65                  70                  75                  80

Lys Glu Thr Gly Met Gly Asn Val Gly His Lys Ile Leu Lys His Gln
            85                  90                  95

Leu Val Ala Glu Lys Thr Pro Gly Thr Glu Asp Ile Thr Thr Lys Ala
        100                 105                 110

```
Trp Ser Gly Asp Arg Gly Leu Thr Leu Ile Glu Met Gly Pro Phe Gly
            115                 120                 125

Val Ile Gly Ala Ile Thr Pro Cys Thr Asn Pro Ser Glu Thr Ile Leu
130                 135                 140

Cys Asn Thr Ile Gly Met Val Ala Gly Gly Asn Thr Val Val Phe Asn
145                 150                 155                 160

Pro His Pro Ala Ala Ile Lys Thr Ser Ile Phe Ala Val Asn Leu Val
                165                 170                 175

Asn Glu Ala Ser Val Glu Ala Gly Gly Pro Asp Asn Ile Ala Cys Thr
            180                 185                 190

Val Glu His Pro Thr Leu Asp Thr Ser Ala Ile Met Met Lys His Lys
        195                 200                 205

Asp Ile His Leu Ile Ala Ala Thr Gly Pro Gly Val Val Thr Ala
    210                 215                 220

Val Leu Ser Ser Gly Lys Arg Gly Ile Gly Ala Gly Ala Gly Asn Pro
225                 230                 235                 240

Pro Ala Leu Val Asp Glu Thr Ala Asp Ile Arg Lys Ala Ala Glu Asp
                245                 250                 255

Ile Val Asn Gly Cys Thr Phe Asp Asn Asn Leu Pro Cys Ile Ala Glu
            260                 265                 270

Lys Glu Ile Val Ala Val Asp Ser Ile Ala Asp Glu Leu Met His Tyr
        275                 280                 285

Met Ile Ser Glu Gln Gly Cys Tyr Leu Ala Ser Ala Lys Glu Gln Glu
    290                 295                 300

Ala Leu Ile Ser Val Val Leu Lys Gly Gly Gln Leu Asn Arg Asp Cys
305                 310                 315                 320

Val Gly Arg Asp Ala Lys Thr Leu Leu Gly Met Ile Gly Val Gln Ala
                325                 330                 335

Pro Asp Asn Ile Arg Cys Ile Thr Phe Glu Gly Pro Lys Glu His Pro
            340                 345                 350

Leu Ile Thr Glu Glu Leu Met Met Pro Ile Leu Gly Val Val Arg Ala
        355                 360                 365

Asp Ser Phe Glu Asp Ala Val Glu Lys Ala Val Trp Leu Glu His Gly
    370                 375                 380

Asn Arg His Ser Ala His Ile His Ser Lys Asn Val Asp His Ile Thr
385                 390                 395                 400

Thr Tyr Ala Lys Ala Ile Asp Thr Ala Ile Leu Val Lys Asn Gly Pro
                405                 410                 415

Ser Tyr Ala Ala Ile Gly Phe Gly Gly Glu Gly Tyr Cys Thr Phe Thr
            420                 425                 430

Ile Ala Ser Arg Thr Gly Glu Gly Leu Thr Ser Ala Ser Ala Phe Thr
        435                 440                 445

Lys Arg Arg Arg Cys Val Met Cys Asp Ser Leu Cys Ile Arg
    450                 455                 460

<210> SEQ ID NO 102
<211> LENGTH: 467
<212> TYPE: PRT
<213> ORGANISM: Thermosediminibacter oceani

<400> SEQUENCE: 102

Met Val Asp Glu Lys Val Val Glu Ala Ile Ala Lys Arg Ile Ile Glu
1               5                   10                  15

Glu Leu Asn Leu Cys Glu Ser Gly Ser Ser Gly Gly Glu Ser Arg Glu
            20                  25                  30
```

```
Glu Leu Gly Ile Phe Asp Asn Leu Asp Asp Ala Val Glu Ala Ala Ser
         35                  40                  45

Gln Ala Gln Lys Arg Phe Ala Ala Leu Asp Leu Glu Lys Arg Glu Glu
 50                  55                  60

Ile Ile Gln Ala Ile Arg Glu Ala Cys Leu Asn Asn Ala Arg Tyr Leu
 65                  70                  75                  80

Ala Glu Leu Thr Val Asn Glu Thr Gly Ile Gly Arg Val Glu Asp Lys
                 85                  90                  95

Ile Val Lys Asn Ile Leu Ala Ala Lys Lys Thr Pro Gly Thr Glu Asp
                100                 105                 110

Leu Arg Pro Ser Cys Trp Thr Gly Asp His Gly Leu Thr Leu Val Glu
                115                 120                 125

Met Ala Pro Val Gly Val Ile Gly Ser Ile Thr Pro Val Thr Asn Pro
130                 135                 140

Val Ala Thr Val Ile Asn Asn Ser Ile Ser Met Leu Ala Ala Gly Asn
145                 150                 155                 160

Ala Val Val Phe Asn Pro His Pro Ser Ala Lys Arg Ser Ser Asn Lys
                165                 170                 175

Ala Val Glu Ile Ile Asn Glu Ala Ile Met Lys Val Gly Gly Pro Arg
                180                 185                 190

His Leu Val Asn Ser Val Ala Glu Pro Thr Ile Glu Thr Ala Lys Ala
                195                 200                 205

Leu Met Ala His Pro Lys Val Asn Leu Val Ser Val Thr Gly Gly Lys
        210                 215                 220

Ala Val Val Ser Glu Ala Leu Arg Ser Gly Lys Lys Val Ile Gly Ala
225                 230                 235                 240

Gly Ala Gly Asn Pro Pro Val Val Val Asp Glu Thr Ala Asp Ile Val
                245                 250                 255

Lys Ala Ala His Asp Ile Tyr Cys Gly Ala Ser Phe Asp Asn Asn Leu
                260                 265                 270

Pro Cys Ile Ala Glu Lys Glu Leu Ile Ala Val Glu Ala Val Ala Asp
        275                 280                 285

Met Leu Leu Glu Arg Leu Ala Arg Glu Gly Ala Tyr Ile Leu Arg Gly
290                 295                 300

Lys Asp Val Glu Lys Ile Thr Glu Val Val Phe Asp Glu Asn His Arg
305                 310                 315                 320

Ile Asn Lys Lys Leu Val Gly Lys Asp Ala Ser Phe Ile Leu Glu Gln
                325                 330                 335

Ile Gly Ile Gln Val Gly Lys Asp Val Arg Leu Val Val Pro Val
                340                 345                 350

Asn Pro Glu His Pro Leu Val His His Glu Gln Leu Met Pro Val Leu
        355                 360                 365

Pro Phe Val Arg Val Pro Asn Ile Gln Glu Ala Val Glu Leu Ala Val
370                 375                 380

Arg Ala Glu Gly Gly Asn Arg His Thr Ala Val Met His Ser Lys Asn
385                 390                 395                 400

Val Asp Asn Met Thr Asn Phe Ala Arg Ala Ile Gln Thr Thr Ile Phe
                405                 410                 415

Val Lys Asn Ala Pro Ser Tyr Ala Gly Ile Gly Phe Gly Gly Glu Gly
                420                 425                 430

Tyr Ala Thr Phe Thr Ile Ala Gly Pro Thr Gly Glu Gly Leu Thr Ser
        435                 440                 445
```

Ala Arg Thr Phe Thr Arg Gln Arg Arg Cys Val Leu Val Asp Ala Phe
450                 455                 460

Arg Ile Ile
465

<210> SEQ ID NO 103
<211> LENGTH: 479
<212> TYPE: PRT
<213> ORGANISM: Clostridium clostridioforme

<400> SEQUENCE: 103

Met Glu Ile Ser Glu Lys Glu Val Glu Ala Ile Val Arg Ser Val Leu
1               5                   10                  15

Ser Gly Leu Gly Gln Lys Ser Phe Gln Ala Glu Ala Leu His Val Lys
            20                  25                  30

Asp Lys Met Cys Ser Asp Gly Glu Asp Gly Ile Phe Glu Leu Val Glu
        35                  40                  45

Asp Ala Ile Glu Ala Ala Ser Lys Ala Gln Lys Glu Trp Val His Arg
    50                  55                  60

Tyr Lys Leu Lys Asp Arg Lys Arg Ile Ile Glu Ala Ile Arg Val Thr
65                  70                  75                  80

Ser Arg Ala His Ala Glu Ser Leu Ala Arg Met Val His Glu Glu Thr
                85                  90                  95

Gly Met Gly Arg Tyr Glu Asp Lys Ile Thr Lys His Met Ala Val Ile
            100                 105                 110

Asp Lys Thr Pro Gly Val Glu Cys Leu Val Thr Asp Ala Ile Ser Gly
        115                 120                 125

Asp Glu Gly Leu Met Ile Glu Glu Pro Ala Pro Phe Gly Val Ile Gly
    130                 135                 140

Ala Ile Thr Pro Ser Thr Asn Pro Thr Glu Thr Met Ile Asn Asn Thr
145                 150                 155                 160

Ile Ser Met Ile Ala Gly Gly Asn Ala Val Val Phe Asn Val His Pro
                165                 170                 175

Gly Ala Lys Lys Cys Cys Ala Tyr Cys Leu Gln Ile Leu His Arg Ala
            180                 185                 190

Ile Val Glu Asn Gly Gly Pro Lys Asn Leu Ile Thr Met Gln Arg Glu
        195                 200                 205

Pro Asp Met Asp Ala Val His Lys Leu Thr Ser Ser Pro His Ile Arg
    210                 215                 220

Leu Met Val Gly Thr Gly Gly Met Gly Met Val His Ala Leu Leu Cys
225                 230                 235                 240

Ser Gly Lys Arg Thr Ile Gly Ala Gly Ala Gly Asn Pro Pro Val Val
                245                 250                 255

Val Asp Asp Thr Ala Asp Leu Ser Leu Ala Ala Arg Glu Leu Tyr Arg
            260                 265                 270

Gly Ala Ser Phe Asp Asn Asn Leu Leu Cys Leu Ala Glu Lys Glu Val
        275                 280                 285

Phe Val Met Asp Asn Val Ala Glu Glu Leu Asp Arg Leu Val Gly
    290                 295                 300

Glu Gly Ala Tyr Leu Leu Asp Asp Leu Gln Leu Lys Lys Ile Thr Glu
305                 310                 315                 320

Leu Ala Met Val Asn Lys Asp Gly Lys Tyr Glu Val Asn Lys Lys Trp
                325                 330                 335

Val Gly Lys Asp Ala Gly Lys Phe Leu Glu Ala Ile Gly Ile Gln Glu
            340                 345                 350

His Arg Glu Pro Arg Leu Leu Ile Cys Val Thr Asp Arg Ser His Pro
            355                 360                 365

Phe Val Lys Val Glu Gln Leu Met Pro Val Leu Pro Ile Val Arg Cys
        370                 375                 380

Gly Ser Phe Glu Lys Cys Val Glu Trp Ala Val Asp Thr Glu Ala Gly
385                 390                 395                 400

Asn Arg His Thr Ala Ser Ile Phe Ser Lys Asn Val Glu His Met Thr
                405                 410                 415

Leu Phe Gly Lys Glu Ile Glu Thr Thr Ile Tyr Thr Lys Asn Gly Ala
            420                 425                 430

Thr Leu Lys Gly Ile Gly Ile Gly Gly Glu Gly His Thr Thr Met Thr
        435                 440                 445

Ile Ala Gly Pro Thr Gly Glu Gly Leu Thr Cys Ala Arg Ser Phe Thr
    450                 455                 460

Arg Arg Arg Arg Cys Met Leu Ala Glu Gly Gly Leu Arg Ile Ile
465                 470                 475

<210> SEQ ID NO 104
<211> LENGTH: 471
<212> TYPE: PRT
<213> ORGANISM: Clostridium clostridioforme

<400> SEQUENCE: 104

Met Asp Met Asp Ile Lys Val Ile Glu Gln Met Val Glu Gln Ala Leu
1               5                   10                  15

Lys Glu Ile Lys Ala Glu Gln Pro Gln Lys Phe Thr Met Pro Lys Ala
            20                  25                  30

Glu Leu Tyr Gly Val Phe Lys Thr Met Asp Glu Ala Ile Ala Ala Ser
        35                  40                  45

Glu Glu Ala Gln Lys Lys Leu Leu Phe Ser Lys Ile Ser Asp Arg Gln
    50                  55                  60

Lys Tyr Val Asp Val Ile Arg Arg Thr Ile Leu Lys Arg Glu Asn Leu
65                  70                  75                  80

Glu Met Ile Ser Arg Leu Ser Val Glu Glu Thr Glu Ile Gly Asp Tyr
                85                  90                  95

Glu His Lys Leu Ile Lys Asn Arg Leu Ala Ala Glu Lys Thr Pro Gly
            100                 105                 110

Thr Glu Asp Leu Leu Thr Glu Ala Met Thr Gly Asp Asn Gly Leu Thr
        115                 120                 125

Leu Val Glu Tyr Cys Pro Phe Gly Val Ile Gly Ala Ile Thr Pro Thr
    130                 135                 140

Thr Asn Pro Thr Glu Thr Ile Ile Asn Asn Ser Ile Ser Met Ile Ala
145                 150                 155                 160

Gly Gly Asn Thr Val Val Phe Ser Pro His Pro Arg Ala Lys Lys Val
                165                 170                 175

Ser Gln Met Thr Val Lys Leu Leu Asn Lys Ala Leu Thr Glu Ser Gly
            180                 185                 190

Ala Pro Glu Asn Leu Ile Thr Met Val Glu Glu Pro Ser Ile Glu Asn
        195                 200                 205

Thr Asn Lys Met Ile Glu Asn Pro Ser Val Arg Leu Leu Val Ala Thr
    210                 215                 220

Gly Gly Pro Ser Ile Val Lys Lys Val Leu Ser Ser Gly Lys Lys Ala
225                 230                 235                 240

Ile Gly Ala Gly Ala Gly Asn Pro Pro Val Val Val Asp Glu Thr Ala

```
                245                 250                 255
Asp Ile Val Lys Ala Lys Asp Ile Val Asp Gly Cys Ser Phe Asp
            260                 265                 270

Asn Asn Val Pro Cys Ile Ala Glu Lys Glu Val Phe Ala Val Asp Ser
        275                 280                 285

Ile Cys Asp Tyr Leu Ile His Asn Met Lys Glu Asn Gly Ala Tyr Gln
    290                 295                 300

Ile Thr Asp Pro Ala Leu Leu Glu Lys Leu Val Thr Leu Val Thr Asn
305                 310                 315                 320

Glu Lys Gly Gly Pro Lys Thr Ser Phe Val Gly Lys Ser Ala Arg Tyr
                325                 330                 335

Ile Leu Asp Lys Leu Gly Ile Thr Ala Asp Ala Ser Val Arg Val Ile
            340                 345                 350

Ile Met Glu Val Pro Lys Glu His Leu Leu Val Gln Glu Met Met
        355                 360                 365

Met Pro Ile Leu Pro Val Val Arg Val Cys Asp Val Asp Thr Ala Ile
    370                 375                 380

Glu Tyr Ala Arg Gln Ala Glu His Gly Asn Arg His Thr Ala Met Met
385                 390                 395                 400

His Ser Arg Asn Val Glu Lys Leu Ser Lys Met Ala Lys Ile Met Glu
                405                 410                 415

Thr Thr Ile Phe Val Lys Asn Ala Pro Ser Tyr Ala Gly Ile Gly Val
            420                 425                 430

Gly Gly Glu Gly Tyr Thr Thr Phe Thr Ile Ala Gly Pro Thr Gly Glu
        435                 440                 445

Gly Leu Thr Ser Pro Arg Ala Phe Cys Arg Lys Arg Lys Cys Val Met
    450                 455                 460

Thr Asp Ala Phe Ser Ile Arg
465                 470

<210> SEQ ID NO 105
<211> LENGTH: 472
<212> TYPE: PRT
<213> ORGANISM: Ilyobacter polytropus

<400> SEQUENCE: 105

Met Asn Leu Asp Ala Asn Asn Leu Asn Asn Ile Val Ser Leu Ile Met
1               5                   10                  15

Lys Glu Leu Asp Lys Asn Asn Ile Asp Asp Thr Gly Gln Gly Cys
            20                  25                  30

Gly Gly Glu Glu Gly Lys Asn Gly Ile Phe Ser Ser Met Asp Thr Ala
        35                  40                  45

Val Ser Lys Ala Lys Glu Ala Gln Val Thr Leu Phe Ala Ser Lys Leu
    50                  55                  60

Glu Leu Arg Glu Arg Ile Ile Lys Ala Ile Arg Glu Asp Val Arg Glu
65                  70                  75                  80

Ala Ala Ala Glu Leu Ala Glu Ile Ala Val Glu Thr Gly Met Gly
                85                  90                  95

Arg Val Asp Asp Lys Thr Leu Lys His Tyr Val Thr Val Asp Lys Thr
            100                 105                 110

Pro Gly Val Glu Asp Leu Arg Ala Phe Ala Tyr Ser Gly Asp Asn Gly
        115                 120                 125

Leu Thr Val Met Glu Leu Ser Pro Tyr Gly Val Ile Gly Ser Ile Thr
    130                 135                 140
```

```
Pro Ser Thr Asn Pro Ser Glu Thr Ile Val Cys Asn Ala Ile Gly Met
145                 150                 155                 160

Ile Ala Ala Gly Asn Ser Val Val Phe Ala Pro His Pro Gly Ala Lys
                165                 170                 175

Lys Thr Ser Leu Arg Ala Val Glu Ile Leu Asn Lys Ala Val Ala Arg
            180                 185                 190

Ala Gly Gly Pro Asn Asn Leu Val Val Thr Ile Phe Glu Pro Ser Ile
        195                 200                 205

Glu Asn Thr Asn Lys Met Val Lys Asn Pro Asp Ile Lys Met Val Val
        210                 215                 220

Ala Thr Gly Gly Pro Gly Val Val Lys Ser Val Met Ser Ser Gly Lys
225                 230                 235                 240

Lys Ala Ile Gly Ala Gly Ala Gly Asn Pro Pro Val Leu Val Asp Glu
                245                 250                 255

Thr Ala Asp Ile Glu Lys Ala Ala Lys Asp Ile Val Asn Gly Cys Ser
            260                 265                 270

Phe Asp Asn Asn Leu Pro Cys Ile Thr Glu Lys Glu Val Val Ala Val
        275                 280                 285

Asp Ser Ile Thr Asp Tyr Leu Ile Phe Glu Met Gln Lys Asn Gly Ala
        290                 295                 300

Tyr Leu Val Gln Asp Ser Lys Thr Ile Lys Lys Leu Cys Glu Met Val
305                 310                 315                 320

Ile Asn Asp Gly Ser Pro Asn Arg Ala Tyr Val Gly Lys Asn Ala Ser
                325                 330                 335

Tyr Ile Leu Lys Asp Leu Gly Ile Asp Val Gly Asp Glu Ile Lys Val
            340                 345                 350

Ile Ile Val Glu Thr Asp Ala Gly His Pro Leu Ala Val Leu Glu Met
        355                 360                 365

Leu Met Pro Val Leu Pro Ile Val Arg Val Lys Asp Ala Leu Glu Gly
        370                 375                 380

Ile Lys Val Cys Lys Lys Leu Glu Asp Gly Leu Arg His Thr Ala Met
385                 390                 395                 400

Ile His Ser Lys Asn Ile Asp Ile Leu Thr Lys Tyr Ala Arg Asp Met
                405                 410                 415

Glu Thr Thr Ile Leu Val Lys Asn Gly Pro Ser Tyr Ser Gly Ile Gly
            420                 425                 430

Val Gly Gly Glu Gly Tyr Thr Thr Phe Thr Ile Ala Gly Pro Thr Gly
        435                 440                 445

Glu Gly Leu Thr Ser Ala Lys Ser Phe Ala Arg Asn Arg Arg Cys Ala
        450                 455                 460

Leu Val Gly Gly Leu Ser Ile Lys
465                 470

<210> SEQ ID NO 106
<211> LENGTH: 462
<212> TYPE: PRT
<213> ORGANISM: Shuttleworthia satelles

<400> SEQUENCE: 106

Met Ala Asp Glu Gln Leu Val Gln Asn Val Val Arg Glu Val Val Ala
1               5                   10                  15

Arg Met Gln Ile Ser Ala Pro Ala Arg Gly Met His Gly Val Phe Ser
                20                  25                  30

Asp Met Glu Glu Ala Ile Glu Ala Ala Arg Thr Ala Gln Gln Thr Val
            35                  40                  45
```

-continued

```
Arg Leu Leu Pro Met Asp Gln Arg Glu Lys Ile Ile Gly Ala Ile Arg
 50              55                  60
Arg Lys Thr Arg Glu Asn Ala Glu Ile Leu Ala Arg Met Ala Val Asn
 65              70                  75                  80
Glu Thr Gly Met Gly Asn Val Gly Asp Lys Ile Leu Lys His Leu Leu
                 85                  90                  95
Val Ala Asp Lys Val Pro Gly Thr Glu Asp Ile Ser Thr Arg Ala Phe
            100                 105                 110
Ser Gly Asp Arg Gly Leu Thr Leu Ile Glu Met Gly Pro Phe Gly Val
            115                 120                 125
Ile Gly Ala Ile Thr Pro Cys Thr Asn Pro Ser Glu Thr Val Leu Cys
130                 135                 140
Asn Thr Ile Gly Met Leu Ala Gly Gly Asn Thr Val Val Phe Asn Pro
145                 150                 155                 160
His Pro Gln Ala Ile Lys Thr Thr Leu Phe Thr Ile Gln Met Val Asn
                165                 170                 175
Glu Ala Ser Leu Glu Ala Gly Gly Pro Asp Asn Ile Ala Cys Thr Val
                180                 185                 190
Asp Ala Pro Thr Leu Ala Thr Ser Glu Ile Met Met Lys Ser Pro His
            195                 200                 205
Ile Lys Leu Leu Val Ala Thr Gly Gly Pro Gly Val Val Thr Ala Val
210                 215                 220
Leu Ser Ser Gly Lys Arg Ala Ile Gly Ala Gly Ala Gly Asn Pro Pro
225                 230                 235                 240
Ala Leu Val Asp Glu Thr Ala Asp Ile Arg Lys Ala Ala Glu Asp Ile
                245                 250                 255
Val Asn Gly Cys Thr Phe Asp Asn Asn Leu Pro Cys Ile Ala Glu Lys
            260                 265                 270
Glu Ile Val Ala Val Asp Ser Ile Ala Asp Glu Leu Leu His Tyr Met
            275                 280                 285
Leu Thr Glu Gln Gly Cys Tyr Gln Ala Ser Glu Glu Glu Leu Asp Arg
290                 295                 300
Leu Thr Lys Ala Val Met Asp Glu Lys Gly Arg Leu Asn Arg Lys Ala
305                 310                 315                 320
Val Gly Arg Ser Ala Arg Lys Leu Leu Ser Met Ile Gly Val Glu Val
                325                 330                 335
Asp Ala Asn Ile Arg Cys Ile Thr Phe Phe Gly Pro Lys Glu His Pro
                340                 345                 350
Leu Ile Thr Thr Glu Leu Met Met Pro Ile Leu Gly Ile Val Arg Val
            355                 360                 365
Lys Asp Phe Ala Glu Gly Leu Glu Thr Ala Ala Trp Leu Glu His Gly
            370                 375                 380
Asn Lys His Ser Ala His Ile His Ser Lys Asn Val Asp Arg Ile Thr
385                 390                 395                 400
Glu Tyr Ala Arg Arg Leu Asp Thr Thr Ile Thr Val Lys Asn Gly Pro
                405                 410                 415
Ser Tyr Ala Ala Leu Gly Phe Gly Gly Glu Ser Tyr Cys Thr Phe Thr
            420                 425                 430
Ile Ala Ser Arg Thr Gly Glu Gly Leu Thr Ser Ala Arg Ser Phe Ile
            435                 440                 445
Lys Ser Arg His Cys Val Met Thr Asp Ser Leu Cys Val Arg
450                 455                 460
```

-continued

<210> SEQ ID NO 107
<211> LENGTH: 472
<212> TYPE: PRT
<213> ORGANISM: Clostridium beijerinckii

<400> SEQUENCE: 107

Met Asp Val Asp Val Leu Val Glu Lys Leu Val Arg Gln Ala Ile
1               5                   10                  15

Glu Glu Val Lys Asn Lys Asn Leu Leu Asn Leu Asp Lys Phe Glu Ser
            20                  25                  30

Val Lys Asn Tyr Gly Ile Phe Gly Thr Met Asp Ala Ala Val Glu Ala
        35                  40                  45

Ser Phe Val Ala Gln Lys Gln Leu Leu Asn Ala Ser Met Thr Asp Lys
    50                  55                  60

Gln Lys Tyr Val Asp Thr Ile Lys Ala Thr Ile Leu Lys Lys Glu Asn
65                  70                  75                  80

Leu Glu Leu Ile Ser Arg Met Ser Val Glu Glu Thr Glu Ile Gly Lys
                85                  90                  95

Tyr Glu His Lys Leu Ile Lys Asn Arg Val Ala Ala Glu Lys Thr Pro
            100                 105                 110

Gly Ile Glu Asp Leu Thr Thr Glu Ala Met Thr Gly Asp Asn Gly Leu
        115                 120                 125

Thr Leu Val Glu Tyr Cys Pro Phe Gly Val Ile Gly Ala Ile Thr Pro
    130                 135                 140

Thr Thr Asn Pro Thr Glu Thr Ile Ile Cys Asn Ser Ile Ser Met Ile
145                 150                 155                 160

Ala Gly Gly Asn Thr Val Val Phe Ser Pro His Pro Arg Ala Lys Asn
                165                 170                 175

Val Ser Ile Lys Leu Val Thr Met Leu Asn Lys Ala Leu Glu Glu Ala
            180                 185                 190

Gly Ala Pro Asp Asn Leu Ile Ala Thr Val Lys Glu Pro Ser Ile Glu
        195                 200                 205

Asn Thr Asn Ile Met Met Glu His Pro Lys Ile Arg Met Leu Val Ala
    210                 215                 220

Thr Gly Gly Pro Ala Ile Val Asn Lys Val Met Ser Thr Gly Lys Lys
225                 230                 235                 240

Ala Ile Gly Ala Gly Ala Gly Asn Pro Pro Val Val Val Asp Glu Thr
                245                 250                 255

Ala Asp Ile Glu Lys Ala Ala Ile Asp Ile Val Asn Gly Cys Ser Phe
            260                 265                 270

Asp Asn Asn Val Pro Cys Ile Ala Glu Lys Glu Val Phe Ala Val Asp
        275                 280                 285

Gln Ile Cys Asp Tyr Leu Ile His Tyr Met Lys Leu Asn Gly Ala Tyr
    290                 295                 300

Glu Ile Lys Asp Arg Asp Leu Ile Gln Lys Leu Leu Asp Leu Val Thr
305                 310                 315                 320

Asn Glu Asn Gly Gly Pro Lys Val Ser Phe Val Gly Lys Ser Ala Pro
                325                 330                 335

Tyr Ile Leu Asn Lys Leu Gly Ile Ser Val Asp Glu Asn Ile Lys Val
            340                 345                 350

Ile Ile Met Glu Val Glu Lys Asn His His Phe Val Leu Glu Glu Met
        355                 360                 365

Met Met Pro Ile Leu Pro Ile Val Arg Thr Lys Asp Val Asp Glu Ala
    370                 375                 380

```
Ile Glu Cys Ala Tyr Val Ala Glu His Gly Asn Arg His Thr Ala Ile
385                 390                 395                 400

Met His Ser Lys Asn Val Asp Lys Leu Thr Lys Met Ala Arg Leu Leu
                405                 410                 415

Glu Thr Thr Ile Phe Val Lys Asn Ala Pro Ser Tyr Ala Gly Ile Gly
            420                 425                 430

Val Gly Gly Glu Gly Thr Thr Thr Phe Thr Ile Ala Gly Pro Thr Gly
        435                 440                 445

Glu Gly Leu Thr Thr Ala Arg Ser Phe Cys Arg Lys Arg Arg Cys Val
    450                 455                 460

Met Val Asp Ala Phe Asn Ile Arg
465                 470

<210> SEQ ID NO 108
<211> LENGTH: 471
<212> TYPE: PRT
<213> ORGANISM: Clostridium clostridioforme

<400> SEQUENCE: 108

Met Asp Met Asp Ile Lys Val Ile Glu Gln Met Val Glu Gln Ala Leu
1               5                   10                  15

Lys Glu Ile Lys Ala Glu Gln Pro Gln Lys Phe Thr Met Pro Lys Ala
            20                  25                  30

Glu Leu Tyr Gly Val Phe Lys Thr Met Asp Glu Ala Ile Ala Ala Ser
        35                  40                  45

Glu Glu Ala Gln Lys Lys Leu Leu Phe Ser Lys Ile Ser Asp Arg Gln
    50                  55                  60

Lys Tyr Val Asp Val Ile Arg Arg Thr Ile Leu Lys Arg Glu Asn Leu
65                  70                  75                  80

Glu Met Ile Ser Arg Leu Ser Val Glu Glu Thr Glu Ile Gly Asp Tyr
                85                  90                  95

Glu His Lys Leu Ile Lys Asn Arg Leu Ala Ala Glu Lys Thr Pro Gly
            100                 105                 110

Thr Glu Asp Leu Leu Thr Glu Ala Met Thr Gly Asp Asn Gly Leu Thr
        115                 120                 125

Leu Val Glu Tyr Cys Pro Phe Gly Val Ile Gly Ala Ile Thr Pro Thr
    130                 135                 140

Thr Asn Pro Thr Glu Thr Ile Ile Asn Asn Ser Ile Ser Met Ile Ala
145                 150                 155                 160

Gly Gly Asn Thr Val Phe Ser Pro His Pro Arg Ala Lys Lys Val
                165                 170                 175

Ser Gln Met Thr Val Lys Leu Leu Asn Lys Ala Leu Thr Glu Ser Gly
            180                 185                 190

Ala Pro Glu Asn Leu Ile Thr Met Val Glu Glu Pro Ser Ile Glu Asn
        195                 200                 205

Thr Asn Lys Met Ile Glu Asn Pro Ser Val Arg Leu Leu Val Ala Thr
    210                 215                 220

Gly Gly Pro Ser Ile Val Lys Lys Val Leu Ser Ser Gly Lys Lys Ala
225                 230                 235                 240

Ile Gly Ala Gly Ala Gly Asn Pro Pro Val Val Asp Glu Thr Ala
                245                 250                 255

Asp Ile Val Lys Ala Ala Lys Asp Ile Val Asp Gly Cys Ser Phe Asp
            260                 265                 270

Asn Asn Val Pro Cys Ile Ala Glu Lys Glu Val Phe Ala Val Asp Ser
```

```
        275                 280                 285

Ile Cys Asp Tyr Leu Ile His Asn Met Lys Glu Asn Gly Ala Tyr Gln
    290                 295                 300

Ile Thr Asp Pro Ala Leu Leu Glu Lys Leu Val Thr Leu Val Thr Asn
305                 310                 315                 320

Glu Lys Gly Gly Pro Lys Thr Ser Phe Val Gly Lys Ser Ala Arg Tyr
                325                 330                 335

Ile Leu Asp Lys Leu Gly Ile Thr Ala Asp Ala Ser Val Arg Val Ile
            340                 345                 350

Ile Met Glu Val Pro Lys Glu His Leu Leu Val Gln Glu Glu Met Met
        355                 360                 365

Met Pro Ile Leu Pro Val Val Arg Val Cys Asp Val Asp Thr Ala Ile
    370                 375                 380

Glu Tyr Ala Arg Gln Ala Glu His Gly Asn Arg His Thr Ala Met Met
385                 390                 395                 400

His Ser Arg Asn Val Glu Lys Leu Ser Lys Met Ala Lys Ile Met Glu
                405                 410                 415

Thr Thr Ile Phe Val Lys Asn Ala Pro Ser Tyr Ala Gly Ile Gly Val
            420                 425                 430

Gly Gly Glu Gly Tyr Thr Thr Phe Thr Ile Ala Gly Pro Thr Gly Glu
        435                 440                 445

Gly Leu Thr Ser Pro Lys Ala Phe Cys Arg Lys Arg Lys Cys Val Met
    450                 455                 460

Thr Asp Ala Phe Ser Ile Arg
465                 470

<210> SEQ ID NO 109
<211> LENGTH: 473
<212> TYPE: PRT
<213> ORGANISM: Clostridium sp.

<400> SEQUENCE: 109

Met Lys Leu Asp Asp Lys Leu Ile Glu Gln Val Ala Arg Leu Val Met
1               5                   10                  15

Glu Glu Met Lys Ser Gly Ser Ala Ala Ala Cys Glu Glu Asn Gly Thr
            20                  25                  30

Cys Gly Asp Ser Tyr Gly Ile Phe Asp Ser Met Asp Asp Ala Val Gln
        35                  40                  45

Ala Ser Glu Ala Ala Gln Arg Lys Tyr Leu Phe Ser Thr Met Glu Asp
    50                  55                  60

Arg Gln Lys Tyr Val Asp Val Ile Arg Gln Thr Val Leu Glu Pro Glu
65                  70                  75                  80

Met Leu Gln Lys Ile Ser Arg Met Ala Val Glu Glu Thr Gly Met Gly
                85                  90                  95

Asn Tyr Glu His Lys Leu Ile Lys Asn Arg Leu Ala Ala Glu Lys Ser
            100                 105                 110

Pro Gly Thr Glu Asp Leu Val Thr Glu Ala Met Thr Gly Asp Arg Gly
        115                 120                 125

Leu Thr Leu Val Glu Tyr Cys Pro Phe Gly Val Ile Gly Ala Val Thr
    130                 135                 140

Pro Ala Thr Asn Pro Thr Glu Thr Ile Ile Cys Asn Ser Ile Ala Met
145                 150                 155                 160

Leu Ala Gly Gly Asn Thr Val Val Phe Ser Pro His Pro Arg Ala Lys
                165                 170                 175
```

Asn Val Thr His Val Leu Val Thr Ala Leu Asn Gln Ala Leu Glu Lys
            180                 185                 190

Val Gly Ala Pro Thr Asn Leu Ile Val Thr Val Arg Glu Pro Ser Val
        195                 200                 205

Glu Asn Thr Asn Leu Met Ile Lys His Pro Lys Ile Arg Val Leu Val
210                 215                 220

Ala Thr Gly Gly Pro Gly Ile Val Lys Met Val Met Ser Thr Gly Lys
225                 230                 235                 240

Lys Ala Ile Gly Ala Gly Ala Gly Asn Pro Pro Val Val Val Asp Glu
            245                 250                 255

Thr Ala Asp Ile Glu Lys Ala Ala Lys Asp Ile Val Asp Gly Cys Ser
        260                 265                 270

Phe Asp Asn Asn Leu Pro Cys Ile Ala Glu Lys Glu Val Ile Ala Val
        275                 280                 285

Asp Thr Ile Ala Asp Cys Leu Ile Trp His Met Lys Arg Val Gly Ala
        290                 295                 300

Phe Glu Leu Lys Glu Glu Ser Ala Ile Ser Arg Leu Leu Gln Leu Val
305                 310                 315                 320

Thr Asn Glu Lys Gly Gly Pro Lys Val Glu Phe Val Gly Lys Ser Ala
            325                 330                 335

Pro Tyr Ile Leu Asn Lys Leu Gly Ile Ser Gly Gly Glu Asn Ala Arg
        340                 345                 350

Val Ile Leu Met Glu Thr Gln Lys Asp His Pro Phe Val Met Glu Glu
        355                 360                 365

Leu Met Met Pro Ile Leu Pro Ile Val Arg Ala Ala Asp Val Asp Glu
370                 375                 380

Ala Ile Glu Ile Ala Leu Val Ala Glu Arg Gly Asn Arg His Thr Ala
385                 390                 395                 400

Met Met His Ser Lys Asn Val Asp Lys Leu Thr Lys Met Ala Lys Leu
            405                 410                 415

Leu Gln Thr Thr Ile Phe Val Lys Asn Ala Pro Ser Tyr Ala Gly Ile
        420                 425                 430

Gly Val Gly Gly Glu Gly Cys Thr Thr Phe Thr Ile Ala Gly Pro Thr
        435                 440                 445

Gly Glu Gly Leu Thr Thr Ala Arg Ser Phe Cys Arg Lys Arg Arg Cys
450                 455                 460

Val Met Ser Asp Ala Leu His Ile Arg
465                 470

<210> SEQ ID NO 110
<211> LENGTH: 471
<212> TYPE: PRT
<213> ORGANISM: Clostridium bolteae

<400> SEQUENCE: 110

Met Asp Met Asp Ile Lys Val Ile Glu Gln Leu Val Glu Gln Ala Leu
1               5                   10                  15

Lys Glu Ile Lys Ala Glu Gln Pro Leu Lys Phe Thr Ala Pro Lys Leu
            20                  25                  30

Glu Arg Tyr Gly Val Phe Lys Thr Met Asp Ala Ile Ala Ala Ser
        35                  40                  45

Glu Glu Ala Gln Lys Lys Leu Leu Phe Ser Lys Ile Ser Asp Arg Gln
50                  55                  60

Lys Tyr Val Asp Val Ile Arg Ser Thr Ile Ile Lys Arg Glu Asn Leu
65                  70                  75                  80

Glu Leu Ile Ser Arg Leu Ser Val Glu Thr Glu Ile Gly Asp Tyr
            85                  90                  95

Glu His Lys Leu Ile Lys Asn Arg Leu Ala Ala Glu Lys Thr Pro Gly
            100                 105                 110

Thr Glu Asp Leu Leu Thr Glu Ala Ile Thr Gly Asp Asn Gly Leu Thr
            115                 120                 125

Leu Val Glu Tyr Cys Pro Phe Gly Val Ile Gly Ala Ile Thr Pro Thr
            130                 135                 140

Thr Asn Pro Thr Glu Thr Ile Ile Asn Asn Ser Ile Ser Met Ile Ala
145                 150                 155                 160

Gly Gly Asn Thr Val Val Phe Ser Pro His Pro Arg Ala Lys Lys Val
            165                 170                 175

Ser Gln Met Thr Val Lys Met Leu Asn Lys Ala Leu Ile Asp Asn Gly
            180                 185                 190

Ala Pro Pro Asn Leu Ile Thr Met Val Glu Glu Pro Ser Ile Glu Asn
            195                 200                 205

Thr Asn Lys Met Ile Asp Asn Pro Ser Val Arg Leu Leu Val Ala Thr
            210                 215                 220

Gly Gly Pro Ser Ile Val Lys Lys Val Leu Ser Ser Gly Lys Lys Ala
225                 230                 235                 240

Ile Gly Ala Gly Ala Gly Asn Pro Pro Val Val Asp Glu Thr Ala
            245                 250                 255

Asp Ile Asp Lys Ala Ala Lys Asp Ile Val Asp Gly Cys Ser Phe Asp
            260                 265                 270

Asn Asn Val Pro Cys Ile Ala Glu Lys Glu Val Phe Ala Val Asp Ser
            275                 280                 285

Ile Cys Asp Tyr Leu Ile His His Met Lys Glu Asn Gly Ala Tyr Gln
            290                 295                 300

Ile Thr Asp Pro Met Leu Leu Glu Gln Leu Val Ala Leu Val Thr Thr
305                 310                 315                 320

Glu Lys Gly Gly Pro Lys Thr Ser Phe Val Gly Lys Ser Ala Arg Tyr
            325                 330                 335

Ile Leu Asp Lys Leu Gly Ile Thr Val Asp Ala Ser Val Arg Val Ile
            340                 345                 350

Ile Met Glu Val Pro Lys Asp His Leu Leu Val Gln Glu Glu Met Met
            355                 360                 365

Met Pro Ile Leu Pro Val Val Arg Val Ser Asp Val Asp Thr Ala Ile
370                 375                 380

Glu Tyr Ala His Gln Ala Glu His Gly Asn Arg His Thr Ala Met Met
385                 390                 395                 400

His Ser Lys Asn Val Glu Lys Leu Ser Lys Met Ala Lys Ile Met Glu
            405                 410                 415

Thr Thr Ile Phe Val Lys Asn Ala Pro Ser Tyr Ala Gly Ile Gly Val
            420                 425                 430

Gly Gly Glu Gly Tyr Thr Thr Phe Thr Ile Ala Gly Pro Thr Gly Glu
            435                 440                 445

Gly Leu Thr Ser Pro Arg Thr Phe Cys Arg Lys Arg Lys Cys Val Met
450                 455                 460

Thr Asp Ala Phe Ser Ile Arg
465                 470

<210> SEQ ID NO 111
<211> LENGTH: 468

```
<212> TYPE: PRT
<213> ORGANISM: Eubacterium hallii

<400> SEQUENCE: 111
```

| | | | | | | | | | | | | | | |
|---|---|---|---|---|---|---|---|---|---|---|---|---|---|---|
|Met|Asn|Ile|Asp|Val|Glu|Leu|Ile|Glu|Lys|Val|Val|Lys|Val|Leu|
|1| | | |5| | | | |10| | | | |15|

| | | | | | | | | | | | | | | |
|---|---|---|---|---|---|---|---|---|---|---|---|---|---|---|
|Asn|Asp|Val|Glu|Thr|Gly|Ser|Ser|Ser|Glu|Tyr|Gly|Tyr|Gly|Ile|
| | | | |20| | | | |25| | | | |30|

| | | | | | | | | | | | | | | |
|---|---|---|---|---|---|---|---|---|---|---|---|---|---|---|
|Phe|Asp|Thr|Met|Asp|Glu|Ala|Ile|Glu|Ala|Ser|Ala|Lys|Ala|Gln|Lys|
| | | | |35| | | | |40| | | | |45|

Met Asn Ile Asp Val Glu Leu Ile Glu Lys Val Val Lys Val Leu
1               5               10              15

Asn Asp Val Glu Thr Gly Ser Ser Ser Glu Tyr Gly Tyr Gly Ile
                20              25              30

Phe Asp Thr Met Asp Glu Ala Ile Glu Ala Ser Ala Lys Ala Gln Lys
            35              40                  45

Glu Tyr Met Asn His Ser Met Ala Asp Arg Gln Arg Tyr Val Glu Gly
        50              55                  60

Ile Arg Glu Val Val Cys Thr Lys Glu Asn Leu Glu Tyr Met Ser Lys
65              70              75                  80

Leu Ala Val Glu Glu Ser Gly Met Gly Ala Tyr Glu Tyr Lys Val Ile
            85              90                  95

Lys Asn Arg Leu Ala Ala Val Lys Ser Pro Gly Val Glu Asp Leu Thr
            100                 105                 110

Thr Glu Ala Leu Ser Gly Asp Asp Gly Leu Thr Leu Val Glu Tyr Cys
            115                 120                 125

Pro Phe Gly Val Ile Gly Ala Ile Pro Thr Thr Asn Pro Thr Glu
            130                 135                 140

Thr Val Ile Cys Asn Ser Ile Ala Met Leu Ala Gly Gly Asn Thr Val
145                 150                 155                 160

Val Phe Ser Pro His Pro Arg Ser Lys Gly Val Ser Ile Trp Leu Ile
                165                 170                 175

Lys Lys Leu Asn Ala Lys Leu Glu Glu Leu Gly Ala Pro Arg Asn Leu
            180                 185                 190

Ile Val Thr Val Lys Glu Pro Ser Ile Glu Asn Thr Asn Ile Met Met
            195                 200                 205

Asn His Pro Lys Val Arg Met Leu Val Ala Thr Gly Gly Pro Gly Ile
210                 215                 220

Val Lys Ala Val Met Ser Thr Gly Lys Lys Ala Ile Gly Ala Gly Ala
225                 230                 235                 240

Gly Asn Pro Pro Val Val Asp Glu Thr Ala Asp Ile Glu Lys Ala
                245                 250                 255

Ala Lys Asp Ile Val Asn Gly Cys Ser Phe Asp Asn Asn Leu Pro Cys
            260                 265                 270

Ile Ala Glu Lys Glu Val Ile Ala Val Asp Gln Ile Ala Asp Tyr Leu
            275                 280                 285

Ile Phe Asn Met Lys Asn Asn Gly Ala Tyr Glu Val Lys Asp Pro Glu
            290                 295                 300

Ile Ile Glu Lys Met Val Asp Leu Val Thr Lys Asp Arg Lys Lys Pro
305                 310                 315                 320

Ala Val Asn Phe Val Gly Lys Ser Ala Gln Tyr Ile Leu Asp Lys Val
                325                 330                 335

Gly Ile Lys Val Gly Pro Glu Val Lys Cys Ile Ile Met Glu Ala Pro
            340                 345                 350

Lys Asp His Pro Phe Val Gln Ile Glu Leu Met Met Pro Ile Leu Pro
            355                 360                 365

Ile Val Arg Val Pro Asn Val Asp Glu Ala Ile Asp Phe Ala Val Glu
            370                 375                 380

Val Glu His Gly Asn Arg His Thr Ala Met Met His Ser Lys Asn Val
385                 390                 395                 400

```
Asp Lys Leu Thr Lys Met Ala Lys Glu Ile Glu Thr Thr Ile Phe Val
            405                 410                 415

Lys Asn Gly Pro Ser Tyr Ala Gly Ile Gly Val Gly Met Gly Tyr
            420                 425                 430

Thr Thr Phe Thr Ile Ala Gly Pro Thr Gly Glu Gly Leu Thr Ser Ala
            435                 440                 445

Lys Ser Phe Cys Arg Lys Arg Arg Cys Val Leu Gln Asp Gly Leu His
            450                 455                 460

Ile Arg Met Lys
465

<210> SEQ ID NO 112
<211> LENGTH: 467
<212> TYPE: PRT
<213> ORGANISM: Halanaerobium saccharolyticum

<400> SEQUENCE: 112

Met Lys Ile Lys Glu Asn Glu Leu Asp Lys Ile Val Asn Gln Val Ile
1               5                   10                  15

Ser Ser Leu Asn Asn Lys Gln Asn Ser Asn Asp Phe Asn Thr Lys Ile
            20                  25                  30

Asn Tyr Gly Ile Phe Ser Thr Met Asp Glu Ala Ile Ala Glu Ala Val
            35                  40                  45

Lys Ala Gln Ala Cys Leu Gln Leu Asn Tyr Ser Thr Glu Ala Arg Glu
        50                  55                  60

Lys Ile Ile Lys Ser Ile Arg Lys Asn Val Ser Lys His Val Glu Lys
65                  70                  75                  80

Ile Ser Glu Met Ala Val Glu Glu Thr Asp Met Gly Arg Ile Glu Asp
                85                  90                  95

Lys Ile Ile Lys Asn Asn Leu Ala Ile Asn Lys Thr Pro Gly Thr Glu
            100                 105                 110

Asp Leu Arg Thr Glu Ala Phe Ser Gly Lys Lys Gly Leu Thr Ile Val
            115                 120                 125

Glu Glu Ala Pro Phe Gly Val Ile Cys Ser Ile Ala Pro Val Thr Asn
130                 135                 140

Pro Thr Glu Thr Ile Ile Ser Asn Ala Ile Ser Met Ile Ala Ser Cys
145                 150                 155                 160

Asn Gly Val Val Phe Asn Ser His Pro Gly Ala Lys Lys Val Ser Lys
                165                 170                 175

Tyr Ile Ile Glu Val Leu Asn Lys Val Ile Met Glu Ala Gly Gly Pro
            180                 185                 190

Glu Asn Leu Leu Thr Ala Val Asn Glu Pro Thr Leu Gln Thr Val Glu
            195                 200                 205

Ser Cys Met Arg Asp Asp Arg Ile Ala Met Ile Val Ala Thr Gly Gly
        210                 215                 220

Pro Gly Val Val Asn Ala Ala Leu Ser Ser Gly Lys Lys Ala Ile Gly
225                 230                 235                 240

Ala Gly Ala Gly Asn Pro Pro Val Leu Val Asp Asp Thr Val Asp Leu
                245                 250                 255

Lys Arg Val Ala Lys Asp Ile Ile Asn Gly Ala Ser Phe Asp Asn Asn
            260                 265                 270

Leu Pro Cys Thr Ser Glu Lys Ala Ile Val Ala Leu Glu Ser Ile Ala
            275                 280                 285

Asp Ser Leu Leu Asn Glu Met Thr Asn Gln Asn Ala Gln Leu Val His
```

```
                 290                 295                 300

Asp Ile Lys Ala Leu Glu Arg Val Ile Leu Asn Asp Asp Gly Ser Ile
305                 310                 315                 320

Asn Lys Ala Leu Val Gly Lys Asp Ala Ala Phe Ile Leu Asn Lys Ala
                325                 330                 335

Gly Leu Lys Ala Lys Ser Glu Asp Leu Arg Leu Val Ile Val Asp Val
                340                 345                 350

Asp Leu Arg His Pro Phe Val Gln Lys Glu Gln Leu Met Pro Val Ile
                355                 360                 365

Pro Leu Val Arg Ala Lys Asn Phe Asn Glu Ala Met Glu Met Gly Val
                370                 375                 380

Asp Ile Glu Glu Gly Asn Arg His Thr Ala Ile Ile His Ser Lys Asn
385                 390                 395                 400

Val Asp Asn Leu Thr Lys Phe Ala Lys Lys Ile Glu Thr Thr Ile Tyr
                405                 410                 415

Val Lys Asn Ala Pro Ser Tyr Ala Gly Ile Gly Ala Gly Gly Glu Gly
                420                 425                 430

Tyr Ala Thr Phe Thr Ile Ala Gly Pro Thr Gly Glu Gly Leu Thr Ser
                435                 440                 445

Ala Arg Ser Phe Thr Arg Lys Arg Arg Cys Val Leu Val Asp Gly Phe
                450                 455                 460

Ser Ile Ile
465

<210> SEQ ID NO 113
<211> LENGTH: 469
<212> TYPE: PRT
<213> ORGANISM: Eubacterium limosum

<400> SEQUENCE: 113

Met Asn Ile Asp Thr Thr Gly Ile Glu Tyr Ile Val Lys Lys Val Met
1               5                   10                  15

Asp Gln Ile Asp Tyr Ala Glu Glu Thr Gly Ala Pro Val Val Asp Gly
                20                  25                  30

Lys Asp Gly Val Phe Gln Thr Met Asp Ala Ala Ile Glu Ala Ala Ala
                35                  40                  45

Val Ala Gln Lys Glu Tyr Met Lys Lys Pro Leu Ala Leu Arg Arg Gln
50                  55                  60

Met Ile Ala Ala Met Arg Glu Ile Met Leu Lys Lys Glu Asn Ile Glu
65                  70                  75                  80

Thr Ile Cys Ala Met Val Val Glu Glu Ser Gly Met Gly Asn Tyr Glu
                85                  90                  95

His Lys Leu Ala Lys His Arg Leu Ala Thr Thr Gly Thr Pro Gly Val
                100                 105                 110

Glu Asp Leu Leu Thr Glu Ala Trp Ala Gly Asp Gly Cys Thr Leu
                115                 120                 125

Leu Glu Leu Ser Pro Phe Gly Val Ile Gly Ala Ile Thr Pro Thr Thr
                130                 135                 140

Asn Pro Asn Glu Thr Ile Val Asn Asn Ser Ile Gly Met Leu Ala Ala
145                 150                 155                 160

Gly Asn Ala Val Val Phe Ser Pro His Pro Lys Ala Leu Lys Thr Ser
                165                 170                 175

Phe Leu Cys Ile Lys Leu Leu Asn Glu Ala Ile Ser Val Gly Gly
                180                 185                 190
```

```
Pro Arg Asn Leu Ile Val Thr Cys Ala Asn Pro Thr Ile Glu Ala Ala
            195                 200                 205

Asn Glu Met Met Val His Pro Lys Ile Arg Met Leu Val Ala Thr Gly
    210                 215                 220

Gly Pro Gly Val Val Lys Ala Val Leu Ser Ser Gly Lys Lys Ala Ile
225                 230                 235                 240

Gly Ala Gly Ala Gly Asn Pro Pro Ala Leu Val Asp Glu Thr Ala Asp
                245                 250                 255

Ile Glu Lys Ala Ala Lys Asp Ile Ile Asp Gly Cys Ser Phe Asp Asn
            260                 265                 270

Asn Leu Pro Cys Ile Ala Glu Lys Glu Val Val Val Asp Gln Val
        275                 280                 285

Ala Asp Tyr Leu Ile Phe Asn Met Lys Lys Asn Gly Ala Tyr Glu Ile
    290                 295                 300

Thr Asp Lys Lys Ala Ile Asp Ala Leu Ala Asp Leu Val Cys Pro Glu
305                 310                 315                 320

Gly Arg Leu Ser Arg Asp Phe Val Gly Lys Ser Ala Lys Tyr Ile Ala
                325                 330                 335

Ala Ala Ala Gly Leu Asp Val Pro Glu Asp Thr Arg Val Leu Ile Cys
            340                 345                 350

Glu Thr Ser Lys Asp His Leu Leu Ala Val Glu Glu Leu Met Met Pro
        355                 360                 365

Ile Leu Pro Ile Val Arg Val Ala Asn Val Asp Glu Gly Ile Asp Val
    370                 375                 380

Ala Val Glu Leu Glu His Gly Asn Arg His Thr Ala Ile Met His Ser
385                 390                 395                 400

Lys Asn Val Asp Lys Leu Thr Glu Met Ala Lys Arg Ile Gln Thr Thr
                405                 410                 415

Ile Phe Val Lys Asn Gly Pro Ser Tyr Ala Gly Ile Gly Phe Gly Gly
            420                 425                 430

Glu Gly Tyr Pro Thr Phe Thr Ile Ala Gly Pro Thr Gly Glu Gly Leu
        435                 440                 445

Thr Ser Ala Lys Ser Phe Ala Arg Arg Arg Cys Val Leu Val Gly
    450                 455                 460

Gly Phe Asp Ile Lys
465

<210> SEQ ID NO 114
<211> LENGTH: 466
<212> TYPE: PRT
<213> ORGANISM: Thermoanaerobacter sp.

<400> SEQUENCE: 114

Met Ile Asp Glu Asn Leu Val Val Thr Ile Thr Lys Lys Ile Leu Asn
1               5                   10                  15

Glu Ile Asn Leu Lys Glu Ala Glu Glu Lys Glu Lys Asp Asn Pro
            20                  25                  30

Asp Leu Gly Ile Phe Asn Asp Val Asn Glu Ala Val Glu Cys Ala Lys
        35                  40                  45

Glu Ala Gln Lys Lys Phe Ala Leu Met Asp Leu Glu Lys Arg Glu Glu
    50                  55                  60

Ile Ile Ala Ala Ile Arg Glu Ala Cys Val Asn Asn Ala Arg Leu Leu
65                  70                  75                  80

Ala Glu Ile Ala Cys Ser Glu Thr Gly Arg Gly Arg Val Glu Asp Lys
                85                  90                  95
```

Val Ala Lys Asn Ile Leu Ala Ala Lys Lys Thr Pro Gly Thr Glu Asp
            100                 105                 110

Leu Lys Pro Thr Ala Trp Thr Gly Asp Arg Gly Leu Thr Leu Val Glu
            115                 120                 125

Met Ala Pro Val Gly Val Ile Ala Ser Ile Thr Pro Val Thr Asn Pro
130                 135                 140

Thr Ala Thr Ile Ile Asn Asn Thr Ile Ser Met Leu Ala Ala Gly Asn
145                 150                 155                 160

Ala Val Val Phe Asn Pro His Pro Ser Ala Lys Lys Thr Ser Asn Lys
                165                 170                 175

Ala Val Glu Ile Ile Asn Glu Ala Ile Leu Lys Val Gly Ala Pro Asn
            180                 185                 190

Gly Leu Val Cys Ser Ile Asn Asn Pro Thr Ile Gln Thr Ala Gln Lys
            195                 200                 205

Leu Met Glu His Pro Glu Val Asn Met Val Val Thr Gly Gly Lys
210                 215                 220

Ala Val Val Gln Thr Ala Leu Arg Cys Gly Lys Lys Val Ile Gly Ala
225                 230                 235                 240

Gly Ala Gly Asn Pro Pro Val Val Val Asp Glu Thr Ala Asp Ile Val
                245                 250                 255

Lys Ala Ala His Asp Ile Ala Cys Gly Ala Ser Phe Asp Asn Asn Leu
            260                 265                 270

Pro Cys Ile Ala Glu Lys Glu Ile Ile Ala Val Glu Arg Ile Ala Asp
            275                 280                 285

Thr Leu Leu Glu Arg Met Lys Arg Glu Gly Ala Tyr Val Leu His Gly
290                 295                 300

Lys Asp Ile Asp Arg Met Thr Glu Leu Ile Phe Gln Gly Gly Ala Ile
305                 310                 315                 320

Asn Lys Asp Leu Ile Gly Arg Asp Ala His Phe Ile Leu Ser Gln Ile
                325                 330                 335

Gly Ile Glu Thr Gly Lys Asp Ile Arg Leu Val Val Met Pro Val Asp
            340                 345                 350

Val Ser His Pro Leu Val Tyr His Glu Gln Leu Met Pro Val Ile Pro
            355                 360                 365

Phe Val Thr Val Pro Thr Val Glu Glu Ala Ile Asn Leu Ala Val Lys
370                 375                 380

Ala Glu Gly Gly Asn Arg His Thr Ala Met Met His Ser Lys Asn Val
385                 390                 395                 400

Glu Asn Met Thr Ala Phe Ala Arg Ala Ile Gln Thr Thr Ile Phe Val
                405                 410                 415

Lys Asn Ala Pro Ser Tyr Ala Gly Ile Gly Phe Gly Gly Glu Gly Tyr
            420                 425                 430

Thr Thr Phe Thr Ile Ala Gly Pro Thr Gly Glu Gly Leu Thr Ser Ala
            435                 440                 445

Arg Thr Phe Thr Arg Gln Arg Arg Cys Val Leu Val Asp Ala Phe Arg
            450                 455                 460

Ile Val
465

<210> SEQ ID NO 115
<211> LENGTH: 529
<212> TYPE: PRT
<213> ORGANISM: Rhodospirillum rubrum

<400> SEQUENCE: 115

```
Met Asn Asp Gly Gln Ile Ala Ala Ala Val Ala Lys Val Leu Glu Ala
1               5                  10                  15
Tyr Gly Val Pro Ala Asp Pro Ser Ala Ala Pro Ala Pro Ala Ala
            20                  25                  30
Pro Val Ala Pro Ala Ala Pro Thr Ala Gly Ser Val Ser Glu Met Ile
        35                  40                  45
Ala Arg Gly Ile Ala Lys Ala Ser Ser Asp Asp Gln Ile Ala Gln Ile
    50                  55                  60
Val Ala Lys Val Val Gly Asp Tyr Ser Ala Gln Ala Ala Lys Pro Ala
65                  70                  75                  80
Val Val Pro Gly Ala Ala Ser Thr Glu Ala Gly Asp Gly Val Phe
            85                  90                  95
Asp Thr Met Asp Ala Ala Val Asp Ala Ala Val Leu Ala Gln Gln Gln
            100                 105                 110
Tyr Leu Leu Cys Ser Met Thr Asp Arg Gln Arg Phe Val Asp Gly Ile
        115                 120                 125
Arg Glu Val Ile Leu Gln Lys Asp Thr Leu Glu Leu Ile Ser Arg Met
    130                 135                 140
Ala Ala Glu Glu Thr Gly Met Gly Asn Tyr Glu His Lys Leu Ile Lys
145                 150                 155                 160
Asn Arg Leu Ala Ala Glu Lys Thr Pro Gly Thr Glu Asp Leu Thr Thr
                165                 170                 175
Glu Ala Phe Ser Gly Asp Asp Gly Leu Thr Leu Val Glu Tyr Ser Pro
            180                 185                 190
Phe Gly Ala Ile Gly Ala Val Ala Pro Thr Thr Asn Pro Thr Glu Thr
        195                 200                 205
Ile Ile Cys Asn Ser Ile Gly Met Leu Ala Ala Gly Asn Ser Val Ile
    210                 215                 220
Phe Ser Pro His Pro Arg Ala Thr Lys Val Ser Leu Leu Thr Val Lys
225                 230                 235                 240
Leu Ile Asn Gln Lys Leu Ala Cys Leu Gly Ala Pro Ala Asn Leu Val
                245                 250                 255
Val Thr Val Ser Lys Pro Ser Val Glu Asn Thr Asn Ala Met Met Ala
            260                 265                 270
His Pro Lys Ile Arg Met Leu Val Ala Thr Gly Gly Pro Gly Ile Val
        275                 280                 285
Lys Ala Val Met Ser Thr Gly Lys Lys Ala Ile Gly Ala Gly Ala Gly
    290                 295                 300
Asn Pro Pro Val Val Val Asp Glu Thr Ala Asp Ile Glu Lys Ala Ala
305                 310                 315                 320
Leu Asp Ile Ile Asn Gly Cys Ser Phe Asp Asn Asn Leu Pro Cys Ile
                325                 330                 335
Ala Glu Lys Glu Ile Ile Ala Val Ala Gln Ile Ala Asp Tyr Leu Ile
            340                 345                 350
Phe Ser Met Lys Lys Gln Gly Ala Tyr Gln Ile Thr Asp Pro Ala Val
        355                 360                 365
Leu Arg Lys Leu Gln Asp Leu Val Leu Thr Ala Lys Gly Gly Pro Gln
    370                 375                 380
Thr Ser Cys Val Gly Lys Ser Ala Val Trp Leu Leu Asn Lys Ile Gly
385                 390                 395                 400
Ile Glu Val Asp Ser Ser Val Lys Val Ile Leu Met Glu Val Pro Lys
                405                 410                 415
```

```
Glu His Pro Phe Val Gln Glu Leu Met Met Pro Ile Leu Pro Leu
        420                 425                 430

Val Arg Val Ser Asp Val Asp Glu Ala Ile Ala Val Ala Ile Glu Val
        435                 440                 445

Glu His Gly Asn Arg His Thr Ala Ile Met His Ser Thr Asn Val Arg
450                 455                 460

Lys Leu Thr Lys Met Ala Lys Leu Ile Gln Thr Thr Ile Phe Val Lys
465                 470                 475                 480

Asn Gly Pro Ser Tyr Ala Gly Leu Gly Val Gly Gly Glu Gly Tyr Thr
                485                 490                 495

Thr Phe Thr Ile Ala Gly Pro Thr Gly Glu Gly Leu Thr Ser Ala Lys
                500                 505                 510

Ser Phe Ala Arg Lys Arg Lys Cys Val Met Val Glu Ala Leu Asn Ile
                515                 520                 525

Arg

<210> SEQ ID NO 116
<211> LENGTH: 466
<212> TYPE: PRT
<213> ORGANISM: Eubacterium yurii

<400> SEQUENCE: 116

Met Asn Pro Glu Leu Leu Glu Asp Val Val Arg Gln Val Leu Ser Glu
1               5                   10                  15

Met Lys Leu Glu Ser Ser Lys Met Val Asp Ile Tyr Asn Tyr Gly Ile
                20                  25                  30

Phe Asp Ser Val Asp Asp Ala Ile Asn Ala Ser Glu Ile Ala Gln Arg
            35                  40                  45

Gln Leu Phe Glu Cys Ser Val Gln Lys Arg Asn Glu Tyr Val Asn Ala
        50                  55                  60

Ile Arg Gln Ile Ile Leu Lys Lys Asp Asn Leu Glu Met Met Ser Arg
65                  70                  75                  80

Asp Ala Val Glu Glu Thr Gly Ile Gly Arg Tyr Glu Asp Lys Ile Leu
                85                  90                  95

Lys Asn Lys Leu Ala Ala Glu Lys Thr Pro Gly Met Glu Asp Leu Ile
                100                 105                 110

Thr Arg Ala Val Ser Gly Gln Asp Gly Leu Thr Leu Glu Glu Tyr Cys
            115                 120                 125

Pro Phe Gly Val Ile Gly Ser Ile Thr Pro Thr Thr Asn Pro Thr Glu
        130                 135                 140

Thr Phe Ile Ser Asn Ser Ile Ser Met Ile Val Gly Asn Thr Val
145                 150                 155                 160

Val Phe Ser Pro His Pro Arg Ala Lys Asn Thr Ser Ile Lys Leu Val
                165                 170                 175

Lys Leu Met Asn Lys Ala Leu Glu Gln Val Gly Ala Pro Arg Asn Leu
                180                 185                 190

Ile Ser Met Val Lys Glu Pro Ser Ile Glu Asn Thr Asn Leu Met Met
            195                 200                 205

Asn His Pro Lys Ile Lys Met Leu Val Ala Thr Gly Gly Pro Ala Ile
        210                 215                 220

Val Lys Thr Val Leu Ser Ser Gly Lys Lys Ala Ile Gly Ala Gly Ala
225                 230                 235                 240

Gly Asn Pro Pro Val Val Val Asp Glu Thr Ala Asp Ile Glu Lys Ala
                245                 250                 255
```

Ala Lys Asp Ile Val Ala Gly Ser Ser Phe Asp Asn Val Pro Cys
            260                 265                 270

Ile Ala Glu Lys Glu Val Phe Ala Val Glu Ser Ile Cys Asp Gln Leu
            275                 280                 285

Ile Tyr His Met Lys Lys Asn Gly Ala Tyr Glu Ile Thr Ser Tyr Glu
            290                 295                 300

Met Ile Glu Lys Leu Asp Lys Leu Val Ser Gln Glu Asn Gly Lys Pro
305                 310                 315                 320

Asn Thr Asp Phe Val Gly Lys Ser Ala Lys Tyr Ile Leu Glu Lys Leu
                325                 330                 335

Gly Ile Ser Val Asp Asp Ser Ile Arg Leu Ile Cys Arg Thr Asn
            340                 345                 350

Lys Asp His His Leu Val Gln Glu Met Leu Met Pro Ile Leu Pro
            355                 360                 365

Ile Val Ser Val Ser Asp Val Asp Val Ala Ile Glu Tyr Ala Tyr Glu
            370                 375                 380

Ala Glu His Arg Asn Arg His Thr Ala Ile Met His Ser Arg Asn Val
385                 390                 395                 400

Glu Lys Leu Ser Lys Met Ala Lys Lys Leu Glu Ala Thr Ile Phe Val
                405                 410                 415

Lys Asn Ala Pro Ser Tyr Ala Gly Ile Gly Val Gly Gly Glu Gly Tyr
            420                 425                 430

Thr Thr Phe Thr Ile Ala Gly Pro Thr Gly Glu Gly Leu Thr Ser Pro
            435                 440                 445

Lys Ser Phe Cys Arg Val Arg Arg Cys Thr Met Ser Asp Ser Phe Ser
450                 455                 460

Ile Arg
465

<210> SEQ ID NO 117
<211> LENGTH: 466
<212> TYPE: PRT
<213> ORGANISM: Eubacterium sp.

<400> SEQUENCE: 117

Met Asn Pro Glu Leu Leu Glu Asp Val Val Arg Gln Val Leu Ser Glu
1               5                   10                  15

Met Lys Leu Glu Ser Ser Lys Met Val Asp Ile Tyr Asn Tyr Gly Ile
                20                  25                  30

Phe Asp Ser Val Asp Asp Ala Ile Asn Ala Ser Glu Ile Ala Gln Arg
            35                  40                  45

Gln Leu Phe Glu Cys Ser Val Gln Lys Arg Asn Glu Tyr Val Asn Ala
        50                  55                  60

Ile Arg Gln Ile Ile Leu Lys Lys Asp Asn Leu Glu Met Met Ser Arg
65                  70                  75                  80

Asp Ala Val Glu Glu Thr Gly Ile Gly Arg Tyr Glu Asp Lys Ile Leu
                85                  90                  95

Lys Asn Lys Leu Ala Ala Glu Lys Thr Pro Gly Met Glu Asp Leu Ile
            100                 105                 110

Thr Arg Ala Val Ser Gly Gln Asp Gly Leu Thr Leu Glu Tyr Cys
            115                 120                 125

Pro Phe Gly Val Ile Gly Ser Ile Thr Pro Thr Asn Pro Thr Glu
            130                 135                 140

Thr Phe Ile Ser Asn Ser Ile Ser Met Ile Val Gly Gly Asn Thr Val

```
            145                 150                 155                 160
       Val Phe Ser Pro His Pro Arg Ala Lys Asn Thr Ser Ile Lys Leu Val
                       165                 170                 175

Lys Leu Met Asn Lys Ala Leu Glu Gln Val Gly Ala Pro Arg Asn Leu
                       180                 185                 190

Ile Ser Met Val Lys Glu Pro Ser Ile Glu Asn Thr Asn Leu Met Met
                       195                 200                 205

Asn His Pro Lys Ile Lys Met Leu Val Ala Thr Gly Pro Ala Ile
           210                 215                 220

Val Lys Thr Val Leu Ser Ser Gly Lys Ala Ile Gly Ala Gly Ala
       225                 230                 235                 240

Gly Asn Pro Pro Val Val Asp Glu Thr Ala Asp Ile Glu Lys Ala
                       245                 250                 255

Ala Lys Asp Ile Val Ala Gly Ser Ser Phe Asp Asn Asn Val Pro Cys
                       260                 265                 270

Ile Ala Glu Lys Glu Val Phe Ala Val Glu Ser Ile Cys Asp Gln Leu
                       275                 280                 285

Ile Tyr His Met Lys Lys Asn Gly Ala Tyr Glu Ile Thr Ser Tyr Glu
                       290                 295                 300

Met Ile Glu Lys Leu Asp Lys Leu Val Ser Gln Glu Asn Gly Lys Pro
       305                 310                 315                 320

Asn Thr Asp Phe Val Gly Lys Ser Ala Lys Tyr Ile Leu Glu Lys Leu
                       325                 330                 335

Gly Ile Asn Val Asp Asp Ser Ile Arg Leu Ile Ile Cys Arg Thr Asn
                       340                 345                 350

Lys Asp His His Leu Val Gln Glu Glu Met Leu Met Pro Ile Leu Pro
                       355                 360                 365

Ile Val Ser Val Ser Asp Val Asp Val Ala Ile Glu Tyr Ala Tyr Glu
                       370                 375                 380

Ala Glu His Arg Asn Arg His Thr Ala Ile Met His Ser Arg Asn Val
       385                 390                 395                 400

Glu Lys Leu Ser Lys Met Ala Lys Lys Leu Glu Ala Thr Ile Phe Val
                       405                 410                 415

Lys Asn Ala Pro Ser Tyr Ala Gly Ile Gly Val Gly Gly Glu Gly Tyr
                       420                 425                 430

Thr Thr Phe Thr Ile Ala Gly Pro Thr Gly Gly Leu Thr Ser Pro
                       435                 440                 445

Lys Ser Phe Cys Arg Val Arg Arg Cys Thr Met Ser Asp Ser Phe Ser
           450                 455                 460

Ile Arg
       465

<210> SEQ ID NO 118
<211> LENGTH: 532
<212> TYPE: PRT
<213> ORGANISM: Vibrio sp.

<400> SEQUENCE: 118

Met Asn Glu Gln Glu Ile Ala His Ala Val Glu Asn Val Leu Ser Lys
1               5                   10                  15

Tyr Thr Asn Val Thr Ala Gln Asn Ala Glu Pro Val Ser Tyr Ser Ser
                20                  25                  30

Asn Ala Ser Leu Glu Asn Ile Val Ser Gln Ala Leu Ala Gly Asn Met
            35                  40                  45
```

```
Val Lys Gln Pro Glu Thr Gln Thr Ala Pro Asp Leu Asn Ser Asn Ile
     50                  55                  60

Glu Asn Ile Val Ser Gln Ile Leu Ala Glu Asn Gln Ala Lys Pro Gln
 65                  70                  75                  80

Ser Val Gln Cys Gln Ser Ala Asn His Gly Thr Thr Glu Tyr Leu Gly
                 85                  90                  95

Cys Phe Ala Ser Met Glu Glu Ala Ile Ser Ala Ala Ser His Ala Gln
                100                 105                 110

Val Gln Tyr Arg His Cys Thr Met Gly Asp Arg Ala Ser Phe Val Lys
            115                 120                 125

Gly Ile Arg Glu Val Phe Thr Gln Asp Asp Val Leu Glu Lys Ile Ser
130                 135                 140

Arg Met Ala Val Glu Glu Thr Gly Met Gly Asn Tyr Ala Asp Lys Leu
145                 150                 155                 160

Thr Lys Asn Arg Ile Ala Ala Thr Lys Thr Pro Gly Ile Glu Asp Leu
                165                 170                 175

Thr Thr Ser Ala Leu Ser Gly Asp Ser Gly Leu Thr Leu Thr Glu Phe
                180                 185                 190

Ser Ala Tyr Gly Val Ile Gly Ser Ile Thr Pro Thr Thr Asn Pro Thr
            195                 200                 205

Glu Thr Ile Ile Asn Asn Ser Ile Gly Met Leu Ala Ala Gly Asn Thr
210                 215                 220

Val Val Tyr Ser Pro His Pro Arg Ser Arg Asn Val Ser Leu Val Ala
225                 230                 235                 240

Val Asp Leu Ile Asn Arg Lys Leu Ala Glu Leu Gly Ala Pro Ala Asn
                245                 250                 255

Leu Val Val Thr Val Leu Glu Pro Ser Ile Asp Asn Thr Asn Ala Met
                260                 265                 270

Met Asn Asp Pro Arg Val Asn Met Leu Val Ala Thr Gly Gly Pro Ser
            275                 280                 285

Ile Val Lys Thr Val Met Ser Thr Gly Lys Lys Ala Ile Gly Ala Gly
290                 295                 300

Ala Gly Asn Pro Pro Ala Val Val Asp Glu Thr Ala Asn Ile Glu Lys
305                 310                 315                 320

Ala Ala Lys Asp Ile Ile Asn Gly Cys Ala Phe Asp Asn Asn Leu Pro
                325                 330                 335

Cys Ile Ala Glu Lys Glu Val Ile Val Val Asn Glu Val Ala Asp Tyr
                340                 345                 350

Leu Ile His Cys Met Lys Lys Ser Gly Ala Tyr Leu Leu Cys Asp Lys
            355                 360                 365

Gln Lys Ile Gln Gln Leu Gln Ser Leu Val Leu Asn Glu Lys Gly Thr
370                 375                 380

Gly Pro Asn Thr Ser Phe Val Gly Lys Gly Ala Arg Tyr Ile Leu Asp
385                 390                 395                 400

Lys Leu Asn Ile Gln Val Ser Asp Asp Ile Lys Val Ile Leu Ile Glu
                405                 410                 415

Thr Glu Arg Asn His Pro Phe Val Val His Glu Leu Met Met Pro Ile
                420                 425                 430

Leu Pro Val Val Arg Val Glu Asn Val Asp Glu Ala Ile Asp Leu Ala
            435                 440                 445

Ile Lys Val Glu His Gly Asn Arg His Thr Ala Ile Met His Ser Thr
450                 455                 460

Asn Val Glu Lys Leu Ser Lys Met Ala Arg Leu Ile Gln Thr Thr Ile
```

```
                465                 470                 475                 480
            Phe Val Lys Asn Gly Pro Ser Tyr Ser Gly Ile Gly Val Gly Gly Glu
                            485                 490                 495
            Gly His Thr Thr Phe Thr Ile Ala Gly Pro Thr Gly Glu Gly Ile Thr
                            500                 505                 510
            Ser Ala Arg Ser Phe Ala Arg Tyr Arg Arg Cys Val Met Val Glu Ala
                            515                 520                 525
            Leu Asn Ile Arg
                            530

<210> SEQ ID NO 119
<211> LENGTH: 467
<212> TYPE: PRT
<213> ORGANISM: Eubacteriaceae bacterium

<400> SEQUENCE: 119

Met Asn Ala Glu Leu Leu Gln Asp Val Val Arg Gln Val Leu Ser Glu
1               5                   10                  15
Met Lys Leu Glu Ser Ser Asn Ile Leu Ser Asn Glu Tyr Asn Tyr Gly
                20                  25                  30
Ile Phe Asp Asp Met Glu Ala Ala Ile Asn Ala Ser Glu Thr Ala Gln
            35                  40                  45
Arg Lys Leu Phe Glu Cys Ser Val Gln Gln Arg Asn Glu Phe Ala Asn
        50                  55                  60
Val Ile Arg Lys Glu Ile Leu Lys Lys Asp Asn Leu Glu Met Ile Ser
65                  70                  75                  80
Arg Asp Ala Val Glu Glu Thr Glu Ile Gly Arg Phe Glu Asp Lys Ile
                85                  90                  95
Leu Lys Asn Lys Val Ala Ala Glu Lys Thr Pro Gly Met Glu Asp Leu
            100                 105                 110
Thr Thr Arg Ala Ile Ser Gly Lys Asp Gly Leu Met Ile Glu Glu Tyr
        115                 120                 125
Cys Pro Phe Gly Val Ile Gly Ser Ile Thr Pro Thr Thr Asn Pro Thr
130                 135                 140
Glu Thr Leu Ile Asn Asn Ser Ile Ser Met Ile Val Gly Gly Asn Thr
145                 150                 155                 160
Val Val Phe Ser Pro His Pro Arg Ala Lys Asn Val Ser Ile Lys Leu
                165                 170                 175
Val Lys Met Met Asn Lys Ala Leu Glu Glu His Gly Ala Pro Arg Asn
            180                 185                 190
Met Ile Thr Met Val Lys Glu Pro Ser Ile Glu Asn Thr Asn Leu Met
        195                 200                 205
Met Ser Asn Pro Lys Val Lys Leu Leu Val Ala Thr Gly Gly Pro Phe
210                 215                 220
Ile Val Asn Thr Val Leu Ser Ser Gly Lys Lys Ala Ile Gly Ala Gly
225                 230                 235                 240
Ala Gly Asn Pro Pro Val Val Asp Glu Thr Ala Asp Ile Glu Lys
                245                 250                 255
Ala Ala Ile Asp Ile Val Ser Gly Ala Ser Phe Asp Asn Asn Val Pro
            260                 265                 270
Cys Ile Ala Glu Lys Glu Val Phe Ala Val Asp Ser Ile Ser Asp Met
        275                 280                 285
Leu Ile Tyr His Met Lys Lys Asn Gly Ala Tyr Glu Ile Val Ser Gln
    290                 295                 300
```

Asp Met Ile Glu Lys Leu Asp Lys Leu Val Ser Gln Glu Asn Gly Lys
305                 310                 315                 320

Pro Lys Thr Glu Phe Val Gly Lys Ser Ala Lys Tyr Ile Leu Glu Lys
            325                 330                 335

Leu Gly Ile Tyr Val Asp Asp Ser Ile Arg Leu Ile Cys Arg Thr
                340                 345                 350

Ser Lys Asn His His Leu Val Gln Glu Met Leu Met Pro Ile Leu
        355                 360                 365

Pro Ile Val Ser Val Ser Val Asp Ile Ala Ile Glu Tyr Ala Tyr
    370                 375                 380

Glu Ala Glu His Gly Asn Arg His Thr Ala Ile Met His Ser Lys Asn
385                 390                 395                 400

Val Glu Lys Leu Ser Lys Met Ala Lys Lys Leu Glu Ala Thr Ile Phe
            405                 410                 415

Val Lys Asn Ala Pro Ser Tyr Ser Gly Ile Gly Val Gly Gly Glu Gly
            420                 425                 430

His Thr Thr Phe Thr Ile Ala Gly Pro Thr Gly Glu Gly Ile Thr Ser
                435                 440                 445

Ala Lys Ser Phe Cys Arg Ile Arg Arg Cys Val Met His Asp Ser Phe
    450                 455                 460

Ser Ile Arg
465

<210> SEQ ID NO 120
<211> LENGTH: 473
<212> TYPE: PRT
<213> ORGANISM: Propionibacterium propionicum

<400> SEQUENCE: 120

Met Lys Ile Asp Pro Ala Gln Leu Glu Ala Thr Ile Arg Glu Val Leu
1               5                   10                  15

Ala Ala Met Leu Pro Gly Asn Asp Asn Gln Thr Glu Ala Pro Ala Thr
            20                  25                  30

Gln Gln Glu Ala Pro Gly Asp Gly Val Phe Ala Asp Met Asp Ser Ala
        35                  40                  45

Val Glu Ala Ala His Leu Ala Gln Arg Glu Tyr Leu Ser His Pro Met
50                  55                  60

Ala Asp Arg Arg Arg Tyr Val Ala Ala Ile Arg Glu Ala Met Leu Ala
65                  70                  75                  80

Pro Glu Ala Leu Asp Tyr Met Ser Glu Gln Ala Val Ala Gln Ser Gly
            85                  90                  95

Met Gly Asp Val Gly His Lys Tyr Leu Lys Asn Lys Val Ala Ala Ala
            100                 105                 110

Glu Thr Pro Gly Val Glu Asp Leu Val Thr Glu Ala Trp Ser Gly Asp
        115                 120                 125

Asp Gly Leu Thr Thr Ile Glu Tyr Ser Pro Tyr Gly Val Ile Gly Ala
    130                 135                 140

Ile Thr Pro Thr Thr Asn Pro Thr Glu Thr Ile Thr Cys Asn Ser Ile
145                 150                 155                 160

Gly Met Leu Ala Ala Gly Asn Ala Val Val Phe Ser Pro His Pro Arg
            165                 170                 175

Val Ala Lys Leu Ser Cys Trp Gln Val Arg Arg Ile Asn Arg Ala Leu
            180                 185                 190

Arg Ala Ala Gly Ala Pro Asp Asn Leu Val Val Thr Val Thr Ala Pro
        195                 200                 205

Ser Leu Glu Asn Thr Asn Ala Met Met Ala His Pro Lys Val Arg Met
210                 215                 220

Leu Val Ala Thr Gly Gly Pro Gly Ile Val Lys Ala Val Leu Ser Ser
225                 230                 235                 240

Gly Lys Lys Ala Ile Gly Ala Gly Ala Gly Asn Pro Pro Ala Val Val
                245                 250                 255

Asp Glu Thr Ala Asp Ile Glu His Ala Ala Lys Cys Ile Val Asp Gly
                260                 265                 270

Ala Ser Phe Asp Asn Asn Leu Pro Cys Thr Ala Glu Lys Glu Ile Ile
            275                 280                 285

Ala Val Asp Ser Ile Ala Asp Met Leu Lys Phe Cys Met Ile Lys His
        290                 295                 300

Gly Ala Tyr Glu Ala Thr Ala Ser Glu Val Ala Glu Leu Glu Lys Leu
305                 310                 315                 320

Leu Val Asn Gly Asp Lys Pro Arg Thr Glu Trp Val Gly Lys Pro Ala
                325                 330                 335

Ala Lys Ile Leu Glu Ala Ile Gly Val Thr Pro Pro Gly Val Arg
                340                 345                 350

Leu Ile Val Cys Glu Ala Ser Ala Thr His Pro Phe Val His Glu
            355                 360                 365

Leu Met Met Pro Val Leu Gly Leu Val Arg Val Pro Asp Val Asp Ala
370                 375                 380

Ala Ile Asp Leu Ala Val Glu Leu Glu His Gly Asn Arg His Thr Ala
385                 390                 395                 400

Val Met His Ser Leu Asn Val Ser Lys Leu Thr Lys Met Gly Lys Leu
                405                 410                 415

Ile Gln Thr Thr Ile Phe Val Lys Asn Gly Pro Ser Tyr Asn Gly Ile
                420                 425                 430

Gly Ile Gly Gly Glu Gly Tyr Pro Thr Phe Thr Ile Ala Gly Pro Thr
            435                 440                 445

Gly Glu Gly Leu Thr Ser Ala Arg Ser Phe Thr Arg Lys Arg Arg Cys
450                 455                 460

Val Leu Val Gly Asp Leu Asn Val Arg
465                 470

<210> SEQ ID NO 121
<211> LENGTH: 467
<212> TYPE: PRT
<213> ORGANISM: Eubacteriaceae bacterium

<400> SEQUENCE: 121

Met Asn Ala Glu Leu Leu Gln Asp Val Val Arg Gln Val Leu Ser Glu
1               5                   10                  15

Met Lys Leu Glu Ser Ser Asn Ile Leu Ser Asn Glu Tyr Asn Tyr Gly
                20                  25                  30

Ile Phe Asp Asp Met Glu Ala Ala Ile Asn Ala Ser Glu Thr Ala Gln
            35                  40                  45

Arg Lys Leu Phe Glu Cys Ser Val Gln Gln Arg Asn Glu Phe Ala Asn
    50                  55                  60

Val Ile Arg Lys Glu Ile Leu Lys Lys Asp Asn Leu Glu Met Ile Ser
65                  70                  75                  80

Arg Asp Ala Val Glu Glu Thr Glu Ile Gly Arg Phe Glu Asp Lys Ile
                85                  90                  95

Leu Lys Asn Lys Val Ala Ala Glu Lys Thr Pro Gly Met Glu Asp Leu

```
                100              105              110
Thr Thr Arg Ala Leu Thr Gly Lys Asp Gly Leu Met Ile Glu Glu Tyr
            115              120              125
Cys Pro Phe Gly Val Ile Gly Ser Ile Thr Pro Thr Thr Asn Pro Thr
            130              135              140
Glu Thr Leu Ile Asn Asn Ser Ile Ser Met Ile Val Gly Gly Asn Thr
145              150              155              160
Val Val Phe Ser Pro His Pro Arg Ala Lys Asn Val Ser Ile Lys Leu
            165              170              175
Val Lys Met Met Asn Lys Ala Leu Glu Glu Tyr Gly Ala Pro Arg Asn
            180              185              190
Met Ile Thr Met Val Lys Glu Pro Ser Ile Glu Asn Thr Asn Leu Met
            195              200              205
Met Ser Asn Pro Lys Val Lys Leu Leu Val Ala Thr Gly Gly Pro Phe
            210              215              220
Ile Val Asn Thr Val Leu Ser Ser Gly Lys Lys Ala Ile Gly Ala Gly
225              230              235              240
Ala Gly Asn Pro Pro Val Val Asp Glu Thr Ala Asp Ile Glu Lys
            245              250              255
Ala Ala Ile Asp Ile Val Ser Gly Ala Ser Phe Asp Asn Asn Val Pro
            260              265              270
Cys Ile Ala Glu Lys Glu Val Phe Ala Val Asp Ser Ile Ser Asp Met
            275              280              285
Leu Ile Tyr His Met Lys Lys Asn Gly Ala Tyr Glu Ile Val Ser Gln
            290              295              300
Asp Met Ile Glu Lys Leu Asp Lys Leu Val Ser Gln Glu Asn Gly Lys
305              310              315              320
Pro Lys Thr Glu Phe Val Gly Lys Ser Ala Lys Tyr Ile Leu Glu Lys
            325              330              335
Leu Gly Ile Tyr Val Asp Asp Ser Ile Arg Leu Ile Ile Cys Arg Thr
            340              345              350
Ser Lys Asn His His Leu Val Gln Glu Glu Met Leu Met Pro Ile Leu
            355              360              365
Pro Ile Val Ser Val Ser Asp Val Asp Ile Ala Ile Glu Tyr Ala Tyr
            370              375              380
Glu Ala Glu His Gly Asn Arg His Thr Ala Ile Met His Ser Lys Asn
385              390              395              400
Val Glu Lys Leu Ser Lys Met Ala Lys Lys Leu Glu Ala Thr Ile Phe
            405              410              415
Val Lys Asn Ala Pro Ser Tyr Ser Gly Ile Gly Val Gly Gly Glu Gly
            420              425              430
His Thr Thr Phe Thr Ile Ala Gly Pro Thr Gly Glu Gly Ile Thr Ser
            435              440              445
Ala Lys Ser Phe Cys Arg Ile Arg Arg Cys Val Met His Asp Ser Phe
            450              455              460
Ser Ile Arg
465

<210> SEQ ID NO 122
<211> LENGTH: 467
<212> TYPE: PRT
<213> ORGANISM: Eubacteriaceae bacterium

<400> SEQUENCE: 122
```

Met Asn Ala Glu Leu Leu Gln Asp Val Val Arg Gln Val Leu Ser Glu
1               5                   10                  15

Met Lys Leu Glu Ser Ser Asn Ile Leu Ser Asn Glu Tyr Asn Tyr Gly
            20                  25                  30

Ile Phe Asp Asp Met Glu Ala Ala Ile Asn Ala Ser Glu Thr Ala Gln
            35                  40                  45

Arg Lys Leu Phe Glu Cys Ser Val Gln Gln Arg Asn Glu Phe Ala Asn
        50                  55                  60

Val Ile Arg Arg Glu Val Leu Lys Lys Asp Asn Leu Glu Met Ile Ser
65                  70                  75                  80

Arg Asp Ala Val Glu Glu Thr Glu Ile Gly Arg Phe Gly Asp Lys Ile
                85                  90                  95

Leu Lys Asn Lys Val Ala Ala Glu Lys Thr Pro Gly Met Glu Asp Leu
            100                 105                 110

Thr Thr Arg Ala Leu Thr Gly Lys Asp Gly Leu Met Ile Glu Glu Tyr
            115                 120                 125

Cys Pro Phe Gly Val Ile Gly Ser Ile Thr Pro Thr Thr Asn Pro Thr
        130                 135                 140

Glu Thr Leu Ile Asn Asn Ser Ile Ser Met Ile Val Gly Gly Asn Thr
145                 150                 155                 160

Val Val Phe Ser Pro His Pro Arg Ala Lys Asn Val Ser Ile Lys Leu
                165                 170                 175

Val Lys Met Met Asn Lys Ala Leu Glu Glu Tyr Gly Ala Pro Arg Asn
            180                 185                 190

Met Ile Thr Met Val Lys Glu Pro Ser Ile Glu Asn Thr Asn Leu Met
            195                 200                 205

Met Ser Asn Pro Lys Val Lys Leu Leu Val Ala Thr Gly Gly Pro Phe
        210                 215                 220

Ile Val Asn Thr Val Leu Ser Ser Gly Lys Lys Ala Ile Gly Ala Gly
225                 230                 235                 240

Ala Gly Asn Pro Pro Val Val Asp Glu Thr Ala Asp Ile Glu Lys
                245                 250                 255

Ala Ala Ile Asp Ile Val Ser Gly Ala Ser Phe Asp Asn Asn Val Pro
            260                 265                 270

Cys Ile Ala Glu Lys Glu Val Phe Ala Val Asp Ser Ile Ser Asp Met
        275                 280                 285

Leu Ile Tyr His Met Lys Lys Asn Gly Ala Tyr Glu Ile Val Ser Gln
        290                 295                 300

Asp Met Ile Glu Lys Leu Asp Lys Leu Val Ser Gln Glu Asn Gly Lys
305                 310                 315                 320

Pro Lys Thr Glu Phe Val Gly Lys Ser Ala Lys Tyr Ile Leu Glu Lys
                325                 330                 335

Leu Gly Ile Tyr Val Asp Asp Ser Ile Arg Leu Ile Ile Cys Arg Thr
            340                 345                 350

Ser Lys Asn His His Leu Val Gln Glu Glu Met Leu Met Pro Ile Leu
        355                 360                 365

Pro Ile Val Ser Val Ser Asp Val Asp Ile Ala Ile Glu Tyr Ala Tyr
        370                 375                 380

Glu Ala Glu His Gly Asn Arg His Thr Ala Ile Met His Ser Lys Asn
385                 390                 395                 400

Val Glu Lys Leu Ser Lys Met Ala Lys Lys Leu Glu Ala Thr Ile Phe
                405                 410                 415

Val Lys Asn Ala Pro Ser Tyr Ser Gly Ile Gly Val Gly Gly Glu Gly

```
                    420                 425                 430
His Thr Thr Phe Thr Ile Ala Gly Pro Thr Gly Glu Gly Ile Thr Ser
                435                 440                 445

Ala Lys Ser Phe Cys Arg Ile Arg Arg Cys Val Met His Asp Ser Phe
            450                 455                 460

Ser Ile Arg
465

<210> SEQ ID NO 123
<211> LENGTH: 468
<212> TYPE: PRT
<213> ORGANISM: Clostridium beijerinckii

<400> SEQUENCE: 123

Met Asn Lys Asp Thr Leu Ile Pro Thr Thr Lys Asp Leu Lys Val Lys
1               5                  10                  15

Thr Asn Gly Glu Asn Ile Asn Leu Lys Asn Tyr Lys Asp Asn Ser Ser
                20                  25                  30

Cys Phe Gly Val Phe Glu Asn Val Glu Asn Ala Ile Ser Ser Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320
```

```
Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
            355                 360                 365

Leu Met Met Pro Ile Leu Pro Ile Val Arg Val Lys Asp Ile Asp Glu
            370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 124
<211> LENGTH: 20
<212> TYPE: PRT
<213> ORGANISM: Clostridium saccharoperbutylacetonicum

<400> SEQUENCE: 124

Leu Gln Lys Asn Asn Glu Thr Gln Glu Tyr Ser Ile Asn Lys Lys Trp
1               5                   10                  15

Val Gly Lys Asp
            20

<210> SEQ ID NO 125
<211> LENGTH: 15
<212> TYPE: PRT
<213> ORGANISM: Lactobacillus brevis

<400> SEQUENCE: 125

Ile Gly Pro Lys Gly Ala Pro Asp Arg Lys Phe Val Gly Lys Asp
1               5                   10                  15

<210> SEQ ID NO 126
<211> LENGTH: 14
<212> TYPE: PRT
<213> ORGANISM: Clostridium phytofermentans

<400> SEQUENCE: 126

Ile Thr Pro Lys Gly Leu Asn Arg Asn Cys Val Gly Lys Asp
1               5                   10

<210> SEQ ID NO 127
<211> LENGTH: 18
<212> TYPE: PRT
<213> ORGANISM: Clostridium saccharoperbutylacetonicum

<400> SEQUENCE: 127

Ser Phe Ala Gly Val Gly Tyr Glu Ala Glu Gly Phe Thr Thr Phe Thr
1               5                   10                  15

Ile Ala
```

```
<210> SEQ ID NO 128
<211> LENGTH: 22
<212> TYPE: PRT
<213> ORGANISM: Lactobacillus brevis

<400> SEQUENCE: 128

Thr Tyr Cys Gly Thr Gly Val Ala Thr Asn Gly Ala His Ser Gly Ala
1               5                   10                  15

Ser Ala Leu Thr Ile Ala
            20

<210> SEQ ID NO 129
<211> LENGTH: 18
<212> TYPE: PRT
<213> ORGANISM: Clostridium phytofermentans

<400> SEQUENCE: 129

Ser Tyr Ala Ala Ile Gly Phe Gly Gly Glu Gly Phe Cys Thr Phe Thr
1               5                   10                  15

Ile Ala
```

ALDEHYDE DEHYDROGENASE VARIANTS AND METHODS OF USING SAME

This application is a U.S. National Stage Application under 35 U.S.C. § 371 of International Patent Application No. PCT/US2019/052829, filed Sep. 25, 2019, which claims the benefit of U.S. Provisional Application No. 62/737,053, filed Sep. 26, 2018, and the benefit of U.S. Provisional Application No. 62/740,830, filed Oct. 3, 2018, the disclosure of each of which is incorporated by reference herein in its entirety.

BACKGROUND OF THE INVENTION

Reference is made to the following provisional and international applications, which are incorporated herein by reference in their entireties: (1) U.S. Provisional Application No. 62/480,194 entitled "ALDEHYDE DEHYDROGENASE VARIANTS AND METHODS OF USE," filed Mar. 31, 2017; (2) U.S. Provisional Application No. 62/480,208 entitled "3-HYDROXYBUTYRYL-COA DEHYDROGENASE VARIANTS AND METHODS OF USE," filed Mar. 31, 2017; (3) U.S. Provisional Application No. 62/480,270 entitled "PROCESS AND SYSTEMS FOR OBTAINING 1,3-BUTANEDIOL FROM FERMENTATION BROTHS," filed Mar. 31, 2017; (4) International Patent Application No. PCT/US2018/025122 entitled "ALDEHYDE DEHYDROGENASE VARIANTS AND METHODS OF USE," filed Mar. 29, 2018; (5) International Patent Application No. PCT/US2018/025086 entitled "3-HYDROXYBUTYRYL-COA DEHYDROGENASE VARIANTS AND METHODS OF USE," filed Mar. 29, 2018; and (6) International Patent Application No. PCT/US2018/025068 entitled, "PROCESS AND SYSTEMS FOR OBTAINING 1,3-BUTANEDIOL FROM FERMENTATION BROTHS," filed on Mar. 29, 2018.

This application incorporates herein by reference a Sequence Listing as an ASCII text file entitled "12956-462-228_SL.TXT" created on Sep. 17, 2019, and having a size of 498,106 bytes.

The present invention relates generally to organisms engineered to produce desired products, engineered enzymes that facilitate production of a desired product, and more specifically to enzymes and cells that produce desired products such as 3-hydroxybutyraldehyde, 1,3-butanediol, 4-hydroxybutyraldehyde, 1,4-butanediol, and related products and products derived therefrom.

Various commodity chemicals are used to make desired products for commercial use. Many of the commodity chemicals are derived from petroleum. Such commodity chemicals have various uses, including use as solvents, resins, polymer precursors, and specialty chemicals. Desired commodity chemicals include 4-carbon molecules such as 1,4-butanediol and 1,3-butanediol, upstream precursors and downstream products. It is desirable to develop methods for production of commodity chemicals to provide renewable sources for petroleum-based products and to provide less energy- and capital-intensive processes.

Thus, there exists a need for methods that facilitate production of desired products. The present invention satisfies this need and provides related advantages as well.

SUMMARY OF INVENTION

The invention provides polypeptides and encoding nucleic acids of aldehyde dehydrogenase variants. The invention also provides cells expressing aldehyde dehydrogenase variants. The invention further provides methods for producing 3-hydroxybutyraldehyde (3-HBal) and/or 1,3-butanediol (1,3-BDO), or an ester or amide thereof, comprising culturing cells expressing an aldehyde dehydrogenase variant or using lysates of such cells. The invention additional provides methods for producing 4-hydroxybutyraldehyde (4-HBal) and/or 1,4-butanediol (1,4-BDO), or an ester or amide thereof, comprising culturing cells expressing an aldehyde dehydrogenase variant or using lysates of such cells.

BRIEF DESCRIPTION OF THE DRAWINGS

FIG. 1 shows pathways from acetoacetyl-CoA to 1,3-butanediol. The enzymes are: (A) acetoacetyl-CoA reductase (CoA-dependent, aldehyde forming); (B) 3-oxobutyraldehyde reductase (ketone reducing); (C) 3-hydroxybutyraldehyde reductase, also referred to herein as 1,3-butanediol dehydrogenase; (D) acetoacetyl-CoA reductase (CoA-dependent, alcohol forming); (E) 3-oxobutyraldehyde reductase (aldehyde reducing); (F) 4-hydroxy, 2-butanone reductase; (G) acetoacetyl-CoA reductase (ketone reducing); (H) 3-hydroxybutyryl-CoA reductase (aldehyde forming), also referred to herein as 3-hydroxybutyraldehyde dehydrogenase; and (I) 3-hydroxybutyryl-CoA reductase (alcohol forming).

FIG. 3 shows a sequence alignment of ALD-1, ALD-2 and ALD-3. The sequences correspond to SEQ ID NOS:1, 2 and 3, respectively. Underlined in the figure are 2 loop regions, the first designated A, the second B, both involved in substrate specificity and enantiomer specificity as determined herein. Loop A in ALD-1 is sequence LQKN-NETQEYSINKKWVGKD (SEQ ID NO:124), in ALD-2 is sequence IGPKGAPDRKFVGKD (SEQ ID NO:125), and in ALD-3 is sequence ITPKGLNRNCVGKD (SEQ ID NO:126). Loop B in ALD-1 is sequence SFAGVGYEAE-GFTTFTIA (SEQ ID NO:127), in ALD-2 is sequence TYCGTGVATNGAHSGASALTIA (SEQ ID NO:128), and in ALD-3 is sequence SYAAIGFGGEGFCTFTIA (SEQ ID NO:129). The sequence and the length of the substrate specificity loop A and B from ALD-2 differ from those of ALD-1 and ALD-3; nevertheless the alignment shows sufficient conservation to facilitate identification of corresponding positions for substitution as described herein, and especially so if combined with 3D modeling as shown in FIG. 6. ALD-3 was used as the template for modeling of crystal structure; see FIG. 6 that shows the two loop regions interacting to affect substrate specificity and enantiomer specificity, especially when modified with exemplary substitutions as described herein. ALD-1 and ALD-3 are 51.9% identical. ALD-1 and ALD-2 are 35.9% identical. ALD-3 and ALD-2 are 40% identical. A consensus for Loop A based on alignment of ALD-1, ALD-2 and ALD-3 is IXPKG-----XXNRKXVGKD (SEQ ID NO:5). A consensus for Loop B based on alignment of ALD-1, ALD-2 and ALD-3 is SYAGXGXXXE----GFXTFTIA (SEQ ID NO:6). It is understood that the specifically identified amino acids in the consensus sequences are conserved residues, whereas the positions marked with "X" are variable, and can correspond to any amino acid, as desired and disclosed herein. It is further understood that "-----" can correspond to the presence or absence of a variable number of amino acid residues. An example of such a variable number of amino acid residues is shown in FIGS. 3 and 4A-4C. Further, it is understood that conserved residues in the consensus sequence can be substituted, for example, with conservative amino acids, as described herein (see, for example, FIGS. 4A-4C).

FIGS. 4A-4C show alignments of exemplary aldehyde deydrogenases (ALD), which representative alignments demonstrate identifying positions in ALDs that correspond to positions in the representative template ALD sequence where substitutions of the invention can be made. As in FIG. 3, underlined are 2 loop regions, the first designated A, the second B, both involved in substrate specificity and enantiomer specificity as determined herein. FIG. 4A shows an alignment of exemplary ALD sequences with a 40-55% cutoff compared to ALD-1. The sequences correspond to SEQ ID NOS: 1 (ALD-1), 13, 20 and 24 as indicated in FIG. 4A. FIG. 4B shows an alignment of exemplary ALD sequences with a 75-90% cutoff compared to ALD-1. The sequences correspond to SEQ ID NOS: 1 (ALD-1), 30, 33 and 37 as indicated in FIG. 4B. Loops A and B are underlined. FIG. 4C shows an alignment of exemplary ALD sequences with a 90% cutoff compared to ALD-1. The sequences correspond to SEQ ID NOS: 1 (ALD-1), 38, 40 and 44 as indicated in FIG. 4C. ALD-1 is 99%, 97%, and 95% identical to SEQ ID NOS: 38, 40 and 44, respectively. FIGS. 4A-4C demonstrate that corresponding positions for substitutions taught herein can be identified in ALDs that have at least 40% identity with ALD-1, especially the Loop A and B regions, and especially the very conserved Loop B region.

FIG. 5A shows the specific activity of ALD-2, ALD-1 and ALD-1 variants on 3 hydroxy-(R)-butyraldehyde (left bar in sets of bars) and 3 hydroxy-(S)-butyraldehyde (right bar in sets of bars). FIG. 5B shows the ratio of activity with the R to S form of 3-hydroxybutyraldehyde.

FIG. 6C shows the same orientation as 3-hydroxy-(R)-butyraldehyde (R3HIB).

DETAILED DESCRIPTION OF THE INVENTION

Figure 1:
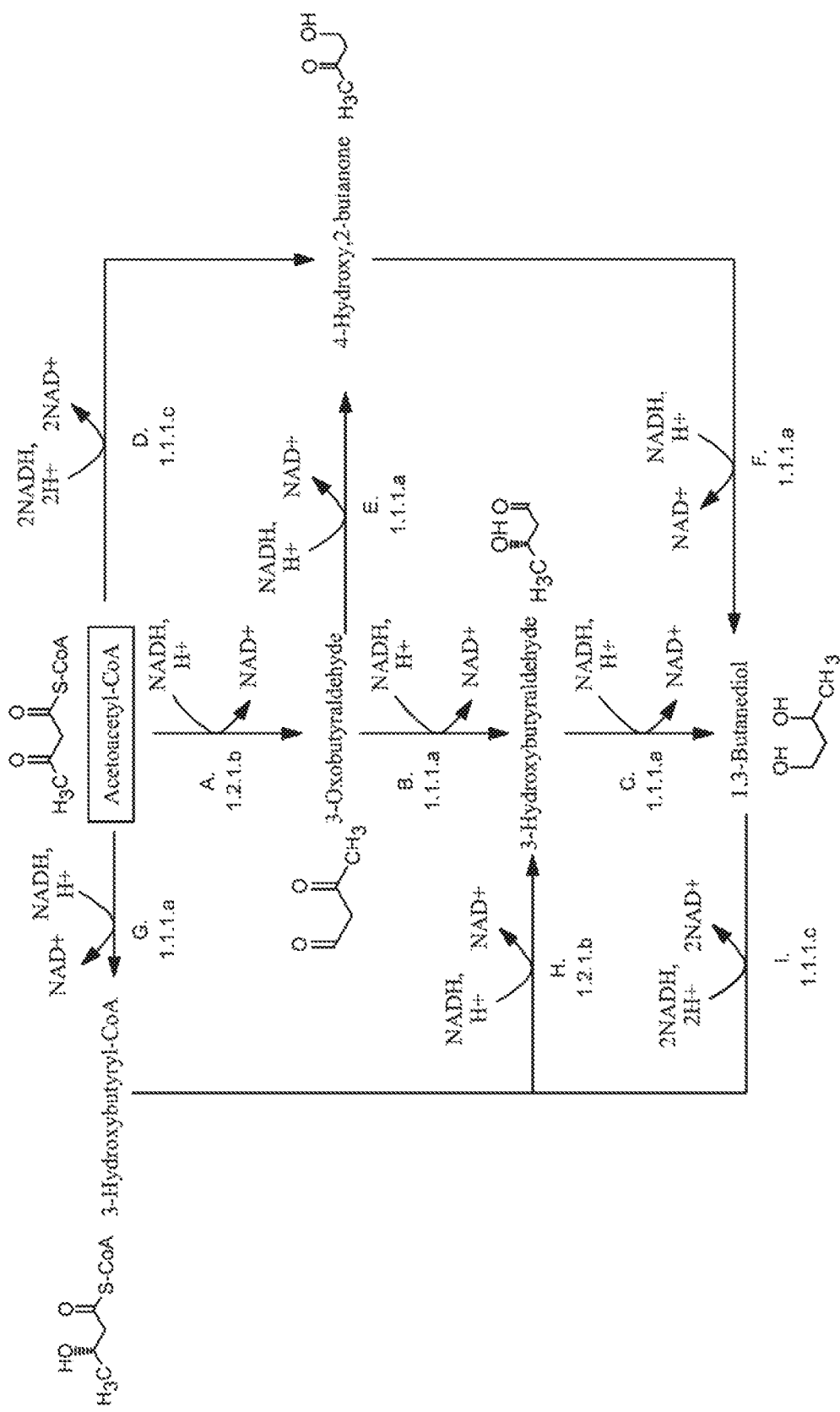
FIG. 1 shows an exemplary 1,3-butanediol (1,3-BDO) pathway that comprise an aldehyde dehydrogenase.

The invention relates to enzyme variants that have desirable properties and are useful for producing desired products. In a particular embodiment, the invention relates to aldehyde dehydrogenase variants, which are enzyme variants that have markedly different structural and/or functional characteristics compared to a wild type enzyme that occurs in nature. Thus, the aldehyde dehydrogenases of the invention or not naturally occurring enzymes. Such aldehyde dehydrogenase variants of the invention are useful in an engineered cell, such as a microbial organism, that has been engineered to produce a desired product. For example, as disclosed herein, a cell, such as a microbial organism, having a metabolic pathway can produce a desired product. An aldehyde dehydrogenase of the invention having desirable characteristics can be introduced into a cell, such as microbial organism, that has a metabolic pathway that uses an aldehyde dehydrogenase enzymatic activity to produce a desired product. Such aldehyde dehydrogenase variants are additionally useful as biocatalysts for carrying our desired reactions in vitro. Thus, the aldehyde dehydrogenase variants of the invention can be utilized in engineered cells, such as microbial organisms, to produce a desired product or as as an in vitro biocatalyst to produce a desired product.

As used herein, the term "non-naturally occurring" when used in reference to a cell, a microbial organism or microorganism of the invention is intended to mean that the cell has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the cell's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a biosynthetic pathway for producing a desired product.

A metabolic modification refers to a biochemical reaction that is altered from its naturally occurring state. Therefore, non-naturally occurring cells can have genetic modifications to nucleic acids encoding metabolic polypeptides, or functional fragments thereof. Exemplary metabolic modifications are disclosed herein.

As used herein, the term "isolated" when used in reference to a cell or microbial organism is intended to mean a cell that is substantially free of at least one component as the referenced cell is found in nature, if such a cell is found in nature. The term includes a cell that is removed from some or all components as it is found in its natural environment. The term also includes a cell that is removed from some or all components as the cell is found in non-naturally occurring environments. Therefore, an isolated cell is partly or completely separated from other substances as it is found in nature or as it is grown, stored or subsisted in non-naturally occurring environments. Specific examples of isolated cells include partially pure cells, substantially pure cells and cells cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. When used in reference to a biosynthetic activity, the term refers to an activity that is introduced into the host reference organism. The source can be, for example, a homologous or heterologous encoding nucleic acid that expresses the referenced activity following introduction into the host cell. Therefore, the term "endogenous" refers to a referenced molecule or activity that is present in the host. Similarly, the term when used in reference to expression of an encoding nucleic acid refers to expression of an encoding nucleic acid contained within the cell. The term "heterologous" refers to a molecule or activity derived from a source other than the referenced species whereas "homologous" refers to a molecule or activity derived from the host cell. Accordingly, exogenous expression of an encoding nucleic acid of the invention can utilize either or both a heterologous or homologous encoding nucleic acid.

It is understood that when more than one exogenous nucleic acid is included in a cell that the more than one exogenous nucleic acids refers to the referenced encoding nucleic acid or biosynthetic activity, as discussed above. It is further understood, as disclosed herein, that such more than one exogenous nucleic acids can be introduced into the host cell on separate nucleic acid molecules, on polycistronic nucleic acid molecules, or a combination thereof, and still be considered as more than one exogenous nucleic acid. For example, as disclosed herein a cell can be engineered to express two or more exogenous nucleic acids encoding a desired enzyme or protein, such as a pathway enzyme or protein. In the case where two exogenous nucleic acids encoding a desired activity are introduced into a host cell, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the non-naturally occurring cells of the invention. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given function. However, the attenuation of the activity or amount of an enzyme or protein that mimics complete disruption, for example, complete disruption for one pathway, can still be sufficient for a separate pathway to continue to function. For example, attenuation of an endogenous enzyme or protein can be sufficient to mimic the complete disruption of the same enzyme or protein for production of a desired product of the invention, but the remaining activity or amount of enzyme or protein can still be sufficient to maintain other pathways, such as a pathway that is critical for the host cell to survive, reproduce or grow. Attenuation of an enzyme or protein can also be weakening, reducing or diminishing the activity or amount of the enzyme or protein in an amount that is sufficient to increase yield of a desired product of the invention, but does not necessarily mimic complete disruption of the enzyme or protein.

The non-naturally occurring cells of the invention can contain stable genetic alterations, which refers to cells that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host cell or organism such as *E. coli* and their corresponding metabolic reactions or a suitable source cell or organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring cell. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring cells of the invention having biosynthetic capability for a desired product, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced cell that encode an enzyme catalyzing a similar or substantially similar metabolic reaction, those skilled in the art also can utilize these evolutionarily related genes. Similarly for a gene disruption, evolutionarily related genes can also be disrupted or deleted in a host cell to reduce or eliminate functional redundancy of enzymatic activities targeted for disruption.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In one embodiment, the invention provides an aldehyde dehydrogenase that is a variant of a wild type or parent aldehyde dehydrogenase. The aldehyde dehydrogenase of the invention converts an acyl-CoA to its corresponding aldehyde. Such an enzyme can also be referred to as an oxidoreductase that converts an acyl-CoA to its corresponding aldehyde. Such an aldehyde dehydrogenase of the invention can be classified as a reaction 1.2.1.b, oxidoreductase (acyl-CoA to aldehyde), where the first three digits correspond to the first three Enzyme Commission number digits which denote the general type of transformation independent of substrate specificity. Exemplary enzymatic conversions of an aldehyde dehydrogenase of the invention include, but are not limited to, the conversion of 3-hydroxybutyryl-CoA to 3-hydroxybutyraldehyde (also referred to as 3-HBal)(see FIG. 1), and the conversion of 4-hydroxybutyryl-CoA to 4-hydroxybutyraldehyde (see FIG. 2). An aldehyde dehydrogenase of the invention can be used to produce desired products such as 3-hydroxybutyraldehyde (3-HBal), 1,3-butanediol (1,3-BDO), 4-hydroxybutyraldehyde (4-HBal), 1,4-butanediol (1,4-BDO), or other desired products such as a downstream product, including an ester or amide thereof, in a cell, such as a microbial organism, containing a suitable metabolic pathway, or in vitro. For example, 1,3-BDO can be reacted with an acid, either in vivo or in vitro, to convert to an ester using, for example, a lipase. Such esters can have nutraceutical, medical and food uses, and are advantaged when R-form of 1,3-butanediol is used since that is the form (compared to S-form or the racemic mixture that is made from petroleum or from ethanol by the acetaldehyde chemical synthesis route) best utilized by both animals and humans as an energy source (e.g., a ketone ester, such as (R)-3-hydroxybutyl-R-1,3-butanediol monoester (which has Generally Recognized As Safe (GRAS) approval in the United States) and (R)-3-hydroxybutyrate glycerol monoester or diester). The ketone esters can be delivered orally, and the ester releases R-1,3-butanediol that is used by the body (see, for example, WO2013150153). Thus the present invention is particularly useful to provide an improved enzymatic route and microorganism to provide an improved composition of 1,3-butanediol, namely R-1,3-butanediol, highly enriched or essentially enantiomerically pure, and further having improved purity qualities with respect to by-products.

1,3-Butanediol, also referred to as butylene glycol, has further food related uses including use directly as a food source, a food ingredient, a flavoring agent, a solvent or solubilizer for flavoring agents, a stabilizer, an emulsifier, and an anti-microbial agent and preservative. 1,3-Butanediol is used in the pharmaceutical industry as a parenteral drug solvent. 1,3-Butanediol finds use in cosmetics as an ingredient that is an emollient, a humectant, that prevents crystallization of insoluble ingredients, a solubilizer for less-water-soluble ingredients such as fragrances, and as an anti-microbial agent and preservative. For example, it can be used as a humectant, especially in hair sprays and setting lotions; it reduces loss of aromas from essential oils, preserves against spoilage by microorganisms, and is used as a solvent for benzoates. 1,3-Butanediol can be use at concentrations from 0.1 percent or less to 50 percent or greater. It is used in hair and bath products, eye and facial makeup, fragrances, personal cleanliness products, and shaving and skin care preparations (see, for example, the Cosmetic Ingredient Review board's report: "Final Report on the Safety Assessment of Butylene Glycol, Hexylene Glycol, Ethoxydiglycol, and Dipropylene Glycol", *Journal of the American College of Toxicology*, Volume 4, Number 5, 1985, which is incorporated herein by reference). This report provides specific uses and concentrations of 1,3-butanediol (butylene glycol) in cosmetics; see for examples the report's Table 2 therein entitled "Product Formulation Data".

In one embodiment, the invention provides an isolated nucleic acid molecule selected from (a) a nucleic acid molecule encoding an amino acid sequence referenced as SEQ ID NO:1, 2 or 3 or in Table 4, wherein said amino acid sequence comprises an amino acid substitution corresponding to position I66; (b) a nucleic acid molecule that hybridizes to the nucleic acid of (a) under highly stringent hybridization conditions and comprises a nucleic acid sequence that encodes an amino acid substitution corresponding to position I66; and (c) a nucleic acid molecule that is complementary to (a) or (b).

In some embodiments of a nucleic acid of the invention, the amino acid substitution at position I66 is an amino acid substitution as set forth in Table 1, 2 and/or 3. In some embodiments, the amino acid sequence, in addition to the substitution at position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3.

In some embodiments of a nucleic acid molecule of the invention, the amino acid sequence, other than the one or more amino acid substitutions, has at least 65%, 70%, 75%, 80%, 85%, 90%, 95%, 98% or 99% sequence identity, or is identical, to an amino acid sequence referenced in SEQ ID NO:1, 2 or 3 or in Table 4. In some embodiments, the amino acid sequence comprises at least 2, 3, 4, 5, 6, 7, 8, 9, 10, 11, 12, 13, 14, 15 or 16 of the amino acid substitutions set forth in Table 1, 2 and/or 3. In some embodiments, the amino acid sequence comprises the amino acid substitutions of a variant as set forth in Table 1, 2 and/or 3.

In one embodiment, an isolated nucleic acid molecule can be selected from: (a) a nucleic acid molecule encoding an amino acid sequence referenced as SEQ ID NO:1, 2 or 3 or in Table 4, wherein the amino acid sequence comprises one or more of the amino acid substitutions set forth in Table 1, 2 and/or 3; (b) a nucleic acid molecule that hybridizes to the nucleic acid of (a) under highly stringent hybridization conditions and comprises a nucleic acid sequence that encodes one or more of the amino acid substitutions set forth in Table 1, 2 and/or 3; (c) a nucleic acid molecule encoding an amino acid sequence comprising the consensus sequence of Loop A (SEQ ID NO:5) and/or Loop B (SEQ ID NO:6), wherein the amino acid sequence comprises one or more of the amino acid substitutions set forth in Table 1, 2 and/or 3; and (d) a nucleic acid molecule that is complementary to (a) or (b). In an embodiment, the amino acid sequence encoded by the nucleic acid molecule, other than the one or more amino acid substitutions, has at least 65%, 70%, 75%, 80%, 85%, 90%, 95%, 98% or 99% sequence identity, or is identical, to an amino acid sequence referenced in SEQ ID NO:1, 2 or 3 or in Table 4. The amino acid sequence can comprise at least 2, 3, 4, 5, 6, 7, 8, 9, 10, 11, 12, 13, 14, 15 or 16, or more, of the amino acid substitutions set forth in Table 1, 2 and/or 3, for example, 17, 18, 19, 20, 21, 22, 23, 24, 25, 26, 27, 28, 29, 30, 31, 32, 33, 34, 35, 36, 37, 38, 39, 40, 41, 42 or 43, i.e., up to all of the amino acid positions having a substitution.

The invention also provides a vector containing the nucleic acid molecule of the invention. In one embodiment, the vector is an expression vector. In one embodiment, the vector comprises double stranded DNA.

The invention also provides a nucleic acid encoding an aldehyde dehydrogenase polypeptide of the invention. A nucleic acid molecule encoding an aldehyde dehydrogenase of the invention can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 700%, 75%, 80%, 85%, 90%, 91%, 92%, 93%, 94%, 95%, 96%, 97%, 98% or 99% sequence identity, or be identical, to a nucleic acid described herein.

Stringent hybridization refers to conditions under which hybridized polynucleotides are stable. As known to those of skill in the art, the stability of hybridized polynucleotides is reflected in the melting temperature ($T_m$) of the hybrids. In general, the stability of hybridized polynucleotides is a function of the salt concentration, for example, the sodium ion concentration, and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamine tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding an aldehyde dehydrogenase of the invention can have at least a certain sequence identity to a nucleotide sequence disclosed herein. Accordingly, in some aspects of the invention, a nucleic acid molecule encoding an aldehyde dehydrogenase of the invention has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity, or is identical, to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+ SwissProtein+SPupdate+PIR. Details of these programs can be found at the National Center for Biotechnology Information (see also Altschul et al., "*J. Mol. Biol.* 215:403410 (1990)).

In some embodiments, the nucleic acid molecule is an isolated nucleic acid molecule. In some embodiments, the isolated nucleic acid molecule is a nucleic acid molecule encoding a variant of a reference polypeptide, wherein (i) the reference polypeptide has an amino acid sequence of SEQ ID NO: 1, 2 or 3 or those in Table 4 (SEQ ID NOS:7-123), (ii) the variant comprises one or more amino acid substitutions relative to SEQ ID NO: 1, 2 or 3 or those in Table 4, and (iii) the one or more amino acid substitutions are selected from the amino acid substitutions shown in Tables 1-3. Tables 1-3 provide non-limiting lists of exemplary variants of SEQ ID NO: 1, 2 or 3 or those in Table 4. In one embodiment, for each variant in Tables 1-3, all positions except for the indicated position(s) are identical to SEQ ID NO: 1, 2 or 3 or those in Table 4. Amino acid substitutions are indicated by a letter indicating the identity of the original amino acid, followed by a number indicating the position of the substituted amino acid in SEQ ID NO: 1, 2 or 3 or those in Table 4, followed by a letter indicating the identity of the substituted amino acid. For example, "D12A" indicates that the aspartic acid at position 12 in SEQ ID NO: 1 or 2 is replaced with an alanine. The single-letter code used to identify amino acids is the standard code known by those skilled in the art. Some variants in Tables 1-3 comprise two or more substitutions, which is indicated by a list of substitutions. The one or more amino acid substitutions can be selected from any one of the variants listed in Tables 1-3, or from any combination of two or more variants listed in Tables 1-3. When selecting from a single variant in Tables 1-3, the resulting variant can comprise one or more of the substitutions of the selected variant in any combination, including all of the indicated substitutions or less than all of the indicated substitutions. When substitutions are selected from those of two or more variants in Tables 1-3, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Tables 1-3. As a further example, the resulting variant can comprise 1, 2, 3, 4, 5, 6, 7, 8, 9, 10, 11, 12, 13, 14, 15, 16, 20, 25, or more substitutions selected from 1, 2, 3, 4, 5, or more selected variants of Tables 1-3. In some embodiments, the resulting variant comprises all of the indicated substitutions of a selected variant in Tables 1-3. In some embodiments, the resulting variant differs from SEQ ID NO: 1, 2 or 3 or those in Table 4 by at least one amino acid substitution, but less than 25, 20, 10, 5, 4, or 3 amino acid substitutions. In some embodiments, the resulting variant comprises, consists essentially of, or consists of a sequence as indicated by a variant selected from Tables 1-3, differing from SEQ ID NO: 1, 2 or 3 or those in Table 4 only at the indicated amino acid substitutions.

In some embodiments, the nucleic acid molecule is an isolated nucleic acid molecule encoding a variant of a reference polypeptide (the reference polypeptide having an amino acid sequence of SEQ ID NO: 1, 2 or 3 or those in Table 4), wherein the variant (i) comprises one or more amino acid substitutions of a corresponding variant selected from Table 1-3, and (ii) has at least 65%, 70%, 75%, 80%, 85%, 90%, 95%, 98% 99%, or 100% sequence identity to the corresponding variant. In cases where the second variant has 100% sequence identity to the corresponding variant, the second variant comprises a sequence as indicated by a variant selected from Table 1-3, and may or may not have one or more additional amino acids at either or both the amino- and carboxy-termini. In some embodiments, the resulting variant has at least 80%, 85%, 90%, or 95% sequence identity to a corresponding variant selected from Table 1-3; in some cases, identity is at least 90% or more. In cases where the resulting variant is less than 100% identical to a corresponding variant selected from Table 1-3, the position of one or more of the amino acid substitutions indicated for the corresponding variant may shift (e.g. in the case of insertion or deletion of one or more amino acids), but still be contained within the resulting variant. For example, the aspartic acid to alanine substitution corresponding to "D12A" (at position 12 relative to SEQ ID NO: 1 or 2) may be present, but at a different position in the resulting variant. Whether an amino acid corresponds to an indicated substitution, albeit at a different position, can be determined by sequence alignment, as is well known in the art. In general, an alignment showing identity or similarity of amino acids flanking the substituted amino acid, such that the flanking sequences are considered to be aligned with a homologous sequence of another polypeptide, will allow the substituted amino acid to be positioned locally with respect to the corresponding variant of Table 1-3 to determine a corresponding position to make the substitution, albeit at a shifted numerical position in a given polypeptide chain. In one embodiment, a region comprising at least three to fifteen amino acids, including the substituted position, will locally align with the corresponding variant sequence with a relatively high percent identity, including at the position of the substituted amino acid along the corresponding variant sequence (e.g. 90%, 95%, or 100% identity). In some embodiments, the one or more amino acid substitutions (e.g. all or less than all of the amino acid substitutions) indicated by a corresponding variant selected from Table 1-3 is considered to be present in a given variant, even if occurring at a different physical position along a polypeptide chain, if the sequence of the polypeptide being compared aligns with the corresponding variant with an identical match or similar amino acid at the indicated position along the corresponding variant sequence when using a BLASTP alignment algorithm with default parameters, where a similar amino acid is one considered to have chemical properties sufficient for alignment with the variant position of interest using default parameters of the alignment algorithm.

In some embodiments, a nucleic acid molecule of the invention is complementary to a nucleic acid described in connection with any of the various embodiments herein.

It is understood that a nucleic acid of the invention or a polypeptide of the invention can exclude a wild type parental sequence, for example a parental sequence such as SEQ ID NOS: 1, 2 or 3 or sequences disclosed in Table 4. One skilled in the art will readily understand the meaning of a parental wild type sequence based on what is well known in the art. It is further understood that such a nucleic acid of the invention can exclude a nucleic acid sequence encoding a naturally occurring amino acid sequence as found in nature. Similarly, a polypeptide of the invention can exclude an amino acid sequence as found in nature. Thus, in a particular embodiment, the nucleic acid or polypeptide of the invention is as set forth herein, with the proviso that the encoded amino acid sequence is not the wild type parental sequence or a naturally occurring amino acid sequence and/or that the nucleic acid sequence is not a wild type or naturally occurring nucleic acid sequence. A naturally occurring amino acid or nucleic acid sequence is understood by those skilled in the art as relating to a sequence that is found in a naturally occurring organism as found in nature. Thus, a nucleic acid or amino acid sequence that is not found in the same state or having the same nucleotide or encoded amino acid sequence as in a naturally occurring organism is included within the meaning of a nucleic acid and/or amino acid sequence of the invention. For example, a nucleic acid or amino acid sequence that has been altered at one or more nucleotide or amino acid positions from a parent sequence, including variants as described herein, are included within the meaning of a nucleic acid or amino acid sequence of the invention that is not naturally occurring. An isolated nucleic acid molecule of the invention excludes a naturally occurring chromosome that contains the nucleic acid sequence, and can further exclude other molecules as found in a naturally occurring cell such as DNA binding proteins, for example, proteins such as histones that bind to chromosomes within a eukaryotic cell.

Thus, an isolated nucleic acid sequence of the invention has physical and chemical differences compared to a naturally occurring nucleic acid sequence. An isolated or non-naturally occurring nucleic acid of the invention does not contain or does not necessarily have some or all of the chemical bonds, either covalent or non-covalent bonds, of a naturally occurring nucleic acid sequence as found in nature. An isolated nucleic acid of the invention thus differs from a naturally occurring nucleic acid, for example, by having a different chemical structure than a naturally occurring nucleic acid sequence as found in a chromosome. A different chemical structure can occur, for example, by cleavage of phosphodiester bonds that release an isolated nucleic acid sequence from a naturally occurring chromosome. An isolated nucleic acid of the invention can also differ from a naturally occurring nucleic acid by isolating or separating the nucleic acid from proteins that bind to chromosomal DNA in either prokaryotic or eukaryotic cells, thereby differing from a naturally occurring nucleic acid by different non-covalent bonds. With respect to nucleic acids of prokaryotic origin, a non-naturally occurring nucleic acid of the invention does not necessarily have some or all of the naturally occurring chemical bonds of a chromosome, for example, binding to DNA binding proteins such as polymerases or chromosome structural proteins, or is not in a higher order structure such as being supercoiled. With respect to nucleic acids of eukaryotic origin, a non-naturally occurring nucleic acid of the invention also does not contain the same internal nucleic acid chemical bonds or chemical bonds with structural proteins as found in chromatin. For example, a non-naturally occurring nucleic acid of the invention is not chemically bonded to histones or scaffold proteins and is not contained in a centromere or telomere. Thus, the non-naturally occurring nucleic acids of the invention are chemically distinct from a naturally occurring nucleic acid because they either lack or contain different van der Waals interactions, hydrogen bonds, ionic or electrostatic bonds, and/or covalent bonds from a nucleic acid as found in nature. Such differences in bonds can occur either internally within separate regions of the nucleic acid (that is cis) or such difference in bonds can occur in trans, for example, interactions with chromosomal proteins. In the case of a nucleic acid of eukaryotic origin, a cDNA is considered to be an isolated or non-naturally occurring nucleic acid since the chemical bonds within a cDNA differ from the covalent bonds, that is the sequence, of a gene on chromosomal DNA. Thus, it is understood by those skilled in the art that an isolated or non-naturally occurring nucleic acid is distinct from a naturally occurring nucleic acid.

In one embodiment, the invention provides an isolated polypeptide comprising an amino acid sequence referenced as SEQ ID NO:1, 2 or 3 or in Table 4, wherein the amino acid sequence comprises an amino acid substitution corresponding to position I66. In some embodiments, the amino acid substitution at position I66 is an amino acid substitution as set forth in Table 1, 2 and/or 3. In some embodiments, the amino acid sequence, in addition to the substitution corresponding to amino acid position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3.

In another embodiment, the invention provides an isolated polypeptide comprising an amino acid sequence referenced as SEQ ID NO:1, 2 or 3 or in Table 4, wherein said amino acid sequence comprises an amino acid substitution corresponding to position I66, wherein the amino acid sequence, other than the amino acid substitution corresponding to position I66, has at least 65%, 70%, 75%, 80%, 85%, 90%, 95%, 98% or 99% sequence identity, or is identical, to an amino acids sequence referenced as SEQ ID NO:1, 2 or 3 or in Table 4.

In some embodiments on of an isolated polypeptide of the invention, the amino acid substitution at position I66 is an amino acid substitution as set forth in Table 1, 2 and/or 3. In some embodiments, the amino acid sequence, in addition to the substitution corresponding to amino acid position I66, comprises one or more amino acid substitutions at other amino acid variant positions set forth in Table 1, 2 and/or 3. In some embodiments, the amino acid sequence, in addition to the substitution at position I66, comprises one or more of the amino acid substitutions set forth in Table 1, 2 and/or 3. In some embodiments, the amino acid sequence further comprises a conservative amino acid substitution in from 1 to 100 amino acid positions, wherein said positions are other than the one or more amino acid substitutions set forth in Table 1, 2 and/or 3.

In some embodiments of an isolated polypeptide of the invention, the amino acid sequence comprises no modification at from 2 to 300 amino acid positions compared to the parent sequence, other than the one or more amino acid substitutions set forth in Table 1, 2 and/or 3, wherein the positions are selected from those that are identical to between 2, 3, 4, or 5 of the amino acid sequences referenced as SEQ ID NO:1, 2 or 3 or in Table 4. In one embodiment, the amino acid sequence comprises at least 2, 3, 4, 5, 6, 7, 8, 9, 10, 11, 12, 13, 14, 15 or 16 of the amino acid substitutions set forth in Table 1, 2 and/or 3. In a particular embodiment, the amino acid sequence comprises the amino acid substitutions of a variant as set forth in Table 1, 2 and/or 3.

In one embodiment, an isolated polypeptide comprises an amino acid sequence referenced as SEQ ID NO:1, 2 or 3 or in Table 4, wherein the amino acid sequence comprises one or more of the amino acid substitutions set forth in Table 1, 2 and/or 3. In one embodiment, an isolated polypeptide comprises the consensus amino acid sequence of Loop A (SEQ ID NO:5) and/or Loop B (SEQ ID NO:6).

In another embodiment, an isolated polypeptide comprises an amino acid sequence referenced as SEQ ID NO:1, 2 or 3 or in Table 4, wherein the amino acid sequence comprises one or more of the amino acid substitutions set forth in Table 1, 2 and/or 3, wherein the amino acid sequence, other than the one or more amino acid substitutions, has at least 65%, 70%, 75%, 80%, 85%, 90%, 95%, 98% or 99% sequence identity, or is identical, to an amino acids sequence referenced as SEQ ID NO:1, 2 or 3 or in Table 4. In one embodiment, the amino acid sequence further comprises a conservative amino acid substitution in from 1 to 100 amino acid positions, wherein the positions are other than the one or more amino acid substitutions set forth in Table 1, 2 and/or 3. In another embodiment, the amino acid sequence comprises no modification at from 2 to 300 amino acid positions compared to the parent sequence, other than the one or more amino acid substitutions set forth in Table 1, 2 and/or 3, wherein the positions are selected from those that are identical to between 2, 3, 4, or 5 of the amino acid sequences referenced as SEQ ID NO:1, 2 or 3 or in Table 4. In one embodiment, the amino acid sequence comprises at least 2, 3, 4, 5, 6, 7, 8, 9, 10, 11, 12, 13, 14, 15 or 16, or more, of the amino acid substitutions set forth in Table 1, 2 and/or 3, for example, 17, 18, 19, 20, 21, 22, 23, 24, 25, 26, 27, 28, 29, 30, 31, 32, 33, 34, 35, 36, 37, 38, 39, 40, 41, 42 or 43, i.e., up to all of the amino acid positions having a substitution.

In one embodiment, the polypeptide of the invention encodes an aldehyde dehydrogenase. In one embodiment, the polypeptide can convert 3-hydroxybutyryl-CoA to 3-hydroxybutyraldehyde. In one embodiment, the polypeptide can convert 4-hydroxybutyryl-CoA to 4-hydroxybutyraldehyde. In one embodiment, the polypeptide has higher activity relative to the parental polypeptide. In one embodiment, the polypeptide has higher activity for 3-hydroxy-(R)-butyryl-CoA over 3-hydroxy-(S)-butyryl-CoA. In one embodiment, the polypeptide has higher specificity for 3-hydroxybutyryl-CoA over acetyl-CoA. In one embodiment, the polypeptide has higher specificity for 4-hydroxybutyryl-CoA over acetyl-CoA. In one embodiment, the polypeptide produces decreased byproducts in a cell or cell extract. In a particular embodiment, the byproduct is ethanol or 4-hydroxy-2-butanone. In one embodiment, the polypeptide has a higher kcat relative to the parental polypeptide.

In some embodiments, the invention provides an isolated polypeptide having an amino acid sequence disclosed herein, such SEQ ID NOS:1, 2 or 3 or those referenced in Table 4, wherein the amino acid sequence includes one or more variant amino acid positions as set forth in Tables 1, 2 and/or 3. In particular, such a polypeptide encodes an aldehyde dehydrogenase, which can convert an acyl-CoA to the corresponding aldehyde, for example, 3-hydroxybutyryl-CoA to 3-hydroxybutyraldehyde, or 4-hydroxybutyryl-CoA to 4-hydroxybutyraldehyde. In some aspects, the isolated polypeptide of the invention includes an amino acid sequence, other than the one or more variant amino acid positions as set forth in Tables 1, 2, and/or 3, with at least 65%, 70%, 75%, 80%, 85%, 90%, 91%, 92%, 93%, 94%, 95%, 96%, 97%, 98% or 99% sequence identity, or is identical, to an amino acids sequence referenced as SEQ ID NOS:1, 2 or 3 or in Table 4. It is understood that a variant amino acid position can include any one of the 20 naturally occurring amino acids, a conservative substitution of a wild type or parental sequence at the corresponding position of the variant amino acid position, or a specific amino acid at the variant amino acid position such as those disclosed herein in Tables 1, 2 and/or 3. It is further understood that any of the variant amino acid positions can be combined to generate further variants. Variants with combinations of two or more variant amino acid positions exhibited activities greater than wild type. Thus, as exemplified herein, generating enzyme variants by combining active variant amino acid positions resulted in enzyme variants with improved properties. One skilled in the art can readily generate polypeptides with single variant positions or combinations of variant positions using methods well known to those skilled in the art to generate polypeptides with desired properties, including increased activity, increased specificity for the R form of 3-hydroxybutyryl-CoA or 3-hydroxybutyraldehyde over the S form, increased specificity for 3-hydroxybutyryl-CoA and/or 4-hydroxybutyryl-CoA over acetyl-CoA, decreased byproduct formation, such as ethanol or 4-hydroxy-2-butanone, increased kcat, increased stability in vivo and/or in vitro and the like, as described herein.

"Homology" or "identity" or "similarity" refers to sequence similarity between two polypeptides or between two nucleic acid molecules. Homology can be determined by comparing a position in each sequence which may be aligned for purposes of comparison. When a position in the compared sequence is occupied by the same base or amino acid, then the molecules are identical at that position. A degree of homology between sequences is a function of the number of matching or homologous positions shared by the sequences. A polypeptide or polypeptide region (or a polynucleotide or polynucleotide region) has a certain percentage (for example, 65%, 70%, 75%, 80%, 85%, 90%, 95%, 98% or 99%) of "sequence identity" to another sequence means that, when aligned, that percentage of amino acids (or nucleotide bases) are the same in comparing the two sequences.

In certain embodiments, the invention provides an isolated polypeptide having an amino acid sequence that includes at least two, three, four, five, six, seven, eight, nine, ten, eleven, twelve, thirteen, fourteen, fifteen, sixteen, seventeen, eighteen, nineteen, twenty or more variants in any combination disclosed herein. The variants can include any combination of the variants set forth in Tables 1, 2, and/or 3. In some embodiments, the isolated polypeptide is a variant of a reference polypeptide, wherein the reference polypeptide has an amino acid sequence of SEQ ID NO: 1, 2 or 3 or those in Table 4, and the polypeptide variant is selected from Table 1-3 and has one or more amino acid substitutions relative to SEQ ID NO: 1, 2 or 3 or those in Table 4.

In some embodiments, the isolated polypeptide is a variant of a reference polypeptide, wherein the reference polypeptide has an amino acid sequence of SEQ ID NO: 1, 2 or 3 or those in Table 4, the polypeptide variant comprises one or more amino acid substitutions relative to SEQ ID NO: 1, 2 or 3 or those in Table 4, where the one or more amino acid substitutions are selected from Table 1-3, and the polypeptide variant has at least 65%, 70%, 75%, 80%, 85%, 90%, 95%, 98%, or 99% sequence identity to a corresponding variant selected from Table 1-3. The one or more amino acid substitutions can be selected from any one of the variants listed in Table 1-3, or from any combination of two or more variants listed in Table 1-3. When selecting from a single variant in Table 1-3, the resulting variant can comprise one or more of the substitutions of the selected variant in any combination, including all of the indicated substitutions or less than all of the indicated substitutions. When substitutions are selected from those of two or more variants in Table 1-3, the resulting variant can comprise one or more of the substitutions of the selected variants, including all of the indicated substitutions or less than all of the indicated substitutions from each of the two or more selected variants, in any combination. For example, the resulting variant can comprise 1, 2, 3, or 4 substitutions from a single variant in Table 1-3. As a further example, the resulting variant can comprise 1, 2, 3, 4, 5, 6, 7, 8, 9, 10, 11, 12, 13, 14, 15, 16, 20, 25, or more substitutions selected from 1, 2, 3, 4, 5, or more selected variants of Table 1-3, including up to all positions being substituted, as disclosed herein. In some embodiments, the resulting variant comprises all of the indicated substitutions of a selected variant in Table 1-3. In some embodiments, the resulting variant differs from SEQ ID NO: 1, 2 or 3 or those in Table 4 by at least one amino acid substitution, but less than 25, 20, 10, 5, 4, or 3 amino acid substitutions. In some embodiments, the resulting variant comprises, consists essentially of, or consists of a sequence as indicated by a variant selected from Table 1-3, differing from SEQ ID NO: 1, 2 or 3 or those in Table 4 only at the indicated amino acid substitution(s).

In some embodiments, the resulting variant has at least 80%, 85%, 90%, or 95% sequence identity to a corresponding variant selected from Table 1-3; in some cases, identity is at least 90% or more. In cases where the resulting variant is less than 100% identical to a corresponding variant selected from Table 1-3, the position of one or more of the amino acid substitutions indicated for the corresponding variant may shift (e.g. in the case of insertion or deletion of one or more amino acids), but still be contained within the resulting variant. For example, the glycine to glutamic acid substitution corresponding to "D12A" (at position 12 relative to SEQ ID NO: 1 or 2) may be present, but at a different position in the resulting variant. Whether an amino acid corresponds to an indicated substitution, albeit at a different position, can be determined by sequence alignment, as described above and as well known in the art. In some embodiments, the one or more amino acid substitutions (e.g., all or less than all of the amino acid substitutions) indicated by a corresponding variant selected from Table 1-3 is considered to be present in a given variant, even if occurring at a different physical position along a polypeptide chain, if the sequence of the polypeptide being compared aligns with the corresponding variant with an identical match or similar amino acid at the indicated position along the corresponding variant sequence when using a BLASTP alignment algorithm with default parameters, where a similar amino acid is one considered to have chemical properties sufficient for alignment with the variant position of interest using default parameters of the alignment algorithm.

The variants alone or in combination can produce an enzyme that retains or improves the activity relative to a reference polypeptide, for example, the wild-type (native) enzyme. In some aspects, the polypeptide of the invention can have any combination of variants set forth in Tables 1, 2, and/or 3. In some aspects, the polypeptide of the invention having any combination of variants set forth in Tables 1, 2, and/or 3 can convert an acyl-CoA to the corresponding aldehyde, for example, 3-hydroxybutyryl-CoA to 3-hydroxybutyraldehyde, or 4-hydroxybutyryl-CoA to 4-hydroxybutyraldehyde. Methods of generating and assaying such polypeptides are well known to one of skill in the art.

In some embodiments, the isolated polypeptide of the invention can further include a conservative amino acid substitution in from 1 to 100 amino acid positions, or alternatively from 2 to 100 amino acid positions, or alternatively from 3 to 100 amino acid positions, or alternatively from 4 to 100 amino acid positions, or alternatively from 5 to 100 amino acid positions, or alternatively from 6 to 100 amino acid positions, or alternatively from 7 to 100 amino acid positions, or alternatively from 8 to 100 amino acid positions, or alternatively from 9 to 100 amino acid positions, or alternatively from 10 to 100 amino acid positions, or alternatively from 15 to 100 amino acid positions, or alternatively from 20 to 100 amino acid positions, or alternatively from 30 to 100 amino acid positions, or alternatively from 40 to 100 amino acid positions, or alternatively from 50 to 100 amino acid positions, or any integer therein, wherein the positions are other than the variant amino acid positions set forth in Tables 1, 2, and/or 3. In some aspects, the conservative amino acid sequence is a chemically conservative or an evolutionary conservative amino acid substitution. Methods of identifying conservative amino acids are well known to one of skill in the art, any one of which can be used to generate the isolated polypeptides of the invention.

In some embodiments, the isolated polypeptide of the invention can include no modification at from 2 to 300 amino acid positions, or alternatively 3 to 300 amino acid positions, or alternatively 4 to 300 amino acid positions, or alternatively 5 to 300 amino acid positions, or alternatively 10 to 300 amino acid positions, or alternatively 20 to 300 amino acid positions, or alternatively 30 to 300 amino acid positions, or alternatively 40 to 300 amino acid positions, or alternatively 50 to 300 amino acid positions, or alternatively 60 to 300 amino acid positions, or alternatively 80 to 300 amino acid positions, or alternatively 100 to 300 amino acid positions, or alternatively 150 to 300 amino acid positions, or alternatively 200 to 300 amino acid positions, or alternatively 250 to 300 amino acid positions, or any integer therein, compared to the parent (wild-type) sequence, wherein the positions are selected from those that are identical to between 2, 3, 4, or 5 of the amino acid sequences referenced as SEQ ID NOS:1, 2 or 3 or in Table 4.

It is understood that the variant polypeptides such as polypeptide variants of aldehyde dehydrogenase, as disclosed herein, can carry out a similar enzymatic reaction as the parent polypeptide, for example, converting an acyl-CoA to its corresponding aldehyde, such as converting 3-hydroxybutyryl-CoA to 3-hydroxybutyraldehyde, or converting 4-hydroxybutyryl-CoA to 4-hydroxybutyraldehyde. It is further understood that the polypeptide variants of the aldehyde dehydrogenase enzyme can include variants that provide a beneficial characteristic to the polypeptide, including but not limited to, increased activity, increased specificity for the R form of 3-hydroxybutyryl-CoA or 3-hydroxybutyraldehyde over the S form, increased specificity for 3-hydroxybutyryl-CoA and/or 4-hydroxybutyryl-CoA over acetyl-CoA, decreased byproduct formation, such as ethanol or 4-hydroxy-2-butanone, increased kcat, increased stability in vivo and/or in vitro and the like (see Example). In a particular embodiment, the aldehyde dehydrogenase variant can exhibit an activity that is at least the same or higher than a wild type or parent polypeptide, that is, is higher than a parent polypeptide without the variant amino acid position(s). For example, the aldehyde dehydrogenase variants of the invention can have 1.2, 1.5, 2, 2.5, 3, 3.5, 4, 4.5, 5, 5.5, 6, 6.5, 7, 7.5, 8, 8.5, 9, 9.5, 10, or even higher fold activity of the variant polypeptide over a wild type or parent polypeptide (see Example). It is understood that activity refers to the ability of an aldehyde dehydrogenase of the invention to convert a substrate to a product relative to a wild type or parent polypeptide under the same assay conditions.

In another particular embodiment, the aldehyde dehydrogenase variant can exhibit increased specificity for the R form of 3-hydroxybutyryl-CoA or 3-hydroxybutyraldehyde over the S form, for example, about 2 to 40 fold higher, for example, 2 to 35, 2 to 30, 2 to 25, 2 to 20, 2 to 15, 2 to 10 or 2 to 5, for example, 2, 3, 4, 5, 6, 7, 8, 9, 10, 11, 12, 13, 14, 15, 20, 25, 30, 35, 40 or even higher fold activity. Such an increased specificity can be measured, for example, by the ratio of activity for the R over the S form of 3-hydroxybutyryl-CoA or 3-hydroxybutyraldehyde.

In another particular embodiment, the aldehyde dehydrogenase variant can exhibit increased specificity for 3-hydroxybutyryl-CoA and/or 4-hydroxybutyryl-CoA over acetyl-CoA, for example, 1.5 to 100, 1.5 to 95, 1.5 to 90, 1.5 to 85, 1.5 to 80, 1.5 to 75, 1.5 to 70, 1.5 to 65, 1.5 to 60, 1.5 to 55, 1.5 to 50, 1.5 to 45, 1.5 to 40, 1.5 to 35, 1.5 to 30, 1.5 to 25, 1.5 to 20, 1.5 to 15, 1.5 to 10, or 1.5 to 5, for example, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, or 100-fold. Such an increased specificity can be measured, for example, by the ratio of activity for 3-hydroxybutyryl-CoA or 4-hydroxybutyryl-CoA over acetyl-CoA. Specificity is indicated by the activity on 3HB-CoA or 4HB-CoA divided by the activity on acetyl-CoA.

In another particular embodiment, the aldehyde dehydrogenase variant can exhibit decreased byproduct formation, such as ethanol and/or 4-hydroxy-2-butanone, for example, a decrease in byproduct formation of 10%, 15%, 20%, 25%, 30%, 35%, 40%, 45%, 50%, 60%, 65%, 70%, 75%, 80%, 85%, 90%, 95%, 96%, 97%, 98%, 99%. Such an aldehyde dehydrogenase variant can exhibit an activity that has decreased byproduct formation, as described above, relative to a wild type or a parent polypeptide, that is, a parent polypeptide without the variant amino acid position.

In another particular embodiment, the aldehyde dehydrogenase variant can exhibit increased kcat, for example, 1.25, 1.5, 1.75, 2, 2.5, 3, 3.5, 4, 4.5, 5, 5.5, 6, 6.5, 7, 7.5, 8, 8.5, 9, 9.5, 10-fold or higher, relative to a wild type or a parent polypeptide, that is, a parent polypeptide without the variant amino acid position(s). The kcat is understood to refer to its well known meaning in enzymology of the turnover number, where kcat=Vmax/[$E_T$], where Vmax is the rate of enzyme reaction with saturating substrate, and [$E_T$] is the total enzyme concentration (see Segel, *Enzyme Kinetics: Behavior and Analysis of Rapid Equilibrium and Steady-State Enzyme Kinetics*, Wiley-Interscience, New York (1975)). Such an aldehyde dehydrogenase variant can exhibit an activity that has increased kcat relative to a wild type or a parent polypeptide, that is, a parent polypeptide without the variant amino acid position(s).

In another particular embodiment, the aldehyde dehydrogenase variant can exhibit increased stability, either in vitro or in vivo, or both, relative to a wild type or a parent polypeptide, that is, a parent polypeptide without the variant amino acid position(s). For example, the aldehyde dehydrogenase variant can exhibit increased stability in vitro in a cell lysate.

It is understood that, in certain embodiments, an aldehyde dehydrogenase variant can exhibit two or more of the characteristics described above, for example, two or more of the characteristics of (1) increased activity, (2) increased specificity for the R form of 3-hydroxybutyryl-CoA or 3-hydroxybutyraldehyde over the S form, (3) increased specificity for 3-hydroxybutyryl-CoA and/or 4-hydroxybutyryl-CoA over acetyl-CoA, (4) decreased byproduct formation, such as ethanol and/or 4-hydroxy-2-butanone, (5) increased kcat, (6) increased stability in vivo and/or in vitro, and the like, in any combination. Such combinations include, for example, characteristics 1 and 2; 1 and 3; 1 and 4; 1 and 5; 1 and 6; 2 and 3; 2 and 4; 2 and 5; 2 and 6; 3 and 4; 3 and 5; 3 and 6; 4 and 5; 4 and 6; 5 and 6; 1, 2 and 3; 1, 2 and 4; 1, 2 and 5; 1, 2 and 6; 1, 3 and 4; 1, 3 and 5; 1, 3 and 6; 1, 4 and 5; 1, 4 and 6; 1, 5 and 6; 2, 3 and 4; 2, 3 and 5; 2, 3 and 6; 2, 4 and 5; 2, 4 and 6; 2, 5 and 6; 3, 4 and 5; 3, 4 and 6; 3, 5 and 6; 4, 5 and 6; 1, 2, 3 and 4; 1, 2, 3 and 5; 1, 2, 3 and 6; 1, 2, 4 and 5; 1, 2, 4 and 6; 1, 2, 5 and 6; 1, 3, 4 and 5; 1, 3, 4 and 6; 1, 4, 5 and 6; 2, 3, 4 and 5; 2, 3, 4 and 6; 2, 3, 5 and 6; 3, 4, 5 and 6; 1, 2, 3, 4 and 5; 1, 3, 4, 5 and 6; 1, 2, 4, 5 and 6; 1, 2, 3, 5 and 6; 1, 2, 3, 4 and 6; 2, 3, 4, 5 and 6; 1, 2, 3, 4, 5 and 6.

The polypeptides of the invention can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology*, Vol. 182, (Academic Press, (1990)). Alternatively, the isolated polypeptides of the present invention can be obtained using well-known recombinant methods (see, for example, Sambrook et al., supra, 1989; Ausubel et al., supra, 1999). The methods and conditions for biochemical purification of a polypeptide of the invention can be chosen by those skilled in the art, and purification monitored, for example, by a functional assay.

One non-limiting example of a method for preparing the invention polypeptide is to express nucleic acids encoding the polypeptide in a suitable host cell, such as a bacterial cell, a yeast cell, or other suitable cell, using methods well known in the art, and recovering the expressed polypeptide, again using well-known purification methods, as described herein. Invention polypeptides can be isolated directly from cells that have been transformed with expression vectors as described herein. Recombinantly expressed polypeptides of the invention can also be expressed as fusion proteins with appropriate affinity tags, such as glutathione S transferase (GST), poly His, streptavidin, and the like, and affinity purified, if desired. A polypeptide of the invention can retain the affinity tag, if desired, or optionally the affinity tag can be removed from the polypeptide using well known methods to remove an affinity tag, for example, using appropriate enzymatic or chemical cleavage. Thus, the invention provides polypeptides of the invention without or optionally with an affinity tag. In some embodiments, the invention provides a host cell expressing a polypeptide of the invention disclosed herein. An invention polypeptide can also be produced by chemical synthesis using a method of polypeptide synthesis well know to one of skill in the art (Merrifield, *J. Am. Chem. Soc.* 85:2149 (1964); Bodansky, M., *Principles of Peptide Synthesis* (Springer-Verlag, 1984); Houghten, *Proc. Natl. Acad Sci., USA* 82:5131 (1985); Grant *Synthetic Peptides: A User Guide*. W.H. Freeman and Co., N.Y. (1992); Bodansky M and Trost B., Ed. *Principles of Peptide Synthesis*. Springer-Verlag Inc., NY (1993)).

In some embodiments, the invention provides using a polypeptide disclosed herein as a biocatalyst. A "biocatalyst," as used herein, refers to a biological substance that initiates or modifies the rate of a chemical reaction. A biocatalyst can be an enzyme. A polypeptide of the invention can be used to increase the rate of conversion of a substrate to a product as disclosed herein. In the context of an industrial reaction, a polypeptide of the invention can be used, absent a host cell expressing the polypeptide, to improve reactions generating 3-HBal, 1,3-BDO, 4-HBal or 1,4-BDO, or a downstream product related thereto such as an ester or amide thereof, for example, using in vitro methods. In one embodiment, the invention provides use of the polypeptide of the invention as a biocatalyst.

In some embodiments of the invention, the polypeptide encoding an aldehyde dehydrogenase of the invention is provided as a cell lysate of a cell expressing the aldehyde dehydrogenase. In such a case, the cell lysate serves as a source of the aldehyde dehydrogenase for carrying out the conversion of 3-hydroxybutyryl-CoA to 3-hydroxybutyraldehyde, or 4-hydroxybutyryl-CoA to 4-hydroxybutyraldehyde, or the reverse reaction, in an in vitro reaction. In another embodiment, the aldehyde dehydrogenase can be provided in a partially purified form, for example, partially purified from a cell lysate. In another embodiment, the aldehyde dehydrogenase can be provided in substantially purified form, in which the aldehyde dehydrogenase is substantially purified from other components, such as the components of a cell extract. Methods for partially purifying or substantially purifying a polypeptide encoding an aldehyde dehydrogenase are well known in the art, as described herein. In some embodiments, the aldehyde dehydrogenase is immobilized to a solid support, for example, a bead, plate or membrane. In a particular embodiment, the aldehyde dehydrogenase comprises an affinity tag, and the affinity tag is used to immobilize the aldehyde dehydrogenase to a solid support. Such an affinity tag can include, but is not limited to, glutathione S transferase (GST), poly His, streptavidin, and the like, as described herein.

In some embodiments, the invention provides a composition having a polypeptide disclosed herein and at least one substrate for the polypeptide. Substrate for each of the polypeptides disclosed herein are described herein and are exemplified in the Figures. The polypeptide within the composition of the invention can react with a substrate under in vitro or in vivo conditions. In this context, an in vitro condition refers to a reaction in the absence of or outside of a cell, including a cell of the invention.

In one embodiment, the invention provides a composition comprising a polypeptide of the invention and at least one substrate for the polypeptide. In one embodiment, the polypeptide can react with the substrate under in vitro conditions. In one embodiment, the substrate is 3-hydroxybutyryl-CoA. In one embodiment, the substrate is 3-hydroxy-(R)-butyryl-CoA. In one embodiment, the substrate is 4-hydroxybutyryl-CoA.

In some embodiments, the invention provides a method of constructing a host strain that can include, among other steps, introducing a vector disclosed herein into a host cell, for example, that is capable of expressing an amino acid sequence encoded by the vector and/or is capable of fermentation. Vectors of the invention can be introduced stably or transiently into a host cell using techniques well known in the art including, but not limited to, conjugation, electroporation, chemical transformation, transduction, transfection, and ultrasound transformation. Additional methods are disclosed herein, any one of which can be used in the method of the invention.

In an additional embodiment, the invention provides a cell that comprises a polypeptide of the invention, that is, an aldehyde dehydrogenase of the invention. Thus, the invention provides a non-naturally occurring cell comprising a polypeptide encoding an aldehyde dehydrogenase of the invention. Optionally, the cell can comprise a 3-HBal or 1,3-BDO pathway, or a 4-HBal or 1,4-BDO pathway, and additionally optionally include a pathway to produce a downstream product related thereto such as an ester or amide thereof. In some embodiments, the non-naturally occurring cell comprises at least one exogenous nucleic acid encoding an aldehyde dehydrogenase that converts an acyl-CoA to its corresponding aldehyde. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, in a particular embodiment, the invention provides a cell, in particular a non-naturally occurring cell, containing at least one exogenous nucleic acid encoding an aldehyde dehydrogenase, where the aldehyde dehydrogenase functions in a 3-HBal, 1,3-BDO, 4-HBal or 1,4-BDO pathway, such as that shown in FIGS. 1 and 2.

In one embodiment, the invention provides a cell comprising a vector of the invention comprising a nucleic acid of the invention. The invention also provides a cell comprising a nucleic acid of the invention. In one embodiment, the nucleic acid molecule is integrated into a chromosome of the cell. In a particular embodiment, the integration is site-specific. In an embodiment of the invention, the nucleic acid molecule is expressed. In one embodiment, the invention provides a cell comprising a polypeptide of the invention.

In one embodiment, the cell comprising a vector, nucleic acid or polypeptide is a microbial organism. In a particular embodiment, the microbial organism is a bacterium, yeast or fungus. In a particular embodiment, the cell is an isolated eukaryotic cell.

In one embodiment, the cell comprises a pathway that produces 3-hydroxybutyraldehyde (3-HBal) and/or 1,3-butanediol (1,3-BDO), or an ester or amide thereof. In another embodiment, the cell comprises a pathway that produces 4-hydroxybutyraldehyde (4-HBal) and/or 1,4-butanediol (1,4-BDO), or an ester or amide thereof. In one embodiment, the cell is capable of fermentation. In one embodiment, the cell further comprises at least one substrate for the polypeptide of the invention expressed in the cell. In a particular embodiment, the substrate is 3-hydroxybutyryl-CoA. In a particular embodiment, the substrate is 3-hydroxy-(R)-butyryl-CoA. In one embodiment, the cell has higher activity for 3-hydroxy-(R)-butyryl-CoA over 3-hydroxy-(S)-butyryl-CoA. In another particular embodiment, the substrate is 4-hydroxybutyryl-CoA. The invention also provides culture medium comprising a cell of the invention.

The aldehyde dehydrogenase of the invention can be utilized in a pathway that converts an acyl-CoA to its corresponding aldehyde. Exemplary pathways for 3-HBal and/or 1,3-BDO that comprise an aldehyde dehydrogenase have been described, for example, in WO 2010/127319, WO 2013/036764, U.S. Pat. No. 9,017,983, US 2013/0066035, each of which is incorporated herein by reference.

Exemplary 3-HBal and/or 1,3-BDO pathways are shown in FIG. 1 and described in WO 2010/127319, WO 2013/036764, U.S. Pat. No. 9,017,983 and US 2013/0066035. Such a 3-HBal and/or 1,3-BDO pathway that comprises an aldehyde dehydrogenase includes, for example, (G) acetoacetyl-CoA reductase (ketone reducing); (H) 3-hydroxybutyryl-CoA reductase (aldehyde forming), also referred to herein as 3-hydroxybutyraldehyde dehydrogenase, an aldehyde dehydrogenase (ALD); and (C) 3-hydroxybutyraldehyde reductase, also referred to herein as a 1,3-BDO dehydrogenase (see FIG. 1). Acetoacetyl-CoA can be formed by converting two molecules of acetyl-CoA into one molecule of acetoacetyl-CoA employing a thiolase. Acetoacetyl-CoA thiolase converts two molecules of acetyl-CoA into one molecule each of acetoacetyl-CoA and CoA (see WO 2013/036764 and US 2013/0066035).

Figure 2:
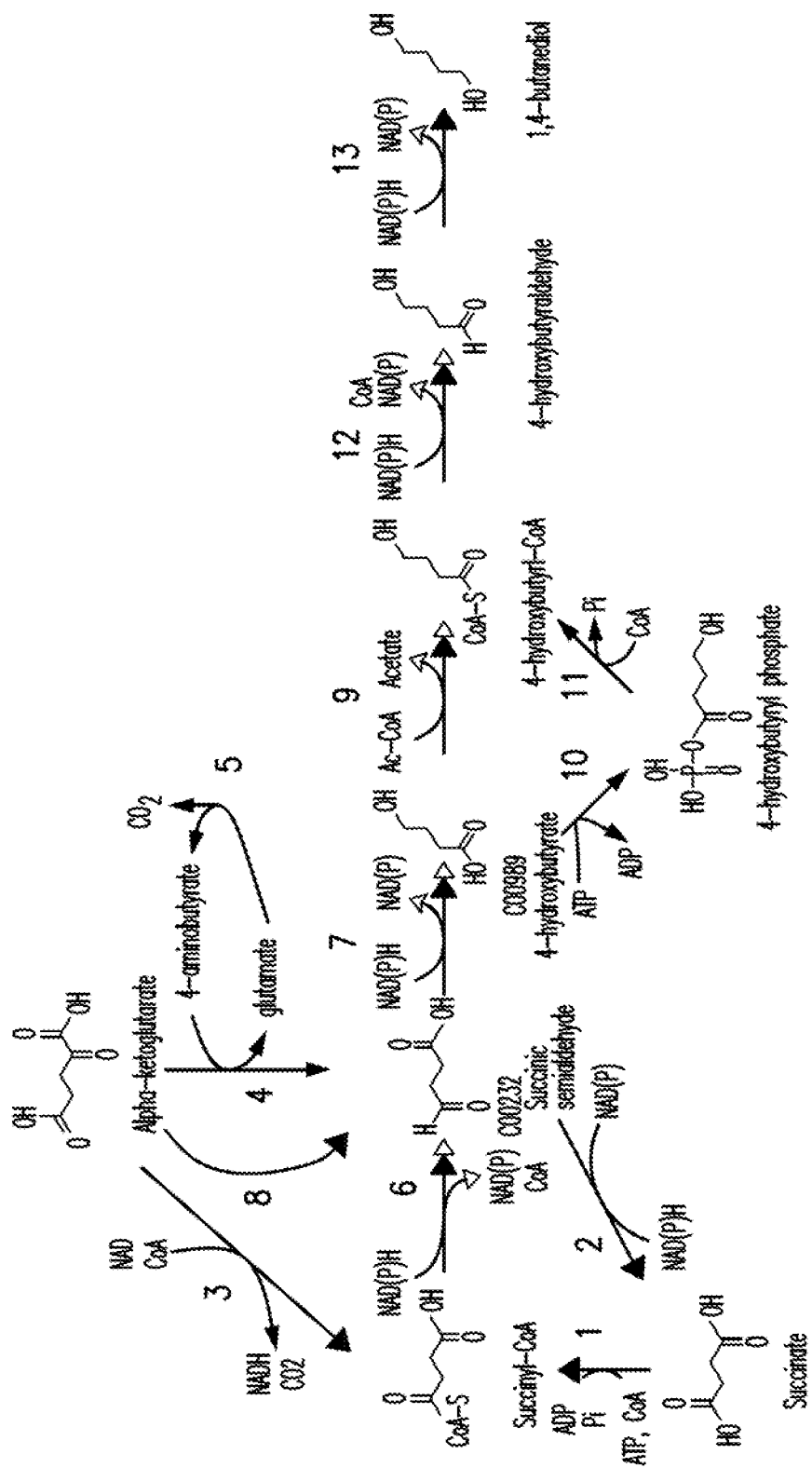
FIG. 2 shows an exemplary 1,4-butanediol (1,4-BDO) pathway that comprises an aldehyde dehydrogenase. Enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase (also referred to as 4-hydroxybutyrate dehydrogenase); (8) α-ketoglutarate decarboxylase; (9) 4-hydroxybutyryl CoA:acetyl-CoA transferase; (10) butyrate kinase (also referred to as 4-hydroxybutyrate kinase); (11) phosphotransbutyrylase (also referred to as phospho-trans-4-hydroxybutyrylase); (12) aldehyde dehydrogenase (also referred to as 4-hydroxybutyryl-CoA reductase); (13) alcohol dehydrogenase (also referred to as 4-hydroxybutanal reductase or 4-hydroxybutyraldehyde reductase).

An exemplary 1,3-BDO pathway is shown in FIG. 2 of WO 2010/127319. Briefly, acetoacetyl-CoA can be converted to 3-hydroxybutyryl-CoA by acetoacetyl-CoA reductase (ketone reducing)(EC 1.1.1.a)(step G of FIG. 1).

3-Hydroxybutyryl-CoA can be converted to 3-hydroxybutyraldehyde by 3-hydroxybutyryl-CoA reductase (aldehyde forming)(EC 1.2.1.b), also referred to herein as 3-hydroxybutyraldehyde dehydrogenase, including an aldehyde dehydrogenase of the invention (step H of FIG. 1). 3-Hydroxybutyraldehyde can be converted to 1,3-butanediol by 3-hydroxybutyraldehyde reductase (EC 1.1.1.a), also referred to herein as 1,3-BDO dehydrogenase (step C of FIG. 1).

As disclosed herein, aldehyde dehydrogenases of the invention can function in a pathway to convert 3-hydroxybutyryl-CoA to 3-hydroxybutyraldehyde. In the pathway described above that comprises an aldehyde dehydrogenase that converts 3-hydroxybutyryl-CoA to 3-hydroxybutyraldehyde, the pathway converts acetoacetyl-CoA to 3-hydroxybutyryl-CoA (see FIG. 1). The aldehyde dehydrogenases of the invention can also be used in other 3-HBal and/or 1,3-BDO pathways that comprise 3-hydroxybutyryl-CoA as a substrate/product in the pathway. One skilled in the art can readily utilize an aldehyde dehydrogenase of the invention to convert 3-hydroxybutyryl-CoA to 3-hydroxybutyraldehyde in any desired pathway that comprises such a reaction.

Exemplary 4-HBal and/or 1,4-BDO pathways are shown in FIG. 2 and described in WO 2008/115840, WO 2010/030711, WO 2010/141920, WO 2011/047101, WO 2013/184602, WO 2014/176514, U.S. Pat. Nos. 8,067,214, 7,858,350, 8,129,169, 8,377,666, US 2013/0029381, US 2014/0030779, US 2015/0148513 and US 2014/0371417. Such a 4-HBal and/or 1,4-BDO pathway that comprises an aldehyde dehydrogenase includes, for example, (1) succinyl-CoA synthetase; (2) CoA-independent succinic semialdehyde dehydrogenase; (3) α-ketoglutarate dehydrogenase; (4) glutamate:succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:acetyl-CoA transferase; (10) butyrate kinase (also referred to as 4-hydroxybutyrate kinase); (11) phosphotransbutyrylase (also referred to as phospho-trans-4-hydroxybutyrylase); (12) aldehyde dehydrogenase (also referred to as 4-hydroxybutyryl-CoA reductase); (13) alcohol dehydrogenase, such as 1,4-butanediol dehydrogenase (also referred to as 4-hydroxybutanal reductase or 4-hydroxybutyraldehyde reductase)(see FIG. 2).

Similar to FIG. 2, exemplary 1,4-BDO pathways are shown in FIG. 8A of WO 2010/141920. Briefly, succinyl-CoA can be converted to succinic semialdehyde by succinyl-CoA reductase (or succinate semialdehyde dehydrogenase) (EC 1.2.1.b). Succinate semialdehyde can be converted to 4-hydroxybutyrate by 4-hydroxybutyrate dehydrogenase (EC 1.1.1.a). Alternatively, succinyl-CoA can be converted to 4-hydroxybutyrate by succinyl-CoA reductase (alcohol forming) (EC 1.1.1.c). 4-Hydroxybutyrate can be converted to 4-hydroxybutyryl-CoA by 4-hydroxybutyryl-CoA transferase (EC 2.8.3.a), by 4-hydroxybutyryl-CoA hydrolase (EC 3.1.2.a) or by 4-hydroxybutyryl-CoA ligase (or 4-hydroxybutyryl-CoA synthetase) (EC 6.2.1.a). Alternatively, 4-hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a). Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), including by an aldehyde dehydrogenase variant of the invention. Alternatively, 4-hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a).

Exemplary 1,4-BDO pathways are also shown in FIG. 8B of WO 2010/141920. Briefly, alpha-ketoglutarate can be converted to succinic semialdehyde by alpha-ketoglutarate decarboxylase (EC 4.1.1.a). Alternatively, alpha-ketoglutarate can be converted to glutamate by glutamate dehydrogenase (EC 1.4.1.a). 4-Aminobutyrate can be converted to succinic semialdehyde by 4-aminobutyrate oxidoreductase (deaminating) (EC 1.4.1.a) or 4-aminobutyrate transaminase (EC 2.6.1.a). Glutamate can be converted to 4-aminobutyrate by glutamate decarboxylase (EC 4.1.1.a). Succinate semialdehyde can be converted to 4-hydroxybutyrate by 4-hydroxybutyrate dehydrogenase (EC 1.1.1.a). 4-Hydroxybutyrate can be converted to 4-hydroxybutyryl-CoA by 4-hydroxybutyryl-CoA transferase (EC 2.8.3.a), by 4-hydroxybutyryl-CoA hydrolase (EC 3.1.2.a), or by 4-hydroxybutyryl-CoA ligase (or 4-hydroxybutyryl-CoA synthetase) (EC 6.2.1.a). 4-Hydroxybutyrate can be converted to 4-hydroxybutyryl-phosphate by 4-hydroxybutyrate kinase (EC 2.7.2.a). 4-Hydroxybutyryl-phosphate can be converted to 4-hydroxybutyryl-CoA by phosphotrans-4-hydroxybutyrylase (EC 2.3.1.a). Alternatively, 4-hydroxybutyryl-phosphate can be converted to 4-hydroxybutanal by 4-hydroxybutanal dehydrogenase (phosphorylating) (EC 1.2.1.d). 4-Hydroxybutyryl-CoA can be converted to 4-hydroxybutanal by 4-hydroxybutyryl-CoA reductase (or 4-hydroxybutanal dehydrogenase) (EC 1.2.1.b), including by an aldehyde dehydrogenase of the invention. 4-Hydroxybutyryl-CoA can be converted to 1,4-butanediol by 4-hydroxybutyryl-CoA reductase (alcohol forming) (EC 1.1.1.c). 4-Hydroxybutanal can be converted to 1,4-butanediol by 1,4-butanediol dehydrogenase (EC 1.1.1.a).

As disclosed herein, aldehyde dehydrogenases of the invention can function in a pathway to convert 4-hydroxybutyryl-CoA to 4-hydroxybutyraldehyde. In the pathways described above that comprise an aldehyde dehydrogenase that converts 4-hydroxybutyryl-CoA to 4-hydroxybutyraldehyde, the pathways convert 4-hydroxybutyrate to 4-hydroxybutyryl-CoA or 4-hydroxybutyryl phosphate to 4-hydroxybutyryl-CoA (see FIG. 2). The aldehyde dehydrogenases of the invention can also be used in other 4-HBal and/or 1,4-BDO pathways that comprise 4-hydroxybutyryl-CoA as a substrate/product in the pathway. One skilled in the art can readily utilize an aldehyde dehydrogenase of the invention to convert 4-hydroxybutyryl-CoA to 4-hydroxybutyraldehyde in any desired pathway that comprises such a reaction. For example, 4-oxobutyryl-CoA can be converted to 4-hydroxybutyryl-CoA as described and shown in WO 2010/141290, FIG. 9A. In addition, 5-hydroxy-2-oxopentanoic acid can be converted to 4-hydroxybutyryl-CoA as described and shown in WO 2010/141290, FIGS. 10 and 11. Also, acetoacetyl-CoA, 3-hydroxybutyryl-CoA, crotonyl-CoA and/or vinylacetyl-CoA can be converted to 4-hydroxybutyryl-CoA as described and shown in WO 2010/141290, FIG. 12. Additionally, 4-hydroxybut-2-enoyl-CoA can be converted to 4-hydroxybutyryl-CoA as described and shown in WO 2010/141290, FIG. 13. Thus, one skilled in the art will readily understand how to use an aldehyde dehydrogenase of the invention in a 4-HBal and/or 1,4-BDO pathway that comprises conversion of 4-hydroxybutyryl-CoA to 4-hydroxybutyraldehyde, as desired.

Enzyme types required to convert common central metabolic intermediates into 1,3-BDO or 1,4-BDO are indicated above with representative Enzyme Commission (EC) numbers (see also WO 2010/127319, WO 2013/036764, WO 2008/115840, WO 2010/030711, WO 2010/141920, WO 2011/047101, WO 2013/184602, WO 2014/176514, U.S. Pat. Nos. 9,017,983, 8,067,214, 7,858,350, 8,129,169, 8,377,666, US 2013/0066035, US 2013/0029381, US 2014/0030779, US 2015/0148513, and US 2014/0371417). The first three digits of each label correspond to the first three Enzyme Commission number digits which denote the general type of transformation independent of substrate specificity. Exemplary enzymes include: 1.1.1.a, Oxidoreductase (ketone to hydroxyl or aldehyde to alcohol); 1.1.1.c, Oxidoreductase (2 step, acyl-CoA to alcohol); 1.2.1.b, Oxidoreductase (acyl-CoA to aldehyde); 1.2.1.c, Oxidoreductase (2-oxo acid to acyl-CoA, decarboxylation); 1.2.1.d, Oxidoreductase (phosphorylating/dephosphorylating); 1.3.1.a, Oxidoreductase operating on CH-CH donors; 1.4.1.a, Oxidoreductase operating on amino acids (deaminating); 2.3.1.a, Acyltransferase (transferring phosphate group); 2.6.1.a, Aminotransferase; 2.7.2.a, Phosphotransferase, carboxyl group acceptor; 2.8.3.a, Coenzyme-A transferase; 3.1.2.a, Thiolester hydrolase (CoA specific); 4.1.1.a, Carboxy-lyase; 4.2.1.a, Hydro-lyase; 4.3.1.a, Ammonia-lyase; 5.3.3.a, Isomerase; 5.4.3.a, Aminomutase; and 6.2.1.a, Acid-thiol ligase.

The aldehyde dehydrogenases of the invention can be utilized in a cell or in vitro to convert an acyl-CoA to its corresponding aldehyde. As disclosed herein, the aldehyde dehydrogenases of the invention have beneficial and useful properties, including but not limited to increased specificity for the R enantiomer of 3-hydroxybutyryl-CoA over the S enantiomer, increased specificity for 3-hydroxybutyryl-CoA and/or 4-hydroxybutyryl-CoA over acetyl-CoA, increased activity, decreased byproduct production, increased kcat, and the like. Aldehyde dehydrogenases of the invention can be used to produce the R-form of 1,3-butanediol (also referred to as (R)-1,3-butanediol), by enzymatically converting the product of an aldehyde dehydrogenase of the invention, 3-hydroxy-(R)-butyraldehyde, to (R)-1,3-butanediol using a 1,3-butanediol dehydrogenase.

The bio-derived R-form of 1,3-butanediol can be utilized for production of downstream products for which the R-form is preferred. In some embodiments, the R-form can be utilized as a pharmaceutical and/or nutraceutical (see WO 2014/190251). For example, (R)-1,3-butanediol can be used to produce (3R)-hydroxybutyl (3R)-hydroxybutyrate, which can have beneficial effects such as increasing the level of ketone bodies in the blood. Increasing the level of ketone bodies can lead to various clinical benefits, including an enhancement of physical and cognitive performance and treatment of cardiovascular conditions, diabetes and treatment of mitochondrial dysfunction disorders and in treating muscle fatigue and impairment (see WO 2014/190251). The bio-derived R-form of 1,3-butanediol can be utilized for production of downstream products in which a non-petroleum based product is desired, for example, by substituting petroleum-derived racemate 1,3-butanediol, its S-form or its R-form, with the bio-derived R-form.

In one embodiment, the invention provides 3-HBal or 1,3-BDO, or downstream products related thereto, such as an ester or amide thereof, enantiomerically enriched for the R form of the compound. In some embodiments, the 3-HBal or 1,3-BDO is a racemate enriched in R-enantiomer, that is, includes more R-enantiomer than S-enantiomer. For example, the 3-HBal or 1,3-BDO racemate can include 55% or more R-enantiomer and 45% or less S-enantiomer. For example, the 3-HBal or 1,3-BDO racemate can include 60% or more R-enantiomer and 40% or less S-enantiomer. For example, the 3-HBal or 1,3-BDO racemate can include 65% or more R-enantiomer and 35% or less S-enantiomer. For example, the 3-HBal or 1,3-BDO racemate can include 70% or more R-enantiomer and 30% or less S-enantiomer. For example, the 3-HBal or 1,3-BDO racemate can include 75% or more R-enantiomer and 25% or less S-enantiomer. For example, the 3-HBal or 1,3-BDO racemate can include 80% or more R-enantiomer and 20% or less S-enantiomer. For example, the 3-HBal or 1,3-BDO racemate can include 85% or more R-enantiomer and 15% or less S-enantiomer. For example, the 3-HBal or 1,3-BDO racemate can include 90% or more R-enantiomer and 10% or less S-enantiomer. For example, the 3-HBal or 1,3-BDO racemate can include 95% or more R-enantiomer and 5% or less S-enantiomer. In some embodiments, the 3-HBal or 1,3-BDO, or downstream products related thereto such as an ester or amide thereof, is greater than 90% R form, for example, greater than 95%, 96%, 97%, 98%, 99% or 99.9% R form. In one embodiment, the 3-HBal and/or 1,3-BDO, or downstream products related thereto, such as an ester or amide thereof, is ≥55% R-enantiomer, ≥60% R-enantiomer, ≥65% R-enantiomer, ≥70% R-enantiomer, ≥75% R-enantiomer, ≥80% R-enantiomer, ≥85% R-enantiomer, ≥90% R-enantiomer, or ≥95% R-enantiomer, and can be highly chemically pure, e.g., ≥99%, for example, ≥95%, ≥96%, ≥97%, ≥98%, ≥99%, ≥99.1%, ≥99.2%, ≥99.3%, ≥99.4%, ≥99.5%, ≥99.6%, ≥99.7%, ≥99.8% or ≥99.9% R-enantiomer.

In one embodiment, a petroleum-derived racemic mixture of a precursor of 3-HBal and/or 1,3-BDO, in particular a racemic mixture of 3-hydroxybutyryl-CoA, is used as a substrate for an aldehyde dehydrogenase of the invention, which exhibits increased specificity for the R form over the S form, to produce 3-HBal or 1,3-BDO, or a downstream product related thereto such as an ester or amide thereof, that is enantiomerically enriched for the R form. Such a reaction can be carried out by feeding a petroleum-derived precursor to a cell that expresses an aldehyde dehydrogenase of the invention, in particular a cell that can convert the precursor to 3-hydroxybutyryl-CoA, or can be carried out in vitro using one or more enzymes to convert the petroleum-derived precursor to 3-hydroxybutyryl-CoA, or a combination of in vivo and in vitro reactions. A reaction to produce 4-hydroxybutyryl-CoA with an aldehyde dehydrogenase of the invention can similarly be carried out by feeding a petroleum-derived precursor to a cell that expresses an aldehyde dehydrogenase of the invention, in particular a cell that can convert the precursor to 4-hydroxybutyryl-CoA, or can be carried out in vitro using one or more enzymes to convert the petroleum-derived precursor to 4-hydroxybutyryl-CoA, or a combination of in vivo and in vitro reactions.

While generally described herein as a cell that contains a 3-HBal, 1,3-BDO, 4-HBal or 1,4-BDO pathway comprising an aldehyde dehydrogenase of the invention, it is understood that the invention also provides a cell comprising at least one exogenous nucleic acid encoding an aldehyde dehydrogenase of the invention. The aldehyde dehydrogenase can be expressed in a sufficient amount to produce a desired product, such a product of a 3-HBal, 1,3-BDO, 4-HBal or 1,4-BDO pathway, or a downstream product related thereto such as an ester or amide thereof. Exemplary 3-HBal, 1,3-BDO, 4-HBal or 1,4-BDO pathways are shown in FIGS. 1 and 2 and are described herein.

It is understood that any of the pathways disclosed herein, as described in the Examples and exemplified in the Figures, including the pathways of FIGS. 1 and 2, can be utilized to generate a cell that produces any pathway intermediate or product, as desired, in particular a pathway that utilizes an aldehyde dehydrogenase of the invention. As disclosed herein, such a cell that produces an intermediate can be used in combination with another cell expressing one or more upstream or downstream pathway enzymes to produce a desired product. However, it is understood that a cell that produces a 3-HBal, 1,3-BDO, 4-HBal or 1,4-BDO pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, a product or pathway intermediate that is a carboxylic acid can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate products or intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Other biosynthetically accessible O-carboxylates can include medium to long chain groups, that is C7-C22, O-carboxylate esters derived from fatty alcohols, such as heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

The cells of the invention can be produced by introducing an expressible nucleic acid encoding an aldehyde dehydrogenase of the invention, and optionally expressible nucleic acids encoding one or more of the enzymes or proteins participating in one or more 3-HBal, 1,3-BDO, 4-HBal or 1,4-BDO biosynthetic pathways, and further optionally a nucleic acid encoding an enzyme that produces a downstream product related to 3-HBal, 1,3-BDO, 4-HBal or 1,4-BDO such as an ester or amide thereof. Depending on the host cell chosen, nucleic acids for some or all of a particular 3-HBal, 1,3-BDO, 4-HBal or 1,4-BDO biosynthetic pathway, or downstream product, can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is included for the deficient enzyme(s) or protein(s) to achieve 3-HBal, 1,3-BDO, 4-HBal or 1,4-BDO biosynthesis, or exogenous expression of endogenously expressed genes can be provided to increase expression of pathway enzymes, if desired. Thus, a cell of the invention can be produced by introducing an aldehyde dehydrogenase of the invention, and optionally exogenous enzyme or protein activities to obtain a desired biosynthetic pathway, or by introducing one or more exogenous enzyme or protein activities, including an aldehyde dehydrogenase of the invention that, together with one or more endogenous enzymes or proteins, produces a desired product such as 3-HBal, 1,3-BDO, 4-HBal or 1,4-BDO, or a downstream product related thereto such as an ester or amide thereof.

Host cells can be selected from, and the non-naturally cells expressing an aldehyde dehydrogenase of the invention generated in, for example, bacteria, yeast, fungus or any of a variety of microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*; the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium eth, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. *E. coli* is a particularly useful host organism since it is a well characterized microbial organism suitable for genetic engineering.

Similarly, exemplary species of yeast or fungi species include any species selected from the order Saccharomycetales, family Saccharomycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccharomycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. A particularly useful host organism that is a yeast includes *Saccharomyces cerevisiae*.

Although generally described herein as utilizing a cell that is a microbial organism as a host cell, particularly for producing 3-HBal, 1,3-BDO, 4-HBal or 1,4-BDO, or a downstream product related thereto such as an ester or amide thereof, it is understood that a host cell can be a cell line of a higher eukaryote, such as a mammalian cell line or insect cell line. Thus, it is understood that reference herein to a host cell that is a microbial organism can alternatively utilize a higher eukaryotic cell line to produce a desired product. Exemplary higher eukaryotic cell lines include, but are not limited to, Chinese hamster ovary (CHO), human (Hela, Human Embryonic Kidney (HEK) 293, Jurkat), mouse (3T3), primate (Vero), insect (Sf9), and the like. Such cell lines are commercially available (see, for example, the American Type Culture Collection (ATCC; Manassas Va.); Life Technologies, Carlsbad Calif.). It is understood that any suitable host cell can be used to introduce an aldehyde dehydrogenase of the invention, and optionally metabolic and/or genetic modifications to produce a desired product.

Depending on the 3-HBal, 1,3-BDO, 4-HBal or 1,4-BDO biosynthetic pathway constituents of a selected host cell, the non-naturally occurring cells of the invention will include at least one exogenously expressed 3-HBal, 1,3-BDO, 4-HBal or 1,4-BDO pathway-encoding nucleic acid and up to all encoding nucleic acids for one or more 3-HBal, 1,3-BDO, 4-HBal or 1,4-BDO biosynthetic pathways, or a downstream product related thereto such as an ester or amide thereof, including an aldehyde dehydrogenase of the invention. For example, 3-HBal, 1,3-BDO, 4-HBal or 1,4-BDO biosynthesis can be established in a host deficient in a pathway enzyme or protein through exogenous expression of the corresponding encoding nucleic acid, including an aldehyde dehydrogenase of the invention. In a host deficient in all enzymes or proteins of a 3-HBal, 1,3-BDO, 4-HBal or 1,4-BDO pathway, or a downstream product related thereto such as an ester or amide thereof, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 3-HBal, 1,3-BDO, 4-HBal or 1,4-BDO pathway, or a downstream product related thereto such as an ester or amide thereof, can be included, including an aldehyde dehydrogenase of the invention.

Given the teachings and guidance provided herein, those skilled in the art will understand that the number of encoding nucleic acids to introduce in an expressible form will, at least, parallel the 3-HBal, 1,3-BDO, 4-HBal or 1,4-BDO pathway deficiencies of the selected host cell if a 3-HBal, 1,3-BDO, 4-HBal or 1,4-BDO pathway is to be included in the cell. Therefore, a non-naturally occurring cell of the invention can have one, two, three, four, five, six, seven, eight, and so forth, depending on the particular pathway, up to all nucleic acids encoding the enzymes or proteins constituting a 3-HBal, 1,3-BDO, 4-HBal or 1,4-BDO biosynthetic pathway disclosed herein. In some embodiments, the non-naturally occurring cells also can include other genetic modifications that facilitate or optimize 3-HBal, 1,3-BDO, 4-HBal or 1,4-BDO biosynthesis or that confer other useful functions onto the host cell. One such other functionality can include, for example, augmentation of the synthesis of one or more of the 3-HBal, 1,3-BDO, 4-HBal or 1,4-BDO pathway precursors such acetyl-CoA or acetoacetyl-CoA.

Generally, a host cell is selected such that it can express an aldehyde dehydrogenase of the invention, and optionally produces the precursor of a 3-HBal, 1,3-BDO, 4-HBal or 1,4-BDO pathway, in a cell containing such a pathway, either as a naturally produced molecule or as an engineered product that either provides de novo production of a desired precursor or increased production of a precursor naturally produced by the host cell. A host organism can be engineered to increase production of a precursor, as disclosed herein. In addition, a cell that has been engineered to produce a desired precursor can be used as a host organism and further engineered to express enzymes or proteins of a 3-HBal, 1,3-BDO, 4-HBal or 1,4-BDO pathway, or a downstream product related thereto such as an ester or amide thereof, if desired.

In some embodiments, a non-naturally occurring cell of the invention is generated from a host that contains the enzymatic capability to synthesize 3-HBal, 1,3-BDO, 4-HBal or 1,4-BDO, or a downstream product related thereto such as an ester or amide thereof. In this specific embodiment it can be useful to increase the synthesis or accumulation of a 3-HBal, 1,3-BDO, 4-HBal or 1,4-BDO pathway product to, for example, drive 3-HBal, 1,3-BDO, 4-HBal or 1,4-BDO pathway reactions toward 3-HBal, 1,3-BDO, 4-HBal or 1,4-BDO production, or a downstream product related thereto such as an ester or amide thereof. Increased synthesis or accumulation can be accomplished by, for example, overexpression of nucleic acids encoding one or more of the above-described 3-HBal, 1,3-BDO, 4-HBal or 1,4-BDO pathway enzymes or proteins, including an aldehyde dehydrogenase of the invention. Overexpression of the enzyme or enzymes and/or protein or proteins of the 3-HBal, 1,3-BDO, 4-HBal or 1,4-BDO pathway can occur, for example, through exogenous expression of the endogenous gene or genes, or through exogenous expression of the heterologous gene or genes, including exogenous expression of an aldehyde dehydrogenase of the invention. Therefore, naturally occurring organisms can be readily converted to non-naturally occurring cells of the invention, for example, producing 3-HBal, 1,3-BDO, 4-HBal or 1,4-BDO or a downstream product related thereto such as an ester or amide thereof, through overexpression of one, two, three, four, five, six, seven, eight, or more, depending on the 3-HBal, 1,3-BDO, 4-HBal or 1,4-BDO pathway, that is, up to all nucleic acids encoding 3-HBal, 1,3-BDO, 4-HBal or 1,4-BDO biosynthetic pathway enzymes or proteins, or enzymes that produce a downstream product related thereto such as an ester or amide thereof. In addition, a non-naturally occurring organism can be generated by mutagenesis of an endogenous gene that results in an increase in activity of an enzyme in the 3-HBal, 1,3-BDO, 4-HBal or 1,4-BDO biosynthetic pathway, or a downstream product related thereto such as an ester or amide thereof.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring cell.

It is understood that any of the one or more exogenous nucleic acids can be introduced into a cell to produce a non-naturally occurring cell of the invention. The nucleic acids can be introduced so as to confer, for example, a 3-HBal, 1,3-BDO, 4-HBal or 1,4-BDO, or a downstream product related thereto such as an ester or amide thereof, biosynthetic pathway onto the cell, including introducing a nucleic acid encoding an aldehyde dehydrogenase of the invention. Alternatively, encoding nucleic acids can be introduced to produce a cell having the biosynthetic capability to catalyze some of the required reactions to confer 3-HBal, 1,3-BDO, 4-HBal or 1,4-BDO biosynthetic capability to produce an intermediate. For example, a non-naturally occurring cell having a 3-HBal, 1,3-BDO, 4-HBal or 1,4-BDO biosynthetic pathway can comprise at least two exogenous nucleic acids encoding desired enzymes or proteins, including an aldehyde dehydrogenase of the invention. Thus, it is understood that any combination of two or more enzymes or proteins of a biosynthetic pathway can be included in a non-naturally occurring cell of the invention, including an aldehyde dehydrogenase of the invention. Similarly, it is understood that any combination of three or more enzymes or proteins of a biosynthetic pathway can be included in a non-naturally occurring cell of the invention, as desired, so long as the combination of enzymes and/or proteins of the desired biosynthetic pathway results in production of the corresponding desired product. Similarly, any combination of four or more enzymes or proteins of a biosynthetic pathway as disclosed herein can be included in a non-naturally occurring cell of the invention, as desired, so long as the combination of enzymes and/or proteins of the desired biosynthetic pathway results in production of the corresponding desired product.

In addition to the biosynthesis of 3-HBal, 1,3-BDO, 4-HBal or 1,4-BDO, or a downstream product related thereto such as an ester or amide thereof, as described herein, the non-naturally occurring cells and methods of the invention also can be utilized in various combinations with each other and/or with other cells and methods well known in the art to achieve product biosynthesis by other routes. For example, one alternative to produce 3-HBal, 1,3-BDO, 4-HBal or 1,4-BDO other than use of the 3-HBal, 1,3-BDO, 4-HBal or 1,4-BDO producers is through addition of another cell capable of converting a 3-HBal, 1,3-BDO, 4-HBal or 1,4-BDO pathway intermediate to 3-HBal, 1,3-BDO, 4-HBal or 1,4-BDO. One such procedure includes, for example, the fermentation of a cell that produces a 3-HBal, 1,3-BDO, 4-HBal or 1,4-BDO pathway intermediate. The 3-HBal, 1,3-BDO, 4-HBal or 1,4-BDO pathway intermediate can then be used as a substrate for a second cell that converts the 3-HBal, 1,3-BDO, 4-HBal or 1,4-BDO pathway intermediate to 3-HBal, 1,3-BDO, 4-HBal or 1,4-BDO. The 3-HBal, 1,3-BDO, 4-HBal or 1,4-BDO pathway intermediate can be added directly to another culture of the second organism or the original culture of the 3-HBal, 1,3-BDO, 4-HBal or 1,4-BDO pathway intermediate producers can be depleted of these cells by, for example, cell separation, and then subsequent addition of the second organism to the fermentation broth can be utilized to produce the final product without intermediate purification steps. A cell that produces a downstream product related to 3-HBal, 1,3-BDO, 4-HBal or 1,4-BDO such as an ester or amide thereof, can optionally be included to produce such a downstream product.

Alternatively, such enzymatic conversions can be carried out in vitro, with a combination of enzymes or sequential exposure of substrates to enzymes that result in conversion of a substrate to a desired product. As another alternative, a combination of cell-based conversions and in vitro enzymatic conversions can be used, if desired.

In other embodiments, the non-naturally occurring cells and methods of the invention can be assembled in a wide variety of subpathways to achieve biosynthesis of, for example, 3-HBal, 1,3-BDO, 4-HBal or 1,4-BDO or a downstream product related thereto such as an ester or amide thereof. In these embodiments, biosynthetic pathways for a desired product of the invention can be segregated into different cells, and the different cells can be co-cultured to produce the final product. In such a biosynthetic scheme, the product of one cell is the substrate for a second cell until the final product is synthesized. For example, the biosynthesis of 3-HBal, 1,3-BDO, 4-HBal or 1,4-BDO, or a downstream product related thereto such as an ester or amide thereof, can be accomplished by constructing a cell that contains biosynthetic pathways for conversion of one pathway intermediate to another pathway intermediate or the product. Alternatively, 3-HBal, 1,3-BDO, 4-HBal or 1,4-BDO also can be biosynthetically produced from cells through co-culture or co-fermentation using two different cells in the same vessel, where the first cell produces a 3-HBal, 1,3-BDO, 4-HBal or 1,4-BDO intermediate and the second cell converts the intermediate to 3-HBal, 1,3-BDO, 4-HBal or 1,4-BDO, or a downstream product related thereto such as an ester or amide thereof.

Given the teachings and guidance provided herein, those skilled in the art will understand that a wide variety of combinations and permutations exist for the non-naturally occurring cells and methods of the invention together with other cells, with the co-culture of other non-naturally occurring cells having subpathways and with combinations of other chemical and/or biochemical procedures well known in the art to produce 3-HBal, 1,3-BDO, 4-HBal or 1,4-BDO, or a downstream product related thereto such as an ester or amide thereof.

Sources of encoding nucleic acids for a 3-HBal, 1,3-BDO, 4-HBal or 1,4-BDO pathway enzyme or protein, or a downstream product related thereto such as an ester or amide thereof, can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Clostridium kluyveri, Clostridium acetobutylicum, Clostridium beierinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum,*

*Clostridium subterminale, Clostridium sticklandi, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzu, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum,* marine gamma proteobacterium, butyrate-producing bacterium, *Nocardia iowensis, Nocardia ffarcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrifcans, Fusobacterium nucleatum, Streptomyces clavuligenus, Acinetobacter baumanu, Mus musculus, Lachancea kluyveri, Trichomonas vaginalis, Trypanosoma brucei, Pseudomonas stutzeri, Bradyrhizobium japonicum, Mesorhizobium loft, Bos taurus, Nicotiana glutnosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2155, *Mycobacterium avium* subsp. paratuberculosis K-10, *Mycobacterium marinum* M, *Tsukamurella paurometabola* D SM 20162, *Cyanobium* PCC7001, *Dictyostelium discoideum* AX4, *Acidaminococcus fermentans, Acinetobacter baylyi, Acinetobacter calcoaceticus, Aquifex aeolicus, Arabidopsis thaliana, Archaeoglobus fulgidus, Aspergillus niger, Aspergillus terreus, Bacillus subtilis, Bos Taurus, Candida albicans, Candida tropicalis, Chlamydomonas reinhardtii, Chlorobium tepidum, Citrobacter koseri, Citrus junos, Clostridium acetobutylicum, Clostridium kluyveri, Clostridium saccharoperbutylacetonicum, Cyanobium* PCC7001, *Desulfatibacillum alkenivorans, Dictyostelum discoideum, Fusobacterium nucleatum, Haloarcula marismortui, Homo sapiens, Hydrogenobacter thermophilus, Klebsiella pneumoniae, Kluyveromyces lactis, Lactobacillus brevis, Leuconostoc mesenteroides, Metallosphaera sedula, Methanothermobacter thermautotrophicus, Mus musculus, Mycobacterium avium, Mycobacterium bovis, Mycobacterium marinum, Mycobacterium smegmatis, Nicotiana tabacum, Nocardia iowensis, Oryctolagus cuniculus, Penicillium chrysogenum, Pichia pastoris, Porphyromonas gingivalis, Porphyromonas gingivalus, Pseudomonas aeruginos, Pseudomonas putida, Pyrobaculum aerophilum, Ralstonia eutropha, Rattus norvegicus, Rhodobacter sphaeroides, Saccharomyces cerevisiae, Salmonella enteric, Salmonella typhimurium, Schizosaccharomyces pombe, Sulfolobus acidocaldarius, Sulfolobus solfataricus, Sulfolobus tokodai, Thermoanaerobacter tengcongensis, Thermus thermophilus, Trypanosoma brucei, Tsukamurella paurometabola, Yarrowia lipolytica, Zoogloea ramigera* and *Zymomonas mobilis, Clostridum* species, including but no limited to *Clostridium saccharoperbutylacetonicum, Clostridium beiernckii, Clostridium saccharobutylicum, Clostridium botulinum, Clostridium methylpentosum, Clostridium sticklandu, Clostridium phytofermentans, Clostridium saccharolyticum, Clostridium asparagiforme, Clostridium celatum, Clostridium carboxidivorans, Clostridium clostridioforme, Clostridium bolteae, Caldalkalibacillus thermarum, Clostridium botulinum, Pelosinus fermentans, Thermoanaerobacterium thermosaccharolyticum, Desulfosporosinus* speices, *Thermoanaerobacterium* species, including but not limited to *Thermoanaerobacterium saccharolyticum, Thermoanaerobacterium xylanolyticum, Acetonema longum, Geobacillus* species, including but not limited to *Geobacillus thermoglucosidans, Bacillus azotoformans, Thermincola potens, Fusobacterium* species, including but not limited to *Fusobacterium nucleatum, Fusobacterium ulcerans, Fusobacterium varium, Ruminococcus* species, including but not limited to *Ruminococcus gnavus, Ruminococcus obeum, Lachnospiraceae bacterium, Flavonifractor plautii, Roseburia inulinivorans, Acetobacterium woodii, Eubacterium* species, including but not limited to *Eubacterium plexicaudatum, Eubacterium halli, Eubacterium limosum, Eubacterium yurii, Eubacteriaceae bacterium, Thermosediminibacter oceani, Ilyobacter polytropus, Shuttleworthia satelles, Halanaerobium saccharolyticum, Thermoanaerobacter ethanolicus, Rhodospirillum rubrum, Vibrio, Propionibacterium propionicum* as well as other exemplary species disclosed herein or available as source organisms for corresponding genes, including the source organisms of the aldehyde dehydrogenases described in Table 4. However, with the complete genome sequence available for now more than 550 species (with more than half of these available on public databases such as the NCBI), including 395 microorganism genomes and a variety of yeast, fungi, plant, and mammalian genomes, the identification of genes encoding the 3-HBal, 1,3-BDO, 4-HBal or 1,4-BDO biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 3-HBal, 1,3-BDO, 4-HBal or 1,4-BDO, or a downstream product related thereto such as an ester or amide thereof, including expression of an aldehyde dehydrogenase of the invention, described herein with reference to a particular organism such as *E. coli* can be readily applied to other cells such as microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 3-HBal, 1,3-BDO, 4-HBal or 1,4-BDO biosynthetic pathway exists in an unrelated species, 3-HBal, 1,3-BDO, 4-HBal or 1,4-BDO biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all cells using the cognate metabolic alterations to those exemplified herein to construct a cell in a species of interest that will synthesize 3-HBal, 1,3-BDO, 4-HBal or 1,4-BDO, or a downstream product related thereto such as an ester or amide thereof, if desired, including introducing an aldehyde dehydrogenase of the invention.

Methods for constructing and testing the expression levels of a non-naturally occurring host producing 3-HBal, 1,3-BDO, 4-HBal or 1,4-BDO, or a downstream product related thereto such as an ester or amide thereof, including an aldehyde dehydrogenase of the invention, can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

An exogenous nucleic acid encoding an aldehyde dehydrogenase of the invention, and optionally exogenous nucleic acid sequences involved in a pathway for production of 3-HBal, 1,3-BDO, 4-HBal or 1,4-BDO, or a downstream product related thereto such as an ester or amide thereof, can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffieister et al., *J Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include a nucleic acid encoding an aldehyde dehydrogenase of the invention, and/or optionally one or more 3-HBal, 1,3-BDO, 4-HBal or 1,4-BDO biosynthetic pathway encoding nucleic acids, or nucleic acids encoding an enzyme that produces a downstream product related to 3-HBal, 1,3-BDO, 4-HBal or 1,4-BDO such as an ester or amide thereof, as exemplified herein operably linked to expression control sequences functional in the host organism. Expression vectors applicable for use in the host cells of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences encoding an aldehyde dehydrogenase of the invention or encoding polypeptides involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

A vector or expression vector can also be used to express an encoded nucleic acid to produce an encoded polypeptide by in vitro transcription and translation. Such a vector or expression vector will comprise at least a promoter, and includes the vectors described herein above. Such a vector for in vitro transcription and translation generally is double stranded DNA. Methods of in vitro transcription and translation are well known to those skilled in the art (see Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999)). Kits for in vitro transcription and translation are also commercially available (see, for example, Promega, Madison, Wis.; New England Biolabs, Ipswich, Mass.; Thermo Fisher Scientific, Carlsbad, Calif.).

In one embodiment, the invention provides a method for producing 3-hydroxybutyraldehyde (3-HBal) and/or 1,3-butanediol (1,3-BDO), or an ester or amide thereof, comprising culturing a cell of the invention to produce 3-HBal and/or 1,3-BDO, or an ester or amide thereof. Such a cell expresses a polypeptide of the invention. In one embodiment, the invention provides a method for producing 4-hydroxybutyraldehyde (4-HBal) and/or 1,4-butanediol (1,4-BDO), or an ester or amide thereof, comprising culturing a cell of the invention to produce 4-HBal and/or 1,4-BDO, or an ester or amide thereof. In one embodiment, the cell is in a substantially anaerobic culture medium. In one embodiment, the method can further comprise isolating or purifying the 3-HBal and/or 1,3-BDO, or the 4-HBal and/or 1,4-BDO, or ester or amide thereof. In a particular embodiment, the isolating or purifying comprises distillation.

In one embodiment, the invention provides a process for producing a product of the invention, comprising chemically reacting the 3-HBal and/or 1,3-BDO, or the 4-HBal and/or 1,4-BDO, with itself or another compound in a reaction that produces the product.

In one embodiment, the invention provides a method for producing 3-hydroxybutyraldehyde (3-HBal) and/or 1,3-butanediol (1,3-BDO), or an ester or amide thereof, comprising providing a substrate to a polypeptide of the invention and converting the substrate to 3-HBal and/or 1,3-BDO, wherein the substrate is a racemic mixture of 1,3-hydroxybutyryl-CoA. In one embodiment, the 3-HBal and/or 1,3-BDO is enantiomerically enriched for the R form. In one embodiment, the invention provides a method for producing 4-hydroxybutyraldehyde (4-HBal) and/or 1,4-butanediol (1,4-BDO), or an ester or amide thereof, comprising providing a substrate to a polypeptide of the invention and converting the substrate to 4-HBal and/or 1,4-BDO, wherein the substrate is 1,4-hydroxybutyryl-CoA. In one embodiment, the polypeptide is present in a cell, in a cell lysate, or is isolated from a cell or cell lysate.

In one embodiment, the invention provides a method for producing 3-HBal and/or 1,3-BDO, or 4-HBal and/or 1,4-BDO, comprising incubating a lysate of a cell of the invention to produce 3-HBal and/or 1,3-BDO, or 4-HBal and/or 1,4-BDO. In one embodiment, the cell lysate is mixed with a second cell lysate, wherein the second cell lysate comprises an enzymatic activity to produce a substrate of a polypeptide of the invention, or a downstream product of 3-HBal and/or 1,3-BDO. or 4-HBal and/or 1,4-BDO.

The invention also provides a method for producing a polypeptide of the invention, comprising expressing the polypeptide in a cell. The invention additionally provides a method for producing a polypeptide of the invention, comprising in vitro transcribing and translating a nucleic acid of the invention or a vector of the invention to produce the polypeptide.

As described herein, a cell can be used to express an aldehyde dehydrogenase of the invention, and optionally the cell can include a metabolic pathway that utilizes an aldehyde dehydrogenase of the invention to produce a desired product, such as 3-HBal and/or 1,3-BDO, or 4-HBal and/or 1,4-BDO. Such methods for expressing a desired product are described herein. Alternatively, an aldehyde dehydrogenase of the invention can be expressed, and/or a desired product produced, in a cell lysate, for example, a cell lysate of a cell expressing an aldehyde dehydrogenase of the invention, or a cell expressing an aldehyde dehydrogenase of the invention and a metabolic pathway to produce a desired product, as described herein. In another embodiment, an aldehyde dehydrogenase of the invention can be expressed by in vitro transcription and translation, in which the aldehyde dehydrogenase is produced in a cell free system. The aldehyde dehydrogenase expressed by in vitro transcription and translation can be used to carry out a reaction in vitro. Optionally, other enzymes, or cell lysate(s) containing such enzymes, can be used to convert the product of the aldehyde dehydrogenase enzymatic reaction to a desired downstream product in vitro.

Suitable purification and/or assays to test for the expression of an aldehyde dehydrogenase, or for production of 3-HBal, 1,3-BDO, 4-HBal or 1,4-BDO, or a downstream product related thereto such as an ester or amide thereof, including assays to test for aldehyde dehydrogenase activity, can be performed using well known methods (see also Example). Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art (see also Example).

The 3-HBal, 1,3-BDO, 4-HBal or 1,4-BDO, or other desired product, such as a downstream product related thereto such as an ester or amide thereof, can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring cells expressing an aldehyde dehydrogenase of the invention described herein can be cultured to produce and/or secrete the biosynthetic products of the invention. For example, the cells that produce 3-HBal, 1,3-BDO, 4-HBal or 1,4-BDO, or a downstream product related thereto such as an ester or amide thereof, can be cultured for the biosynthetic production of 3-HBal, 1,3-BDO, 4-HBal or 1,4-BDO, or a downstream product related thereto such as an ester or amide thereof. Accordingly, in some embodiments, the invention provides culture medium containing the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate described herein. In some aspects, the culture medium can also be separated from the non-naturally occurring cells of the invention that produced the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. Methods for separating a cell from culture medium are well known in the art. Exemplary methods include filtration, flocculation, precipitation, centrifugation, sedimentation, and the like.

For the production of an aldehyde dehydrogenase of the invention, or of 3-HBal, 1,3-BDO, 4-HBal or 1,4-BDO, or a downstream product related thereto such as an ester or amide thereof, in a cell expressing an aldehyde dehydrogenase of the invention, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United States publication 2009/0047719, filed Aug. 10, 2007. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high yields of a desired product such as 3-HBal, 1,3-BDO, 4-HBal or 1,4-BDO, or a downstream product related thereto such as an ester or amide thereof.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring cell. Such sources include, for example: sugars such as glucose, xylose, arabinose, galactose, mannose, fructose, sucrose and starch; or glycerol, and it is understood that a carbon source can be used alone as the sole source of carbon or in combination with other carbon sources described herein or known in the art. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the cells of the invention for the expression of an aldehyde dehydrogenase of the invention, and optionally production of 3-HBal, 1,3-BDO, 4-HBal or 1,4-BDO, or a downstream product thereof, such as an ester or amide thereof.

In addition to renewable feedstocks such as those exemplified above, the cells of the invention that produce 3-HBal, 1,3-BDO, 4-HBal or 1,4-BDO or a downstream product thereof, such as an ester or amide thereof, also can be modified for growth on syngas as its source of carbon. In this specific embodiment, one or more proteins or enzymes are expressed in the 3-HBal, 1,3-BDO, 4-HBal or 1,4-BDO producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2$/$H_2$ mixtures through the same basic set of enzymes and trans-formations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

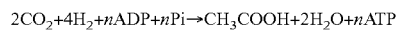

$$2CO_2+4H_2+n\text{ADP}+n\text{Pi} \rightarrow CH_3COOH+2H_2O+n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC)(see WO2009/094485). Following the teachings and guidance provided herein for introducing a sufficient number of encoding nucleic acids to generate a 3-HBal, 1,3-BDO, 4-HBal or 1,4-BDO pathway, or a downstream product related thereto such as an ester or amide thereof, including a nucleic acid encoding an aldehyde dehydrogenase of the invention, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the cells of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to glyceraldehyde-3-phosphate, phosphoenolpyruvate, and pyruvate, by pyruvate:ferredoxin oxidoreductase and the enzymes of gluconeogenesis. Acetyl-CoA can also be converted to acetoacetyl-CoA by, for example, acetoacetyl-CoA thiolase to funnel into a 1,3-BDO pathway, as disclosed herein (see FIG. 1). Following the teachings and guidance provided herein for introducing a sufficient number of encoding nucleic acids to generate a 3-HBal, 1,3-BDO, 4-HBal or 1,4-BDO pathway, or pathway to generate a downstream product related thereto such as an ester or amide thereof, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the cells of the invention can be performed such that the modified organism contains a reductive TCA pathway.

Accordingly, given the teachings and guidance provided herein, those skilled in the art will understand that a non-naturally occurring cell can be produced that produces and/or secretes the biosynthesized compounds of the invention when grown on a carbon source such as a carbohydrate. Such compounds include, for example, 3-HBal, 1,3-BDO, 4-HBal or 1,4-BDO, or a downstream product related thereto such as an ester or amide thereof, and any of the intermediate metabolites in the 3-HBal, 1,3-BDO, 4-HBal or 1,4-BDO pathway. All that is required is to engineer in one or more of the required enzyme or protein activities to achieve biosynthesis of the desired compound or intermediate including, for example, inclusion of some or all of the biosynthetic pathways for 3-HBal, 1,3-BDO, 4-HBal or 1,4-BDO, or a downstream product related thereto such as an ester or amide thereof, including an aldehyde dehydrogenase of the invention. Accordingly, the invention provides a non-naturally occurring cell that produces and/or secretes 3-HBal, 1,3-BDO, 4-HBal or 1,4-BDO, or a downstream product related thereto such as an ester or amide thereof, when grown on a carbohydrate or other carbon source and produces and/or secretes any of the intermediate metabolites shown in the 3-HBal, 1,3-BDO, 4-HBal or 1,4-BDO pathway when grown on a carbohydrate or other carbon source. The cells producing 3-HBal, 1,3-BDO, 4-HBal or 1,4-BDO, or a downstream product related thereto such as an ester or amide thereof, of the invention can initiate synthesis from an intermediate of a 3-HBal, 1,3-BDO, 4-HBal or 1,4-BDO pathway.

The non-naturally occurring cells of the invention are constructed using methods well known in the art as exemplified herein to exogenously express an aldehyde dehydrogenase of the invention, and optionally at least one nucleic acid encoding a 3-HBal, 1,3-BDO, 4-HBal or 1,4-BDO pathway enzyme or protein, or a downstream product related thereto such as an ester or amide thereof. The enzymes or proteins can be expressed in sufficient amounts to produce 3-HBal, 1,3-BDO, 4-HBal or 1,4-BDO, or a downstream product related thereto such as an ester or amide thereof. It is understood that the cells of the invention are cultured under conditions sufficient to express an aldehyde dehydrogenase of the invention or produce 3-HBal, 1,3-BDO, 4-HBal or 1,4-BDO, or a downstream product related thereto such as an ester or amide thereof. Following the teachings and guidance provided herein, the non-naturally occurring cells of the invention can achieve biosynthesis of 3-HBal, 1,3-BDO, 4-HBal or 1,4-BDO, or a downstream product related thereto such as an ester or amide thereof, resulting in intracellular concentrations between about 0.1-300 mM or more, for example, 0.1-1.3 M or higher. Generally, the intracellular concentration of 3-HBal, 1,3-BDO, 4-HBal or 1,4-BDO, or a downstream product related thereto such as an ester or amide thereof, is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring cells of the invention. For example, the intracellular concentration of 3-HBal, 1,3-BDO, 4-HBal or 1,4-BDO, or a downstream product related thereto such as an ester or amide thereof, can be between about 100 mM to 1.3 M, including about 100 mM, 200 mM, 500 mM, 800 mM, 1 M, 1.1 M, 1.2 M, 1.3 M, or higher.

A cell of the invention is cultured using well known methods. The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring cells as well as other anaerobic conditions well known in the art. Under such anaerobic or substantially anaerobic conditions, the 3-HBal, 1,3-BDO, 4-HBal or 1,4-BDO producers can synthesize 3-HBal, 1,3-BDO, 4-HBal or 1,4-BDO, or a downstream product related thereto such as an ester or amide thereof, at intracellular concentrations of 5-10 mM or more as well as all other concentrations exemplified herein. It is understood that, even though the above description refers to intracellular concentrations, 3-HBal, 1,3-BDO, 4-HBal or 1,4-BDO producing cells can produce 3-HBal, 1,3-BDO, 4-HBal or 1,4-BDO, or a downstream product related thereto such as an ester or amide thereof, intracellularly and/or secrete the product into the culture medium.

As described herein, one exemplary growth condition for achieving biosynthesis of 3-HBal, 1,3-BDO, 4-HBal or 1,4-BDO, or a downstream product related thereto such as an ester or amide thereof, includes anaerobic culture or fermentation conditions. In certain embodiments, the non-naturally occurring cells of the invention can be sustained, cultured or fermented under anaerobic or substantially anaerobic conditions. Briefly, an anaerobic condition refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 3-HBal, 1,3-BDO, 4-HBal or 1,4-BDO, or a downstream product related thereto such as an ester or amide thereof, by a cell of the invention. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 3-HBal, 1,3-BDO, 4-HBal or 1,4-BDO, or a downstream product related thereto such as an ester or amide thereof. Generally, and as with non-continuous culture procedures, the continuous and/or near-continuous production of 3-HBal, 1,3-BDO, 4-HBal or 1,4-BDO, or a downstream product related thereto such as an ester or amide thereof, will include culturing a non-naturally occurring cell producing 3-HBal, 1,3-BDO, 4-HBal or 1,4-BDO, or a downstream product related thereto such as an ester or amide thereof, of the invention in sufficient nutrients and medium to sustain and/or nearly sustain growth in an exponential phase. Continuous culture under such conditions can include, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the cell of the invention is for a sufficient period of time to produce a sufficient amount of product for a desired purpose.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, $N_2/CO_2$ mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermentation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

Fermentation procedures are well known in the art. Briefly, fermentation for the biosynthetic production of 3-HBal, 1,3-BDO, 4-HBal or 1,4-BDO, or a downstream product related thereto such as an ester or amide thereof, can be utilized in, for example, fed-batch fermentation and batch separation; fed-batch fermentation and continuous separation, or continuous fermentation and continuous separation. Examples of batch and continuous fermentation procedures are well known in the art and described herein.

In addition to the fermentation procedures described herein using the producers of 3-HBal, 1,3-BDO, 4-HBal or 1,4-BDO, or a downstream product related thereto such as an ester or amide thereof, of the invention for continuous production of substantial quantities of 3-HBal, 1,3-BDO, 4-HBal or 1,4-BDO, or a downstream product related thereto such as an ester or amide thereof, the 3-HBal, 1,3-BDO, 4-HBal or 1,4-BDO, or a downstream product related thereto such as an ester or amide, producers also can be, for example, simultaneously subjected to chemical synthesis and/or enzymatic procedures to convert the product to other compounds, or the product can be separated from the fermentation culture and sequentially subjected to chemical and/or enzymatic conversion to convert the product to other compounds, if desired.

In addition to the culturing and fermentation conditions disclosed herein, growth condition for achieving expression of an aldehyde dehydrogenase of the invention or biosynthesis of 3-HBal, 1,3-BDO, 4-HBal or 1,4-BDO, or a downstream product related thereto such as an ester or amide thereof, can include the addition of an osmoprotectant to the culturing conditions. In certain embodiments, the non-naturally occurring cells of the invention can be sustained, cultured or fermented as described herein in the presence of an osmoprotectant. Briefly, an osmoprotectant refers to a compound that acts as an osmolyte and helps a cell as described herein survive osmotic stress. Osmoprotectants include, but are not limited to, betaines, amino acids, and the sugar trehalose. Non-limiting examples of such are glycine betaine, praline betaine, dimethylthetin, dimethylsulfonioproprionate, 3-dimethylsulfonio-2-methyl-proprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a cell described herein from osmotic stress will depend on the cell used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in 3-HBal, 1,3-BDO, 4-HBal or 1,4-BDO, or a downstream product related thereto such as an ester or amide thereof, or any 3-HBal, 1,3-BDO, 4-HBal or 1,4-BDO pathway intermediate. The various carbon feedstock and other uptake sources enumerated above will be referred to herein, collectively, as "uptake sources." Uptake sources can provide isotopic enrichment for any atom present in the product 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate, or for side products generated in reactions diverging away from a 3-HBal, 1,3-BDO, 4-HBal or 1,4-BDO pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios.

In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased source derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$) Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b)

normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950)$^{14}$C/$^{12}$C ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx H is −17.8 per mil. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content of a compound or material and/or prepared downstream products that utilize a compound or material of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 3-HBal, 1,3-BDO, 4-HBal or 1,4-BDO or a downstream product related thereto such as an ester or amide thereof, or a 3-HBal, 1,3-BDO, 4-HBal or 1,4-BDO pathway intermediate, produced by a cell of the invention, that has a carbon-12, carbon-13, and carbon-14 ratio that reflects an atmospheric carbon, also referred to as environmental carbon, uptake source. For example, in some aspects the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate that has a carbon-12, carbon-13, and carbon-14 ratio that reflects petroleum-based carbon uptake source. In this aspect, the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate as disclosed herein, and to the products derived therefrom, wherein the 3-HBal, 1,3-BDO, 4-HBal or 1,4-BDO, or a downstream product related thereto such as an ester or amide thereof, or a 3-HBal, 1,3-BDO, 4-HBal or 1,4-BDO pathway intermediate has a carbon-12, carbon-13, and carbon-14 isotope ratio of about the same value as the $CO_2$ that occurs in the environment. For example, in some aspects the invention provides bioderived 3-HBal, 1,3-BDO, 4-HBal or 1,4-BDO, or a downstream product related thereto such as an ester or amide thereof, or a bioderived 3-HBal, 1,3-BDO, 4-HBal of 1,4-BDO intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived 3-HBal, 1,3-BDO, 4-HBal or 1,4-BDO, or a downstream product related thereto such as an ester or amide thereof, or a bioderived 3-HBal, 1,3-BDO, 4-HBal or 1,4-BDO pathway intermediate as disclosed herein, wherein the bioderived product is chemically modified to generate a final product. Methods of chemically modifying a bioderived product of 3-HBal, 1,3-BDO, 4-HBal or 1,4-BDO, or a downstream product related thereto such as an ester or amide thereof, or an intermediate of a 3-HBal, 1,3-BDO, 4-HBal or 1,4-BDO, to generate a desired product are well known to those skilled in the art, as described herein. The invention further provides plastics, elastic fibers, polyurethanes, polyesters, including polyhydroxyalkanoates, nylons, organic solvents, polyurethane resins, polyester resins, hypoglycaemic agents, butadiene and/or butadiene-based products, which can be based on 3-HBal and/or 1,3-BDO, or a downstream product related thereto such as an ester or amide thereof, and plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, and the like, which can be based on 4-HBal and/or 1,4-BDO, or a downstream product related thereto such as an ester or amide thereof, having a carbon-12 versus carbon-13 versus carbon-14 isotope ratio of about the same value as the $CO_2$ that occurs in the environment, wherein the plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene, and/or butadiene-based products are generated directly from or in combination with bioderived 3-HBal, 1,3-BDO, 4-HBal or 1,4-BDO, or a downstream product related thereto such as an ester or amide thereof, or a bioderived 3-HBal, 1,3-BDO, 4-HBal or 1,4-BDO pathway intermediate as disclosed herein. Methods for producing butadiene and/or butadiene-based products have been described previously (see, for example, WO 2010/127319, WO 2013/036764, U.S. Pat. No. 9,017,983, US 2013/0066035, WO/2012/018624, US 2012/0021478, each of which is incorporated herein by reference). 1,3-BDO can be reacted with an acid, either in vivo or in vitro, to convert to an ester using, for example, a lipase. Such esters can have nutraceutical, pharmaceutical and food uses, and are advantaged when R-form of 1,3-BDO is used since that is the form (compared to S-form or the racemic mixture) best utilized by both animals and humans as an energy source (e.g., a ketone ester, such as (R)-3-hydroxybutyl-R-1,3-butanediol monoester (which has Generally Recognized As Safe (GRAS) approval in the United States) and (R)-3-hydroxybutyrate glycerol monoester or diester). The ketone esters can be delivered orally, and the ester releases R-1,3-butanediol that is used by the body (see, for example, WO2013150153). Methods of producing amides are well known in the art (see, for example, Goswami and Van Lanen, *Mol. Biosyst.* 11(2):338-353 (2015)).

Thus the present invention is particularly useful to provide an improved enzymatic route and microorganism to provide an improved composition of 1,3-BDO, namely R-1,3-butanediol, highly enriched or essentially enantiomerically pure, and further having improved purity qualities with respect to by-products. 1,3-BDO has further food related uses including use directly as a food source, a food ingredient, a flavoring agent, a solvent or solubilizer for flavoring agents, a stabilizer, an emulsifier, and an antimicrobial agent and preservative. 1,3-BDO is used in the pharmaceutical industry as a parenteral drug solvent. 1,3-BDO finds use in cosmetics as an ingredient that is an emollient, a humectant, that prevents crystallization of insoluble ingredients, a solubilizer for less-water-soluble ingredients such as fragrances, and as an anti-microbial agent and preservative. For example, it can be used as a humectant, especially in hair sprays and setting lotions; it reduces loss of aromas from essential oils, preserves against spoilage by microorganisms, and is used as a solvent for benzoates. 1,3-BDO can be used at concentrations from 0.1% to 50%, and even less than 0.1% and even more than 50%. It is used in hair and bath products, eye and facial makeup, fragrances, personal cleanliness products, and shaving and skin care preparations (see, for example, the Cosmetic Ingredient Review board's report: "Final Report on the Safety Assessment of Butylene Glycol, Hexylene Glycol, Ethoxydiglycol, and Dipropylene Glycol", *Journal of the American College of Toxicology*, Volume 4, Number 5, 1985, which is incorporated herein by reference). This report provides specific uses and concentrations of 1,3-BDO in cosmetics; see for examples the report's Table 2 therein entitled "Product Formulation Data".

In one embodiment, the invention provides culture medium comprising bioderived 3-HBal and/or 1,3-BDO, or 4-HBal and/or 1,4-BDO, wherein the bioderived 3-HBal and/or 1,3-BDO, or 4-HBal and/or 1,4-BDO, has a carbon-12, carbon-13 and carbon-14 isotope ratio that reflects an atmospheric carbon dioxide uptake source, and wherein the bioderived 3-HBal and/or 1,3-BDO, or 4-HBal and/or 1,4-BDO is produced by a cell, or in a cell lysate, of the invention or a method of the invention. In one embodiment, the culture medium is separated from the cell.

In one embodiment, the invention provides 3-hydroxybutyraldeyde (3-HBal) and/or 1,3-butanediol (1,3-BDO), or 4-hydroxybutyraldeyde (4-HBal) and/or 1,4-butanediol (1,4-BDO), having a carbon-12, carbon-13 and carbon-14 isotope ratio that reflects an atmospheric carbon dioxide uptake source, wherein the 3-HBal and/or 1,3-BDO, or the 4-HBal and/or 1,4-BDO, is produced by a cell, or in a cell lysate, of the invention or a method of the invention. In one embodiment, the 3-HBal and/or 1,3-BDO, or the 4-HBal and/or 1,4-BDO, has an Fm value of at least 80%, at least 85%, at least 90%, at least 95% or at least 98%.

In one embodiment, the invention provides 3-hydroxybutyraldehyde (3-HBal) and/or 1,3-butanediol (1,3-BDO), or 4-hydroxybutyraldehyde (4-HBal) and/or 1,4-butanediol (1,4-BDO), produced by a cell, or in a cell lysate of the invention or a method of the invention. In one embodiment, the invention provides 3-hydroxybutyraldeyde (3-HBal) and/or 1,3-butanediol (1,3-BDO) having a carbon-12, carbon-13 and carbon-14 isotope ratio that reflects an atmospheric carbon dioxide uptake source, wherein the 3-HBal and/or 1,3-BDO is produced by a cell, or in a cell lysate, of the invention or a method of the invention, wherein the 3-HBal and/or 1,3-BDO is enantiomerically enriched for the R form. In one embodiment, the 3-HBal and/or 1,3-BDO has an Fm value of at least 80%, at least 85%, at least 90%, at least 95% or at least 98%.

In one embodiment, the invention provides 3-hydroxybutyraldehyde (3-HBal) and/or 1,3-butanediol (1,3-BDO) produced by a cell, or in a cell lysate, of the invention or a method of the invention, wherein the 3-HBal and/or 1,3-BDO is enantiomerically enriched for the R form. In one embodiment, the R form is greater than 95%, 96%, 97%, 98%, 99%, 99.1%, 99.2%, 99.3%, 99.4%, 99.5%, 99.6%, 99.7%, 99.8% or 99.9% of the 3-HBal and/or 1,3-BDO. In one embodiment, the 3-HBal and/or 1,3-BDO is ≥55% R-enantiomer, ≥60% R-enantiomer, ≥65% R-enantiomer, ≥70% R-enantiomer, ≥75% R-enantiomer, ≥80% R-enantiomer, ≥85% R-enantiomer, ≥90% R-enantiomer, or ≥95% R-enantiomer, and can be highly chemically pure, e.g., ≥99%, for example, ≥95%, ≥96%, ≥97%, ≥98%, ≥99%, ≥99.1%, ≥99.2%, ≥99.3%, ≥99.4%, ≥99.5%, ≥99.6%, ≥99.7%, ≥99.8% or ≥99.9% R-enantiomer.

In one embodiment, the invention provides a composition comprising 3-HBal and/or 1,3-BDO, or the 4-HBal and/or 1,4-BDO, produced by a cell, or in a cell lysate, of the invention or a method of the invention and a compound other than the 3-HBal and/or 1,3-BDO, or 4-HBal or 1,4-BDO, respectively. In one embodiment, the compound other than the 3-HBal and/or 1,3-BDO, or the 4-HBal and/or 1,4-BDO, is a portion of a cell that produces the 3-HBal and/or 1,3-BDO, or the 4-HBal and/or 1,4-BDO, respectively, or that expresses a polypeptide of the invention.

In one embodiment, the invention provides a composition comprising 3-HBal and/or 1,3-BDO, or the 4-HBal and/or 1,4-BDO, produced by a cell, or in a cell lysate, of the invention or a method of the invention, or a cell lysate or culture supernatant of a cell producing the 3-HBal and/or 1,3-BDO, or the 4-HBal and/or 1,4-BDO.

In one embodiment, the invention provides a product comprising 3-HBal and/or 1,3-BDO, or the 4-HBal and/or 1,4-BDO, produced by a cell, or in a cell lysate of the invention or a method of the invention, wherein the product is a plastic, elastic fiber, polyurethane, polyester, polyhydroxyalkanoate, poly-4-hydroxybutyrate (P4HB) or a co-polymer thereof, poly(tetramethylene ether) glycol (PTMEG), polybutylene terephthalate (PBT), polyurethane-polyurea copolymer, nylon, organic solvent, polyurethane resin, polyester resin, hypoglycaemic agent, butadiene or butadiene-based product. In one embodiment, the product is a cosmetic product or a food additive. In one embodiment, the product comprises at least 0.1%, at least 0.5%, at least 1%, at least 5%, at least 10%, at least 20%, at least 30%, at least 40% or at least 50% bioderived 3-HBal and/or 1,3-BDO, or bioderived 4-HBal and/or 1,4-BDO. In one embodiment, the product comprises a portion of the produced 3-HBal and/or 1,3-BDO, or the produced 4-HBal and/or 1,4-BDO, as a repeating unit. In one embodiment, the invention provides a molded product obtained by molding a product made with or derived from 3-HBal and/or 1,3-BDO, or 4-HBal and/or 1,4-BDO produced by a cell, or in a cell lysate of the invention or a method of the invention.

The invention further provides a composition comprising bioderived 3-HBal, 1,3-BDO, 4-HBal or 1,4-BDO, or a downstream product related thereto such as an ester or amide thereof, and a compound other than the bioderived 3-HBal, 1,3-BDO, 4-HBal or 1,4-BDO, or a downstream product related thereto such as an ester or amide thereof. The compound other than the bioderived product can be a cellular portion, for example, a trace amount of a cellular portion of, or can be fermentation broth or culture medium or a purified or partially purified fraction thereof produced in the presence of, a non-naturally occurring cell of the invention having a pathway that produces 3-HBal, 1,3-BDO, 4-HBal or 1,4-BDO, or a downstream product related thereto such as an ester or amide thereof. The composition can comprise, for example, a reduced level of a byproduct when produced by an organism having reduced byproduct formation, as disclosed herein. The composition can comprise, for example, bioderived 3-HBal, 1,3-BDO, 4-HBal or 1,4-BDO, or a downstream product related thereto such as an ester or amide thereof, or a cell lysate or culture supernatant of a cell of the invention.

3-HBal, 1,3-BDO, 4-HBal or 1,4-BDO, or a downstream product related thereto such as an ester or amide thereof, is a chemical used in commercial and industrial applications. Non-limiting examples of such applications include production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Moreover, 3-HBal, 1,3-BDO, 4-HBal or 1,4-BDO is also used as a raw material in the production of a wide range of products including plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Accordingly, in some embodiments, the invention provides biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products comprising one or more bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate produced by a non-naturally occurring cell of the invention, for example, expressing an aldehyde dehydrogenase of the invention, or produced using a method disclosed herein.

As used herein, the term "bioderived" means derived from or synthesized by a biological organism and can be considered a renewable resource since it can be generated by a biological organism. Such a biological organism, in particular the cells of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products comprising bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate, wherein the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate includes all or part of the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate used in the production of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. For example, the final plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products can contain the bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate, or a portion thereof that is the result of the manufacturing of plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Such manufacturing can include chemically reacting the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate (e.g. chemical conversion, chemical functionalization, chemical coupling, oxidation, reduction, polymerization, copolymerization and the like) into the final plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products. Thus, in some aspects, the invention provides a biobased plastic, elastic fiber, polyurethane, polyester, including polyhydroxyalkanoate such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymer, referred to as spandex, elastane or Lycra™, nylon, polyurethane resin, polyester resin, hypoglycaemic agent, butadiene and/or butadiene-based product comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate as disclosed herein.

Additionally, in some embodiments, the invention provides a composition having a bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate disclosed herein and a compound other than the bioderived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. For example, in some aspects, the invention provides biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products wherein the 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate used in its production is a combination of bioderived and petroleum derived 3-HBal, 1,3-BDO, 4-HBal or 1,4-BDO, or a downstream product related thereto such as an ester or amide thereof, or 3-HBal, 1,3-BDO, 4-HBal or 1,4-BDO pathway intermediate. For example, biobased plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products can be produced using 50% bioderived 3-HBal, 1,3-BDO, 4-HBal or 1,4-BDO, or a downstream product related thereto such as an ester or amide thereof, and 50% petroleum derived 3-HBal, 1,3-BDO, 4-HBal or 1,4-BDO, or a downstream product related thereto such as an ester or amide thereof, or other desired ratios such as 60%/40%, 70%/30%, 80/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the cells disclosed herein. It is understood that methods for producing plastics, elastic fibers, polyurethanes, polyesters, including polyhydroxyalkanoates such as poly-4-hydroxybutyrate (P4HB) or co-polymers thereof, poly(tetramethylene ether) glycol (PTMEG)(also referred to as PTMO, polytetramethylene oxide), polybutylene terephthalate (PBT), and polyurethane-polyurea copolymers, referred to as spandex, elastane or Lycra™, nylons, organic solvents, polyurethane resins, polyester resins, hypoglycaemic agents, butadiene and/or butadiene-based products using the bioderived 3-HBal, 1,3-BDO, 4-HBal or 1,4-BDO, or a downstream product related thereto such as an ester or amide thereof, or bioderived 3-HBal, 1,3-BDO, 4-HBal or 1,4-BDO pathway intermediate of the invention are well known in the art.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 3-HBal, 1,3-BDO, 4-HBal or 1,4-BDO, or a downstream product related thereto such as an ester or amide thereof.

One computational method for identifying and designing metabolic alterations favoring biosynthesis of a desired product is the OptKnock computational framework (Burgard et al., *Biotechnol. Bioeng.* 84:647-657 (2003)). OptKnock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring cells for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. publication 2002/0168654, filed Jan. 10, 2002, in International Patent No. PCT/US02/00660, filed Jan. 10, 2002, and U.S. publication 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host cells. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, the invention relates to aldehyde dehydrogenase variants (see Example). The generation of such variants is described in the Example. Any of a variety of methods can be used to generate an aldehyde dehydrogenase variant such as the aldehyde dehydrogenase variants disclosed herein. Such methods include, but are not limited to, site-directed mutagenesis, random mutagenesis, combinatorial libraries, and other mutagenesis methods described below (see Sambrook et al., *Molecular Cloning: A Laboratory Manual*, Third Ed., Cold Spring Harbor Laboratory, New York (2001); Ausubel et al., *Current Protocols in Molecular Biology*, John Wiley and Sons, Baltimore, Md. (1999); Gillman et al., *Directed Evolution Library Creation: Methods and Protocols* (*Methods in Molecular Biology*) Springer, 2nd ed (2014).

As disclosed herein, a nucleic acid encoding a desired activity of a pathway for 3-HBal, 1,3-BDO, 4-HBal or 1,4-BDO, or a downstream product related thereto such as an ester or amide thereof, can be introduced into a host organism. In some cases, it can be desirable to modify an activity of a 3-HBal, 1,3-BDO, 4-HBal or 1,4-BDO, or a downstream product related thereto such as an ester or amide thereof, pathway enzyme or protein to increase production of 3-HBal, 1,3-BDO, 4-HBal or 1,4-BDO, or a downstream product related thereto such as an ester or amide thereof. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >10$^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl. Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a pathway enzyme or protein for producing 3-HBal, 1,3-BDO, 4-HBal or 1,4-BDO, or a downstream product thereof such as an ester or amide thereof, or an aldehyde dehydrogenase of the invention. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751(1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Nat. Acad Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also provided within the definition of the invention provided herein. Accordingly, the following examples are intended to illustrate but not limit the present invention.

EXAMPLE

Aldehyde Dehydrogenase Variants

This example describes generation of aldehyde dehydrogenase variants with desirable properties.

Mutagenesis techniques were used to generate variant aldehyde dehydrogenases based on template ALD-1. Variants were generated using error prone PCR, site directed mutagenesis, and by spontaneous mutations during genetic selection. Template ALD-1 corresponds to the aldehyde dehydrogenase provided below:

```
                                        (SEQ ID NO: 1)
MIKDTLVSITKDLKLKTNVENANLKNYKDDSSCFGVFENVENAI

SNAVHAQKILSLHYTKEQREKIITEIRKAALENKEILATMILEE

THMGRYEDKILKHELVAKYTPGTEDLTTTAWSGDNGLTVVEMSP

YGVIGAITPSTNPTETVICNSIGMIAAGNTVVFNGHPGAKKCVA

FAVEMINKAIISCGGPENLVTTIKNPTMDSLDAIIKHPSIKLLC

GTGGPGMVKTLLNSGKKAIGAGAGNPPVIVDDTADIEKAGKSII

EGCSFDNNLPCIAEKEWWENVADDLISNMLKNNAVIINEDQVSK

LIDLVLQKNNETQEYSINKKWVGKDAKLFLDEIDVESPSSVKCI

ICEVSASFIPFVMTELMMPILPIVRVKDIDEAIEYAKIAEQNRK

HSAYIYSKNIDNLNRFEREIDTTIFVKNAKSFAGVGYEAEGFTT

FTIAGSTGEGITSARNFTRQRRCVLAG.
```

Additional ALD sequences for ALD-2 and ALD-3 are provided below:

```
ALD-2
                                        (SEQ ID NO: 2)
MNTENIEQAIRKILSEELSNPQSSTATNTTVPGKNGIFKTVNEA

IAATKAAQENYADQPISVRNKVIDAIREGFRPYIEDMAKRIHDE

TGMGTVSAKIAKLNNALYNTPGPEILQPEAETGDGGLVMYEYAP

FGVIGAVGPSTNPSETVIANAIMMLAGGNTLFFGAHPGAKNITR

WTIEKLNELVADATGLHNLVVSLETPSIESVQEVMQHPDVAMLS

ITGGPAVVHQALISGKKAVGAGAGNPPAMVDATANIALAAHNIV

DSAAFDNNILCTAEKEVVVEAAVKDELIMRMQQEGAFLVTDSAD

IEKLAQMTIGPKGAPDRKFVGKDATYILDQAGISYTGTPTLIIL

EAAKDHPLVTTEMLMPILPWCCPDFDSVLATATEVEGGLHHTAS

IHSENLPHINKAAFIRLNTSIFWNGPTYCGTGVATNGAHSGASA

LTIATPTGEGTATSKTYTRRRRLNSPEGFSLRTWEA

ALD-3
                                        (SEQ ID NO: 3)
MTVNEQLVQDIIKNVVASMQLTQTNKTELGVFDDMNQAIEAAKE

AQLVVKKMSMDQREKIISAIRKKTIEHAETLARMAVEETGMGNV

GHKILKHQLVAEKTPGTEDITTTAWSGDRGLTLVEMGPFGVIGA

ITPCTNPSETIICNTIGMLAGGNTWFNPHPAAIKTSNFAVQLIN

EASLSAGGPVNIACSVRKPTLDSSKIMMSHQDIPLIAATGGPGW

TAVLQSGKRGIGAGAGNPPVLVDETADIRKAAEDIINGCTFDNN

LPCIAEKEWAIDAIANELMNYMVKEQGCYAITKEQQEKLTNLVI

TPKGLNRNCVGKDARTLLGMIGIDVPSNTRCIIFEGEKEHPLIS

EELMMPILGIVRAKSFDDAVEKAVWLEHGNRHSAHIHSKNVDRI

TTYAKAIDTAILVKNAPSYAAIGFGGEGFCTFTIASRTGEGLTS

ASTFTKRRRCVMSDSLCIR
```

ALD-1 is slightly more specific for the R enantiomer of 3-hydroxybutyryl-CoA compared to the S enantiomer. A sequence alignment of ALD-1 to ALD-2 and ALD-3 is shown in FIG. 3. The sequences correspond to SEQ ID NOS:1, 2 and 3, respectively. A crystal structure also exists for ALD-3 (PDBID 4C3S), and ALD-2 is more closely related to ALD-3 than ALD-1. Therefore ALD-3 was used as the template. Underlined in FIG. 3 are 2 loop regions, the first designated A, the second B, both involved in substrate specificity and enantiomer specificity as determined herein. Loop A in ALD-1 is sequence LQKNNETQEY-SINKKWVGKD (SEQ ID NO:124), in ALD-2 is sequence IGPKGAPDRKFVGKD (SEQ ID NO:125) and in ALD-3 is sequence ITPKGLNRNCVGKD (SEQ ID NO:126). Loop B in ALD-1 is sequence SFAGVGYEAEGFTTFTIA (SEQ ID NO:127), in ALD-2 is sequence TYCGTGVATNGAHSGA-SALTIA (SEQ ID NO:128), and in ALD-3 is sequence SYAAIGFGGEGFCTFTIA (SEQ ID NO:129). The sequence and the length of the substrate specificity loop A and B from ALD-2 differs from those of ALD-1 and ALD-3; nevertheless the alignment shows sufficient conservation to facilitate identification of corresponding positions for substitution as described herein, and especially so if combined with 3D modeling as shown in FIG. 6, which shows the two loop regions interacting to affect substrate specificity and enantiomer specificity, especially when modified with exemplary substitutions as described herein. ALD-1 and ALD-3 are 51.9% identical. ALD-1 and ALD-2 are 35.9% identical. ALD-3 and ALD-2 are 40% identical. A consensus ALD sequence based on the alignment of FIG. 3 was generated. A consensus for Loop A based on alignment of ALD-1, ALD-2 and ALD-3 is IXPKG-----XXNRKXVGKD (SEQ ID NO:5). A consensus for Loop B based on alignment of ALD-1, ALD-2 and ALD-3 is SYAGXGXXXE----GFXTF-TIA (SEQ ID NO:6).

Additional alignments were performed (FIG. 4). FIG. 4A shows an alignment with a 40-55% cutoff compared to ALD-1. FIG. 4B shows an alignment with a 75-90% cutoff compared to ALD-1. FIG. 4C shows an alignment with a 90% cutoff compared to ALD-1. The alignments of exemplary aldehyde deydrogenases (ALD) shown in FIGS. 4A-4C demonstrate identifying positions in ALDs that correspond to positions in the representative template ALD sequence where substitutions of the invention can be made. Underlined are two key loop regions, the first designated A, the second B, both involved in substrate specificity and enantiomer specificity as determined herein. FIGS. 4A-4C demonstrate that corresponding positions for substitutions taught herein can be identified in ALDs that are at least 40% identical with ALD-1, especially the Loop A and B regions, and especially the very conserved Loop B region.

Mutagenesis to increase the specificity of variant 45 for 3HB-CoA relative to acetyl-CoA led to several variants with increased 1,3 BDO production and decreased ethanol. Mutations that increase specificity of 3-hydroxybutyryl-CoA over acetyl-CoA provide a decrease in ethanol, since the acetaldehyde generated from acetyl-CoA can be converted to ethanol by enzymes natively in the host cell or by a pathway enzyme that converts 3-hydroxybutyraldehyde to 1,3-butanediol. Variants that increase enzymatic activity of aldehyde dehydrogenase or increase its specificity for 3-hydroxybutyryl-CoA decrease 4-hydroxy-2-butanone by increasing flux through an enzymatic pathway to 1,3-butanediol which pulls acetoacetyl-CoA towards 1,3-butanediol formation, decreasing its availability for two-step conversion to 4-hydroxy-2-butanone by native enzymes or less-specific pathway enzymes. The sequence of variant 45 is provided below:

```
                                       (SEQ ID NO: 4)
MIKDTLVSITKDLKLKTNVENANLKNYKDDSSCFGVFENVENAI

SNAVHAQKILSLHYTKEQREKIITEIRKAALENKEILATMILEE

THMGRYEDKILKHELVAKYTPGTEDLTTTAWSGDNGLTWEMSPY

GVIGAITPSTNPTETVICNSIGMIAAGNTWFNGHPGAKKSVAFA

VEMINKAIISCGGPENLVTTIKNPTRDSLDAIIKHPSIKLLVGT

GGPGMVKTLLNSGKKAIGAGAGNPPVIVDDTADIEKAGKSIIEG

ASFDNNLPCIAEKEVFVFENVADDLISNMLKNNAVIINEDQVSK

LIDLVLQKNNETQEYSINKKWVGKDAKLFLDEIDVESPSSVKCI

ITEVSASHPFVMTELMMPILPIVRVKDIDEAIEYAKIAEQNHKH

SAYIYSKNIDNLNRFEREIDTTIFVKNAKSFAGVGYEAPGFTTF

TIAGSTGEGITSARNFTRQRRIVLVG
```

The assay performed is an in vitro assay to examine the activity on 3HB-CoA by monitoring a decrease in absorbance as NADH is converted to NAD. Assays were also performed with acetyl-CoA (AcCoA) as a substrate, and improved enzymes were identified as an improvement in the ratio of activity for 3HB-CoA vs. AcCoA. Mutations that increase specificity of 3-hydroxybutyryl-CoA over acetyl-CoA provide a decrease in ethanol, since the acetaldehyde generated from acetyl-CoA can be converted to ethanol by enzymes natively in the host cell or by a pathway enzyme that converts 3-hydroxybutyraldehyde to 1,3-butanediol.

Figure 5A:
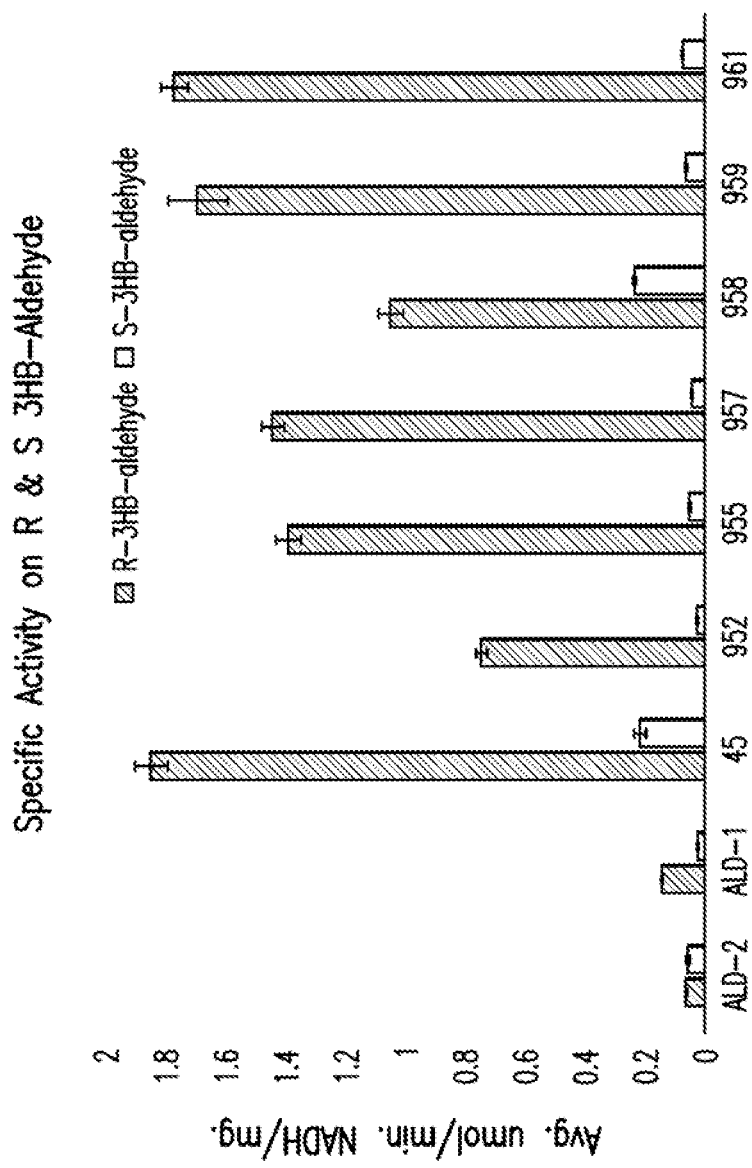
FIGS. 5A and 5B show enzyme activities of various exemplary aldehyde dehydrogenases.
Figure 5B:
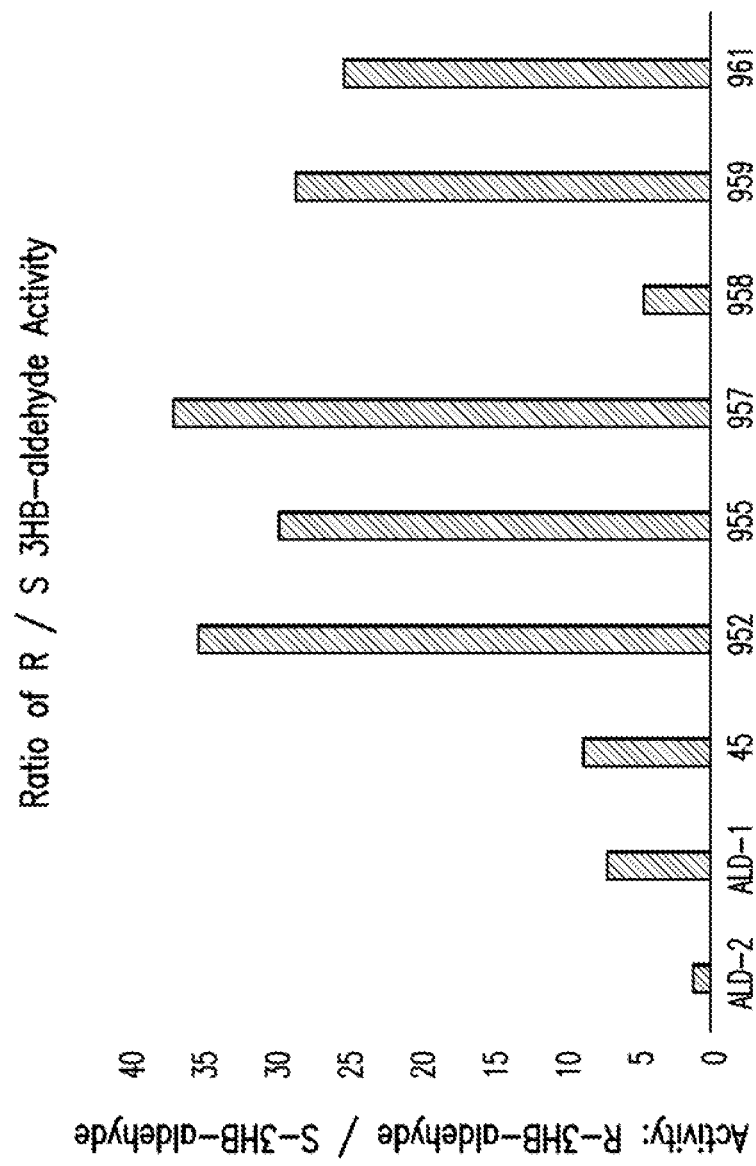

Further investigation of a subset of these variants with (R) and (S) 3-hydroxybutyraldehyde showed that five of the tested variants (952, 955, 957, 959, 961) had improved selectivity for the R enantiomer compared to the parent enzyme (variant 45) and wildtype ALD-1 (FIG. 5). FIG. 5A shows the specific activity of ALD-2, ALD-1 and ALD-1 variants on 3 hydroxy-(R)-butyraldehyde (left bars in sets of bars) and 3 hydroxy-(S)-butyraldehyde (right bars in sets of bars). Purified streptavidin-tagged proteins were assayed at 35° C. in IVI buffer pH 7.5, 0.5 mM NAD$^+$, 2 mM CoA in the presence of either 10 mM R or S 3-hydroxybutyraldehyde, and activity was monitored by change in NADH absorbance at 340 nm. IV buffer contains 5 mM potassium phosphate monobasic, 20 mM potassium phosphate dibasic, 10 mM sodium glutamate, monohydrate, and 150 mM potassium chloride, pH 7.5. Thus, the enzyme reaction in the assay was carried out in the reverse direction from that shown in FIG. 1, that is, the reaction measured the conversion of 3-hydroxybutyraldehyde to 3-hydroxybutyryl-CoA. As shown in FIG. 5B, certain aldehyde dehydrogenase variants exhibited selectivity for R-3-hydroxybutyraldehyde (R-3BIB-aldehyde) over S-3-hydroxybutyraldehyde (S-3BIB-aldehyde).

Figure 6A:
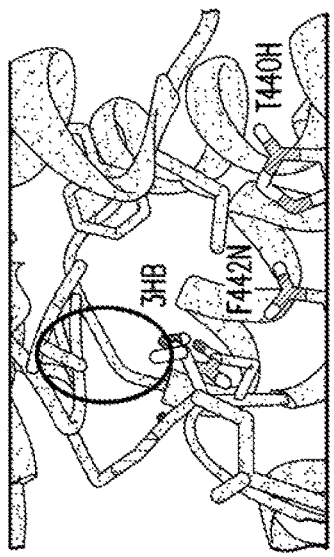
FIGS. 6A-6C show ribbon diagrams of the structure of the aldehyde dehydrogenase 959. The diagrams show docking of 3-hydroxy-(R)-butyraldehyde (FIG. 6A) or 3-hydroxy-(S)-butyraldehyde (FIG. 6B) into the structure of 959.
Figure 6B:
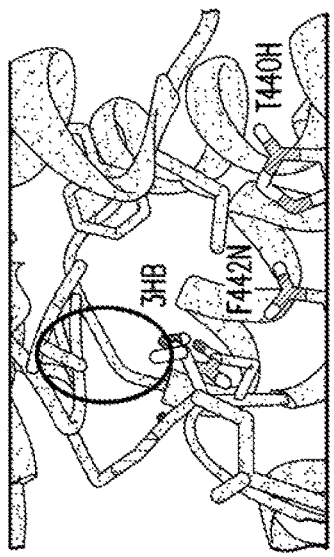
Figure 6C:
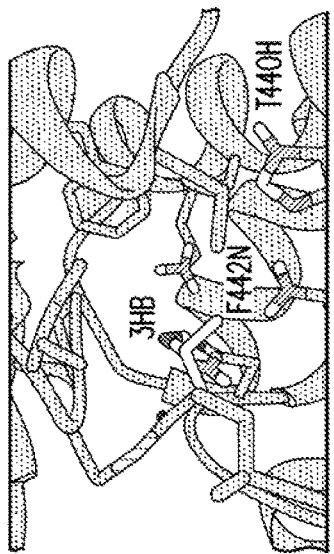

Computational modeling of the mutant 959 using an ALD-1 crystal structure suggests that the amino acid substitution F442N allows a hydrogen bond network to be formed with the hydroxyl on carbon 3 of the R isomer but not the (S) isomer (FIG. 6). FIGS. 6A-6C show ribbon diagrams of the structure of the aldehyde dehydrogenase 959. The diagrams show docking of 3-hydroxy-(R)-butyraldehyde (FIG. 6A) or 3-hydroxy-(S)-butyraldehyde (FIG. 6B) into the structure of 959. FIG. 6C shows that when the 3-hydroxy-(S)-butyraldehyde is docked in the same orientation most energetically favored for docking of 3-hydroxy-(R)-butyraldehyde as shown in FIG. 6A an unfavorable interaction (circled) is created with an isoleucine located in the active site. The model indicates that mutation F442N creates a hydrogen bond between the protein and a hydroxyl of 3-hydroxy-(R)-butyraldehyde that is not possible with the S enantiomer.

Exemplary aldehyde dehydrogenase variants are shown in Tables 1A-1D.

TABLE 1A

Exemplary ALD Variants

| Variant | \multicolumn{13}{c}{Position} |
|---|---|---|---|---|---|---|---|---|---|---|---|---|---|
| | 12 | 19 | 33 | 44 | 65 | 66 | 72 | 73 | 107 | 122 | 129 | 139 | 143 |
| 12 | D12A | | | | | | | | | | | I139S | |
| 16 | D12A | | C33R | | | | | | | | | I139S | |
| 17 | D12A | | C33R | | | | | | | | | I139V | T143N |
| 30 | | | | | | | | | | | E129I | | |
| 34 | D12A | | | | | | | | | | | I139S | |
| 56 | D12A | | | | | | | | | | | I139S | |
| 71 | | | | | | | | | Y107K | | | | |
| 80 | | | | | | | | | Y107K | | | | |
| 93 | D12A | | | | | | | | | | | I139S | |
| 156 | D12A | | | | | | | | Y107K | | | | |
| 166 | D12A | | | | | | | | Y107K | | | | |
| 180 | D12A | | | | | | | | | | | I139S | |
| 182 | | | | | | | | | | | | | |
| 184 | D12A | | | | | | | | | | | I139S | |
| 194 | | | | | | | | | | | | I139S | |
| 199 | | | | | | | | | | | | | |
| 203 | | | | | | | | | | | | | |
| 205 | D12A | | | | | | | | | | | I139S | |
| 208 | | | | | | | | | | | | | |
| 213 | | | | | | | | | | | | | T143S |
| 235 | D12A | | | | | | | | | | | I139S | |
| 240 | D12A | | | | | | | | | | | I139V | |
| 321 | D12V | | | | | | | | | | | I139S | |
| 331 | | | | | K65A | I66M | | | | | | | |
| 598 | D12A | | | | | | | | | | | I139S | |
| 601 | | | | | K65A | I66Q | | | | | | | |
| 602 | | | | | K65A | I66N | | | | | | | |
| 603 | | | | | K65A | I66H | | | | | | | |
| 604 | | | | | K65A | I66T | | | | | | | |
| 605 | | | | | K65A | I66S | | | | | | | |
| 45 | | | | | | | | | | | | | |
| 681 | | | | | K65A | I66M | | A73S | | | | | |
| 682 | | | | | K65A | I66Q | | A73S | | | | | |
| 683 | | | | | K65A | I66N | | A73S | | | | | |
| 684 | | | | | K65A | I66H | | A73S | | | | | |
| 685 | | | | | K65A | I66T | | A73S | | | | | |
| 686 | | | | | K65A | I66S | | A73S | | | | | |
| 687 | | | | | | | | | | | | | |
| 688 | | | | | K65A | | | | | | | | |
| 721 | | | | | | I66M | | | | | | | |
| 722 | | | | | | I66Q | | | | | | | |
| 723 | | | | | | I66N | | | | | | | |
| 724 | | | | | | I66H | | | | | | | |
| 725 | | | | | | I66T | | | | | | | |
| 726 | | | | | | I66S | | | | | | | |
| 775 | | | | | | I66Q | | | | | | | |
| 776 | | | | | | I66N | | | | | | | |
| 777 | | | | | | I66H | | | | | | | |
| 778 | | | | | | I66T | | | | | | | |
| 779 | | | | | | I66S | | | | | | | |
| 780 | | | | | | I66M | | | | | | | |
| 781 | | | | | K65A | | | | | | | | |
| 782 | | | | | K65A | I66M | | | | | | | |
| 783 | D12A | | | | | I66M | | | | | | I139V | |
| 784 | D12A | | | | K65A | | | | | | | I139V | |
| 785 | D12A | | | | K65A | I66M | | | | | | I139V | |
| 921 | | | | | K65A | I66Q | | | | | | | |
| 922 | | | | | K65A | I66N | | | | | | | |
| 923 | | | | | K65A | I66H | | | | | | | |
| 924 | | | | | K65A | I66T | | | | | | | |
| 925 | | | | | K65A | I66S | | | | | | | |
| 951 | | | | | | | | | | | | | |
| 952 | | | | | | | | | | | | | |
| 953 | | | | | | | | | | | | | |
| 954 | | | | | | | | | | | | | |
| 955 | | | | | | | | | | | | | |
| 956 | | | | | | | | | | | | | |
| 957 | | | | | | | | | | | | | |

TABLE 1A-continued

Exemplary ALD Variants

| Variant | 12 | 19 | 33 | 44 | 65 | 66 | 72 | 73 | 107 | 122 | 129 | 139 | 143 |
|---|---|---|---|---|---|---|---|---|---|---|---|---|---|
| 960 | | V19I | | | | | | | | D122N | | | |
| 975 | D12A | | | | | | | | | | | I139V | |
| 991 | D12A | | | | | | | | | | | I139L | T143N |
| 992 | | | | | | | | A73S | | | | | |
| 997 | | | | I44L | | | | | | | | | |
| 999 | | | | | K65A | | | | | | | | |
| 1007 | | | | | | I66M | | | | | | | |
| 1008 | | | | | K65A | | | | | | | | |
| 1009 | | | | | K65A | I66M | | | | | | | |
| 1012 | | | | | | I66M | | | | | | | |
| 1013 | | | | | K65A | | | | | | | | |
| 1014 | | | | | K65A | I66M | | | | | | | |
| 1037 | | | | | | | K72N | | | | | | |

TABLE 1A-continued

Exemplary ALD Variants

| Variant | 12 | 19 | 33 | 44 | 65 | 66 | 72 | 73 | 107 | 122 | 129 | 139 | 143 |
|---|---|---|---|---|---|---|---|---|---|---|---|---|---|
| 1061 | | | | | | | | | | | | | |
| 1062 | | | | | | | | | | | | | |
| 1063 | | | | | | | | | | | | | |
| 1064 | | | | | | | | | | | | | |
| 1065 | | | | | | | | | | | | | |
| 1066 | | | | | | | | | | | | | |
| 1067 | | | | | | | | | | | | | |
| 1068 | | | | | | | | | | | | | |
| 1069 | | | | | | | | | | | | | |
| 1070 | | | | | | | | | | | | | |
| 1071 | | | | | | | | | | | | | |
| 1072 | | | | | | | | | | | | | |
| 1073 | | | | | | | | | | | | | |
| 1074 | | | | | | | | | | | | | |
| 1075 | | | | | | | | | | | | | |
| 1076 | | | | | | | | | | | | | |
| 1077 | | | | | | | | | | | | | |
| 1078 | | | | | | | | | | | | | |
| 1079 | | | | | | | | A73D | | | | | |
| 1080 | | | | | | | | A73G | | | | | |
| 1081 | | | | | | | | A73L | | | | | |
| 1082 | | | | | | | | A73Q | | | | | |
| 1083 | | | | | | | | A73F | | | | | |
| 1084 | | | | | | | | A73G | | | | | |
| 1085 | | | | | | | | A73E | | | | | |
| 1086 | | | | | | | | A73W | | | | | |
| 1087 | | | | | | | | | | | | | |
| 1088 | | | | | | | | | | | | | |
| 1089 | | | | | | | | | | | | | |
| 1090 | | | | | | | | | | | | | |
| 1091 | | | | | | | | | | | | | |
| 1092 | | | | | | | | | | | | | |
| 1093 | | | | | | | | A73L | | | | | |
| 1094 | | | | | | | | A73R | | | | | |
| 1095 | | | | | | | | A73C | | | | | |
| 1096 | | | | | | | | | | | | | |
| 1097 | | | | | | | | A73W | | | | | |
| 1098 | | | | | | | | A73M | | | | | |
| 1099 | | | | | | | | | | | | | |
| 1100 | | | | | | | | A73F | | | | | |
| 1101 | | | | | | | | | | | | | |

TABLE 1B

Exemplary ALD Variants

| Variant | 145 | 155 | 163 | 167 | 174 | 189 | 204 | 220 | 227 | 229 |
|---|---|---|---|---|---|---|---|---|---|---|
| 12 | | | | | | | M204R | | | |
| 16 | | | | | C174S | C189A | M204R | C220V | | |
| 17 | | | | G167S | C174S | | M204R | C220V | | |
| 30 | | | | | C174S | | | C220V | | |
| 34 | | | | | C174S | | M204R | C220V | | |
| 56 | | | | | C174S | | M204R | C220V | | |
| 71 | | | | | C174S | | M204R | C220V | | |
| 80 | | | | | C174S | | | C220V | | |
| 93 | | | | | C174S | | M204R | C220V | | |
| 156 | | | | | C174S | | M204R | C220V | | |
| 166 | | | | | C174S | | | C220V | | |
| 180 | | | | | C174S | | M204R | C220V | | |
| 182 | | | | | C174S | | M204R | C220V | | |
| 184 | | | | | C174S | | M204R | C220V | | |
| 194 | | | | | C174S | | M204R | C220V | | |
| 199 | | | | | C174S | | M204R | C220V | | |
| 203 | | | | | C174S | | M204R | C220V | | |
| 205 | | | | | C174S | | M204R | C220V | | |
| 208 | | | | | C174S | | M204R | C220V | | |
| 213 | | | | | C174S | | M204R | C220V | | |
| 235 | | | | | C174S | | M204R | C220V | | |

TABLE 1B-continued

Exemplary ALD Variants

| Variant | 145 | 155 | 163 | 167 | 174 | 189 | 204 | 220 | 227 | 229 |
|---|---|---|---|---|---|---|---|---|---|---|
| 240 | | | | | C174S | | M204R | C220V | M227K | |
| 321 | | | | | | | M204R | | | |
| 331 | | | | | C174S | | M204R | C220V | | |
| 598 | | | | | C174S | | M204R | C220V | M227Q | |
| 601 | | | | | C174S | | M204R | C220V | | |
| 602 | | | | | C174S | | M204R | C220V | | |
| 603 | | | | | C174S | | M204R | C220V | | |
| 604 | | | | | C174S | | M204R | C220V | | |
| 605 | | | | | C174S | | M204R | C220V | | |
| 45 | | | | | C174S | | M204R | C220V | | |
| 681 | | | | | C174S | | M204R | C220V | M227I | |
| 682 | | | | | C174S | | M204R | C220V | M227I | |
| 683 | | | | | C174S | | M204R | C220V | M227I | |
| 684 | | | | | C174S | | M204R | C220V | M227I | |
| 685 | | | | | C174S | | M204R | C220V | M227I | |
| 686 | | | | | C174S | | M204R | C220V | M227I | |
| 687 | | | | | C174S | | M204R | C220V | | |
| 688 | | | | | C174S | | M204R | C220V | | |
| 721 | | | | | C174S | | M204R | C220V | | |
| 722 | | | | | C174S | | M204R | C220V | | |
| 723 | | | | | C174S | | M204R | C220V | | |
| 724 | | | | | C174S | | M204R | C220V | | |
| 725 | | | | | C174S | | M204R | C220V | | |
| 726 | | | | | C174S | | M204R | C220V | | |
| 775 | | | | | C174S | | M204R | C220V | | |
| 776 | | | | | C174S | | M204R | C220V | | |
| 777 | | | | | C174S | | M204R | C220V | | |
| 778 | | | | | C174S | | M204R | C220V | | |
| 779 | | | | | C174S | | M204R | C220V | | |
| 780 | | | | | C174S | | M204R | C220V | | |
| 781 | | | | | C174S | | M204R | C220V | | |
| 782 | | | | | C174S | | M204R | C220V | | |
| 783 | | | | | C174S | | M204R | C220V | M227Q | |
| 784 | | | | | C174S | | M204R | C220V | M227Q | |
| 785 | | | | | C174S | | M204R | C220V | M227Q | |
| 921 | | | | | C174S | | M204R | C220V | | |
| 922 | | | | | C174S | | M204R | C220V | | |
| 923 | | | | | C174S | | M204R | C220V | | |
| 924 | | | | | C174S | | M204R | C220V | | |
| 925 | | | | | C174S | | M204R | C220V | | |
| 951 | | | | | C174S | | M204R | C220V | | |
| 952 | | | | | C174S | | M204R | C220V | | |
| 953 | | | | | C174S | | M204R | C220V | | |
| 954 | | | | | C174S | | M204R | C220V | | |
| 955 | | | | | C174S | | M204R | C220V | | |
| 956 | | | | | C174S | | M204R | C220V | | |
| 957 | | | | | C174S | | M204R | C220V | | |
| 958 | | | | | C174S | | M204R | C220V | | |
| 959 | | | | | C174S | | M204R | C220V | | |
| 960 | | | | | C174S | | M204R | C220V | | |
| 961 | | | | | C174S | | M204R | C220V | | |
| 975 | | | | | C174S | | M204R | C220V | M227Q | |
| 991 | | | | | C174S | | M204R | C220V | | |
| 992 | | | | | C174S | | M204R | C220V | | |
| 993 | | | | | C174S | | M204R | C220V | | |
| 994 | | | V163C | | C174S | | M204R | C220V | | |
| 995 | | | | | C174S | | M204R | C220V | | K229S |
| 996 | | | | | C174S | | M204R | C220V | | |
| 997 | | | | | C174S | | M204R | C220V | | |
| 998 | | | | | C174S | | M204R | C220V | | |
| 999 | | | | | C174S | | M204R | C220V | | |
| 1000 | | | V163C | | C174S | | M204R | C220V | | |
| 1001 | | | | | C174S | | M204R | C220V | | |
| 1002 | | | | | C174S | | M204R | C220V | | |
| 1003 | | G155G | | | C174S | | M204R | C220V | | |
| 1004 | P145P | | | | C174S | | M204R | C220V | | |
| 1005 | | | | | C174S | | M204R | C220V | | |
| 1006 | | | | | C174S | | M204R | C220V | | |
| 1007 | | | | | C174S | | M204R | C220V | | |
| 1008 | | | | | C174S | | M204R | C220V | | |
| 1009 | | | | | C174S | | M204R | C220V | | |
| 1011 | | | | | C174S | | M204R | C220V | | |
| 1012 | | | | | C174S | | M204R | C220V | | |
| 1013 | | | | | C174S | | M204R | C220V | | |

TABLE 1B-continued

Exemplary ALD Variants

| Variant | 145 | 155 | 163 | 167 | 174 | 189 | 204 | 220 | 227 | 229 |
|---|---|---|---|---|---|---|---|---|---|---|
| 1014 | | | | | C174S | | M204R | C220V | | |
| 1015 | | | | | C174S | | M204R | C220V | M227I | |
| 1016 | | | | | C174S | | M204R | C220V | | |
| 1017 | | | | | C174S | | M204R | C220V | | |
| 1018 | | | | | C174S | | M204R | C220V | | |
| 1019 | | | | | C174S | | M204R | C220V | | |
| 1020 | | | | | C174S | | M204R | C220V | | |
| 1021 | | | | | C174S | | M204R | C220V | M227V | |
| 1022 | | | | | C174S | | M204R | C220V | M227V | |
| 1023 | | | | | C174S | | M204R | C220V | M227I | |
| 1024 | | | | | C174S | | M204R | C220V | M227I | |
| 1025 | | | | | C174S | | M204R | C220V | | |
| 1026 | | | | | C174S | | M204R | C220V | | |
| 1027 | | | | | C174S | | M204R | C220V | M227I | |
| 1028 | | | | | C174S | | M204R | C220V | | |
| 1029 | | | | | C174S | | M204R | C220V | | |
| 1030 | | | | | C174S | | M204R | C220V | | |
| 1031 | | | | | C174S | | M204R | C220V | | |
| 1032 | | | | | C174S | | M204R | C220V | | |
| 1033 | | | | | C174S | | M204R | C220V | | |
| 1034 | | | | | C174S | | M204R | C220V | M227I | |
| 1035 | | | | | C174S | | M204R | C220V | | |
| 1036 | | | | | C174S | | M204R | C220V | | |
| 1037 | | | | | C174S | | M204R | C220V | | |
| 1038 | | | | | C174S | | M204R | C220V | | |
| 1039 | | | | | C174S | | M204R | C220V | | |
| 1040 | | | | | C174S | | M204R | C220V | | |
| 1041 | | | | | C174S | | M204R | C220V | | |
| 1042 | | | | | C174S | | M204R | C220V | | |
| 1043 | | | | | C174S | | M204R | C220V | M227V | |
| 1044 | | | | | C174S | | M204R | C220V | | |
| 1045 | | | | | C174S | | M204R | C220V | | |
| 1046 | | | | | C174S | | M204R | C220V | | |
| 1047 | | | | | C174S | | M204R | C220V | M227C | |
| 1048 | | | | | C174S | | M204R | C220V | M227L | |
| 1049 | | | | | C174S | | M204R | C220V | | |
| 1050 | | | | | C174S | | M204R | C220V | M227C | |
| 1051 | | | | | C174S | | M204R | C220V | | |
| 1052 | | | | | C174S | | M204R | C220V | | |
| 1053 | | | | | C174S | | M204R | C220V | M227C | |
| 1054 | | | | | C174S | | M204R | C220V | M227C | |
| 1055 | | | | | C174S | | M204R | C220V | | |
| 1056 | | | | | C174S | | M204R | C220V | | |
| 1057 | | | | | C174S | | M204R | C220V | | |
| 1058 | | | | | C174S | | M204R | C220V | | |
| 1059 | | | | | C174S | | M204R | C220V | | |
| 1060 | | | | | C174S | | M204R | C220V | M227L | |
| 1061 | | | | | C174S | | M204R | C220V | M227A | |
| 1062 | | | | | C174S | | M204R | C220V | | |
| 1063 | | | | | C174S | | M204R | C220V | | |
| 1064 | | | | | C174S | | M204R | C220V | | |
| 1065 | | | | | C174S | | M204R | C220V | | |
| 1066 | | | | | C174S | | M204R | C220V | M227I | |
| 1067 | | | | | C174S | | M204R | C220V | M227I | |
| 1068 | | | | | C174S | | M204R | C220V | M227I | |
| 1069 | | | | | C174S | | M204R | C220V | | |
| 1070 | | | | | C174S | | M204R | C220V | M227V | |
| 1071 | | | | | C174S | | M204R | C220V | M227C | |
| 1072 | | | | | C174S | | M204R | C220V | | |
| 1073 | | | | | C174S | | M204R | C220V | | |
| 1074 | | | | | C174S | | M204R | C220V | | |
| 1075 | | | | | C174S | | M204R | C220V | | |
| 1076 | | | | | C174S | | M204R | C220V | M227L | |
| 1077 | | | | | C174S | | M204R | C220V | | |
| 1078 | | | | | C174S | | M204R | C220V | M227V | |
| 1079 | | | | | C174S | | M204R | C220V | M227I | |
| 1080 | | | | | C174S | | M204R | C220V | M227I | |
| 1081 | | | | | C174S | | M204R | C220V | M227I | |
| 1082 | | | | | C174S | | M204R | C220V | M227I | |
| 1083 | | | | | C174S | | M204R | C220V | M227I | |
| 1084 | | | | | C174S | | M204R | C220V | M227I | |
| 1085 | | | | | C174S | | M204R | C220V | M227I | |
| 1086 | | | | | C174S | | M204R | C220V | M227I | |
| 1087 | | | V163G | | C174S | | M204R | C220V | M227I | |

TABLE 1B-continued

Exemplary ALD Variants

| Variant | 145 | 155 | 163 | 167 | 174 | 189 | 204 | 220 | 227 | 229 |
|---|---|---|---|---|---|---|---|---|---|---|
| 1088 | | V163T | | | C174S | | M204R | C220V | M227I | |
| 1089 | | | | | C174S | | M204R | C220V | M227L | |
| 1090 | | | | | C174S | | M204R | C220V | | |
| 1091 | | | | | C174S | | M204R | C220V | | |
| 1092 | | | | | C174S | | M204R | C220V | | |
| 1093 | | | | | C174S | | M204R | C220V | M227I | |
| 1094 | | | | | C174S | | M204R | C220V | M227I | |
| 1095 | | | V163C | | C174S | | M204R | C220V | M227I | |
| 1096 | | | V163C | | C174S | | M204R | C220V | M227I | |
| 1097 | | | V163C | | C174S | | M204R | C220V | M227I | |
| 1098 | | | V163C | | C174S | | M204R | C220V | M227I | |
| 1099 | | | V163C | | C174S | | M204R | C220V | M227I | |
| 1100 | | | V163C | | C174S | | M204R | C220V | M227I | |
| 1101 | | | V163C | | C174S | | M204R | C220V | M227I | |

TABLE 1C

Exemplary ALD Variants

| Variant | 230 | 243 | 244 | 254 | 267 | 315 | 353 | 356 | 396 | 429 |
|---|---|---|---|---|---|---|---|---|---|---|
| 12 | | | | | | | | | R396H | |
| 16 | | | | | C267A | | | C356T | R396H | |
| 17 | T230R | | | | C267A | | C353A | C356T | R396H | F429Y |
| 30 | | | | | C267A | | | C356T | R396H | |
| 34 | | | | | C267A | | | C356T | R396H | |
| 56 | | | | | C267A | | | C356T | R396H | F429Y |
| 71 | | | | | C267A | | | C356T | | |
| 80 | | | | | C267A | | | C356T | | |
| 93 | T230R | | | | C267A | | | C356T | R396H | F429Y |
| 156 | | | | | C267A | | | C356T | | |
| 166 | | | | | C267A | | | C356T | | |
| 180 | | | | | C267A | | | C356T | R396H | |
| 182 | | A243P | | | C267A | | | C356T | R396H | |
| 184 | | | | | C267A | | | C356T | R396H | |
| 194 | | | | | C267A | | | C356T | R396H | |
| 199 | | | | | C267A | | | C356T | R396H | F429Q |
| 203 | | | | | C267A | | | C356T | R396H | F429Y |
| 205 | | A243P | | | C267A | | | C356T | R396H | F429Y |
| 208 | | | | | C267A | | | C356T | R396H | |
| 213 | | | | | C267A | | | C356T | R396H | |
| 235 | | A243P | | | C267A | | | C356T | R396H | |
| 240 | | | | | C267A | | | C356T | R396H | F429Y |
| 321 | | | | | | | | | R396H | |
| 331 | | A243Q | | | C267A | | | C356T | R396H | |
| 598 | T230R | A243P | | | C267A | | | C356T | R396H | F429Y |
| 601 | | A243Q | | | C267A | | | C356T | R396H | |
| 602 | | A243Q | | | C267A | | | C356T | R396H | |
| 603 | | A243Q | | | C267A | | | C356T | R396H | |
| 604 | | A243Q | | | C267A | | | C356T | R396H | |
| 605 | | A243Q | | | C267A | | | C356T | R396H | |
| 45 | | | | | C267A | | | C356T | R396H | |
| 681 | T230C | A243P | | | C267A | | | C356T | R396H | |
| 682 | T230C | A243P | | | C267A | | | C356T | R396H | |
| 683 | T230C | A243P | | | C267A | | | C356T | R396H | |
| 684 | T230C | A243P | | | C267A | | | C356T | R396H | |
| 685 | T230C | A243P | | | C267A | | | C356T | R396H | |
| 686 | T230C | A243P | | | C267A | | | C356T | R396H | |
| 687 | | | | | C267A | | | C356T | R396H | |
| 688 | | A243Q | | | C267A | | | C356T | R396H | |
| 721 | | A243Q | | | C267A | | | C356T | R396H | |
| 722 | | A243Q | | | C267A | | | C356T | R396H | |
| 723 | | A243Q | | | C267A | | | C356T | R396H | |
| 724 | | A243Q | | | C267A | | | C356T | R396H | |
| 725 | | A243Q | | | C267A | | | C356T | R396H | |
| 726 | | A243Q | | | C267A | | | C356T | R396H | |
| 775 | | A243P | | | C267A | | | C356T | R396H | |
| 776 | | A243P | | | C267A | | | C356T | R396H | |
| 777 | | A243P | | | C267A | | | C356T | R396H | |

TABLE 1C-continued

Exemplary ALD Variants

| Variant | 230 | 243 | 244 | 254 | 267 | 315 | 353 | 356 | 396 | 429 |
|---|---|---|---|---|---|---|---|---|---|---|
| 778 | | A243P | | | C267A | | | C356T | R396H | |
| 779 | | A243P | | | C267A | | | C356T | R396H | |
| 780 | | | | | C267A | | | C356T | R396H | F429H |
| 781 | | | | | C267A | | | C356T | R396H | F429H |
| 782 | | | | | C267A | | | C356T | R396H | F429H |
| 783 | T230R | A243P | | | C267A | | | C356T | R396H | F429Y |
| 784 | T230R | A243P | | | C267A | | | C356T | R396H | F429Y |
| 785 | T230R | A243P | | | C267A | | | C356T | R396H | F429Y |
| 921 | | A243P | | | C267A | | | C356T | R396H | |
| 922 | | A243P | | | C267A | | | C356T | R396H | |
| 923 | | A243P | | | C267A | | | C356T | R396H | |
| 924 | | A243P | | | C267A | | | C356T | R396H | |
| 925 | | A243P | | | C267A | | | C356T | R396H | |
| 951 | | | | | C267A | | | C356T | R396H | F429H |
| 952 | | | | | C267A | | | C356T | R396H | F429M |
| 953 | | | | | C267A | | | C356T | R396H | F429M |
| 954 | | | | | C267A | | | C356T | R396H | F429Q |
| 955 | | | | | C267A | | | C356T | R396H | |
| 956 | | | | | C267A | | | C356T | R396H | |
| 957 | | | | | C267A | | | C356T | R396H | |
| 958 | | | | | C267A | | | C356T | R396H | |
| 959 | | | | | C267A | | | C356T | R396H | |
| 960 | | | | | C267A | | | C356T | R396H | F429D |
| 961 | | | | | C267A | V315A | | C356T | R396H | |
| 975 | T230R | A243P | | | C267A | | | C356T | R396H | F429Y |
| 991 | T230R | A243P | | | C267A | | | C356T | R396H | F429Y |
| 992 | | | | | C267A | | | C356T | R396H | |
| 993 | | | | A254T | C267A | | | C356T | R396H | |
| 994 | | | | | C267A | | | C356T | R396H | |
| 995 | | | | | C267A | | | C356T | R396H | |
| 996 | | | | | C267A | | | C356L | R396H | |
| 997 | | | | | C267A | | | C356T | R396H | |
| 998 | | | | | C267A | | | C356T | R396H | |
| 999 | | | | | C267A | | | C356T | R396H | |
| 1000 | | | | | C267A | | | C356T | R396H | |
| 1001 | | | | | C267A | | | C356T | R396H | |
| 1002 | | | | | C267A | | | C356T | R396H | |
| 1003 | | | | | C267A | | | C356T | R396H | |
| 1004 | | | | | C267A | | | C356T | R396H | |
| 1005 | | | G244G | | C267A | | | C356T | R396H | |
| 1006 | | | | | C267A | | | C356T | R396H | |
| 1007 | | | | | C267A | | | C356T | R396H | |
| 1008 | | | | | C267A | | | C356T | R396H | |
| 1009 | | | | | C267A | | | C356T | R396H | |
| 1011 | | A243P | | | C267A | | | C356T | R396H | |
| 1012 | | A243P | | | C267A | | | C356T | R396H | |
| 1013 | | A243P | | | C267A | | | C356T | R396H | |
| 1014 | | A243P | | | C267A | | | C356T | R396H | |
| 1015 | T230K | | | | C267A | | | C356T | R396H | |
| 1016 | T230R | A243Q | | | C267A | | | C356T | R396H | |
| 1017 | T230H | A243Q | | | C267A | | | C356T | R396H | |
| 1018 | T230A | A243E | | | C267A | | | C356T | R396H | |
| 1019 | T230M | A243S | | | C267A | | | C356T | R396H | |
| 1020 | T230H | A243N | | | C267A | | | C356T | R396H | |
| 1021 | T230C | | | | C267A | | | C356T | R396H | |
| 1022 | T230H | | | | C267A | | | C356T | R396H | |
| 1023 | T230L | | | | C267A | | | C356T | R396H | |
| 1024 | T230C | | | | C267A | | | C356T | R396H | |
| 1025 | T230M | A243E | | | C267A | | | C356T | R396H | |
| 1026 | T230S | A243Q | | | C267A | | | C356T | R396H | |
| 1027 | T230A | | | | C267A | | | C356T | R396H | |
| 1028 | T230K | | | | C267A | | | C356T | R396H | |
| 1029 | T230Y | A243Q | | | C267A | | | C356T | R396H | |
| 1030 | T230G | A243Q | | | C267A | | | C356T | R396H | |
| 1031 | T230M | A243K | | | C267A | | | C356T | R396H | |
| 1032 | T230T | A243L | | | C267A | | | C356T | R396H | |
| 1033 | T230I | | | | C267A | | | C356T | R396H | |
| 1034 | T230K | | | | C267A | | | C356T | R396H | F429L |
| 1035 | T230H | | | | C267A | | | C356T | R396H | |
| 1036 | T230Y | A243E | | | C267A | | | C356T | R396H | |
| 1037 | | A243S | | | C267A | | | C356T | R396H | |
| 1038 | T230C | A243K | | | C267A | | | C356T | R396H | |
| 1039 | T230H | A243K | | | C267A | | | C356T | R396H | |
| 1040 | T230H | A243C | | | C267A | | | C356T | R396H | |

TABLE 1C-continued

Exemplary ALD Variants

| Variant | 230 | 243 | 244 | 254 | 267 | 315 | 353 | 356 | 396 | 429 |
|---|---|---|---|---|---|---|---|---|---|---|
| 1041 | T230A | A243Q | | | C267A | | | C356T | R396H | |
| 1042 | T230S | A243C | | | C267A | | | C356T | R396H | |
| 1043 | T230S | | | | C267A | | | C356T | R396H | |
| 1044 | T230H | A243M | | | C267A | | | C356T | R396H | |
| 1045 | T230A | A243K | | | C267A | | | C356T | R396H | |
| 1046 | T230W | | | | C267A | | | C356T | R396H | |
| 1047 | T230R | | | | C267A | | | C356T | R396H | |
| 1048 | T230N | | | | C267A | | | C356T | R396H | |
| 1049 | T230N | | | | C267A | | | C356T | R396H | |
| 1050 | T230L | | | | C267A | | | C356T | R396H | |
| 1051 | T230V | | | | C267A | | | C356T | R396H | |
| 1052 | T230L | | | | C267A | | | C356T | R396H | |
| 1053 | T230K | | | | C267A | | | C356T | R396H | |
| 1054 | T230V | | | | C267A | | | C356T | R396H | |
| 1055 | T230T | A243N | | | C267A | | | C356T | R396H | |
| 1056 | T230T | A243I | | | C267A | | | C356T | R396H | |
| 1057 | T230T | A243C | | | C267A | | | C356T | R396H | |
| 1058 | T230G | A243K | | | C267A | | | C356T | R396H | |
| 1059 | T230R | A243K | | | C267A | | | C356T | R396H | |
| 1060 | | A243P | | | C267A | | | C356T | R396H | |
| 1061 | | A243P | | | C267A | | | C356T | R396H | |
| 1062 | | A243Q | | | C267A | | | C356T | R396H | |
| 1063 | T230Q | | | | C267A | | | C356T | R396H | |
| 1064 | T230N | A243I | | | C267A | | | C356T | R396H | |
| 1065 | T230C | A243C | | | C267A | | | C356T | R396H | |
| 1066 | T230R | | | | C267A | | | C356T | R396H | |
| 1067 | | A243L | | | C267A | | | C356T | R396H | |
| 1068 | | A243M | | | C267A | | | C356T | R396H | |
| 1069 | | A243M | | | C267A | | | C356T | R396H | |
| 1070 | | | | | C267A | | | C356T | R396H | |
| 1071 | | A243Q | | | C267A | | | C356T | R396H | |
| 1072 | T230R | A243C | | | C267A | | | C356T | R396H | |
| 1073 | T230L | A243M | | | C267A | | | C356T | R396H | |
| 1074 | T230I | A243M | | | C267A | | | C356T | R396H | |
| 1075 | T230M | A243Q | | | C267A | | | C356T | R396H | |
| 1076 | T230W | | | | C267A | | | C356T | R396H | |
| 1077 | T230V | A243M | | | C267A | | | C356T | R396H | |
| 1078 | T230I | | | | C267A | | | C356T | R396H | |
| 1079 | T230K | | | | C267A | | | C356T | R396H | |
| 1080 | T230K | | | | C267A | | | C356T | R396H | |
| 1081 | T230K | | | | C267A | | | C356T | R396H | |
| 1082 | T230K | | | | C267A | | | C356T | R396H | |
| 1083 | T230K | | | | C267A | | | C356T | R396H | |
| 1084 | T230K | | | | C267A | | | C356T | R396H | |
| 1085 | T230K | | | | C267A | | | C356T | R396H | |
| 1086 | T230K | | | | C267A | | | C356T | R396H | |
| 1087 | T230K | | | | C267A | | | C356T | R396H | |
| 1088 | T230K | | | | C267A | | | C356T | R396H | |
| 1089 | T230S | | | | C267A | | | C356T | R396H | |
| 1090 | | A243E | | | C267A | | | C356T | R396H | |
| 1091 | T230T | A243E | | | C267A | | | C356T | R396H | |
| 1092 | | A243K | | | C267A | | | C356T | R396H | |
| 1093 | T230K | | | | C267A | | | C356T | R396H | |
| 1094 | T230K | | | | C267A | | | C356T | R396H | |
| 1095 | T230K | | | | C267A | | | C356T | R396H | |
| 1096 | T230K | | | | C267A | | | C356T | R396H | |
| 1097 | T230K | | | | C267A | | | C356T | R396H | |
| 1098 | T230K | | | | C267A | | | C356T | R396H | |
| 1099 | T230K | | | | C267A | | | C356T | R396H | |
| 1100 | T230K | | | | C267A | | | C356T | R396H | |
| 1101 | T230K | | | | C267A | | | C356T | R396H | |

TABLE 1D

Exemplary ALD Variants

| Variant | 432 | 437 | 440 | 441 | 442 | 444 | 447 | 450 | 460 | 464 | 467 |
|---|---|---|---|---|---|---|---|---|---|---|---|
| 12 | | | | | | | | | | | |
| 16 | | | | | | | | | | C464V | |
| 17 | | E437P | | | F442T | | | | | C464I | A467V |
| 30 | | | | | | | | | | C464I | A467V |
| 34 | | | | | | | | | | C464I | |
| 56 | | E437P | | | F442T | | | | | C464I | A467V |
| 71 | | | | | | | | | | C464I | A467V |
| 80 | | | | | | | | | | C464I | |
| 93 | | E437P | | | F442T | | | | | C464I | A467V |
| 156 | | | | | | | | | | C464I | A467V |
| 166 | | | | | | | | | | C464I | |
| 180 | | | | | | | | | | C464I | A467V |
| 182 | | E437P | | | | | | | | C464I | A467V |
| 184 | | E437P | | | | | | | | C464I | A467V |
| 194 | | E437P | | | | | | | | C464I | A467V |
| 199 | | E437P | | | | | | | | C464I | A467V |
| 203 | | E437P | | | F442T | | | | | C464I | A467V |
| 205 | | E437P | | | F442T | | | | | C464I | A467V |
| 208 | | E437P | | | F442Y | | | | | C464I | A467V |
| 213 | | E437P | | | | | | | | C464I | A467V |
| 235 | | E437P | | | | | | | | C464I | A467V |
| 240 | | E437P | | | F442T | | | | | C464I | A467V |
| 321 | | | | | | | | | | | |
| 331 | | E437P | | | F442N | | | | | C464I | A467V |
| 598 | | E437P | | | F442T | | | | | C464I | A467V |
| 601 | | E437P | | | F442N | | | | | C464I | A467V |
| 602 | | E437P | | | F442N | | | | | C464I | A467V |
| 603 | | E437P | | | F442N | | | | | C464I | A467V |
| 604 | | E437P | | | F442N | | | | | C464I | A467V |
| 605 | | E437P | | | F442N | | | | | C464I | A467V |
| 45 | | E437P | | | | | | | | C464I | A467V |
| 681 | | E437P | | | F442N | | S447P | | | C464I | A467V |
| 682 | | E437P | | | F442N | | S447P | | | C464I | A467V |
| 683 | | E437P | | | F442N | | S447P | | | C464I | A467V |
| 684 | | E437P | | | F442N | | S447P | | | C464I | A467V |
| 685 | | E437P | | | F442N | | S447P | | | C464I | A467V |
| 686 | | E437P | | | F442N | | S447P | | | C464I | A467V |
| 687 | | E437P | | | F442M | | | | | C464I | A467V |
| 688 | | E437P | | | F442N | | | | | C464I | A467V |
| 721 | | E437P | | | F442N | | | | | C464I | A467V |
| 722 | | E437P | | | F442N | | | | | C464I | A467V |
| 723 | | E437P | | | F442N | | | | | C464I | A467V |
| 724 | | E437P | | | F442N | | | | | C464I | A467V |
| 725 | | E437P | | | F442N | | | | | C464I | A467V |
| 726 | | E437P | | | F442N | | | | | C464I | A467V |
| 775 | | E437P | | | F442N | | | | | C464I | A467V |
| 776 | | E437P | | | F442N | | | | | C464I | A467V |
| 777 | | E437P | | | F442N | | | | | C464I | A467V |
| 778 | | E437P | | | F442N | | | | | C464I | A467V |
| 779 | | E437P | | | F442N | | | | | C464I | A467V |
| 780 | | E437P | | | F442H | | | | | C464I | A467V |
| 781 | | E437P | | | F442H | | | | | C464I | A467V |
| 782 | | E437P | | | F442H | | | | | C464I | A467V |
| 783 | | E437P | | | F442T | | | | | C464I | A467V |
| 784 | | E437P | | | F442T | | | | | C464I | A467V |
| 785 | | E437P | | | F442T | | | | | C464I | A467V |
| 921 | | E437P | | | F442N | | | | | C464I | A467V |
| 922 | | E437P | | | F442N | | | | | C464I | A467V |
| 923 | | E437P | | | F442N | | | | | C464I | A467V |
| 924 | | E437P | | | F442N | | | | | C464I | A467V |
| 925 | | E437P | | | F442N | | | | | C464I | A467V |
| 951 | | E437P | | | F442H | | | | | C464I | A467V |
| 952 | | E437P | | | F442H | | | | | C464I | A467V |
| 953 | | E437P | | | F442N | | | | | C464I | A467V |
| 954 | | E437P | | | | | | | | C464I | A467V |
| 955 | | E437P | | | F442N | | | | | C464I | A467V |
| 956 | | E437P | | | F442N | | | | | C464I | A467V |
| 957 | | E437P | | | F442Q | | | | | C464I | A467V |
| 958 | | E437P | | | | i444V | | | | C464I | A467V |
| 959 | | E437P | T440H | | F442N | | | | | C464I | A467V |
| 960 | | E437P | | | F442Q | | | E450E | | C464I | A467V |
| 961 | | E437P | T440H | | F442N | | | | | C464I | A467V |
| 975 | | E437P | | | F442T | | | | | C464I | A467V |
| 991 | | E437P | | | F442T | | | | | C464I | A467V |

TABLE 1D-continued

Exemplary ALD Variants

| Variant | 432 | 437 | 440 | 441 | 442 | 444 | 447 | 450 | 460 | 464 | 467 |
|---|---|---|---|---|---|---|---|---|---|---|---|
| 992 | | E437P | | | F442M | | S447M | | | C464I | A467V |
| 993 | | E437P | | | F442M | | | | | C464I | A467V |
| 994 | | E437P | | | F442M | | | | | C464I | A467V |
| 995 | | E437P | | | F442N | | | | | C464I | A467V |
| 996 | | E437P | | | F442N | | | | | C464I | A467V |
| 997 | | E437P | | T441G | | | | | | C464I | A467V |
| 998 | | E437P | | | F442M | | | | | C464I | A467V |
| 999 | | E437P | | | F442N | | | | | C464I | A467V |
| 1000 | | E437P | | | F442N | | | | | C464I | A467V |
| 1001 | | E437P | | | F442M | | | | R460K | C464I | A467V |
| 1002 | | E437P | | | F442M | | S447M | | | C464I | A467V |
| 1003 | | E437P | | | F442F | | | | | C464I | A467V |
| 1004 | | E437P | | | | | | | | C464I | A467V |
| 1005 | | E437P | | | | | | | | C464I | A467V |
| 1006 | V432V | E437P | | | | | | | | C464I | A467V |
| 1007 | V432V | E437P | | | | | | | | C464I | A467V |
| 1008 | V432V | E437P | | | | | | | | C464I | A467V |
| 1009 | V432V | E437P | | | | | | | | C464I | A467V |
| 1011 | | E437P | | | F442N | | | | | C464I | A467V |
| 1012 | | E437P | | | F442N | | | | | C464I | A467V |
| 1013 | | E437P | | | F442N | | | | | C464I | A467V |
| 1014 | | E437P | | | F442N | | | | | C464I | A467V |
| 1015 | | E437P | | | F442N | | | | | C464I | A467V |
| 1016 | | E437P | | | F442N | | | | | C464I | A467V |
| 1017 | | E437P | | | F442N | | | | | C464I | A467V |
| 1018 | | E437P | | | F442N | | | | | C464I | A467V |
| 1019 | | E437P | | | F442N | | | | | C464I | A467V |
| 1020 | | E437P | | | F442N | | | | | C464I | A467V |
| 1021 | | E437P | | | F442N | | | | | C464I | A467V |
| 1022 | | E437P | | | F442N | | | | | C464I | A467V |
| 1023 | | E437P | | | F442N | | | | | C464I | A467V |
| 1024 | | E437P | | | F442N | | | | | C464I | A467V |
| 1025 | | E437P | | | F442N | | | | | C464I | A467V |
| 1026 | | E437P | | | F442N | | | | | C464I | A467V |
| 1027 | | E437P | | | F442N | | | | | C464I | A467V |
| 1028 | | E437P | | | F442N | | | | | C464I | A467V |
| 1029 | | E437P | | | F442N | | | | | C464I | A467V |
| 1030 | | E437P | | | F442N | | | | | C464I | A467V |
| 1031 | | E437P | | | F442N | | | | | C464I | A467V |
| 1032 | | E437P | | | F442N | | | | | C464I | A467V |
| 1033 | | E437P | | | F442N | | | | | C464I | A467V |
| 1034 | V432N | E437P | | | F442N | | | | | C464I | A467V |
| 1035 | | E437P | | | F442N | | | | | C464I | A467V |
| 1036 | | E437P | | | F442N | | | | | C464I | A467V |
| 1037 | | E437P | | | F442N | | | | | C464I | A467V |
| 1038 | | E437P | | | F442N | | | | | C464I | A467V |
| 1039 | | E437P | | | F442N | | | | | C464I | A467V |
| 1040 | | E437P | | | F442N | | | | | C464I | A467V |
| 1041 | | E437P | | | F442N | | | | | C464I | A467V |
| 1042 | | E437P | | | F442N | | | | | C464I | A467V |
| 1043 | | E437P | | | F442N | | | | | C464I | A467V |
| 1044 | | E437P | | | F442N | | | | | C464I | A467V |
| 1045 | | E437P | | | F442N | | | | | C464I | A467V |
| 1046 | | E437P | | | F442N | | | | | C464I | A467V |
| 1047 | | E437P | | | F442N | | | | | C464I | A467V |
| 1048 | | E437P | | | F442N | | | | | C464I | A467V |
| 1049 | | E437P | | | F442N | | | | | C464I | A467V |
| 1050 | | E437P | | | F442N | | | | | C464I | A467V |
| 1051 | | E437P | | | F442N | | | | | C464I | A467V |
| 1052 | | E437P | | | F442N | | | | | C464I | A467V |
| 1053 | | E437P | | | F442N | | | | | C464I | A467V |
| 1054 | | E437P | | | F442N | | | | | C464I | A467V |
| 1055 | | E437P | | | F442N | | | | | C464I | A467V |
| 1056 | | E437P | | | F442N | | | | | C464I | A467V |
| 1057 | | E437P | | | F442N | | | | | C464I | A467V |
| 1058 | | E437P | | | F442N | | | | | C464I | A467V |
| 1059 | | E437P | | | F442N | | | | | C464I | A467V |
| 1060 | | E437P | | | F442N | | | | | C464I | A467V |
| 1061 | | E437P | | | F442N | | | | | C464I | A467V |
| 1062 | | E437P | | | F442N | | | | | C464I | A467V |
| 1063 | | E437P | | | F442N | | | | | C464I | A467V |
| 1064 | | E437P | | | F442N | | | | | C464I | A467V |
| 1065 | | E437P | | | F442N | | | | | C464I | A467V |
| 1066 | | E437P | | | F442N | | | | | C464I | A467V |

TABLE 1D-continued

Exemplary ALD Variants

| | | | | | | Position | | | | | |
|---|---|---|---|---|---|---|---|---|---|---|---|
| Variant | 432 | 437 | 440 | 441 | 442 | 444 | 447 | 450 | 460 | 464 | 467 |
| 1067 | | E437P | | | F442N | | | | | C464I | A467V |
| 1068 | | E437P | | | F442N | | | | | C464I | A467V |
| 1069 | | E437P | | | F442N | | | | | C464I | A467V |
| 1070 | | E437P | | | F442N | | | | | C464I | A467V |
| 1071 | | E437P | | | F442N | | | | | C464I | A467V |
| 1072 | | E437P | | | F442N | | | | | C464I | A467V |
| 1073 | | E437P | | | F442N | | | | | C464I | A467V |
| 1074 | | E437P | | | F442N | | | | | C464I | A467V |
| 1075 | | E437P | | | F442N | | | | | C464I | A467V |
| 1076 | | E437P | | | F442N | | | | | C464I | A467V |
| 1077 | | E437P | | | F442N | | | | | C464I | A467V |
| 1078 | | E437P | | | F442N | | | | | C464I | A467V |
| 1079 | | E437P | | | F442N | | S447P | | | C464I | A467V |
| 1080 | | E437P | | | F442N | | S447H | | | C464I | A467V |
| 1081 | | E437P | | | F442N | | S447K | | | C464I | A467V |
| 1082 | | E437P | | | F442N | | S447R | | | C464I | A467V |
| 1083 | | E437P | | | F442N | | S447K | | | C464I | A467V |
| 1084 | | E437P | | | F442N | | S447K | | | C464I | A467V |
| 1085 | | E437P | | | F442N | | S447K | | | C464I | A467V |
| 1086 | | E437P | | | F442N | | S447R | | | C464I | A467V |
| 1087 | | E437P | | | F442N | | S447P | | | C464I | A467V |
| 1088 | | E437P | | | F442N | | S447P | | | C464I | A467V |
| 1089 | | E437P | | | F442N | | | | | C464I | A467V |
| 1090 | | E437P | | | F442N | | | | | C464I | A467V |
| 1091 | | E437P | | | F442N | | | | | C464I | A467V |
| 1092 | | E437P | | | F442N | | | | | C464I | A467V |
| 1093 | | E437P | | | F442N | | S447P | | | C464I | A467V |
| 1094 | | E437P | | | F442N | | S447T | | | C464I | A467V |
| 1095 | | E437P | | | F442N | | | | | C464I | A467V |
| 1096 | | E437P | | | F442N | | S447E | | | C464I | A467V |
| 1097 | | E437P | | | F442N | | S447K | | | C464I | A467V |
| 1098 | | E437P | | | F442N | | S447R | | | C464I | A467V |
| 1099 | | E437P | | | F442N | | S447P | | | C464I | A467V |
| 1100 | | E437P | | | F442N | | S447P | | | C464I | A467V |
| 1101 | | E437P | | | F442N | | S447S | | | C464I | A467V |

Various activities of the ALD variants were determined and are shown in Table 2.

TABLE 2

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 12 | D12A, I139S, M204R, R396H | yes | | | |
| 16 | D12A, C33R, I139S, C174S, C189A, M204R, C220V, C267A, C353A, C356T, R396H, C464V | | | | |
| 17 | D12A, I139V, T143N, G167S, C174S, M204R, C220V, T230R, C267A, C356T, R396H, F429Y, F442T, E437P, C464I, A467V | | | | |
| 30 | E129I, C174S, C220V, C267A, C356T, R396H, C464I, A467V | * | | | |
| 34 | D12A, I139S, C174S, M204R, C220V, C267A, C356T, R396H, C464I | Yes | | | |
| 56 | D12A, I139S, C174S, M204R, C220V, C267A, C356T, R396H, F429Y, , E437P, F442T, C464I, A467V | yes | | | |
| 71 | Y107K, C174S, M204R, C220V, C267A, C356T, C464I, A467V | | | | |
| 80 | Y107K, C174S, C220V, C267A, C356T, C464I | * | | | |
| 93 | D12A, I139S, C174S, M204R, T230R, C220V, C267A, C356T, R396H, F429Y, F442T, E437P, C464I, A467V | * | | | |
| 156 | D12A, Y107K, C174S, M204R, C220V, C267A, C356T, C464I, A467V | * | | | |
| 166 | D12A, Y107K, C174S, C220V, C267A, C356T, C464I | * | | | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 180 | D12A, I139S, C174S, M204R, C220V, C267A, C356T, R396H, C464I, A467V | * | | | |
| 182 | C174S, M204R, C220V, A243P, C267A, C356T, R396H, E437P, C464I, A467V | * | | | |
| 184 | D12A, I139S, C174S, M204R, C220V, C267A, C356T, R396H, E437P, C464I, A467V | * | | | |
| 194 | I139S, C174S, M204R, C220V, C267A, C356T, R396H, E437P, C464I, A467V | * | | | |
| 199 | C174S, M204R, C220V, C267A, C356T, R396H, F429Q, E437P, C464I, A467V | * | | | |
| 203 | C174S, M204R, C220V, C267A, C356T, R396H, F429Y, E437P, F442T, C464I, A467V | * | | | |
| 205 | D12A, I139S, C174S, M204R, C220V, A243P, C267A, C356T, R396H, F429Y, F442T, E437P, C464I, A467V | * | | | |
| 208 | C174S, M204R, C220V, C267A, C356T, R396H, E437P, F442Y, C464I, A467V | * | | | |
| 213 | T143S, C174S, M204R, C220V, C267A, C356T, R396H, E437P, C464I, A467V | * | | | |
| 235 | D12A, I139S, C174S, M204R, C220V, A243P, C267A, C356T, R396H, E437P, C464I, A467V | * | | | |
| 240 | D12A, I139V, C174S, M204R, M227K, C220V, C267A, C356T, R396H, F429Y, F442T, E437P, C464I, A467V | * | | | |
| 321 | D12V, I139S, M204R, R396H | * | | | |
| 598 | D12A, I139S, C174S, M204R, M227Q, T230R, A243P, C220V, C267A, C356T, R396H, F429Y, F442T, E437P, C464I, A467V | Yes | + | | |
| 45 | C174S, M204R, C220V, C267A, C356T, R396H, E437P, C464I, A467V | Yes | +++ | + | |
| 951 | C174S, M204R, C220V, C267A, C356T, R396H, F429H, E437P, F442H, C464I, A467V | | + | + | |
| 952 | C174S, M204R, C220V, C267A, C356T, R396H, F429M, E437P, F442H, C464I, A467V | | + | | |
| 953 | C174S, M204R, C220V, C267A, C356T, R396H, F429M, E437P, F442N, C464I, A467V | | + | | |
| 954 | C174S, M204R, C220V, C267A, C356T, R396H, F429Q, E437P, C464I, A467V | | + | | |
| 955 | C174S, M204R, C220V, C267A, C356T, R396H, E437P, F442N, C464I, A467V | Yes | +++ | + | |
| 957 | C174S, M204R, C220V, C267A, C356T, R396H, E437P, F442Q, C464I, A467V | | + | + | |
| 958 | C174S, M204R, C220V, C267A, C356T, R396H, E437P, I444V, C464I, A467V | | + | + | |
| 959 | C174S, M204R, C220V, C267A, C356T, R396H, E437P, T440H, F442N, C464I, A467V | | + | + | |
| 960 | V19I, D122N, C174S, M204R, C220V, C267A, C356T, R396H, F429D, E437P, F442Q, E450E, C464I, A467V | | + | | |
| 961 | C174S, M204R, C220V, C267A, V315A, C356T, R396H, E437P, T440H, F442N, C464I, A467V | | + | + | |
| 975 | D12A, I139V, C174S, M204R, C220V, M227Q, T230R, A243P, C267A, C356T, R396H, F429Y, F442T, E437P, C464I, A467V | Yes | | | |
| 991 | D12A, I139L, T143N, C174S, M204R, C220V, T230R, A243P, C267A, C356T, R396H, F429Y, F442T, E437P, C464I, A467V | | | | |
| 992 | A73S, C174S, M204R, C220V, C267A, C356T, R396H, E437P, F442M, S447M, C464I, A467V | | + | `+ | |
| 993 | C174S, M204R, C220V, A254T, C267A, C356T, R396H, E437P, F442M, C464I, A467V | | + | | |
| 994 | V163C, C174S, M204R, C220V, C267A, C356T, R396H, E437P, F442M, C464I, A467V | | + | | |
| 995 | C174S, M204R, C220V, K 229S, C267A, C356T, R396H, E437P, F442N, C464I, A467V | | + | | |
| 996 | C174S, M204R, C220V, C267A, C356L, R396H, E437P, F442N, C464I, A467V | | + | | |
| 997 | C174S, M204R, C220V, C267A, C356T, R396H, E437P, T441G, I44L, C464I, A467V | | + | | |
| 998 | C174S, M204R, C220V, C267A, C356T, R396H, E437P, F442M, C464I, A467V | | + | `+ | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 999 | K65A, C174S, M204R, C220V, C267A, C356T, R396H, E437P, F442N, C464I, A467V | | + | | |
| 1000 | V163C, C174S, M204R, C220V, C267A, C356T, R396H, E437P, F442N, C464I, A467V | | + | `+ | |
| 1001 | C174S, M204R, C220V, C267A, C356T, R396H, E437P, F442M, R460K, C464I, A467V | | + | | |
| 1002 | C174S, M204R, C220V, C267A, C356T, R396H, E437P, F442M, S447M, C464I, A467V | Yes | + | `+ | |
| 1003 | G155G, C174S, M204R, C220V, C267A, C356T, R396H, E437P, F442F, C464I, A467V | | | | |
| 1004 | P145P, C174S, M204R, C220V, C267A, C356T, R396H, E437P, C464I, A467V | | | | |
| 1005 | G244G, C174S, M204R, C220V, C267A, C356T, R396H, E437P, C464I, A467V | | | | |
| 1006 | C174S, M204R, C220V, C267A, C356T, R396H, V432V, E437P, C464I, A467V | | | | |
| 1015 | C174S, M204R, C220V, M227I, T230K, C267A, C356T, R396H, E437P, F442N, C464I, A467V | yes | `+++ | `- | |
| 1016 | C174S, M204R, C220V, T230R, A243Q, C267A, C356T, R396H, E437P, F442N, C464I, A467V | yes | `+++ | `- | |
| 1017 | C174S, M204R, C220V, T230H, A243Q, C267A, C356T, R396H, E437P, F442N, C464I, A467V | yes | `++ | `- | |
| 1018 | C174S, M204R, C220V, T230A, A243E, C267A, C356T, R396H, E437P, F442N, C464I, A467V | yes | `++ | `- | |
| 1019 | C174S, M204R, C220V, T230M, A243S, C267A, C356T, R396H, E437P, F442N, C464I, A467V | yes | `+++ | `- | |
| 1020 | C174S, M204R, C220V, T230H, A243N, C267A, C356T, R396H, E437P, F442N, C464I, A467V | yes | `++ | `- | |
| 1021 | C174S, M204R, C220V, M227V, T230C, C267A, C356T, R396H, E437P, F442N, C464I, A467V | yes | `++ | `- | |
| 1022 | C174S, M204R, C220V, M227V, T230H, C267A, C356T, R396H, E437P, F442N, C464I, A467V | yes | `++ | `- | |
| 1023 | C174S, M204R, C220V, M227I, T230L, C267A, C356T, R396H, E437P, F442N, C464I, A467V | yes | `++ | `- | |
| 1024 | C174S, M204R, C220V, M227I, T230C, C267A, C356T, R396H, E437P, F442N, C464I, A467V | yes | `++ | `- | |
| 1025 | C174S, M204R, C220V, T230M, A243E, C267A, C356T, R396H, E437P, F442N, C464I, A467V | yes | `++ | `- | |
| 1026 | C174S, M204R, C220V, T230S, A243Q, C267A, C356T, R396H, E437P, F442N, C464I, A467V | yes | `+++ | `- | |
| 1027 | C174S, M204R, C220V, M227I, T230A, C267A, C356T, R396H, E437P, F442N, C464I, A467V | yes | `+++ | `- | |
| 1028 | C174S, M204R, C220V, T230K, C267A, C356T, R396H, E437P, F442N, C464I, A467V | yes | `- | `- | |
| 1029 | C174S, M204R, C220V, T230Y, A243Q, C267A, C356T, R396H, E437P, F442N, C464I, A467V | yes | `++ | `- | |
| 1030 | C174S, M204R, C220V, T230G, A243Q, C267A, C356T, R396H, E437P, F442N, C464I, A467V | yes | `++ | `- | |
| 1031 | C174S, M204R, C220V, T230M, A243K, C267A, C356T, R396H, E437P, F442N, C464I, A467V | yes | `+++ | `- | |
| 1032 | C174S, M204R, C220V, T230T, A243L, C267A, C356T, R396H, E437P, F442N, C464I, A467V | yes | `++ | `- | |
| 1033 | C174S, M204R, C220V, T230I, C267A, C356T, R396H, E437P, F442N, C464I, A467V | yes | `++ | `- | |
| 1034 | C174S, M204R, C220V, M227I, T230K, C267A, C356T, R396H, F429L, V432N, E437P, F442N, C464I, A467V | yes | `++ | `- | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1035 | C174S, M204R, C220V, T230H, C267A, C356T, R396H, E437P, F442N, C464I, A467V | yes | `+++ | `− | |
| 1036 | C174S, M204R, C220V, T230Y, A243E, C267A, C356T, R396H, E437P, F442N, C464I, A467V | yes | `++ | `− | |
| 1037 | K72N, C174S, M204R, C220V, A243S, C267A, C356T, R396H, E437P, F442N, C464I, A467V | yes | `++ | `− | |
| 1038 | C174S, M204R, C220V, T230C, A243K, C267A, C356T, R396H, E437P, F442N, C464I, A467V | yes | `+++ | `− | |
| 1039 | C174S, M204R, C220V, T230H, A243K, C267A, C356T, R396H, E437P, F442N, C464I, A467V | yes | `+++ | `− | |
| 1040 | C174S, M204R, C220V, T230H, A243C, C267A, C356T, R396H, E437P, F442N, C464I, A467V | yes | `+++ | `− | |
| 1041 | C174S, M204R, C220V, T230A, A243Q, C267A, C356T, R396H, E437P, F442N, C464I, A467V | yes | `+++ | `− | |
| 1042 | C174S, M204R, C220V, T230S, A243C, C267A, C356T, R396H, E437P, F442N, C464I, A467V | yes | `+++ | `− | |
| 1043 | C174S, M204R, C220V, M227V, T230S, C267A, C356T, R396H, E437P, F442N, C464I, A467V | yes | `++ | `− | |
| 1044 | C174S, M204R, C220V, T230H, A243M, C267A, C356T, R396H, E437P, F442N, C464I, A467V | yes | `+++ | `− | |
| 1045 | C174S, M204R, C220V, T230A, A243K, C267A, C356T, R396H, E437P, F442N, C464I, A467V | yes | `+++ | `− | |
| 1046 | C174S, M204R, C220V, T230W, C267A, C356T, R396H, E437P, F442N, C464I, A467V | yes | `++ | `− | |
| 1047 | C174S, M204R, C220V, M227T, T230R, C267A, C356T, R396H, E437P, F442N, C464I, A467V | yes | `++ | `− | |
| 1048 | C174S, M204R, C220V, M227L, T230N, C267A, C356T, R396H, E437P, F442N, C464I, A467V | yes | `++ | `− | |
| 1049 | C174S, M204R, C220V, T230N, C267A, C356T, R396H, E437P, F442N, C464I, A467V | yes | `++ | `− | |
| 1050 | C174S, M204R, C220V, M227C, T230L, C267A, C356T, R396H, E437P, F442N, C464I, A467V | yes | `++ | `− | |
| 1051 | C174S, M204R, C220V, T230V, C267A, C356T, R396H, E437P, F442N, C464I, A467V | yes | `++ | `− | |
| 1052 | C174S, M204R, C220V, T230L, C267A, C356T, R396H, E437P, F442N, C464I, A467V | yes | `++ | `− | |
| 1053 | C174S, M204R, C220V, M227C, T230K, C267A, C356T, R396H, E437P, F442N, C464I, A467V | yes | `+ | `− | |
| 1054 | C174S, M204R, C220V, M227C, T230V, C267A, C356T, R396H, E437P, F442N, C464I, A467V | yes | `+++ | `− | |
| 1055 | C174S, M204R, C220V, T230T, A243N, C267A, C356T, R396H, E437P, F442N, C464I, A467V | yes | `+++ | `− | |
| 1056 | C174S, M204R, C220V, T230T, A243I, C267A, C356T, R396H, E437P, F442N, C464I, A467V | yes | `+++ | `− | |
| 1057 | C174S, M204R, C220V, T230T, A243C, C267A, C356T, R396H, E437P, F442N, C464I, A467V | yes | `+ | `− | |
| 1058 | C174S, M204R, C220V, T230G, A243K, C267A, C356T, R396H, E437P, F442N, C464I, A467V | yes | `++ | `− | |
| 1059 | C174S, M204R, C220V, T230R, A243K, C267A, C356T, R396H, E437P, F442N, C464I, A467V | yes | `++ | `− | |
| 1060 | C174S, M204R, C220V, M227L, A243P, C267A, C356T, R396H, E437P, F442N, C464I, A467V | yes | `+ | `− | |
| 1061 | C174S, M204R, C220V, M227A, A243P, C267A, C356T, R396H, E437P, F442N, C464I, A467V | yes | `+++ | `− | |
| 1062 | C174S, M204R, C220V, A243Q, C267A, C356T, R396H, E437P, F442N, C464I, A467V | yes | `+ | `− | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1063 | C174S, M204R, C220V, T230Q, C267A, C356T, R396H, E437P, F442N, C464I, A467V | yes | `++ | `− | |
| 1064 | C174S, M204R, C220V, T230N, A243I, C267A, C356T, R396H, E437P, F442N, C464I, A467V | yes | `++ | `− | |
| 1065 | C174S, M204R, C220V, T230C, A243C, C267A, C356T, R396H, E437P, F442N, C464I, A467V | yes | `+++ | `− | |
| 1066 | C174S, M204R, C220V, M227I, T230R, C267A, C356T, R396H, E437P, F442N, C464I, A467V | yes | `++ | `− | |
| 1067 | C174S, M204R, C220V, M227I, A243L, C267A, C356T, R396H, E437P, F442N, C464I, A467V | yes | `+++ | `− | |
| 1068 | C174S, M204R, C220V, M227I, A243M, C267A, C356T, R396H, E437P, F442N, C464I, A467V | yes | `++ | `− | |
| 1069 | C174S, M204R, C220V, A243M, C267A, C356T, R396H, E437P, F442N, C464I, A467V | yes | `++ | `− | |
| 1070 | C174S, M204R, C220V, M227V, C267A, C356T, R396H, E437P, F442N, C464I, A467V | yes | `++ | `− | |
| 1071 | C174S, M204R, C220V, M227C, A243Q, C267A, C356T, R396H, E437P, F442N, C464I, A467V | yes | `+++ | `− | |
| 1072 | C174S, M204R, C220V, T230R, A243C, C267A, C356T, R396H, E437P, F442N, C464I, A467V | yes | `++ | `− | |
| 1073 | C174S, M204R, C220V, T230L, A243M, C267A, C356T, R396H, E437P, F442N, C464I, A467V | yes | `++ | `− | |
| 1074 | C174S, M204R, C220V, T230I, A243M, C267A, C356T, R396H, E437P, F442N, C464I, A467V | yes | `+++ | `− | |
| 1075 | C174S, M204R, C220V, T230M, A243Q, C267A, C356T, R396H, E437P, F442N, C464I, A467V | yes | `++ | `− | |
| 1076 | C174S, M204R, C220V, M227L, T230W, C267A, C356T, R396H, E437P, F442N, C464I, A467V | yes | `++ | `− | |
| 1077 | C174S, M204R, C220V, T230V, A243M, C267A, C356T, R396H, E437P, F442N, C464I, A467V | yes | `++ | `− | |
| 1078 | C174S, M204R, C220V, M227V, T230I, C267A, C356T, R396H, E437P, F442N, C464I, A467V | yes | `++ | `− | |
| 1079 | A73D, C174S, M204R, C220V, M227I, T230K, C267A, C356T, R396H, E437P, F442N, S447P, C464I, A467V | yes | `++ | `+ | |
| 1080 | A73G, C174S, M204R, C220V, M227I, T230K, C267A, C356T, R396H, E437P, F442N, S447H, C464I, A467V | yes | `+ | `− | |
| 1081 | A73L, C174S, M204R, C220V, M227I, T230K, C267A, C356T, R396H, E437P, F442N, S447K, C464I, A467V | yes | `+ | `− | |
| 1082 | A73Q, C174S, M204R, C220V, M227I, T230K, C267A, C356T, R396H, E437P, F442N, S447R, C464I, A467V | yes | `++ | `− | |
| 1083 | A73F, C174S, M204R, C220V, M227I, T230K, C267A, C356T, R396H, E437P, F442N, S447K, C464I, A467V | yes | `+ | `− | |
| 1084 | A73G, C174S, M204R, C220V, M227I, T230K, C267A, C356T, R396H, E437P, F442N, S447K, C464I, A467V | yes | `+ | `− | |
| 1085 | A73E, C174S, M204R, C220V, M227I, T230K, C267A, C356T, R396H, E437P, F442N, S447K, C464I, A467V | yes | `+ | `− | |
| 1086 | A73W, C174S, M204R, C220V, M227I, T230K, C267A, C356T, R396H, E437P, F442N, S447R, C464I, A467V | yes | `++ | `− | |
| 1087 | V163G, C174S, M204R, C220V, M227I, T230K, C267A, C356T, R396H, E437P, F442N, S447P, C464I, A467V | yes | `+ | `− | |

TABLE 2-continued

Activities of Exemplary ALD Variants.

| Variant | Mutations Relative to Wild-Type Ald | Small Scale In Vivo 1,3 BDO Production[1] | 3HBCoA/ AcCoA Specificity[2] | R-3HB Aldehyde/ S-3HB Aldehyde | Specific activity[3] |
|---|---|---|---|---|---|
| 1088 | V163T, C174S, M204R, C220V, M227I, T230K, C267A, C356T, R396H, E437P, F442N, S447P, C464I, A467V | yes | `+ | | `− |
| 1089 | C174S, M204R, C220V, M227L, T230S, C267A, C356T, R396H, E437P, F442N, C464I, A467V | yes | `+ | | `− |
| 1090 | C174S, M204R, C220V, A243E, C267A, C356T, R396H, E437P, F442N, C464I, A467V | yes | `+ | | `+ |
| 1091 | C174S, M204R, C220V, T230T, A243E, C267A, C356T, R396H, E437P, F442N, C464I, A467V | yes | `+ | | `− |
| 1092 | C174S, M204R, C220V, A243K, C267A, C356T, R396H, E437P, F442N, C464I, A467V | yes | `+ | | `+ |
| 1093 | A73L, C174S, M204R, C220V, M227I, T230K, C267A, C356T, R396H, E437P, F442N, S447P, C464I, A467V | yes | `+ | | `+ |
| 1094 | A73R, C174S, M204R, C220V, M227I, T230K, C267A, C356T, R396H, E437P, F442N, S447T, C464I, A467V | yes | `+ | | `+ |
| 1095 | A73C, V163C, C174S, M204R, C220V, M227I, T230K, C267A, C356T, R396H, E437P, F442N, C464I, A467V | yes | `+ | | `+ |
| 1096 | V163C, C174S, M204R, C220V, M227I, T230K, C267A, C356T, R396H, E437P, F442N, S447E, C464I, A467V | yes | `+ | | `− |
| 1097 | A73W, V163C, C174S, M204R, C220V, M227I, T230K, C267A, C356T, R396H, E437P, F442N, S447K, C464I, A467V | yes | `+ | | `+ |
| 1098 | A73M, V163C, C174S, M204R, C220V, M227I, T230K, C267A, C356T, R396H, E437P, F442N, S447R, C464I, A467V | yes | `+ | | `+ |
| 1099 | V163C, C174S, M204R, C220V, M227I, T230K, C267A, C356T, R396H, E437P, F442N, S447P, C464I, A467V | yes | `+ | | `+ |
| 1100 | A73F, V163C, C174S, M204R, C220V, M227I, T230K, C267A, C356T, R396H, E437P, F442N, S447P, C464I, A467V | yes | `+ | | `− |
| 1101 | V163C, C174S, M204R, C220V, M227I, T230K, C267A, C356T, R396H, E437P, F442N, S447S, C464I, A467V | yes | `+++ | | `− |

[1]* active on other diols
[2]` − = specificity < 1'
` + = specificity between 1.0-2.0'
` ++ = specificity between 2.0-3.0'
` +++ = specificity > 3.0
[3]` − = relative activity < 1'
` + = relative activity > 1'

Additional activities of exemplary ALD variants are shown in Table 3. Levels of 1,3-BDO production at 48 hours were obtained with ALD variants as high as greater than 50 g/liter, greater than 60 g/liter, greater than 70 g/liter, greater than 80 g/liter, and greater than 90 g/liter.

TABLE 3

Activities of Exemplary ALD Variants.

| Variant | Mutations Relative to Wild-Type Ald | Stable Enzyme Activity in Crude Lysates | Cofactor Preference | 3HBCoA/ AcCoA Specificity | R-3HB Aldehyde/ S-3HB Aldehyde | Increased 1,3-BDO produced in vivo | Increased enyzme activity in vitro |
|---|---|---|---|---|---|---|---|
| 45 | C174S, M204R, C220V, C267A, C356T, R396H, E437P, C464I, A467V | + | NADH | + | + | | + |
| 331 | K65A, I66M, C174S, M204R, C220V, A243Q, C267A, C356T, R396H, E437P, F442N, C464I, A467V | + | NADH | + | | | |

TABLE 3-continued

Activities of Exemplary ALD Variants.

| Variant | Mutations Relative to Wild-Type Ald | Stable Enzyme Activity in Crude Lysates | Cofactor Preference | 3HBCoA/ AcCoA Specificity | R-3HB Aldehyde/ S-3HB Aldehyde | Increased 1,3-BDO produced in vivo | Increased enyzme activity in vitro |
|---|---|---|---|---|---|---|---|
| 681 | K65A, I66M, A73S, C174S, M204R, C220V, M227I, T230C, A243P, C267A, C356T, R396H, E437P, F442N, S447P, C464I, A467V | + | NADH | + | | | |
| 687 | C174S, M204R, C220V, C267A, C356T, R396H, E437P, F442M, C464I, A467V | + | NADH | + | | | |
| 688 | K65A, C174S, M204R, C220V, A243Q, C267A, C356T, R396H, E437P, F442N, C464I, A467V | + | NADH | + | | | |
| 721 | 66M, C174S, M204R, C220V, A243Q, C267A, C356T, R396H, E437P, F442N, C464I, A467V | + | NADH | + | | | |
| 951 | C174S, M204R, C220V, C267A, C356T, R396H, F429H, E437P, F442H, C464I, A467V | + | NADH | + | + | | + |
| 952 | C174S, M204R, C220V, C267A, C356T, R396H, F429M, E437P, F442H, C464I, A467V | + | NADH | + | | | + |
| 953 | C174S, M204R, C220V, C267A, C356T, R396H, F429M, E437P, F442N, C464I, A467V | + | NADH | + | | | + |
| 954 | C174S, M204R, C220V, C267A, C356T, R396H, F429Q, E437P, C464I, A467V | + | NADH | + | | | + |
| 955 | C174S, M204R, C220V, C267A, C356T, R396H, E437P, F442N, C464I, A467V | + | NADH | + | + | | + |
| 956 | C174S, M204R, C220V, C267A, C356T, R396H, E437P, F442N, C464I, A467V | + | NADH | + | | | |
| 957 | C174S, M204R, C220V, C267A, C356T, R396H, E437P, F442Q, C464I, A467V | + | NADH | + | + | | + |
| 958 | C174S, M204R, C220V, C267A, C356T, R396H, E437P, I444V, C464I, A467V | + | NADH | + | + | | + |
| 959 | C174S, M204R, C220V, C267A, C356T, R396H, E437P, T440H, F442N, C464I, A467V | + | NADH | + | + | | + |
| 960 | V19I, D122N, C174S, M204R, C220V, C267A, C356T, R396H, F429D, E437P, F442Q, E450E, C464I, A467V | + | NADH | + | | | + |
| 961 | C174S, M204R, C220V, C267A, V315A, C356T, R396H, E437P, T440H, F442N, C464I, A467V | + | NADH | + | + | | + |
| 962 | A73S, C174S, M204R, C220V, C267A, C356T, R396H, E437P, F442M, S447M, C464I, A467V | + | | + | | + | |
| 963 | C174S, M204R, C220V, A254T, C267A, C356T, R396H, E437P, F442M, C464I, A467V | + | | + | | + | |
| 964 | V163C, C174S, M204R, C220V, C267A, C356T, R396H, E437P, F442M, C464I, A467V | + | | + | | + | |
| 965 | C174S, M204R, C220V, K 229S, C267A, C356T, R396H, E437P, F442N, C464I, A467V | + | | + | | + | |
| 966 | C174S, M204R, C220V, C267A, C356L, R396H, E437P, F442N, C464I, A467V | + | | + | | + | |
| 967 | C174S, M204R, C220V, C267A, C356T, R396H, E437P, T441G, I44L, C464I, A467V | + | | + | | + | |
| 968 | C174S, M204R, C220V, C267A, C356T, R396H, E437P, F442M, C464I, A467V | + | | + | | + | |
| 969 | K65A, C174S, M204R, C220V, C267A, C356T, R396H, E437P, F442N, C464I, A467V | + | | + | | + | |
| 970 | V163C, C174S, M204R, C220V, C267A, C356T, R396H, E437P, F442N, C464I, A467V | + | | + | | + | |
| 971 | C174S, M204R, C220V, C267A, C356T, R396H, E437P, F442M, R460K, C464I, A467V | + | | + | | + | |
| 972 | C174S, M204R, C220V, C267A, C356T, R396H, E437P, F442M, S447M, C464I, A467V | + | | + | | + | |
| 598 | D12A, I139S, C174S, M204R, M227Q, T230R, A243P, C220V, C267A, C356T, R396H, F429Y, F442T, E437P, C464I, A467V | + | NADH/ NADPH | + | | | + |
| 973 | C174S, M204R, C220V, C267A, A243K, C356T, R396H, E437P, F442N, C464I, A467V | + | NADH | + | | | + |
| 974 | Y107N, C174S, M204R, C220V, C267A, C356T, R396H, E437P, F442N, C464I, A467V | + | NADPH | + | | | + |
| 975 | D122G, C174S, M204R, C220V, C267A, C356T, R396H, E437P, F442N, C464I, A467V | + | NADPH | + | | | + |
| 976 | C174S, M204R, C220V, C267A, S349T, C356T, R396H, E437P, F442N, C464I, A467V | + | | + | | | + |
| 977 | C174S, N201D, M204R, C220V, C267A, C356T, R396H, E437P, F442N, C464I, A467V | + | | + | | | + |
| 978 | C174S, M204R, C220V, C267A, D313R, C356T, R396H, E437P, C464I, A467V | | NADH | + | | | + |
| 979 | C174S, M204R, C220V, C267A, P348G, C356T, R396H, E437P, C464I, A467V | | NADH | + | | | + |
| 980 | C174S, M204R, C220V, C267A, C356L, R396H, E437P, C464I, A467V | | NADH | + | | | + |

TABLE 3-continued

Activities of Exemplary ALD Variants.

| Variant | Mutations Relative to Wild-Type Ald | Stable Enzyme Activity in Crude Lysates | Cofactor Preference | 3HBCoA/ AcCoA Specificity | R-3HB Aldehyde/ S-3HB Aldehyde | Increased 1,3-BDO produced in vivo | Increased enzyme activity in vitro |
|---|---|---|---|---|---|---|---|
| 981 | C174S, M204R, C220V, C267A, C356T, A360K, R396H, E437P, C464I, A467V | | NADH | + | | | + |
| 982 | C174S, M204R, C220V, A243K, C267A, C356T, R396H, E437P, C464I, A467V | | NADH | + | | | + |
| 983 | C174S, M204R, C220V, K258W, C267A, C356T, R396H, E437P, C464I, A467V | | NADH | + | | | + |
| 984 | Y107N, C174S, M204R, C220V, C267A, C356T, R396H, E437P, C464I, A467V | | NADH | + | | | + |
| 985 | C174S, M204R, C220V, N223Q, C267A, C356T, R396H, E437P, C464I, A467V | | NADH | + | | | + |
| 986 | S131A, C174S, M204R, C220V, C267A, C356T, R396H, E437P, F442N, C464I, A467V | | NADH | + | | | + |
| 1011 | C174S, M204R, C220V, A243P, C267A, C356T, R396H, E437P, F442N, C464I, A467V | + | NADH | + | | | |
| 1062 | C174S, M204R, C220V, A243Q, C267A, C356T, R396H, E437P, F442N, C464I, A467V | + | NADH | + | | | |

Such aldehyde dehydrogenase variants as described above, which can act on the R form of 3-hydroxybutyraldehyde, can be used to produce a stereoisomer of R-3-hydroxybutyraldehyde or a mixture of R and S forms with a higher proportion of the R form. Such a stereoisomer can be utilized to make stereoisomers of downstream products, such as R-1,3-butanediol. Such stereoisomers have usefulness as pharmaceuticals or nutraceuticals.

These results demonstrate the production of aldehyde dehydrogenase variants having desirable properties, which are useful for commercial production of 3-hydroxybutyraldehyde, 1,3-butanediol, 4-hydroxybutyraldehyde or 1,4-butanediol or other desired products that are produced by metabolic pathways comprising an aldehyde dehydrogenase.

The variants described above are based on the ALD-1 parental sequence. It is understood that variant amino acid positions as shown in Tables 1, 2 or 3 can be applied to homologous aldehyde dehydrogenase sequences. Table 4 provides exemplary ALD sequences based on homology. One skilled in the art will readily understand that such sequences can be analyzed with routine and well known methods for aligning sequences (for example BLAST, blast.ncbi.nlm.nih.gov; Altschul et al., "J. Mol. Biol. 215: 403-410 (1990)). Furthermore, additional homologous ALD sequences can be identified by searching publicly available sequence databases such as found at the National Center for Biotechnology Information (NCBI) GenBank database, European Molecular Biology Laboratory (EMBL), ExPasy Prosite, or other publicly available sequence databases using BLAST. Such alignments can provide information on conserved residues that can be utilized to identify a consensus sequence for preserving enzyme activity as well as positions for generating further enzyme variants.

TABLE 4

Exemplary Aldehyde Dehydrogenase (ALD) Sequences.

| | |
|---|---|
| butyraldehyde dehydrogenase [Clostridium saccharoperbutylacetonicum N1-4(HMT)] | AAP42563.1 GI:31075383 (SEQ ID NO: 7) |
| hypothetical protein ROSEINA2194_01708 [Roseburia inulinivorans DSM 16841] | EEG94445.1 (SEQ ID NO: 8) |
| aldehyde dehydrogenase [Bacillus sp. FJAT-21945] | KOP84001.1 (SEQ ID NO: 9) |
| aldehyde dehydrogenase [Bacillus solani] | KQL21940.1 (SEQ ID NO: 10) |
| aldehyde dehydrogenase [Terrisporobacter othiniensis] | WP_039679531.1 (SEQ ID NO: 11) |
| aldehyde dehydrogenase [Roseburia inulinivorans DSM 16841] | ABC25528.1 GI:83596371 (SEQ ID NO: 12) |
| propionaldehyde dehydrogenase [Clostridium sp. ASF502] | WP_004073235.1 (SEQ ID NO: 13) |
| aldehyde dehydrogenase [[Bacillus] selenitireducens] | WP_013174003.1 (SEQ ID NO: 14) |
| aldehyde dehydrogenase [Blautia obeum] | WP_005427729.1 (SEQ ID NO: 15) |
| hypothetical protein CLOBOL_07248 [[Clostridium] bolteae ATCC BAA-613] | EDP12494.1 (SEQ ID NO: 16) |
| aldehyde dehydrogenase [Jeotgalibacillus alimentarius] | WP_041123321.1 (SEQ ID NO: 17) |
| aldehyde dehydrogenase (NAD) family protein [[Clostridium] hiranonis DSM 13275] | EEA85935.1 (SEQ ID NO: 18) |

TABLE 4-continued

| Exemplary Aldehyde Dehydrogenase (ALD) Sequences. | |
|---|---|
| MULTISPECIES: aldehyde dehydrogenase [*Thermoanaerobacter*] | WP_003870148.1 (SEQ ID NO: 19) |
| MULTISPECIES: aldehyde dehydrogenase [Clostridiales] | WP_008705584.1 (SEQ ID NO: 20) |
| Aldehyde Dehydrogenase [Sebaldella termitidis ATCC 33386] | ACZ07905.1 (SEQ ID NO: 21) |
| propionaldehyde dehydrogenase [*Eubacterium plexicaudatum*] | WP_004061597.1 (SEQ ID NO: 22) |
| MULTISPECIES: aldehyde dehydrogenase [*Escherichia*] | WP_000997839.1 (SEQ ID NO: 23) |
| aldehyde dehydrogenase [Rhodospirillum rubrum] | WP_011388669.1 (SEQ ID NO: 24) |
| aldehyde dehydrogenase [*Clostridium beijerinckii*] | WP_012060202.1 (SEQ ID NO: 25) |
| aldehyde dehydrogenase [[*Eubacterium*] *hallii*] | WP_005344386.1 (SEQ ID NO: 26) |
| aldehyde dehydrogenase [*Vibrio* sp. EJY3] | WP_014232054.1 (SEQ ID NO: 27) |
| aldehyde dehydrogenase [Rhodopseudomonas palustris BisB18] | ABD86737.1 (SEQ ID NO: 28) |
| aldehyde dehydrogenase EutE [Desulfatibacillum alkenivorans] | WP_015949695.1 (SEQ ID NO: 29) |
| aldehyde dehydrogenase Ald [*Clostridium saccharobutylicum*] | WP_022747467.1 (SEQ ID NO: 30) |
| aldehyde dehydrogenase [*Clostridium* sp. DL-VIII] | WP_009171375.1 (SEQ ID NO: 31) |
| aldehyde dehydrogenase EutE [*Clostridium taeniosporum*] | WP_069679818.1 (SEQ ID NO: 32) |
| aldehyde dehydrogenase [*Clostridium botulinum*] | WP_012425099.1 (SEQ ID NO: 33) |
| aldehyde dehydrogenase [*Clostridium botulinum*] | WP_035786720.1 (SEQ ID NO: 34) |
| aldehyde dehydrogenase [*Clostridium botulinum*] | WP_039308447.1 (SEQ ID NO: 35) |
| aldehyde dehydrogenase [*Clostridium botulinum*] | WP_035792132.1 (SEQ ID NO: 36) |
| aldehyde dehydrogenase [*Clostridium pasteurianum*] | WP_023973059.1 (SEQ ID NO: 37) |
| NAD-dependent aldehyde dehydrogenase [*Clostridium saccharoperbutylacetonicum*] | WP_015395720.1 (SEQ ID NO: 38) |
| MULTISPECIES: aldehyde dehydrogenase [*Clostridium*] | WP_023975647.1 (SEQ ID NO: 39) |
| aldehyde dehydrogenase [*Clostridium beijerinckii*] | WP_026888070.1 (SEQ ID NO: 40) |
| *Clostridium beijerinckii* strain NRRL B593 hypothetical protein, coenzyme A acylating aldehyde dehydrogenase (ald), acetoacetate: butyrate/acetate coenzyme A transferase (ctfA), acetoacetate: butyrate/acetate coenzyme A transferase (ctfB), and acetoacetate decarboxylase (adc) genes (AF157306 AF132754) | AF157306.2 (SEQ ID NO: 41) |
| aldehyde dehydrogenase [*Clostridium beijerinckii*] | WP_012059995.1 (SEQ ID NO: 42) |
| aldehyde dehydrogenase [*Clostridium beijerinckii*] | WP_041898834.1 (SEQ ID NO: 43) |
| aldehyde dehydrogenase [*Clostridium beijerinckii*] | WP_017211959.1 (SEQ ID NO: 44) |
| aldehyde dehydrogenase EutE [*Clostridium beijerinckii*] | WP_065419149.1 (SEQ ID NO: 45) |
| NAD-dependent aldehyde dehydrogenase [*Clostridium saccharoperbutylacetonicum* N1-4(HMT)]>gb\|AGF59413.1\| NAD-dependent aldehyde dehydrogenase [*Clostridium saccharoperbutylacetonicum* N1-4(HMT)] | YP_007458667.1 GI:451822466 (WP_015395720.1) (SEQ ID NO: 46) |
| aldehyde dehydrogenase [*Clostridium beijerinckii* NCIMB 8052]>gb\|AAQ12068.1\| coenzyme A acylating aldehyde dehydrogenase [*Clostridium beijerinckii* NCIMB 8052]>gb\|AAQ12072.1\| coenzyme A acylating aldehyde dehydrogenase [*Clostridium beijerinckii*]>gb\|AAT48939.1\| aldehyde dehydrogenase [*Clostridium beijerinckii*]>gb\|AAT66436.1\| coenzyme A-acylating aldehyde dehydrogenase [*Clostridium beijerinckii*]>gb\|ABR35947.1\| aldehyde dehydrogenase [*Clostridium beijerinckii* NCIMB 8052] | YP_001310903.1 GI:150018649 (WP_012059995.1) (SEQ ID NO: 47) |
| coenzyme A acylating aldehyde dehydrogenase [*Clostridium beijerinckii*] | AAD31841.1 GI:4884855 (SEQ ID NO: 48) |
| Acetaldehyde dehydrogenase (acetylating) [*Clostridium* sp. DL-VIII]>gb\|EHJ00721.1\| Acetaldehyde dehydrogenase (acetylating) [*Clostridium* sp. DL-VIII] | ZP_09206127.1 GI:359413662 (SEQ ID NO: 49) |
| coenzyme A acylating aldehyde dehydrogenase [*Clostridium saccharobutylicum*] | CAQ57983.1 GI:189310620 (SEQ ID NO: 50) |
| ethanolamine utilization protein EutE [*Clostridium botulinum* B str. Eklund 17B]>gb\|ACD24339.1\| ethanolamine utilization protein EutE [*Clostridium botulinum* B str. Eklund 17B] | YP_001886323.1 GI:187934965 (WP_012425099.1) (SEQ ID NO: 51) |

TABLE 4-continued

Exemplary Aldehyde Dehydrogenase (ALD) Sequences.

| Description | Accession |
|---|---|
| Aldehyde Dehydrogenase [*Caldalkalibacillus thermarum* TA2.A1]>gb\|EGL82399.1\| Aldehyde Dehydrogenase [*Caldalkalibacillus thermarum* TA2.A1] | ZP_08533507.1 GI:335040377 (SEQ ID NO: 52) |
| Aldehyde Dehydrogenase [Pelosinus fermentans DSM 17108]>ref\|ZP___15517111.1\| Aldehyde Dehydrogenase [Pelosinus fermentans B4]>ref\|ZP_15521980.1\| Aldehyde Dehydrogenase [Pelosinus fermentans B3]>ref\|ZP_15526533.1\| Aldehyde Dehydrogenase [Pelosinus fermentans A12]>ref\|ZP___15534416.1\| Aldehyde Dehydrogenase [Pelosinus fermentans A11]>gb\|EIW18982.1\| Aldehyde Dehydrogenase [Pelosinus fermentans B4]>gb\|EIW21808.1\| Aldehyde Dehydrogenase [Pelosinus fermentans A11]>gb\|EIW29163.1\| Aldehyde Dehydrogenase [Pelosinus fermentans DSM 17108]>gb\|EIW35484.1\| Aldehyde Dehydrogenase [Pelosinus fermentans B3]>gb\|EIW36902.1\| Aldehyde Dehydrogenase [Pelosinus fermentans A12] NAD-dependent aldehyde dehydrogenase [Thermoanaerobacterium thermosaccharolyticum M0795]>gb\|AGB19701.1\| NAD-dependent aldehyde dehydrogenase [Thermoanaerobacterium thermosaccharolyticum M0795] | ZP_10327808.1 GI:392962372 (SEQ ID NO: 53) YP_007299398.1 GI:433655690 (WP_015312185.1) (SEQ ID NO: 54) |
| Aldehyde Dehydrogenase [Pelosinus fermentans JBW45]>gb\|EIW48189.1\| Aldehyde Dehydrogenase [Pelosinus fermentans JBW45] | ZP_15537951.1 GI:421076976 (SEQ ID NO: 55) |
| aldehyde dehydrogenase family protein [*Desulfosporosinus* sp. OT]>gb\|EGW35902.1\| aldehyde dehydrogenase family protein [*Desulfosporosinus* sp. OT] | ZP_08814704.1 GI:345862484 (SEQ ID NO: 56) |
| hypothetical protein CLOSTMETH_00016 [*Clostridium methylpentosum* DSM 5476]>gb\|EEG32278.1\| hypothetical protein CLOSTMETH_00016 [*Clostridium methylpentosum* DSM 5476] | ZP_03705305.1 GI:225016072 (SEQ ID NO: 57) |
| aldehyde dehydrogenase [Thermoanaerobacterium saccharolyticum JW/SL-YS485]>gb\|AFK85255.1\| Aldehyde Dehydrogenase [Thermoanaerobacterium saccharolyticum JW/SL-YS485] | YP_006390854.1 GI:390933349 (WP_014757178.1) (SEQ ID NO: 58) |
| acetaldehyde dehydrogenase [Thermoanaerobacterium xylanolyticum LX-11]>gb\|AEF18105.1\| Acetaldehyde dehydrogenase (acetylating) [Thermoanaerobacterium xylanolyticum LX-11] | YP_004471777.1 GI:333897903 (WP_013788835.1) (SEQ ID NO: 59) |
| aldehyde dehydrogenase EutE [Acetonema longum DSM 6540]>gb\|EGO64744.1\| aldehyde dehydrogenase EutE [Acetonema longum DSM 6540] | ZP_08623980.1 GI:338811775 (SEQ ID NO: 60) |
| ethanolamine utilization protein eutE [*Geobacillus thermoglucosidans* TNO-09.020]>gb\|EID44455.1\| ethanolamine utilization protein eutE [*Geobacillus thermoglucosidans* TNO-09.020] | ZP_17694107.1 GI:423719925 (SEQ ID NO: 61) |
| aldehyde dehydrogenase [*Geobacillus* sp. Y4.1MC1]>gb\|ADP74637.1\| Aldehyde Dehydrogenase [*Geobacillus* sp. Y4.1MC1] | YP_003989248.1 GI:312110932 (WP_013400810.1) (SEQ ID NO: 62) |
| acetaldehyde dehydrogenase [*Geobacillus thermoglucosidasius* C56-YS93]>gb\|AEH47899.1\| Acetaldehyde dehydrogenase (acetylating) [*Geobacillus thermoglucosidasius* C56-YS93] | YP_004587980.1 GI:336235364 (WP_013876899.1) (SEQ ID NO: 63) |
| aldehyde dehydrogenase EutE [*Bacillus azotoformans* LMG 9581]>gb\|EKN64472.1\| aldehyde dehydrogenase EutE [*Bacillus azotoformans* LMG 9581] | ZP_11313951.1 GI:410460269 (SEQ ID NO: 64) |
| putative aldehyde dehydrogenase, ethanolamine utilization protein [[*Clostridium*] *sticklandii*]>emb\|CBH20800.1\| putative aldehyde dehydrogenase, ethanolamine utilization protein [[*Clostridium*] *sticklandii*] | YP_003935705.1 GI:310657984 (WP_013360893.1) (SEQ ID NO: 65) |
| Aldehyde Dehydrogenase [Thermincola potens JR]>gb\|ADG81503.1\| Aldehyde Dehydrogenase [Thermincola potens JR] | YP_003639404.1 GI:296132157 (WP_013119524.1) (SEQ ID NO: 66) |
| CoA-dependent propionaldehyde dehydrogenase [*Clostridium* sp. D5]>gb\|EGB92558.1\| CoA-dependent propionaldehyde dehydrogenase [*Clostridium* sp. D5] | ZP_08130302.1 GI:325263568 (SEQ ID NO: 67) |
| acetaldehyde dehydrogenase (acetylating) [*Fusobacterium* sp. 3_1_33]>gb\|EEW94895.1\| acetaldehyde dehydrogenase (acetylating) [*Fusobacterium* sp. 3_1_33] | ZP_05815063.1 GI:260494934 (SEQ ID NO: 68) |
| ethanolamine utilization protein eutE [*Fusobacterium* sp. 7_1]>gb\|EEO43449.1\| ethanolamine utilization protein eutE [*Fusobacterium* sp. 7_1] | ZP_04573939.1 GI:237743458 (SEQ ID NO: 69) |
| NAD-dependent aldehyde dehydrogenases [*Ruminococcus* sp. SR1/5]>emb\|CBL20089.1\| NAD-dependent aldehyde dehydrogenases [*Ruminococcus* sp. SR1/5] | YP_007783752.1 GI:479153977 (WP_015525955.1) (SEQ ID NO: 70) |
| hypothetical protein HMPREF9942_01197 [*Fusobacterium nucleatum* subsp. *animalis* F0419]>gb\|EHO78009.1\| hypothetical protein HMPREF9942_01197 [*Fusobacterium nucleatum* subsp. *animalis* F0419] | ZP_17125059.1 GI:423137416 (SEQ ID NO: 71) |
| possible aldehyde dehydrogenase [*Fusobacterium nucleatum* subsp. *polymorphum* ATCC 10953]>gb\|EDK87521.1\| possible aldehyde dehydrogenase [*Fusobacterium nucleatum* subsp. *polymorphum* ATCC 10953] | ZP_04969437.1 GI:254302079 (SEQ ID NO: 72) |
| ethanolamine utilization protein eutE [*Fusobacterium* sp. D11]>gb\|EFD80567.1\| ethanolamine utilization protein eutE [*Fusobacterium* sp. D11] | ZP_06524378.1 GI:289765000 (SEQ ID NO: 73) |

TABLE 4-continued

Exemplary Aldehyde Dehydrogenase (ALD) Sequences.

| Description | Accession |
|---|---|
| aldehyde dehydrogenase EutE [*Fusobacterium nucleatum* ChDC F128]>gb\|EJU08233.1\| aldehyde dehydrogenase EutE [*Fusobacterium nucleatum* ChDC F128] | ZP_15972610.1 GI:421526001 (SEQ ID NO: 74) |
| CoA-dependent propionaldehyde dehydrogenase [*Fusobacterium nucleatum* subsp. *polymorphum* F0401]>gb\|EHG19190.1\| CoA-dependent propionaldehyde dehydrogenase [*Fusobacterium nucleatum* subsp. *polymorphum* F0401] | ZP_16419680.1 GI:422338720 (SEQ ID NO: 75) |
| CoA-dependent propionaldehyde dehydrogenase [*Fusobacterium* sp. 11_3_2]>gb\|EGN65750.1\| CoA-dependent propionaldehyde dehydrogenase [*Fusobacterium* sp. 11_3_2] | ZP_08600044.1 GI:336419790 (SEQ ID NO: 76) |
| hypothetical protein CLOSTASPAR_02210 [*Clostridium asparagiforme* DSM 15981]>gb\|EEG55710.1\| hypothetical protein CLOSTASPAR_02210 [*Clostridium asparagiforme* DSM 15981] | ZP_03758198.1 GI:225388474 (SEQ ID NO: 77) |
| aldehyde dehydrogenase [*Clostridium phytofermentans* ISDg]>gb\|ABX41556.1\| Aldehyde Dehydrogenase_[*Clostridium phytofermentans* ISDg] | YP_001558295.1 GI:160879327 (WP_012199204.1) (SEQ ID NO: 78) |
| CoA-dependent propionaldehyde dehydrogenase [*Fusobacterium* sp. 1_1_41FAA]>gb\|EFG28139.1\| CoA-dependent propionaldehyde dehydrogenase [*Fusobacterium* sp. 1_1_41FAA] | ZP_06748808.1 GI:294783484 (SEQ ID NO: 79) |
| hypothetical protein HMPREF0991_01940 [Lachnospiraceae bacterium 2_1_58FAA]>gbEGN47419.1\| hypothetical protein HMPREF0991_01940 [Lachnospiraceae bacterium 2_1_58FAA] | ZP_08612821.1 GI:336432991 (SEQ ID NO: 80) |
| hypothetical protein RUMGNA_01022 [*Ruminococcus gnavus* ATCC 29149]>gb\|EDN78612.1\| aldehyde dehydrogenase (NAD) family protein [*Ruminococcus gnavus* ATCC 29149] | ZP_02040258.1 GI:154503198 (SEQ ID NO: 81) |
| NAD-dependent aldehyde dehydrogenases [*Ruminococcus obeum* A2-162]>emb\|CBL23217.1\| NAD-dependent aldehyde dehydrogenases [*Ruminococcus obeum* A2-162] | YP_007805199.1 GI:479177598 (WP_015542038.1) (SEQ ID NO: 82) |
| aldehyde dehydrogenase [*Clostridium saccharolyticum* WM1]>gb\|ADL04402.1\| Aldehyde Dehydrogenase [*Clostridium saccharolyticum* WM1] | YP_003822025.1 GI:302386203 (WP_013272491.1) (SEQ ID NO: 83) |
| aldehyde dehydrogenase family protein [*Flavonifractor plautii* ATCC 29863]>gb\|EHM40040.1\| aldehyde dehydrogenase family protein [*Flavonifractor plautii* ATCC 29863] | ZP_09385796.1 GI:365844997 (SEQ ID NO: 84) |
| hypothetical protein RUMOBE_00094 [*Ruminococcus obeum* ATCC 29174]>gb\|EDM88971.1\| aldehyde dehydrogenase (NAD) family protein [*Ruminococcus obeum* ATCC 29174] | ZP_01962381.1 GI:153809713 (SEQ ID NO: 85) |
| Aldehyde Dehydrogenase [*Clostridium carboxidivorans* P7]>ref\|ZP_06856832.1\| aldehyde dehydrogenase (NAD) family protein [*Clostridium carboxidivorans* P7]>gb\|EET88516.1\| Aldehyde Dehydrogenase [*Clostridium carboxidivorans* P7]>gb\|EFG86154.1\| aldehyde dehydrogenase (NAD) family protein [*Clostridium carboxidivorans* P7]>gb\|ADO12117.1\| CoA-acylating aldehyde dehydrogenase [*Clostridium carboxidivorans* P7] | ZP_05391061.1 GI:255524100 (SEQ ID NO: 86) |
| hypothetical protein FUAG_00592 [*Fusobacterium ulcerans* ATCC 49185]>gb\|EFS25077.1\| hypothetical protein FUAG_00592 [*Fusobacterium ulcerans* ATCC 49185] | ZP_10974295.1 GI:404368948 (SEQ ID NO: 87) |
| hypothetical protein HMPREF0402_0608 [*Fusobacterium* sp. 12_1B]>gb\|EHO83590.1\| hypothetical protein HMPREF0402_00608 [*Fusobacterium* sp. 12_1B] | ZP_09586735.1 GI:373496187 (SEQ ID NO: 88) |
| Aldehyde Dehydrogenase [*Clostridium carboxidivorans* P7]>ref\|ZP_06855343.1\| aldehyde dehydrogenase (NAD) family protein [*Clostridium carboxidivorans* P7]>gb\|EET85788.1\| Aldehyde Dehydrogenase [*Clostridium carboxidivorans* P7]>gb\|EFG87815.1\| aldehyde dehydrogenase (NAD) family protein [*Clostridium carboxidivorans* P7] | ZP_05393779.1 GI:255526882 (SEQ ID NO: 89) |
| NAD-dependent aldehyde dehydrogenases [*Clostridium* cf. *saccharolyticum* K10]>emb\| CBK77787.1\| NAD-dependent aldehyde dehydrogenases [*Clostridium* cf. *saccharolyticum* K10] | YP_007849785.1 GI:479338567 (WP_015574070.1) (SEQ ID NO: 90) |
| ethanolamine utilization protein eutE [*Fusobacterium varium* ATCC 27725]>gb\| EES62817.1\| ethanolamine utilization protein eutE [*Fusobacterium varium* ATCC 27725] | ZP_08693593.1 GI:340756989 (SEQ ID NO: 91) |
| aldehyde dehydrogenase family protein [*Clostridium celatum* DSM 1785]>gb\|EKY29259.1\| aldehyde dehydrogenase family protein [*Clostridium celatum* DSM 1785] | ZP_19296595.1 GI:429764274 (SEQ ID NO: 92) |
| propionaldehyde dehydrogenase [*Clostridium* sp. ASF502] | EMZ20682.1 GI:476613570 (SEQ ID NO: 93) |
| hypothetical protein HMPREF0988_02063 [Lachnospiraceae bacterium 1_4_56FAA]>gb\|EGN36620.1\| hypothetical protein HMPREF0988_02063 [Lachnospiraceae bacterium 1_4_56FAA] | ZP_08616478.1 GI:336436768 (SEQ ID NO: 94) |
| hypothetical protein HMPREF0994_03038 [Lachnospiraceae bacterium 3_1_57FAA_CT1]>gb\|EGN40215.1\| hypothetical protein HMPREF0994_03038 [Lachnospiraceae bacterium 3_1_57FAA_CT1] | ZP_08607032.1 GI:336427027 (SEQ ID NO: 95) |
| aldehyde dehydrogenase [*Ruminococcus* sp. 5_1_39B_FAA]>gb\|EES77009.1\| aldehyde dehydrogenase [*Ruminococcus* sp. 5_1_39B_FAA] | ZP_04856816.1 GI:253579547 (SEQ ID NO: 96) |
| CoA-dependent propionaldehyde dehydrogenase PduP [*Acetobacterium woodii* DSM 1030]>gb\|AFA49334.1\| CoA-dependent proprionaldehyde dehydrogenase PduP [*Acetobacterium woodii* DSM 1030] | YP_005270223.1 GI:379012411 (WP_014356934.1) (SEQ ID NO: 97) |

TABLE 4-continued

| Exemplary Aldehyde Dehydrogenase (ALD) Sequences. | |
|---|---|
| ethanolamine utilization protein EutE [*Clostridium botulinum* E1 str. 'BoNT E Beluga']>gb\|EES50221.1\| ethanolamine utilization protein EutE [*Clostridium botulinum* E1 str. 'BoNT E Beluga'] | ZP_04822936.1 GI:251780016 (SEQ ID NO: 98) |
| ethanolamine utilization protein EutE [*Clostridium botulinum* B str. Eklund 17B]>gb\|ACD22415.1\| ethanolamine utilization protein EutE [*Clostridium botulinum* B str. Eklund 17B] | YP_001885942.1 GI:187933041 (WP_012423269.1) (SEQ ID NO: 99) |
| ethanolamine utilization protein EutE [*Clostridium botulinum* E3 str. Alaska E43] >gb\|ACD53952.1\| ethanolamine utilization protein EutE [*Clostridium botulinum* E3 str. Alaska E43] | YP_001921227.1 GI:188590535 (WP_012451752.1) (SEQ ID NO: 100) |
| propionaldehyde dehydrogenase [*Eubacterium plexicaudatum* ASF492] | EMZ27833.1 GI:476621007 (SEQ ID NO: 101) |
| Aldehyde Dehydrogenase [Thermosediminibacter oceani DSM 16646]>gb\|ADL07333.1\| Aldehyde Dehydrogenase [Thermosediminibacter oceani DSM 16646] | YP_003824956.1 GI:302389135 (WP_013275382.1) (SEQ ID NO: 102) |
| hypothetical protein HMPREF1090_01637 [*Clostridium clostridioforme* 90A8] | ENZ17687.1 GI:480674262 (SEQ ID NO: 103) |
| hypothetical protein HMPREF9467_03550 [*Clostridium clostridioforme* 2_1_49FAA]>gb\|EHG29726.1\| hypothetical protein HMPREF9467_03550 [*Clostridium clostridioforme* 2_1_49FAA] | ZP_09116578.1 GI:357055510 (SEQ ID NO: 104) |
| Aldehyde Dehydrogenase [Ilyobacter polytropus DSM 2926]>gb\|ADO84118.1\| Aldehyde Dehydrogenase [Ilyobacter polytropus DSM 2926] | YP_003968466.1 GI:310780134 (WP_013388777.1) (SEQ ID NO: 105) |
| hypothetical protein GCWU000342_00651 [Shuttleworthia satelles DSM 14600]>gb\|EEP29295.1\| hypothetical protein GCWU000342_00651 [Shuttleworthia satelles DSM 14600] | ZP_04454656.1 GI:229828587 (SEQ ID NO: 106) |
| aldehyde dehydrogenase [*Clostridium beijerinckii* NCIMB 8052]>gb\|ABR36155.1\| aldehyde dehydrogenase [*Clostridium beijerinckii* NCIMB 8052] | YP_001311111.1 GI:150018857 (WP_012060202.1) (SEQ ID NO: 107) |
| propionaldehyde dehydrogenase [*Clostridium clostridioforme* CM201]>gb\|ENZ04399.1\| propionaldehyde dehydrogenase [*Clostridium clostridioforme* 90B1]>gb\|ENZ17257.1\| propionaldehyde dehydrogenase [*Clostridium clostridioforme* 90A8]>gb\|ENZ22132.1\| propionaldehyde dehydrogenase [*Clostridium clostridioforme* 90A3]>gb\|ENZ29200.1\| propionaldehyde dehydrogenase [*Clostridium clostridioforme* 90A1]>gb\|ENZ64224.1\| propionaldehyde dehydrogenase[*Clostridium clostridioforme* 90A4]>gb\|ENZ70105.1\| propionaldehyde dehydrogenase [*Clostridium clostridioforme* 90A6] | ENY83847.1 GI:480639338 (SEQ ID NO: 108) |
| aldehyde dehydrogenase (NAD) domain protein [*Clostridium* sp. MSTE9]>gb\|EJF40077.1\| aldehyde dehydrogenase (NAD) domain protein [*Clostridium* sp. MSTE9] | ZP_14663848.1 GI:420157008 (SEQ ID NO: 109) |
| propionaldehyde dehydrogenase [*Clostridium bolteae* 90B8]>gb\|ENZ57487.1\| propionaldehyde dehydrogenase [*Clostridium bolteae* 90A5]>gb\|ENZ67775.1\| propionaldehyde dehydrogenase [*Clostridium bolteae* 90B7] | ENZ31577.1 GI:480688660 (SEQ ID NO: 110) |
| hypothetical protein EUBHAL_00514 [*Eubacterium hallii* DSM 3353]>gb\|EEG37590.1\| aldehyde dehydrogenase (NAD) family protein [*Eubacterium hallii* DSM 3353] | ZP_03715465.1 GI:225026273 (SEQ ID NO: 111) |
| CoA-acylating propionaldehyde dehydrogenase [*Halanaerobium saccharolyticum* subsp. *saccharolyticum* DSM 6643]>emb\|CCU77919.1\| CoA-acylating propionaldehyde dehydrogenase [*Halanaerobium saccharolyticum* subsp. *saccharolyticum* DSM 6643] | ZP_23773859.1 GI:470960332 (SEQ ID NO: 112) |
| hypothetical protein [*Eubacterium limosum* KIST612]>gb\|ADO39014.1\| hypothetical protein ELI_4072 [*Eubacterium limosum* KIST612] | YP_003961977.1 GI:310829620 (WP_013382321.1) (SEQ ID NO: 113) |
| aldehyde dehydrogenase [*Thermoanaerobacter* sp. X514]>ref\|ZP_07131928.1\| Aldehyde Dehydrogenase [*Thermoanaerobacter* sp. X561]>ref\|YP_003903905.1\| aldehyde dehydrogenase [*Thermoanaerobacter* sp. X513]>ref\|ZP_08212082.1\| Aldehyde Dehydrogenase [*Thermoanaerobacter ethanolicus* JW 200]>gb\|ABY93220.1\| aldehyde dehydrogenase [*Thermoanaerobacter* sp. X514]>gb\|EFK84693.1\| Aldehyde Dehydrogenase [*Thermoanaerobacter* sp. X561]>gb\|ADN54614.1\| Aldehyde Dehydrogenase [*Thermoanaerobacter* sp. X513]>gb\|EGD51928.1\| Aldehyde Dehydrogenase [*Thermoanaerobacter ethanolicus* JW200] | YP_001663556.1 GI:167040571 (WP_003870148.1) (SEQ ID NO: 114) |
| aldehyde dehydrogenase [Rhodospirillum rubrum ATCC 11170]>ref\|YP_006047210.1\| aldehyde dehydrogenase EutE [Rhodospirillum rubrum F11]>gb\|ABC21715.1\| Aldehyde dehydrogenase [Rhodospirillum rubrum ATCC 11170]>gb\|AEO47413.1\| aldehyde dehydrogenase EutE [Rhodospirillum rubrum F11] | YP_426002.1 GI:83592250 (SEQ ID NO: 115) |
| CoA-dependent propionaldehyde dehydrogenase [*Eubacterium yurii* subsp. *margaretiae* ATCC 43715]>gb\|EFM39950.1\| CoA-dependent propionaldehyde dehydrogenase [*Eubacterium yurii* subsp. *margaretiae* ATCC 43715] | ZP_07453625.1 GI:306819974 (SEQ ID NO: 116) |
| aldehyde dehydrogenase (NAD) domain protein [*Eubacterium* sp. AS15]>gb\|EJP26117.1\| aldehyde dehydrogenase (NAD) domain protein [*Eubacterium* sp. AS15] | ZP_10828060.1 GI:402309064 (SEQ ID NO: 117) |
| aldehyde dehydrogenase EutE [*Vibrio* sp. EJY3]>gb\|AEX22176.1\| aldehyde dehydrogenase EutE [*Vibrio* sp. EJY3] | YP_005023154.1 GI:375265711 (WP_014232054.1) (SEQ ID NO: 118) |
| hypothetical protein HMPREF9629_00032 [Eubacteriaceae bacterium ACC19a]>gb\|EHL16790.1\| hypothetical protein HMPREF9629_00032 [Eubacteriaceae bacterium ACC19a] | ZP_09320518.1 GI:363893420 (SEQ ID NO: 119) |

TABLE 4-continued

Exemplary Aldehyde Dehydrogenase (ALD) Sequences.

| | |
|---|---|
| aldehyde-alcohol dehydrogenase domain protein [Propionibacterium propionicum F0230a]>gb\|AFN47240.1\| aldehyde-alcohol dehydrogenase domain protein [Propionibacterium propionicum F0230a] | YP_006513121.1<br>GI:397671586<br>(WP_014847902.1)<br>(SEQ ID NO: 120) |
| hypothetical protein HMPREF9628_01348 [Eubacteriaceae bacterium CM5]>gb\|EHL19659.1\| hypothetical protein HMPREF9628_01348 [Eubacteriaceae bacterium CM5] | ZP_09316712.1<br>GI:363889349<br>(SEQ ID NO: 121) |
| aldehyde dehydrogenase (NAD) family protein [Eubacteriaceae bacterium OBRC8]>gb\|EJU23517.1\| aldehyde dehydrogenase (NAD) family protein [Eubacteriaceae bacterium OBRC8] | ZP_10886417.1<br>GI:402837902<br>(SEQ ID NO: 122) |
| aldehyde dehydrogenase [*Clostridium beijerinckii*] | AAT48939.1<br>(SEQ ID NO: 123) |

It is understood that the individual ALD variants such as those described above can be used alone, or can be combined with any other variant amino acid position, including 2, 3, 4, 5, 6, 7, 8, 9, 10, 11, 12, 13, 14, 15 or 16, that is, up to all variant amino acid positions as disclosed herein (see Tables 1-3), to generate additional variants having desirable activities. Exemplary ALD variants include, but are not limited to, single substitutions, or a combination of one or more of the substitutions, at amino acid positions disclosed in any of Tables 1-3, for example, at amino acid position 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1) (see Tables 1-3). For example, the ALD variants include, but are not limited to amino acid substitution, single substitutions, or a combination of one or more of the substitutions, at amino acid positions D12, V19, C33, I44, K65, I66, K72, A73, Y107, D122, E129, I139, T143, P145, G155, V163, G167, C174, C189, M204, C220, M227, K229, T230, A243, G244, A254, C267, V315, C353, C356, R396, F429, V432, E437, T440, T441, F442, I444, S447, E450, R460, C464, or A467 corresponding to the amino acid sequence of ALD-1 (SEQ ID NO:1) (see Tables 1-3). It is understood that any substitution of the other 19 amino acids can be done at one or more desired amino acid positions.

In one embodiment, the variant ALD comprises an amino acid substitution at position 12 that is D12A. In one embodiment, the variant ALD comprises an amino acid substitution at position 19 that is V19I. In one embodiment, the variant ALD comprises an amino acid substitution at position 33 that is C33R. In one embodiment, the variant ALD comprises an amino acid substitution at position 44 that is I44L. In one embodiment, the variant ALD comprises an amino acid substitution at position 65 that is K65A. In one embodiment, the variant ALD comprises an amino acid substitution at position 66 selected from I66M, I66Q, I66N, I66H, I66T and I66S. In one embodiment, the variant ALD comprises an amino acid substitution at position 72 that is K72N. In one embodiment, the variant ALD comprises an amino acid substitution at position 73 selected from A73S, A73D, A73G, A73L, A73Q, A73F, A73E, A73W, A73R, A73C, and A73M. In one embodiment, the variant ALD comprises an amino acid substitution at position 107 that is Y107K. In one embodiment, the variant ALD comprises an amino acid substitution at position 122 that is D122N. In one embodiment, the variant ALD comprises an amino acid substitution at position 129 that is E129I. In one embodiment, the variant ALD comprises an amino acid substitution at position 139 selected from I139S, I139V, and I139L. In one embodiment, the variant ALD comprises an amino acid substitution at position 143 that is T143N or T143S. In one embodiment, the variant ALD comprises an amino acid substitution at position 163 selected from V163C, V163G and V163T. In one embodiment, the variant ALD comprises an amino acid substitution at position 167 that is G167S. In one embodiment, the variant ALD comprises an amino acid substitution at position 174 that is C174S. In one embodiment, the variant ALD comprises an amino acid substitution at position 189 that is C189A. In one embodiment, the variant ALD comprises an amino acid substitution at position 204 that is M204R. In one embodiment, the variant ALD comprises an amino acid substitution at position 220 that is C220V. In one embodiment, the variant ALD comprises an amino acid substitution at position 227 selected from M227K, M227Q, M227I, M227V, M227C, M227L, and M227A. In one embodiment, the variant ALD comprises an amino acid substitution at position 229 that is K 229S. In one embodiment, the variant ALD comprises an amino acid substitution at position 230 selected from T230R, T230K, T230H, T230A, T230M, T230C, T230L, T230S, T230Y, T230G, T230T, T230I, T230W, T230N, T230V, and T230Q. In one embodiment, the variant ALD comprises an amino acid substitution at position 243 selected from A243P, A243Q, A243E, A243S, A243N, A243K, A243L, A243C, A243M, and A243I. In one embodiment, the variant ALD comprises an amino acid substitution at position 254 that is A254T. In one embodiment, the variant ALD comprises an amino acid substitution at position 267 that is C267A. In one embodiment, the variant ALD comprises an amino acid substitution at position 315 that is V315A. In one embodiment, the variant ALD comprises an amino acid substitution at position 353 that is C353A. In one embodiment, the variant ALD comprises an amino acid substitution at position 356 that is C356T or C356L. In one embodiment, the variant ALD comprises an amino acid substitution at position 396 that is R396H. In one embodiment, the variant ALD comprises an amino acid substitution at position 429 selected from F429Y, F429Q, F429H, F429M, F429D, and F429L. In one embodiment, the variant ALD comprises an amino acid substitution at position 432 that is V432V or V432N. In one embodiment, the variant ALD comprises an amino acid substitution at position 437 that is E437P. In one embodiment, the variant ALD comprises an amino acid substitution at position 440 that is T440H. In one embodiment, the variant ALD comprises an amino acid substitution at position 441 that is T441G. In one embodiment, the variant ALD comprises an amino acid substitution at position 442 selected from F442T, F442Y, F442H, F442N, F442Q, F442M, and F442F. In one embodiment, the variant ALD comprises an amino acid substitution at position 444 that is I444V. In one embodiment, the variant ALD comprises an amino acid substitution at position 447 selected from S447M, S447P, S447H, S447K, S447R, S447T, S447E, and S447S. In one embodiment, the variant ALD comprises an amino acid substitution at position 460 that is R460K. In one embodiment, the variant ALD comprises an amino acid substitution at position 464 that is C464V or C464I. In one embodiment, the variant ALD comprises an amino acid substitution at position 467 that is A467V. Any of the above-described amino acid positions can be used for single amino acid substitutions, or a combination of one or more of the substitutions, to generate an ALD variant of the invention.

For example, an ALD variant can comprise two or more amino acid substitutions, such as D12 and I139; K65 and C174; M204 and C220; C464 and A467; R396 and F442; C356 and F442; C174 and A243; K65 and I66; I66 and A73; I66 and C174; I66 and M204; I66 and C220; I66 and M227; I66 and T230; I66 and A243; I66 and A243; I66 and C267; I66 and C356; I66 and R396; I66 and E437; I66 and F442; I66 and S447; I66 and C464; I66 and A467, and the like. For example, an ALD variant can comprise two or more amino acid substitutions, such as D12A and I139L; K65A and C174S; M204R and C220V; C464I and A467V; R396H and F442N; C356T and F442M; C174S and A243Q; K65A and I66H; I66H and A73S; I66H and C174S; I66H and M204R; I66H and C220V; I66H and M227I; I66H and T230C; I66H and A243Q; I66H and A243P; I66H and C267A; I66H and C356T; I66H and R396H; I66H and E437P; I66H and F442N; I66H and S447P; I66H and C464I; I66H and A467V; K65A and I66T; I66M and A73S; I66T and C174S; I66T and M204R; I66T and C220V; I66T and M227I; I66T and T230C; I66T and A243Q; I66T and A243P; I66T and C267A; I66T and C356T; I66T and R396H; I66T and E437P; I66T and F442N; I66T and S447P; I66T and C464I; I66T and A467V; K65A and I66M; I66M and A73S; I66M and C174S; I66M and M204R; I66M and C220V; I66M and M227I; I66M and T230C; I66M and A243Q; I66M and A243P; I66M and C267A; I66M and C356T; I66M and R396H; I66M and E437P; I66M and F442N; I66M and S447P; I66M and C464I; I66M and A467V; K65A and I66N; I66N and A73S; I66N and C174S; I66N and M204R; I66N and C220V; I66N and M227I; I66N and T230C; I66N and A243Q; I66N and A243P; I66N and C267A; I66N and C356T; I66N and R396H; I66N and E437P; I66N and F442N; I66N and S447P; I66N and C464I; I66N and A467V, K65A and I66Q; I66Q and A73S; I66Q and C174S; I66Q and M204R; I66Q and C220V; I66Q and M227I; I66Q and T230C; I66Q and A243Q; I66Q and A243P; I66Q and C267A; I66Q and C356T; I66Q and R396H; I66Q and E437P; I66Q and F442N; I66Q and S447P; I66Q and C464I; I66Q and A467V; K65A and I66S; I66S and A73S; I66S and C174S; I66S and M204R; I66S and C220V; I66S and M227I; I66S and T230C; I66S and A243Q; I66S and A243P; I66S and C267A; I66S and C356T; I66S and R396H; I66S and E437P; I66S and F442N; I66S and S447P; I66S and C464I; I66S and A467V, and the like.

An ALD variant can also comprise three or more amino acid substitutions such as D12, I139 and R396; K65, C174 and C356; M204, C220 and A243; C174, C464 and A467; A243, R396 and F442; C220, C356 and F442; C174, A243 and E437; K65, I66 and A243; I66, A73 and E437; I66, C174 and F442; I66, M204 and R396; I66, C220 and S447; I66, M227 and C267; I66, T230 and A243; I66, A243 and C464; I66, A243 and A467; I66, M204 and C267; I66, C356 and R396; I66, R396 and F442; I66, E437 and A467; I66, C220 and F442; I66, S447 and C464; I66, M204 and C464; I66, C174 and A467. For example, an ALD variant can comprise three or more amino acid substitutions, such as D12A, I139L and R396H; K65A, C174S and C356T; M204R, C220V and A243Q; C174S, C464I and A467V; A243P, R396H and F442N; C220V, C356T and F442M; C174S, A243Q and E437P; K65A, I66H and A243Q; I66H, A73S and E437P; I66H, C174S and F442N; I66H, M204R and R396H; I66H, C220V and S447P; I66H, M227I and C267A; I66H, T230C and A243P; I66H, A243Q and C464I; I66H, A243P and A467V; I66H, M204R and C267A; I66H, C356T and R396M; I66H, R396H and F442N; I66H, E437P and A467V; I66H, C220V and F442N; I66H, S447P and C464I; I66H, M204R and C464I; I66H, C174S and A467V; K65A, I66T and A243Q; I66M, A73S and E437P; I66T, C174S and F442N; I66T, M204R and R396I; I66T, C220V and S447P; I66T, M227I and C267A; I66T, T230C and A243P; I66T, A243Q and C464I; I66T, A243P and A467V; I66T, M204R and C267A; I66T, C356T and R396M; I66T, R396H and F442N; I66T, E437P and A467V; I66T, C220V and F442N; I66T, S447P and C464I; I66T, M204R and C464I; I66T, and C174S and A467V; K65A, I66M and A243Q; I66M, A73S and E437P; I66M, C174S and F442N; I66M, M204R and R396I; I66M, C220V and F442N; I66M, M227I and C267A; I66M, T230C and A243P; I66M, A243Q and C464I; I66M, A243P and A467V; I66M, M204R and C267A; I66M, C356T and R396M; I66M, R396H and F442N; I66M, E437P and A467V; I66M, C220V and F442N; I66M, S447P and C464I; I66M, M204R and C464I; I66M, C174S and A467V; K65A, I66N and A243Q; I66N, A73S and M227I; I66N, C174S and E437P; I66N, M204R and R396H; I66N, C220V and S447P; I66N, C174S and M227I; I66N, T230C and C356T; I66N, M204R and A243Q; I66N, A243P and S447P; I66N, C267A and C356T; I66N, C220V and C356T; I66N, R396H and E437P; I66N, M227I and E437P; I66N, F442N and A467V; I66N, M227I and S447P; I66N, M227I and C464I; I66N, A73S and A467V, K65A, I66Q and C220V; I66Q, A73S and M227I; I66Q, C174S and R396H; I66Q, M204R and C220V; I66Q, C220V and E437P; I66Q, M227I and F442N; I66Q, C174S and T230C; I66Q, A243Q and C356T; I66Q, A243P and C267A; I66Q, C267A and C356T; I66Q, C220V and C356T; I66Q, R396H and E437P; I66Q, M204R and E437P; I66Q, M227I and F442N; I66Q, F442N and S447P; I66Q, C256A and C464I; I66Q, A73S and A467V; K65A, I66S and A73S; I66S, A73S and C220V; I66S, C174S and C267A; I66S, M204R and R396H; I66S, C220V and T230C; I66S, C220V and M227I; I66S, T230C and A243P; I66S, A243Q and C356T; I66S, M227I and A243P; I66S, C267A and F442N; I66S, M204R and C356T; I66S, T230C and R396I; I66S, M204R and E437P; I66S, C220V and F442N; I66S, A73S and S447P; I66S, C174S and C464I; I66S, C356T and A467V, and the like. It is understood that such combinations two or more, or three or more combinations of amino acid substitutions as described above are merely exemplary and that a person skilled in the art can readily determine desired combinations of amino acid substitutions for a desired ALD.

Based on the teachings herein, a person skilled in the art can readily identify amino acid positions corresponding to any of amino acid positions 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1) in homologous ALD sequences. For example, as shown in the alignment in FIG. 4A, amino acid 1139 of ALD-1 corresponds to amino acid 1133 of SEQ ID NO:13 and 20. For SEQ ID NO:24, the corresponding position is V199. Using well known methods for aligning amino acid sequences, generally using default parameters as disclosed herein, a person skilled in the art can readily determine an amino acid position in another ALD sequence that corresponds to any of amino acid positions 12, 19, 33, 44, 65, 66, 72, 73, 107, 122, 129, 139, 143, 145, 155, 163, 167, 174, 189, 204, 220, 227, 229, 230, 243, 244, 254, 267, 315, 353, 356, 396, 429, 432, 437, 440, 441, 442, 444, 447, 450, 460, 464, or 467 corresponding to the amino acid sequence of ALD-1 (SEQ ID NO:1).

It is further understood that an ALD variant can contain 2, 3, 4, 5, 6, 7, 8, 9, 10, 11, 12, 13, 14, 15, or 16, that is, up to all variant amino acid positions as disclosed herein, for example, in Tables 1-3. A person skilled in the art can readily generate an ALD variant based on any single or combination of amino acid substitutions, as disclosed herein, such as the amino acid variant positions described above and in Tables 1-3. In a particular embodiment, the ALD variants are those disclosed in Tables 1-3.

Throughout this application various publications have been referenced. The disclosures of these publications in their entireties, including GenBank accession.version designations and/or GI number publications, are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. An isolated nucleic acid molecule selected from:
   (a) a nucleic acid molecule encoding a polypeptide comprising an amino acid sequence that is a variant of SEQ ID NO: 1, wherein said amino acid sequence comprises the amino acid substitution I66M, wherein the amino acid sequence has at least 90% sequence identity to the amino acid sequence of SEQ ID NO: 1 and wherein said polypeptide has aldehyde dehydrogenase activity and
   (b) a nucleic acid molecule that is complementary to (a).

2. The isolated nucleic acid molecule of claim 1, wherein the amino acid sequence, in addition to the substitution I66M, comprises one or more amino acid substitutions at other amino acid variant positions set forth in Table 1, 2 and/or 3.

3. The isolated nucleic acid molecule of claim 1, wherein the amino acid sequence comprises at least 2, 3, 4, 5, 6, 7, 8, 9, 10, 11, 12, 13, 14, 15 or 16 of the amino acid substitutions set forth in Table 1, 2 and/or 3.

4. The isolated nucleic acid molecule of claim 1, wherein the amino acid sequence comprises the amino acid substitutions of a variant as set forth in Table 1, 2 and/or 3.

5. A vector containing the nucleic acid molecule of claim 1.

6. An isolated polypeptide comprising an amino acid sequence that is a variant of SEQ ID NO: 1, wherein said amino acid sequence comprises the amino acid substitution I66M, wherein the amino acid sequence has at least 90% sequence identity to the amino acid sequence of SEQ ID NO:1 and wherein the isolated polypeptide has aldehyde dehydrogenase activity.

7. The isolated polypeptide of claim 6, wherein the amino acid sequence, in addition to the substitution I66M, comprises one or more amino acid substitutions at other amino acid variant positions set forth in Table 1, 2 and/or 3.

8. The isolated polypeptide of claim 6, wherein the amino acid sequence comprises at least 2, 3, 4, 5, 6, 7, 8, 9, 10, 11, 12, 13, 14, 15 or 16 of the amino acid substitutions set forth in Table 1, 2 and/or 3.

9. The isolated polypeptide of claim 6, wherein the amino acid sequence comprises the amino acid substitutions of a variant as set forth in Table 1, 2 and/or 3.

10. The isolated polypeptide of claim 6, wherein the polypeptide:
    (a) can convert 3-hydroxybutyryl-CoA to 3-hydroxybutyraldehyde;
    (b) can convert 4-hydroxybutyryl-CoA to 4-hydroxybutyraldehyde;
    (c) has higher activity relative to the parental a polypeptide consisting of SEQ ID NO: 1;
    (d) has higher activity for 3-hydroxy-(R)-butyryl-CoA over 3-hydroxy-(S)-butyryl-CoA;
    (e) has higher specificity for 4-hydroxybutyryl-CoA over acetyl-CoA;
    (f) produces decreased byproducts in a cell or cell extract relative to a cell or cell extract comprising a polypeptide consisting of SEQ ID NO: 1, wherein optionally the byproduct is ethanol or 4-hydroxy-2-butanone; and/or
    (g) has a higher kcat relative to a polypeptide consisting of SEQ ID NO: 1.

11. A cell comprising the nucleic acid claim 1.

12. The cell of claim 11, wherein the cell is a microbial organism.

13. The cell of claim 11, wherein said cell:
    (a) comprises a pathway that produces 3-hydroxybutyraldehyde (3-HBal) and/or 1,3-butanediol (1,3-BDO), or an ester or amide thereof;
    (b) comprises a pathway that produces 4-hydroxybutyraldehyde (4-HBal) and/or 1,4-butanediol (1,4-BDO), or an ester or amide thereof;
    (c) is capable of fermentation;
    (d) comprising at least one substrate for said polypeptide, wherein optionally the substrate is 3-hydroxybutyryl-CoA or 3-hydroxy-(R)-butyryl-CoA; 4-hydroxybutyryl-CoA; or
    (e) has higher activity for 3-hydroxy-(R)-butyryl-CoA over 3-hydroxy-(S)-butyryl-CoA.

14. A composition comprising the polypeptide of claim 6 and at least one substrate for said polypeptide.

15. A culture medium comprising the cell of claim 11.

16. A method of constructing a host strain comprising introducing the nucleic acid of claim 1 into a cell that is capable of fermentation.

17. A method for producing 3-hydroxybutyraldehyde (3-HBal) and/or 1,3-butanediol (1,3-BDO), or an ester or amide thereof, comprising culturing the cell of claim 11 to produce 3-HBal and/or 1,3-BDO, or an ester or amide thereof.

18. A method for producing 4-hydroxybutyraldehyde (4-HBal) and/or 1,4-butanediol (1,4-BDO), or an ester or amide thereof, comprising culturing the cell of claim 11 to produce 4-HBal and/or 1,4-BDO, or an ester or amide thereof.

19. A method for producing 3-hydroxybutyraldehyde (3-HBal) and/or 1,3-butanediol (1,3-BDO), or an ester or amide thereof, comprising providing a substrate to the polypeptide of claim 6 and converting the substrate to 3-HBal and/or 1,3-BDO, wherein the substrate is a racemic mixture of 1,3-hydroxybutyryl-CoA.

20. A method for producing 4-hydroxybutyraldehyde (4-HBal) and/or 1,4-butanediol (1,4-BDO), or an ester or amide thereof, comprising providing a substrate to the polypeptide of claim 6 and converting the substrate to 4-HBal and/or 1,4-BDO, wherein the substrate is 1,4-hydroxybutyryl-CoA.

21. A method for producing 3-HBal and/or 1,3-BDO, or 4-HBal and/or 1,4-BDO, comprising incubating a lysate of the cell of claim 11 to produce 3-HBal and/or 1,3-BDO, or 4-HBal and/or 1,4-BDO.

22. A method for producing the isolated polypeptide of claim 6, comprising:
  (a) expressing the polypeptide in a cell; or
  (b) in vitro transcribing and translating a nucleic acid encoding the isolated polypeptide.

23. The isolated polypeptide of claim 6, wherein the amino acid sequence has at least 95% sequence identity to the amino acid sequence of SEQ ID NO: 1.

24. The isolated polypeptide of claim 6, wherein the amino acid sequence has at least 98% sequence identity to the amino acid sequence of SEQ ID NO:1.

25. The isolated polypeptide of claim 6, wherein the amino acid sequence has at least 99% sequence identity to the amino acid sequence of SEQ ID NO:1.

26. The isolated polypeptide of claim 6, wherein the amino acid sequence is identical to the amino acid sequence referenced as SEQ ID NO:1 with the exception of the amino acid substitution I66M.

\* \* \* \* \*